(12) United States Patent
Kim et al.

(10) Patent No.: US 11,053,285 B2
(45) Date of Patent: Jul. 6, 2021

(54) NUCLEIC ACIDS ENCODING HUMAN IMMUNODEFICIENCY VIRUS TYPE 1 (HIV-1) N-TERMINAL DELETED GP120 IMMUNOGENS AND METHODS OF USE

(71) Applicants: Duke University, Durham, NC (US); The Government of the United States, as represented by the Secretary of the Army, Fort Detrick, MD (US); Children's Medical Center Corporation, Boston, MA (US)

(72) Inventors: Jerome Kim, Fort Detrick, MD (US); Stephen Harrison, Boston, MA (US); Barton F. Haynes, Durham, NC (US); Georgia D. Tomaras, Durham, NC (US); Nelson Michael, Fort Detrick, MD (US)

(73) Assignees: Duke University, Durham, NC (US); THE GOVERNMENT OF THE UNITED STATES, AS REPRESENTED BY THE SECRETARY OF THE ARMY, Fort Detrick, MD (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/020,543

(22) Filed: Jun. 27, 2018

(65) Prior Publication Data

US 2018/0305411 A1 Oct. 25, 2018

Related U.S. Application Data

(62) Division of application No. 14/130,338, filed as application No. PCT/US2012/045530 on Jul. 5, 2012, now Pat. No. 10,040,826.

(60) Provisional application No. 61/529,137, filed on Aug. 30, 2011, provisional application No. 61/457,906, filed on Jul. 5, 2011.

(51) Int. Cl.

| C07K 14/16 | (2006.01) |
|---|---|
| C07K 14/005 | (2006.01) |
| A61K 39/12 | (2006.01) |
| A61K 39/21 | (2006.01) |
| C07K 16/10 | (2006.01) |
| A61K 39/00 | (2006.01) |
| A61K 38/00 | (2006.01) |

(52) U.S. Cl.
CPC ............ *C07K 14/005* (2013.01); *A61K 39/12* (2013.01); *A61K 39/21* (2013.01); *C07K 14/162* (2013.01); *C07K 16/1063* (2013.01); *A61K 38/00* (2013.01); *A61K 2039/6075* (2013.01); *C07K 2317/21* (2013.01); *C07K 2317/55* (2013.01); *C07K 2317/92* (2013.01); *C07K 2319/40* (2013.01); *C12N 2710/16622* (2013.01); *C12N 2740/16122* (2013.01); *C12N 2740/16134* (2013.01)

(58) Field of Classification Search
CPC .................. C07K 14/162; A61K 39/21; C12N 2740/16122; C12N 2740/16134
See application file for complete search history.

(56) References Cited

U.S. PATENT DOCUMENTS

| 5,858,366 | A | 1/1999 | Sodroski et al. |
|---|---|---|---|
| 6,042,836 | A | 3/2000 | Berman et al. |
| 6,806,055 | B2 | 10/2004 | Berman et al. |
| 7,847,085 | B2 | 12/2010 | Zolla-Pazner et al. |
| 7,951,377 | B2 | 5/2011 | Korber et al. |
| 8,048,431 | B2 | 11/2011 | Haynes |
| 8,071,107 | B2 | 12/2011 | Haynes et al. |
| 8,092,813 | B1 | 1/2012 | Novicki |
| 8,119,140 | B2 | 2/2012 | Korber et al. |
| 9,963,501 | B2 | 5/2018 | Haynes et al. |
| 2002/0106629 | A1 | 8/2002 | Murphy et al. |
| 2004/0052821 | A1 | 3/2004 | Berman |
| 2005/0025779 | A1 | 2/2005 | Berman et al. |
| 2009/0198042 | A1 | 8/2009 | Korber et al. |
| 2011/0044994 | A1 | 2/2011 | Chan-Hui et al. |
| 2011/0195090 | A1 | 8/2011 | Dimitrov |
| 2012/0167237 | A1 | 6/2012 | Bradley et al. |
| 2012/0177681 | A1 | 7/2012 | Singh et al. |
| 2012/0308593 | A1 | 12/2012 | Tartaglia et al. |
| 2012/0321699 | A1 | 12/2012 | Haynes et al. |
| 2013/0251726 | A1 | 9/2013 | Mascola et al. |
| 2013/0273103 | A1* | 10/2013 | Liao ..................... C07K 14/005 |
| 2013/0308593 | A1 | 11/2013 | Takeda et al. |
| 2014/0205607 | A1 | 7/2014 | Mascola et al. |

(Continued)

FOREIGN PATENT DOCUMENTS

| WO | WO-1990/006358 A1 | 6/1990 |
|---|---|---|
| WO | WO-1997/013852 A1 | 4/1997 |

(Continued)

OTHER PUBLICATIONS

Berman, P. W., et al., Jul. 1992, Neutralization of multiple laboratory and clinical isolates of human immunodeficiency virus type 1 (HIV-1) by antisera raised against gp120 from the MN isolate of HIV-1, J. Virol. 66(7):4464-4469.*

Murphy, C. I., et al., 1993, Enhanced expression, secretion, and large-scale purification of recombinant HIV-1 gp120 in insect cells using the baculovirus egtand p67 signal peptides, Prot. Exp. Purif. 4:349-357.*

(Continued)

*Primary Examiner* — Jeffrey S Parkin
(74) *Attorney, Agent, or Firm* — Wilmer Cutler Pickering Hale and Dorr LLP

(57) ABSTRACT

The present invention relates, in general, to human immunodeficiency virus (HIV), and in particular to a vaccine for HIV-1 and to methods of making and using same.

25 Claims, 56 Drawing Sheets

Specification includes a Sequence Listing.

(56) References Cited

U.S. PATENT DOCUMENTS

| | | | |
|---|---|---|---|
| 2014/0221625 | A1 | 8/2014 | Haynes et al. |
| 2014/0248301 | A1 | 9/2014 | Haynes et al. |
| 2015/0246111 | A1 | 9/2015 | Berman et al. |
| 2016/0271244 | A1 | 9/2016 | Haynes et al. |

FOREIGN PATENT DOCUMENTS

| | | |
|---|---|---|
| WO | WO-2001/060838 A2 | 8/2001 |
| WO | WO-2005/028625 A2 | 3/2005 |
| WO | WO-2010/019262 A2 | 2/2010 |
| WO | WO-2011/106100 A2 | 9/2011 |
| WO | WO-2012/071521 A2 | 5/2012 |
| WO | WO-2012/141798 | 10/2012 |
| WO | WO-2013006688 A2 | 1/2013 |
| WO | WO-2013/052095 A2 | 4/2013 |
| WO | WO-2014/124156 A1 | 8/2014 |
| WO | WO-2015/143193 A1 | 9/2015 |

OTHER PUBLICATIONS

Da Silva, J.X., et al., "Sequence variations of Env signal peptide alleles in different clinical stages of HIV infection," Peptides, vol. 32, pp. 1800-1806 (published online Jul. 26, 2011).

Coico, R., et al., "The Genetic Basis of Antibody Structure," Immunology—A Short Course, Fifth Edition, published by John Wiley & Sons, Inc., Hoboken, New Jersey, Chapter 6, pp. 79-89, 13 total pages (2003).

Alam, S. M., et al., "The Role of Antibody Polyspecificity and Lipid Reactivity in Binding of Broadly Neutralizing Anti-HIV-1 Envelope Human Monoclonal Antibodies 2F5 and 4E10 to Glycoprotein 41 Membrane Proximal Envelope Epitopes," Journal of Immunology, 178 (7), pp. 4424-4435, Author Manuscript—25 total pages (Apr. 1, 2007).

Alam, S. M., et al., "Human Immunodeficiency Virus Type 1 gp41 Antibodies That Mask Membrane Proximal Region Epitopes: Antibody Binding Kinetics, Induction, and Potential for Regulation in Acute Infection," Journal of Virology, vol. 82, No. 1, pp. 115-125 (Jan. 2008).

Alam, S.M., et al., "Antigenicity and Immunogenicity of RV144 Vaccine AIDSVAX Clade E Envelope Immunogen Is Enhanced by a gp120 N-Terminal Deletion," Journal of Virology, vol. 87, No. 3, pp. 1554-1568 (Feb. 2013).

Alam, S.M., et al., "Role of HIV Membrane in Neutralization by Two Broadly Neutralizing Antibodies," Proceedings of The National Academy of Sciences of the United States of America, vol. 106, No. 48, pp. 20234-20239 (Dec. 1, 2009).

Barefoot B., et al., "Comparison of Multiple Vaccine Vectors in a Single Heterologous Prime Boost Trial," Vaccine vol. 26, No. 48, pp. 6108-6118, Author Manuscript—23 total pages (Nov. 11, 2008).

Barouch, D.H., et al. "Mosaic HIV-1 Vaccines Expand the Breadth and Depth of Cellular Immune Responses in Rhesus Monkeys," Nature Med., vol. 16, No. 3, pp. 319-323, Author Manuscript—15 total pages (Mar. 2010).

Berman, P.W., "Development of Bivalent rpg120 Vaccines to Prevent HIV Type 1 Infection," AIDS Research and Human Retroviruses, vol. 14, Supplement 3, pp. S-277-S-289 (1998).

Berman, P.W., et al, "Development of Bivalent (B/E) Vaccines Able to Neutralize CCR5-Dependent Viruses from the United States and Thailand," Virology, vol. 265, pp. 1-9 (1999).

Billings, E.A., et al., "Surface Plasmon Resonance Analysis of Anti-gp120 V2-Specific IgG Antibodies Generated in the RV144 Thai Trial", AIDS Research and Human Retroviruses, vol. 27, No. 10, Abstracts from AIDS Vaccine Conference 2011, Bangkok, Thailand, pp. A-21 and A-22, 4 total pages (Sep. 12-15, 2011).

Bonsignori, M., et al., "Analysis of a Clonal Lineage of HIV-1 Envelope V2/V3 Conformational Epitope-Specific Broadly Neutralizing Antibodies and Their Inferred Unmutated Common Ancestors," Journal of Virology, vol. 85, No. 19, pp. 9998-10009, 13 total pages (Oct. 2011).

Bonsignori, M., et al., "Isolation of CD4-Binding Site and V2/V3 Conformational (Quaternary) Broadly Neutralizing Antibodies from the Same HIV-1 Infected African Subject", AIDS Research and Human Retroviruses, vol. 27, No. 10, Abstracts from AIDS Vaccine Conference 2011, Bangkok, Thailand, p. A-120, 3 total pages (Sep. 12-15, 2011).

Davenport, T., "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107, (Jul. 2011).

Ewing, B. and Green, P., "Base-Calling of Automated Sequencer Traces Using Phred. II. Error Probabilities," Genome Research, vol. 8, pp. 186-194, 10 total pages (1998).

Ewing, B., et al., "Base-Calling of Automated Sequencer Traces Using Phred. I. Accuracy Assessment," Genome Research, vol. 8, pp. 175-185, 12 total pages (1998).

Ferrari, G., et al., "An HIV-1 gp120 Envelope Human Monoclonal Antibody That Recognizes a C1 Conformational Epitope Mediates Potent Antibody-Dependent Cellular Cytotoxicity (ADCC) Activity and Defines a Common ADCC Epitope in Human HIV-1 Serum," Journal of Virology, vol. 85, No. 14, pp. 7029-7036 (Jul. 2011).

Finzi, A., et al., "Conformational Characterization of Aberrant Disulfide-Linked HIV-1 gp120 Dimers Secreted from Overexpressing Cells," J. Virol. Methods, vol. 168, Nos. 1-2, 155-161, Author Manuscript—15 total pages (Sep. 2010).

Flynn, B. J., et al., "Immunization with HIV Gag Targeted to Dendritic Cells Followed by Recombinant New York Vaccinia Virus Induces Robust T-cell Immunity in Nonhuman Primates," Proceedings of the National Academy of Sciences, vol. 108, No. 17, pp. 7131-7136 (Apr. 26, 2011).

Flynn, et al., "Placebo-Controlled Phase 3 Trial of a Recombinant Glycoprotein 120 Vaccine to Prevent HIV-1 Infection," The Journal of Infectious Diseases, vol. 191, pp. 654-665 (Mar. 1, 2005).

Francis, D.P., et al., "Advancing AIDSVAX to Phase 3. Safety, Immunogenicity, and Plans for Phase 3," AIDS Research and Human Retroviruses, vol. 14, Supplement 3, pp. S325-S331 (1998).

Gorny, M. K., et al., "Functional and Immunochemical Cross-Reactivity of V2-Specific Monoclonal Antibodies from HIV-1-Infected Individuals," Virology, vol. 427, No. 2, pp. 198-207, Author Manuscript—26 total pages (Jun. 5, 2012).

Gorny, M. K., et al., "Human Anti-V2 Monoclonal Antibody That Neutralizes Primary but Not Laboratory Isolates of Human Immunodeficiency Virus Type 1," Journal of Virology, vol. 68, No. 12, pp. 8312-8320, (Dec. 1994).

Gorny, M. K., et al., "Identification of a New Quaternary Neutralizing Epitope on Human Immunodeficiency Virus Type 1 Virus Particles," Journal of Virology, vol. 79, No. 8, pp. 5232-5237, (Apr. 2005).

Harris, A., et al., "Trimeric HIV-1 Glycoprotein gp140 Immunogens and Native HIV-1 Envelope Glycoproteins Display the Same Closed and Open Quaternary Molecular Architectures," Proceedings of the National Academy of Sciences, vol. 108, No. 28, pp. 11440-11445, (Jul. 12, 2011).

Haynes B.F., "Case control study of the RV144 trial for immune correlates: the analysis and way forward" presented at Plenary Session 01 Novel Approaches in Clinical Evaluation through Global Collaboration at the AIDS Vaccine Conference 2011, Bangkok, Thailand (<http://www.aidsvaxwebcasts.org>), 9 total pages (Sep. 12-15, 2011).

Honnen, W. J., et al., "Type-Specific Epitopes Targeted by Monoclonal Antibodies with Exceptionally Potent Neutralizing Activities for Selected Strains of Human Immunodeficiency Virus Type 1 Map to a Common Region of the V2 Domain of gp120 and Differ Only at Single Positions from the Clade B Consensus Sequence," Journal of Virology, vol. 81, No. 3, pp. 1424-1432 (Feb. 2007).

Jeffs, S.A., et al: "Antigenicity of truncated forms of the human immunodeficiency virus type 1 envelope glycoprotein," Journal of General Virology, vol. 77, pp. 1403-1410 (1996).

Kasturi, S. P., et al, "Programming the Magnitude and Persistence of Antibody Responses with Innate Immunity," Nature, vol. 470, No. 7335, pp. 543-547, Author Manuscript—20 total pages (Feb. 24, 2011).

(56) References Cited

OTHER PUBLICATIONS

Kayman, S. C., et al., "Presentation of Native Epitopes in the V1/V2 and V3 Regions of Human Immunodeficiency Virus Type 1 gp120 by Fusion Glycoproteins Containing Isolated gp120 Domains," Journal of Virology, vol. 68, No. 1, pp. 400-410, (Jan. 1994).

Keele, B. F., et al., "Identification and Characterization of Transmitted and Early Founder Virus Envelopes in Primary HIV-1 Infection," Proceedings of the National Academy of Sciences, vol. 105, No. 21, pp. 7552-7557 (May 27, 2008).

Kwong, P.D., et al., "HIV-1 evades antibody-mediated neutralization through conformational masking of receptor-binding sites," Nature, vol. 420, pp. 678-682 (Dec. 12, 2002).

Lasky, L.A. et al., "Neutralization of the AIDS Retrovirus by Antibodies to a Recombinant Envelope Glycoprotein," Science, vol. 233, No. 4760, pp. 209-212, 5 total pages (Jul. 11, 1986).

Liao H.-X., et al, "A Group M Consensus Envelope Glycoprotein Induces Antibodies That Neutralize subsets of Subtype B and C HIV-1 Primary Viruses," Virology, vol. 353, pp. 268-282 (2006).

Liao, H. X., et al., "High-throughput Isolation of Immunoglobulin Genes from Single Human B Cells and Expression as Monoclonal Antibodies," Journal of Virology Methods, vol. 158, Nos. 1-2, pp. 171-179, Author Manuscript—22 total pages (Jun. 2009).

Liu, J., et al., "Molecular Architecture of Native HIV-1 gp120 Trimers," Nature, vol. 455, No. 7209, pp. 109-113, Author Manuscript—12 total pages (Sep. 4, 2008).

Liu, P., et al., "Dynamic Antibody Specificities and Virion Concentrations in Circulating Immune Complexes in Acute to Chronic HIV-1 Infection," Journal of Virology, vol. 85, No. 21, pp. 11196-11207 (Nov. 2011).

Ma, B.-J., et al., "Envelope Deglycosylation Enhances Antigenicity of HIV-1 gp41 Epitopes for Both Broad Neutralizing Antibodies and Their Unmutated Ancestor Antibodies," PLoS Pathogens, vol. 7, Issue 9, pp. e1002200, pp. 1-16 (Sep. 2011).

McCutchan, F.E., et al., "Genetic Variants of HIV-1 in Thailand," AIDS Research and Human Retroviruses, vol. 8, No. 11, pp. 1887-1895, 18 pages (1992).

McElrath, J. and Haynes, B.F., "Induction of Immunity to Human Immunodeficiency Virus Type-1 by Vaccination," Immunity, vol. 33, No. 4, pp. 542-554, Author Manuscript—25 total pages (Oct. 29, 2010).

McLellan, J.S., et al., "Structure of HIV-1 gp120 Vi/V2 Domain with Broadly Neutralizing Antibody PG9," Nature, vol. 480, No. 7377, pp. 336-343, Author Manuscript—17 total pages (Dec. 15, 2012).

Munshaw, S. and Kepler, T.B., "SoDA2: A Hidden Markov Model Approach for Identification of Immunoglobulin Rearrangements," Bioinformatics, vol. 26, No. 7, pp. 867-872, (Feb. 9, 2010).

Pinter, A., et al., "Potent neutralization of primary HIV-1 isolates by antibodies directed against epitopes present in the V1/V2 domain of HIV-1 gp120," Vaccine, vol. 16, No. 19, pp. 1803-1811 (1998).

Pinter, A., et al., "The V1/V2 Domain of gp120 Is a Global Regulator of the Sensitivity of Primary Human Immunodeficiency Virus Type 1 Isolates to Neutralization by Antibodies Commonly Induced upon Infection," Journal of Virology, vol. 78, No. 10, pp. 5205-5215 (May 2004).

Pitisuttithum, P., "HIV vaccine research in Thailand: lessons learned," Expert Rev. Vaccines, vol. 7, No. 3, pp. 311-317 (2008).

Rerks-Ngarm, S., et al, "Vaccination with ALVAC and AIDSVAX to Prevent HIV-1 Infection in Thailand," The New England Journal of Medicine, vol. 361, No. 23, pp. 2209-2220 (Dec. 3, 2009).

Safsten, P., et al. "Screening Antibody-Antigen Interactions in Parallel Using Biacore A100," Anal. Biochem., vol. 353, pp. 181-190 (2006).

Santra, S., et al., "Mosaic Vaccines Elicit CD8+ T Lymphocyte Responses in Monkeys that Confer Enhanced Immune Coverage of Diverse HIV Strains," Nature Med., vol. 16, No. 3, pp. 324-328, Author Manuscript—13 total pages (Mar. 2010).

Shields, R.L., et al., "High Resolution Mapping of the Binding Site on Human IgG1 for FcγRI, FcγRII, FcγRIII, and FcRn and Design of IgG1 Variants with Improved Binding to the FcγR," Journal of Biological Chemistry, vol. 276, pp. 6591-6604, 27 total pages (Nov. 28, 2000).

Smith, T. F. and Waterman, M.S., "Identification of Common Molecular Subsequences," Journal of Molecular Biology, vol. 147, pp. 195-197 (1981).

Tomaras, G.D., et al., "Initial B-Cell Responses to Transmitted Human Immunodeficiency Virus Type 1: Virion-Binding Immunoglobulin M (IgM) and IgG Antibodies Followed by Plasma Anti-gp41 Antibodies with Ineffective Control of Initial Viremia," Journal of Virology, vol. 82, No. 24, pp. 12449-12463 (Dec. 2008).

Torrieri-Dramard, L., et al., "Intranasal DNA Vaccination Induces Potent Mucosal and Systemic Immune Responses and Cross-protective Immunity Against Influenza Viruses," Molecular Therapy, vol. 19, No. 3, pp. 602-611 (Mar. 2011).

Tsao, C., et al., "Antigenicity and immunogenicity of transmitted/founder HIV envelope oligomers compared to chronic HIV envelopes", AIDS Research and Human Retroviruses, vol. 26, No. 10, Abstracts from AIDS Vaccine Conference 2010, Atlanta, Georgia, p. A-26, 2 total pages (Sep. 28-Oct. 1, 2010).

VanCott, T. C., et al., "Dissociation rate of antibody-gp120 binding interactions is predictive of V3-mediated neutralization of HIV-1," J. Immunol., vol. 153, pp. 449-459, 12 total pages (1994).

Verkoczy L., et al., "Role of Immune Mechanisms in Induction of HIV-1 Broadly Neutralizing Antibodies," Current Opinion Immunology, vol. 23, No. 3, pp. 383-390, Author Manuscript—12 total pages (Jun. 2011).

Volpe, J. M., et al., "SoDA: Implementation of a 3D Alignment Algorithm for Inference of Antigen Receptor Recombinations," Bioinformatics, vol. 22, No. 4, pp. 438-444, (Dec. 15, 2005).

Walker, L. M., et al., "Broad and Potent Neutralizing Antibodies from an African Donor Reveal a New HIV-1 Vaccine Target," Science, vol. 326, No. 5950, pp. 285-289, Author Manuscript—10 total pages (Oct. 9, 2009).

Wrammert, J., et al., "Rapid Cloning of High-Affinity Human Monoclonal Antibodies Against Influenza Virus," Nature, vol. 453, No. 7195, pp. 667-671, Author Manuscript—15 total pages (May 29, 2008).

Yu, J.-S., et al., "Generation of Mucosal Anti-Human Immunodeficiency Virus Type 1 T-Cell Responses by Recombinant *Mycobacterium smegmatis*," Clinical and Vaccine Immunology, vol. 13, No. 11, pp. 1204-1211 (Nov. 2006).

Yu, J.S., et al., "Recombinant *Mycobacterium bovis* Bacillus Calmette-Guérin Elicits Human Immunodeficiency Virus Type 1 Envelope-Specific T Lymphocytes at Mucosal Sites," Clinical and Vaccine Immunol., vol. 14, No. 7, pp. 886-893 (Jul. 2007).

Zhu, P., et al., "Distribution and Three-Dimensional Structure of AIDS Virus Envelope Spikes," Nature, vol. 441: pp. 847-852, (Jun. 15, 2006).

Zolla-Pazner, S., et al., "V2-Reactive Antibodies in RV144 Vaccinees' Plasma", AIDS Research and Human Retroviruses, vol. 27, No. 10, Abstracts from AIDS Vaccine 2011, Bangkok, Thailand, p. A-21, 3 total pages (Sep. 12-15, 2011).

Adams, E., et al., "Intrinsic B-cell hyporesponsiveness accounts for self-tolerance in lysozyme/anti-lysozyme double-transgenic mice," Proc. Natl. Acad. Sci. USA, vol. 87, pp. 5687-5691 (Aug. 1990).

Alam, S. M., et al., "Differential reactivity of germ line allelic variants of a broadly neutralizing HIV-1 antibody to a gp41 fusion intermediate conformation, "Journal of Virology, vol. 85, No. 22, pp. 11725-11731 (Nov. 2011).

Alt, F. W. et al., "Development of the primary antibody repertoire," Science, vol. 238, No. 4830, pp. 1079-1087 (Nov. 20, 1987).

Alt, F. W. et al. "Ordered rearrangement of immunoglobulin heavy chain variable region segments," EMBO J., vol. 3, No. 6, pp. 1209-1219 (1984).

Batista, F. D. & Neuberger, M.S., "Affinity dependence of the B cell response to antigen: a threshold, a ceiling, and the importance of off-rate," Immunity, vol. 8, pp. 751-759 (Jun. 1998).

Berman, P. W. et al., "Expression of Membrane-Associated and Secreted Variants of gp160 of Human Immunodeficiency Virus Type 1 In Vitro and in Continuous Cell Lines", Journal of Virology, vol. 62, No. 9, pp. 3135-3142 (1988).

(56) References Cited

OTHER PUBLICATIONS

Boekel, E., et al., "Changes in the $V_H$ gene repertoire of developing precursor B lymphocytes in mouse bone marrow mediated by the pre-B cell receptor," Immunity, vol. 7, pp. 357-368 (Sep. 1997).
Burton, D. R., et al., "Antibody vs. HIV in a clash of evolutionary titans," Proc. Natl. Acad. Sci. USA, vol. 102, No. 42, pp. 14943-14948, (Oct. 18, 2005).
Calarese, D. A., et al., "Dissection of the carbohydrate specificity of the broadly neutralizing anti-HIV-1 antibody 2G12," Proc. Natl. Acad. Sci. USA, vol. 102, No. 38, pp. 13372-13377, 9 total pages (Sep. 20, 2005).
Carsetti, R., et al., "Transitional B cells are the target of negative selection in the B cell compartment," J. Exp. Med., vol. 181, pp. 2129-2140 (Jun. 1995).
Changela, A., et al., "Crystal structure of human antibody 2909 reveals conserved features of quaternary structure-specific antibodies that potently neutralize HIV-1," J. Virol., vol. 85, No. 6, pp. 2524-2535, 16 total pages (Mar. 2011).
Chen, C., et al., "Deletion and editing of B cells that express antibodies to DNA," J. Immunol., vol. 152, pp. 1970-1982 (1994).
Clarke, S. H., et al., "Inter- and intraclonal diversity in the antibody response to influenza hemagglutinin," J. Exp. Med., vol. 161, pp. 687-704 (Apr. 1985).
Clarke, S. H., et al., "V region gene usage and somatic mutation in the primary and secondary responses to influenza virus hemagglutinin," J. Immunol., vol. 144, No. 7, pp. 2795-2801 (Apr. 1, 1990).
Crotty, Shane, "Follicular helper CD4 T cells ($T_{FH}$)," Annu. Rev. Immunol., vol. 29, pp. 621-663, 45 total pages (2011).
Dal Porto, J. M., et al., "Antigen drives very low affinity B cells to become plasmacytes and enter germinal centers," J. Immunol., vol. 161, pp. 5373-5381 (1998).
Dal Porto, J. M., et al., "Very low affinity B cells form germinal centers, become memory B cells, and participate in secondary immune responses when higher affinity competition is reduced," J. Exp. Med., vol. 195, No. 9, pp. 1215-1221, 9 total pages (May 6, 2002).
Dell'Era, L., et al., "Immunogenicity, safety and tolerability of MF59-adjuvanted seasonal influenza vaccine in children with juvenile idiopathic arthritis," Vaccine, vol. 30, pp. 936-940 (Dec. 3, 2011).
Di Noia, J. M. & Neuberger, M.S., "Molecular Mechanisms of Antibody Somatic Hypermutation," Annual Review of Biochemistry, vol. 76, pp. 1-22, 25 total pages (2007).
Dimitrov, Dimiter S., "Therapeutic antibodies, vaccines and antibodyomes," mAbs, vol. 2, No. 3, pp. 347-356 (May/Jun. 2010).
Ehlich, A. et al., "Analysis of the B-cell progenitor compartment at the level of single cells," Curr. Biol., vol. 4, No. 7, pp. 573-583 (1994).
Ekiert, D. C., et al., "Antibody recognition of a highly conserved influenza virus epitope: implications for universal prevention and therapy," Science, vol. 324, No. 5924, pp. 246-251 (Apr. 10, 2009), Author Manuscript—9 total pages.
European Search Report dated Apr. 22, 2015 in European Application No. 12837722.3, 6 total pages.
Fleishman, S.J., et al., "Computational Design of Proteins Targeting the Conserved Stem Region of Influenza Hemaqqlutinin", Science, vol. 332, No. 6031, pp. 816-821 (May 13, 2011).
Frey G. et al., "A fusion-intermediate state of HIV-1 gp41 targeted by broadly neutralizing antibodies," Proc. Natl. Acad. Sci. USA, vol. 105, No. 10, pp. 3739-3744 (Mar. 11, 2008).
Goodnow, C. C., "Transgenic mice and analysis of B-cell tolerance," Annu. Rev. Immunol., vol. 10, pp. 489-518 (1992).
Gray, E. S., et al., "Isolation of a monoclonal antibody that targets the alpha-2 helix of gp120 and represents the initial autologous neutralizing-antibody response in an HIV-1 subtype C-infected individual," J. Virol., vol. 85, No. 15, pp. 7719-7729, consisting of 15 total pages (May 2011).
Gray, E. S., et al., "The neutralization breadth of HIV-1 develops incrementally over four years and is associated with CD4+ T cell decline and high viral load during acute infection," J. Virol., vol. 85, No. 10, pp. 4828-4840 (May 2011).
Gu, H., et al., "Most peripheral B cells in mice are ligand selected," J. Exp. Med., vol. 173, pp. 1357-1371 (Jun. 1991).
Halliday, J., et al., "Vaccination for hepatitis C virus: closing in on an evasive target," Expert Rev. Vaccines, vol. 10, No. 5, pp. 659-672, 20 pages, Author Manuscript—20 total pages (May 2011).
Han, S., et al., "In situ studies of the primary immune response to (4-hydroxy-3-nitrophenyl)acetyl IV. Affinity-dependent, antigen-driven B cell apoptosis in germinal centers as a mechanism for maintaining self-tolerance," J. Exp. Med., vol. 182, No. 6, pp. 1635-1644 (Dec. 1, 1995).
Hardy, R. R., et al., "Resolution and characterization of pro-B and pre-pro-B cell stages in normal mouse bone marrow," J. Exp. Med., vol. 173, pp. 1213-1225 (May 1991).
Hardy, R.R. and Hayakawa, K., "B cell development pathways," Annu. Rev. Immunol., vol. 19, pp. 595-621 (2001).
Hayakawa, K., et al., "Positive selection of natural autoreactive B cells," Science, vol. 285, pp. 113-116 (1999).
Haynes, B. F., et al., "B-cell-lineage immunogen design in vaccine development with HIV-1 as a case study," Nature Biotechnology, vol. 30, No. 5, pp. 423-433, Author Manuscript—30 total pages (May 7, 2013).
Haynes, B. F. et al., "Cardiolipin polyspecific autoreactivity in two broadly neutralizing HIV-I antibodies," Science, vol. 308, pp. 1906-1908 (Jun. 24, 2005).
Haynes, B. F., et al., "HIV Type 1 V3 Region Primer-Induced Antibody Suppression Is Overcome by Administration of C4-V3 Peptides as a Polyvalent Immunogen," AIDS Res. Human Retroviruses, vol. 11, No. 2, pp. 211-221 (1995).
Haynes, B. F., et al., "Immune-Correlates Analysis of an HIV-1 Vaccine Efficacy Trial," The New England Journal of Medicine, vol. 366, No. 14, pp. 1275-1286 (Apr. 5, 2012).
Haynes, B.F. et al., "Antibody polyspecificity and neutralization of HIV-1: A hypothesis", Human Antibodies, vol. 14, pp. 59-67, Author Manuscript—12 total pages (2005).
Hessell, A. J., et al., "Broadly neutralizing human anti-HIV antibody 2G12 is effective in protection against mucosal SHIV challenge even at low serum neutralizing titers," PLoS Pathog., vol. 5, Issue 5, e1000433, pp. 1-9 (May 2009).
Hessell, A. J., et al., "Broadly neutralizing monoclonal antibodies 2F5 and 4E10 directed against the human immunodeficiency virus type 1 gp41 membrane-proximal external region protect against mucosal challenge by simian-human immunodeficiency virus SHIVBa-L," J. Virol., vol. 84, No. 3, pp. 1302-1313 (Feb. 2010).
Hessell, A. J., et al., "Effective, low-titer antibody protection against low-dose repeated mucosal SHIV challenge in macaques," Nature Med., vol. 15, No. 8, pp. 951-954, 5 total pages (Aug. 2009).
Hessell, A. J., et al., "Fc receptor but not complement binding is important in antibody protection against HIV," Nature, vol. 449, pp. 101-104, 5 total pages (Sep. 6, 2007).
Hilleman, Maurice R., "Overview of the needs and realities for developing new and improved vaccines in the 21st century," Intervirology, vol. 45, pp. 199-211 (2002).
Hioe, C. E., et al., "Anti-V3 Monoclonal Antibodies Display Broad Neutralizing Activities against Multiple HIV-1 Subtypes", PLOS ONE, vol. 5, No. 4, e10254, 14 total pages (Apr. 21, 2010).
International Preliminary Report on Patentability for PCT/US2014/015133 dated Aug. 20, 2015, 8 total pages.
International Search Report and Written Opinion issued by the European Patent Office as Searching Authority in PCT/US2014/015133, 10 total pages (dated Apr. 2, 2014).
International Search Report for PCT/US2012/000442, 4 total pages (dated Mar. 28, 2013).
Karasuyama, H., et al., "A complex of glycoproteins is associated with VpreB/λ□ surrogate light chain on the surface of μ heavy chain-negative early precursor B cell lines," J. Exp. Med., vol. 178, pp. 469-478 (Aug. 1993).
Karasuyama, H., et al., "The proteins encoded by the VpreB and λ□pre-B cell-specific genes can associate with each other and with μ heavy chain," J. Exp. Med., vol. 172, pp. 969-972 (Sep. 1990).
Kashyap, A. K., et al., "Combinatorial antibody libraries from survivors of the Turkish H5N1 avian influenza outbreak reveal virus

(56) References Cited

OTHER PUBLICATIONS neutralization strategies," Proc. Natl. Acad. Sci. USA, vol. 105, No. 16, pp. 5986-5991 (Apr. 22, 2008).

Kelsoe, Garnett, "In situ studies of the germinal center reaction," Adv. Immunol., vol. 60, pp. 267-288, 24 pages in total (Apr. 21, 1995).

Kepler, T. B. & Perelson, A. S., "Somatic hypermutation in B cells: an optimal control treatment," J. Theor. Biol., vol. 164, No. 1, pp. 37-64 (Sep. 7, 1993).

Kepler, Thomas B., "Codon bias and plasticity in immunoglobulins," Molecular Biology and Evolution, vol. 14, No. 6, pp. 637-643 (1997).

Klein, F., et al., "Antibodies in HIV-1 Vaccine Development and Therapy," Science, vol. 341, No. 6151, pp. 1199-1204, Author Manuscript—17 total pages (2013).

Korber, B.T., et al., Sequences 119, 120 and 219 listed in Sequence Listing for U.S. Pat. No. 7,951,377 issued May 31, 2011, pp. 1-681.

Land A. et al., "Folding of HIV-1 Envelope Glycoprotein Involves Extensive Isomerization of Disulfide Bonds and Conformation-Dependent Leader Peptide Cleavage," The FASEB Journal, vol. 17, pp. 1058-1067 (2003).

Leroux-Roels, I., et al., "Strong and persistent CD4+ T-cell response in healthy adults immunized with a candidate H IV-1 vaccine containing gp120, Nef and Tat antigens formulated in three Adjuvant Systems," Vaccine, vol. 28, pp. 7016-7024 (Aug. 20, 2010).

Levine, M. H., et al., "A B-cell receptor-specific selection step governs immature to mature B cell differentiation," Proc. Natl. Acad. Sci. USA, vol. 97, No. 6, pp. 2743-2748 (Mar. 14, 2000).

Li, Y. et al., "Control of Expression, Glycosylation, and Secretion of HIV-1 gp120 by Homologous and Heterologous Signal Sequences," Virology, pp. 266-278 (1994).

Li, Y. et al., "Effects of Inefficient Cleavage of the Signal Sequence of HIV-1 gp120 on its Association with Calnexin, Folding, and Intracellular Transport," Proc. Natl. Acad. Sci. USA, vol. 93, pp. 9606-9611 (Sep. 1996).

Li, Y. S., et al., "The regulated expression of B lineage associated genes during B cell differentiation in bone marrow and fetal liver," J. Exp. Med., vol. 178, pp. 951-960 (Sep. 1993).

Li, Z. et al., "A conserved degradation signal regulates RAG-2 accumulation during cell division and links V(D)J recombination to the cell cycle," Immunity, vol. 5, pp. 575-589 (Dec. 1996).

Liao, H. X., et al., "Initial antibodies binding to HIV-1 gp41 in acutely infected subjects are polyreactive and highly mutated," J. Exp. Med., pp. 1-13 (Oct. 10, 2011).

Loder, F., et al., "B cell development in the spleen takes place in discrete steps and is determined by the quality of B cell receptor-derived signals," J. Exp. Med., vol. 190, No. 1, pp. 75-89 (Jul. 5, 1999).

Meffre, E., et al., "Surrogate light chain expressing human peripheral B cells produce self-reactive antibodies," J. Exp. Med., vol. 199, No. 1, pp. 145-150 (Jan. 5, 2004).

Messmer, B. T., et al., "Multiple distinct sets of stereotyped antigen receptors indicate a role for in antigen promoting chronic lymphocytic leukemia," J. Exp. Med., vol. 200, No. 4, pp. 519-525 (Aug. 16, 2004).

Mietzner, B., et al., "Autoreactive IgG memory antibodies in patients with systemic lupus erythematosus arise from nonreactive and polyreactive precursors," Proc. Natl. Acad. Sci. USA, vol. 105, No. 28, pp. 9727-9732 (Jul. 15, 2008).

Montefiori, D. C., et al., "Magnitude and Breadth of the Neutralizing Antibody Response in the RV144 and Vax003 HIV-1 Vaccine Efficacy Trials," J. Inf. Dis., vol. 206, pp. 431-441 (Aug. 1, 2012).

Moody, M., et al., "H3N2 Influenza Infection Elicits More Cross-reactive and Less Clonally Expanded Anti-hemagglutinin Antibodies Than Influenza Vaccination," PLoS One, vol. 6, Issue 10, e25797, pp. 1-14 (Oct. 2011).

Nabel, G. J. & Fauci, A. S., "Induction of unnatural immunity: prospects for a broadly protective universal influenza vaccine," Nat. Med., vol. 16, No. 12, pp. 1389-1391 (Dec. 2010).

Nemazee, D. & Weigert, M., "Revising B cell receptors," J. Exp. Med., vol. 191, No. 11, pp. 1813-1817 (Jun. 5, 2000).

Nemazee, D. A. and Buerki, K., "Clonal deletion of B lymphocytes in a transgenic mouse bearing anti-MHC class I antibody genes," Letters to Nature, vol. 337, pp. 562-566 (Feb. 9, 1989).

Ofek, G. et al., "Elicitation of structure-specific antibodies by epitope scaffolds," Proc. Natl. Acad. Sci. USA, vol. 107, No. 42, pp. 17880-17887 (Oct. 19, 2010).

Ohno, T., et al., "A Broadly Neutralizing Monoclonal Antibody that Recognizes the V3 Region of Human Immunodeficiency Virus Type 1 Glycoprotein gp120," Proc. Natl. Adac. Sci. USA, vol. 88, pp. 10726-10729 (Dec. 1991).

Pancera, M. et al., Crystal structure of PG 16 and chimeric dissection with somatically related PG9: structure-function analysis of two quaternary specific antibodies that effectively neutralize HIV-1, J. Virol., vol. 84, pp. 8098-8110 (Aug. 2010).

Perez-Andres, M., et al., "Human peripheral blood B-cell compartments: a crossroad in B-cell traffic," Cytometry Part B (Clin. Cytom.), vol. 78B, Suppl. 1, pp. S47-S60 (2010).

Phillips, Robert S., "Structure, mechanism, and substrate specificity of kynureninase," Biochem. Biophys. Acta., vol. 1814, No. 11, pp. 1481-1488, Author Manuscript—19 total pages (Nov. 2011).

Plotkin, Stanley A., "Correlates of protection induced by vaccination," Clin. Vaccine Immunol., vol. 17, No. 7, pp. 1055-1065 (Jul. 2010).

Plotkin, Stanley A., "Correlates of vaccine-induced immunity," Clin. Infect. Dis., vol. 47, pp. 401-409 (2008).

Plotkin, Stanley A., "Vaccines: the fourth century," Clin, Vaccine Immunol., vol. 16, No. 12, pp. 1709-1719 (Dec. 2009).

Pulendran, B. et al., "Soluble Antigen Can Cause Enhanced Apoptosis of Germinal-Centre B Cells," Nature, vol. 375, pp. 331-334 (May 25, 1995).

Radic, M. et al., "B Lymphocytes May Escape Tolerance by Revising Their Antigen Receptors," J. Exp. Med., vol. 177, pp. 1165-1173 (1993).

Rajewsky, Klaus, "Clonal Selection and Learning in the Antibody System," Nature, vol. 381, pp. 751-758 (Jun. 27, 1996).

Reth, M. et al., "Activation of $V^x$ Gene Rearrangement in pre-B Cells Follows the Expression of Membrane-bound immunoglobulin Heavy Chains," EMBO J., vol. 6, No. 11, pp. 3299-3305 (1987).

Richman, D. D. et al., "Rapid Evolution of the Neutralizing Antibody Response to HIV Type 1 Infection," Proc. Natl. Acad. Sci. USA, vol. 100, No. 7, pp. 4144-4149 (Apr. 1, 2003).

Rogozin, I. B., et al., "Somatic Hypermutagenesis in immunoglobulin Genes: II. Influence of Neighbouring Base Sequences on Mutagenesis," Biochimica et Biophysica Acta (BBA)—Gene Structure and Expression, vol. 1171, pp. 11-18 (1992).

Rolink, A.G., et al., "Characterization of Immature B Cells by a Novel Monoclonal Antibody, by Turnover and by Mitogen Reactivity," Eur. J. Immunol., vol. 28, pp. 3738-3748 (Nov. 1998).

Rolland M., et al., "Increased HIV-1 vaccine efficacy against viruses with genetic signatures in Env V2," Nature, vol. 490, pp. 417-421 (Oct. 18, 2012).

Scheid, J. F. et al., "Broad Diversity of Neutralizing Antibodies Isolated from Memory B Cells in HIV-Infected Individuals," Nature, vol. 458, pp. 636-640 (2009).

Schlissel, M. S., et al., "Activation of immunoglobulin Kappa Gene Rearrangement Correlates with Induction of Germline Kappa Gene Transcription," Cell, vol. 58, pp. 1001-1007 (Sep. 8, 1989).

Schwickert, T. A. et al., "A Dynamic T Cell-Limited Checkpoint Regulates Affinity-Dependent B Cell Entry into the Germinal Center," J. Exp. Med., vol. 208, No. 6, pp. 1243-1252 (2011).

Shih, T.-A. Y., et al., "Role of BCR Affinity in T Cell-Dependent Antibody Responses in Vivo," Nat. Immunol., vol. 3, No. 6, pp. 570-575 (Jun. 2002).

Shlomchik, M. et al., "Anti-DNA Antibodies from Autoimmune Mice Arise by Clonal Expansion and Somatic Mutation," J. Exp. Med., vol. 171, pp. 265-292 (1990).

Shokat, K. M., et al., "Antigen-Induced B-Cell Death and Elimination during Germinal-Centre Immune Responses," Nature, vol. 375, pp. 334-338 (May 25, 1995).

Smith, G. P. et al., "Phage Display", Chemical Reviews, vol. 97, No. 2, pp. 391-410 (1997).

(56) References Cited

OTHER PUBLICATIONS

Sui, J. et al., "Structural and Functional Bases for Broad-Spectrum Neutralization of Avian and Human Influenza A Viruses," Nat. Struct. Mal. Biol., vol. 16, Issue 3, pp. 265-273, Author Manuscript—22 total pages (Mar. 2009).

Tarlinton, D. et al., "Diversity Among Memory B Cells: Origin, Consequences, and Utility", Science, vol. 341, pp. 1205-1211, 8 total pages (Sep. 2013).

Thomas, S. J. and Endy, T. P., "Critical Issues in Dengue Vaccine Development," Curr. Opin. Infect. Dis., vol. 24, No. 5, 17 total pages (Oct. 2011).

Throsby, M. et al., "Heterosubtypic Neutralizing Monoclonal Antibodies Cross—Protective against H5N1 and H1N1 Recovered from Human IgM+ Memory B Cells," PLoS One, vol. 3, Issue 12, e3942, pp. 1-15 (Dec. 2008).

Tiegs, S. L., et al., "Receptor Editing in Self-Reactive Bone Marrow B Cells," J. Exp. Med., vol. 177, pp. 1009-1020 (Apr. 1993).

Tiller, T. et al., "Autoreactivity in Human IgG+ Memory B Cells", Immunity, vol. 26, pp. 205-213 (Feb. 2007).

Tobin, G. et al., "Subsets with Restricted immunoglobulin Gene Rearrangement Features Indicate a Role for Antigen Selection in the Development of Chronic Lymphocytic Leukemia," Blood, vol. 104, No. 9, pp. 2879-2885 (Nov. 1, 2004).

Tomaras, G. D. et al., "Polyclonal B Cell Responses to Conserved Neutralization Epitopes in a Subset of HIV-1 Infected Individuals," J. Virol., in press, vol. 85, No. 21, pp. 11502-11519 (Nov. 2011).

Tsuiji, M. et al., "A Checkpoint for Autoreactivity in Human IgM+ Memory B Cell Development," J. Exp. Med., vol. 203, No. 2, pp. 393-400 (Feb. 20, 2006).

U.S. Appl. No. 61/542,469, filed Oct. 3, 2011, 42 total pages.

Verkoczy, L. et al., "Rescue of HIV-1 Broad Neutralizing Antibody-Expressing B Cells in 2F5 VH x VL Knockin Mice Reveals Multiple Tolerance Controls.," J. Immunol., vol. 187, pp. 3785-3797 (2011).

Verkoczy, L., et al., "Autoreactivity in an HIV-1 broadly reactive neutralizing antibody variable region heavy chain induces immunologic tolerance," Proc. Natl. Acad. Sci. USA, vol. 107, No. 1, pp. 181-186 (Jan. 5, 2010).

Victora, G. D. et al., "Germinal Center Dynamics Revealed by Multiphoton Microscopy with a Photoactivatable Fluorescent Reporter," Cell, vol. 143, pp. 592-605 (Nov. 12, 2010).

Walker, B. D. and Burton, D. R., "Toward an AIDS Vaccine," Science, vol. 320, pp. 760-764 (May 9, 2008).

Walker, L. M. et al., "A Limited Number of Antibody Specificities Mediate Broad and Potent Serum Neutralization in Selected HIV-1 Infected Individuals," PLoS Pathog., vol. 6, Issue 8, e1001028, pp. 1-14 (Aug. 2010).

Walker, L. M. et al., "Broad Neutralization Coverage of HIV by Multiple Highly Potent Antibodies," Nature, vol. 477, Issue 7365, pp. 466-470, Author Manuscript—14 total pages (Sep. 22, 2011).

Wang, H. et al., "Transitional B Cells Lose Their Ability to Receptor Edit but Retain Their Potential for Positive and Negative Selection", J. Immunol., vol. 179, pp. 7544-7552 (2007).

Wang, P. et al., "A Promising General Solution to the Problem of Ligating Peptides and Glycopeptides," J. Am. Chem. Soc., vol. 132, No. 47, pp. 17045-17051, Author Manuscript—15 total pages (Dec. 1, 2010).

Wardemann, H. and Nussenzweig, M. C., "B-cell Self-Tolerance in Humans," Adv. Immunol., vol. 95, Chapter 3, pp. 83-110 (2007).

Wardemann, H. et al., "Human Autoantibody Silencing by Immunoglobulin Light Chains," J. Exp. Med., vol. 200, No. 2, pp. 191-199 (Jul. 19, 2004).

Wardemann, H., et al,. "Predominant Autoantibody Production by Early Human B cell Precursors," Science, vol. 301, pp. 1374-1377 (Sep. 5, 2003).

Wei, X. et al., "Antibody Neutralization and Escape by HIV-1 ", Nature, vol. 422, pp. 307-312 (Mar. 20, 2003).

Whittle, J. R. et al., "Broadly Neutralizing Human Antibody that Recognizes the Receptor-Binding Pocket of Influenza Virus Hemagglutinin," Proc. Natl. Acad. Sci. USA, vol. 108, No. 34, pp. 14216-14221 (Aug. 23, 2011).

Written Opinion of the International Searching Authority for PCT/US2012/000442, dated Mar. 28, 2013, 6 total pages.

Wu, X. et al., "Focused Evolution of HIV-1 Neutralizing Antibodies Revealed by Structures and Deep Sequencing," Science, vol. 333, No. 6049, pp. 1593-1602, Author Manuscript—17 total pages (Sep. 16, 2011).

Wu X. et al., Rational Design of Envelope Identifies Broadly Neutralizing Human Monoclonal antibodies to HIV-1, Science, vol. 329, pp. 856-861 (Aug. 13, 2010).

Xiao, X. et al., "Germline-like Predecessors of Broadly Neutralizing Antibodies Lack Measurable Binding to HIV-1 Envelope Glycoproteins: Implications for Evasion of Immune Responses and Design of Vaccine immunogens," Biochem. Biophys. Res. Commun., vol. 390, Issue 3, pp. 404-409, Author Manuscript—14 total pages (Dec. 18, 2009).

Xiao, X. et al., "Maturation Pathways of Cross-Reactive HIV-1 Neutralizing Antibodies," Viruses, vol. 1, pp. 802-817 (Nov. 6, 2009).

Yuan, Y., et al., "Toward Homogeneous Erythropoietin: Fine Tuning of the C-Terminal Acyl Donor in the Chemical Synthesis of the $Cy^{29}$-$Gly^{77}$ Glycopeptide Domain, Glycopeptide Domain," J. Am. Chem. Soc., vol. 131, No. 15, pp. 5432-5437, Author Manuscript—13 total pages (Apr. 22, 2009).

Zhang, J. et al., "Optimality of Mutation and Selection in Germinal Centers," PLoS Comput. Biol., vol. 6, Issue 6, e1000800, pp. 1-9 (Jun. 2010).

Zwick, M. B. et al., "Broadly Neutralizing Antibodies Targeted to the Membrane-Proximal External Region of Human Immunodeficiency Virus Type 1 Glycoprotein gp41," J. Virol., vol. 75, No. 22, pp. 10892-10905 (Nov. 2001).

International Search Report for PCT/US2012/045530, dated Jan. 29, 2013 (4 total pages).

Haynes et al., "Aiming to induce broadly reactive neutralizing antibody responses with HIV-1 vaccine candidates", Expert Review of Vaccines, 2006, vol. 5, No. 3, pp. 347-363 (Author Manuscript—27 total pages).

Notification Concerning Transmittal of International Preliminary Report on Patentability (Form PCT/IB/326) dated Jan. 16, 2014 issued in connection with PCT/US2012/045530 (1 total page).

International Preliminary Report on Patentability dated Jan. 7, 2014 in connection with PCT/US2012/045530 (1 total page).

Written Opinion of the International Searching Authority dated Jan. 30, 2013 in connection with PCT/US2012/045530 (5 total pages).

Wu, X. et al., Supporting Online Material for Rational Design of Envelope Identifies Broadly Neutralizing Human Monoclonal Antibodies to HIV-1 , Science, (Aug. 13, 2010), vol. 329, 35 pages.

Rudikoff, S., et al., "Single amino acid substitution altering antigen-binding specificity," Proc. Nat'l. Acad. Sci. USA, vol. 79, pp. 1979-1983 (Mar. 1982).

Goel, M., et al., "Plasticity within the Antigen-Combining Site May Manifest as Molecular Mimicry in the Humoral Immune Response," J. Immunol., vol. 173, pp. 7358-7367—11 total pages (2004).

Lloyd, C., et al., "Modelling the human immune response: performance of a $10^{11}$ human antibody repertoire against a broad panel of therapeutically relevant antigens," Protein Engineering, Design & Selection, vol. 22, No. 3: 159-168 (2009).

Edwards, B.M., et al.. "The Remarkable Flexibility of the Human Antibody Repertoire; Isolation of Over One Thousand Different Antibodies to a Single Protein, BLyS," J. Mol. Biol., vol. 334, pp. 103-118 (2003).

Burton, D.R., "Antibodies, viruses and vaccines," Nat. Rev. Immunol. vol. 2, pp. 706-713 (Sep. 2002).

Definition of Infer by Merriam-Webster downloaded from https://www.merriam-webster.com/dictionary/infer last retrieved on Apr. 6, 2020 (11 total pages).

(56) References Cited

OTHER PUBLICATIONS

Definition of Computational by Merriam-Webster downloaded from https://www.merriam-webster.com/dictionary/computational last retrieved on Apr. 6, 2020 (10 total pages).

* cited by examiner

Figure 1

Dissociation Constants (Kd) of CH01, PG9, A32 and 697D mAbs binding to RV144 black-and-white ribbon diagram of gp120, based on Peter Kwong structure deposited in NCBI database as 3JWD.pdb. It included the full N- and C-terminal segments of gp120 (but NOT V1-V2 or V3). Residues 31-41 stick out into space, as do residues 494-511. Residues 31-41 are the residues deleted in Δ11 A244 gp120 which are relatively hydrophobic and which would, in gp160, interact with gp41, likely lead to some misfolding or aggregation of gp120 in the endoplamic reticuium, so that disulfides form between two gp120s. The C-terminal extension, which would also interact with gp41 (it leads to the cleavage point), is very polar (indeed, charged), so it may even help solubilize the expressed protein. The Δ11 substitution apparently eliminated (or at least partly eliminated) the aggregation and/or misfolding tendency and the addition of the HSV gD tag in gD+ A244 gp120 did not cause disulfide formation to the extent that the whole gp120 does.

Figures 4A-B
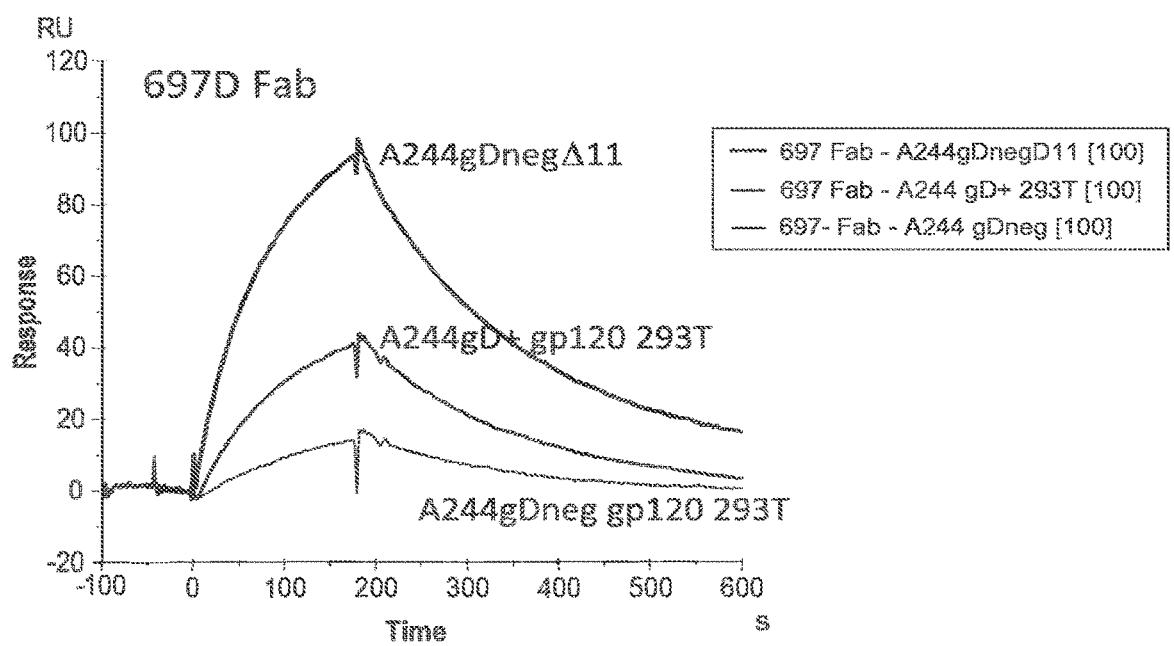
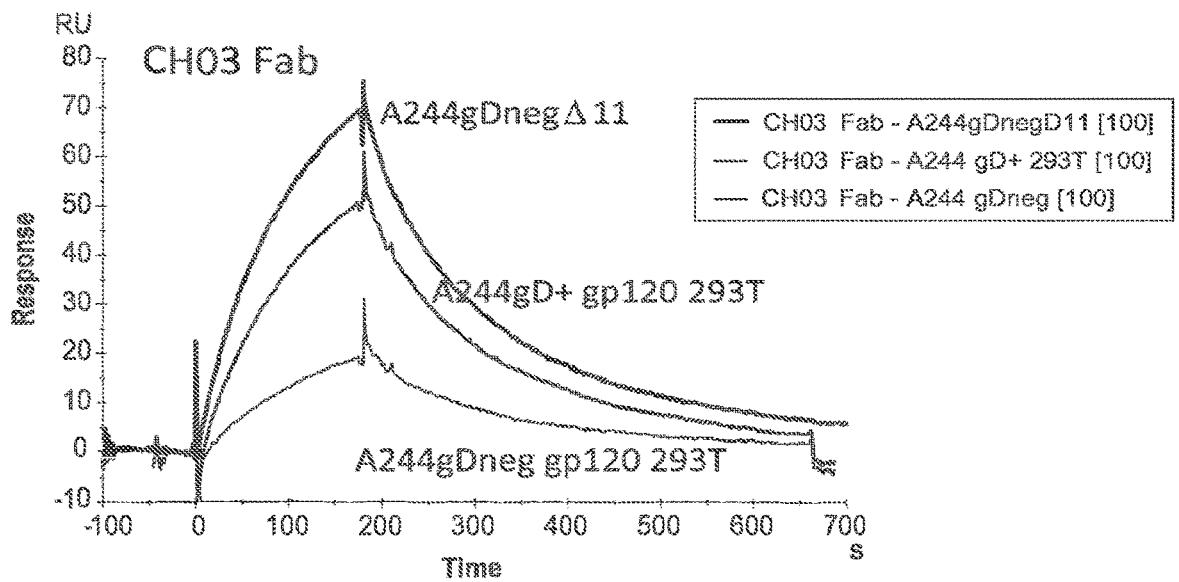

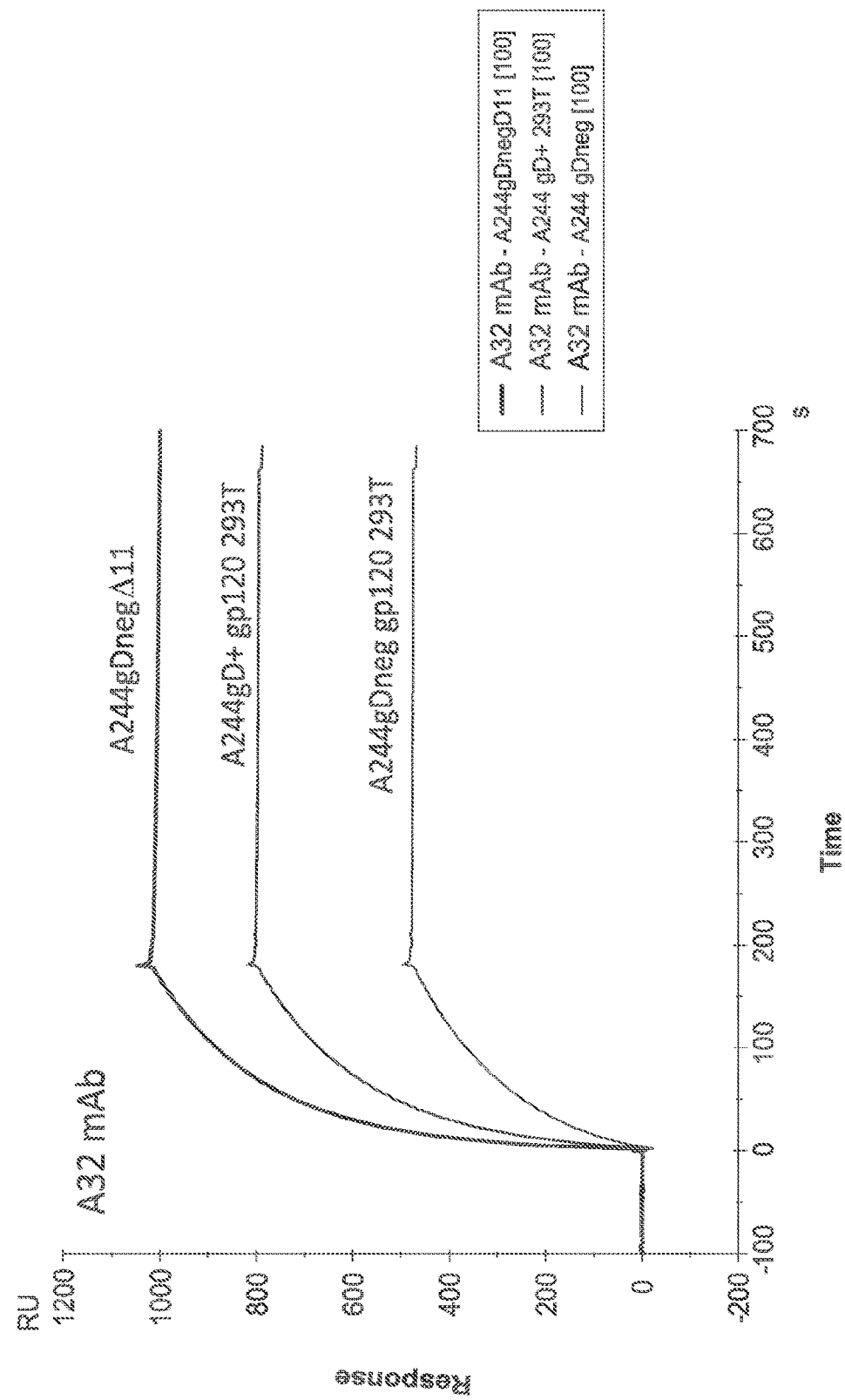

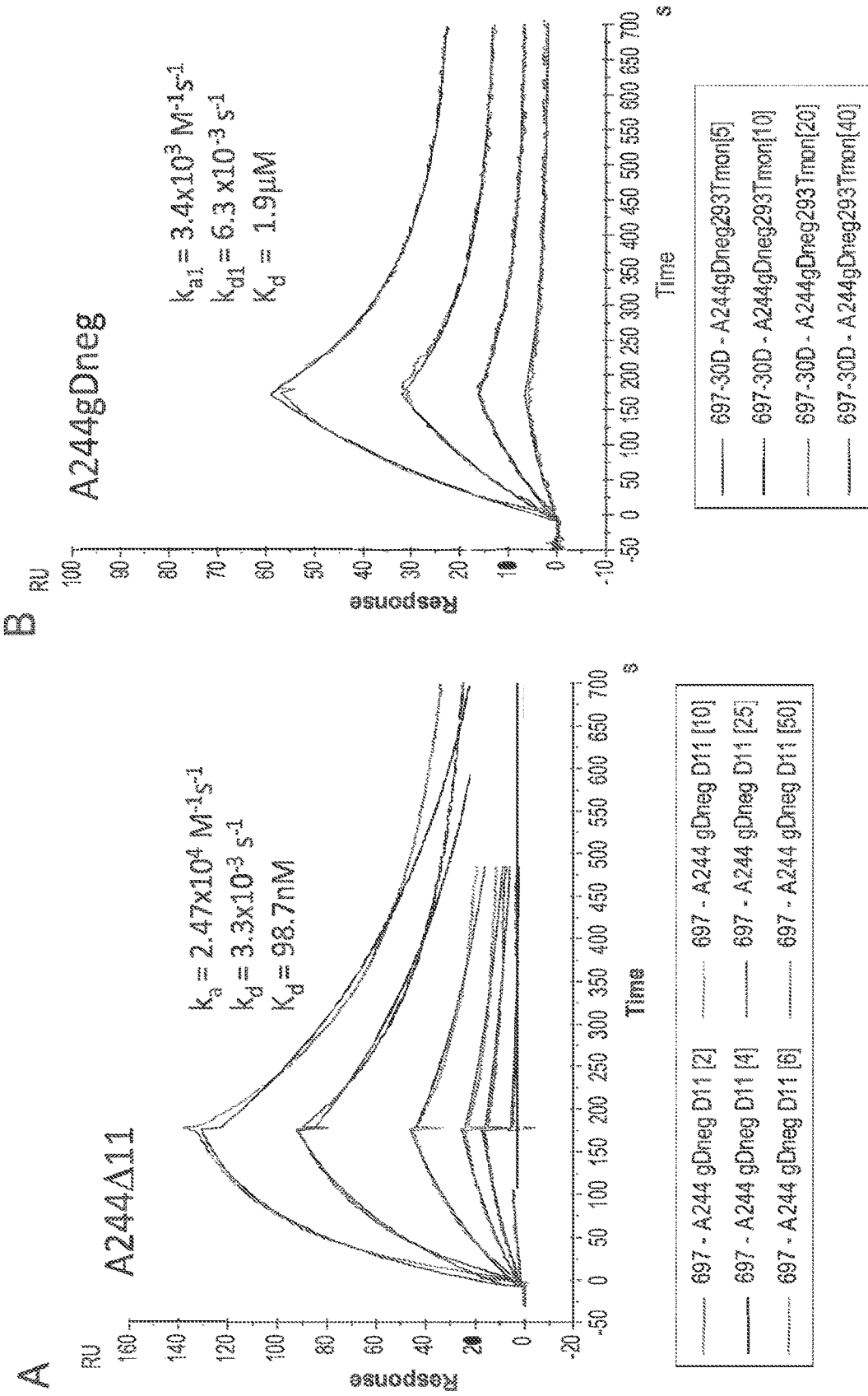
Figure 13A-B

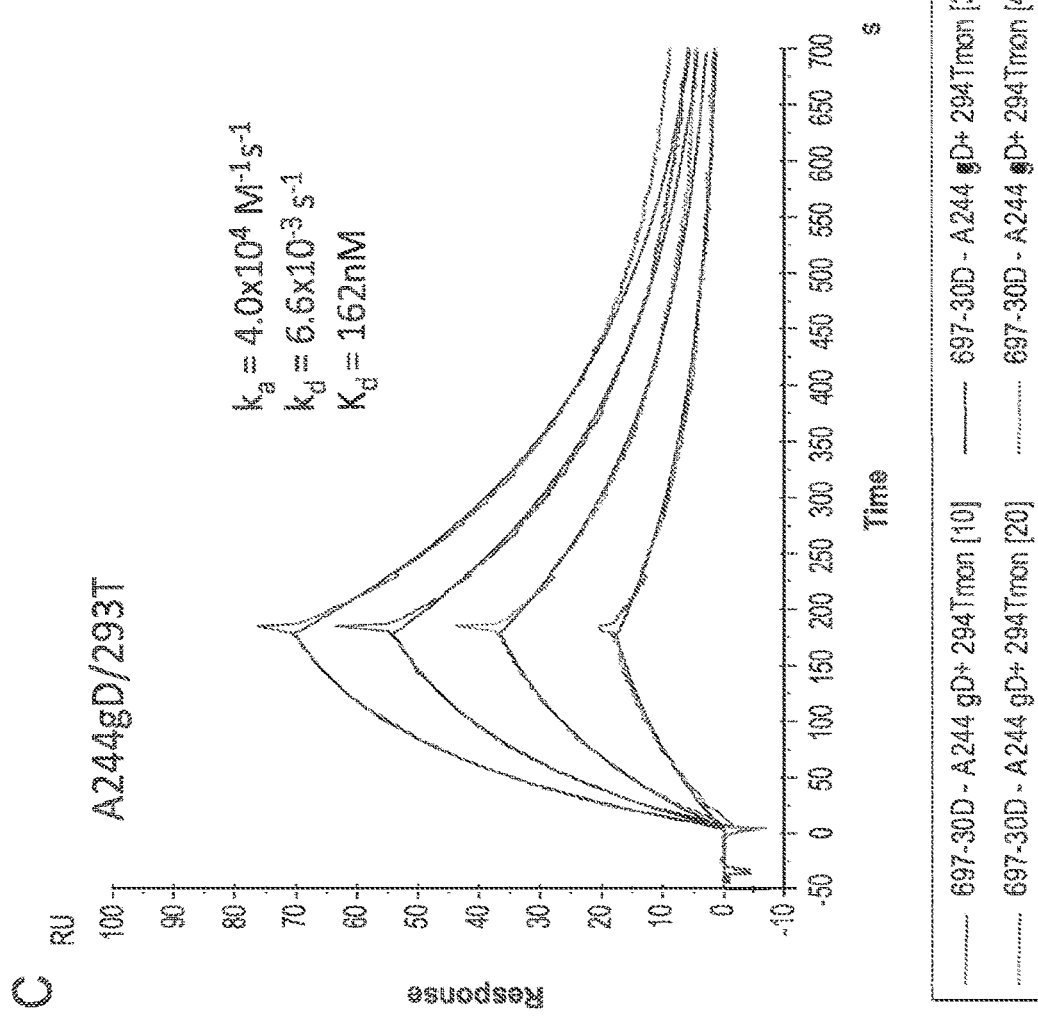

Figures 14A-B
Binding to PG9 mAb
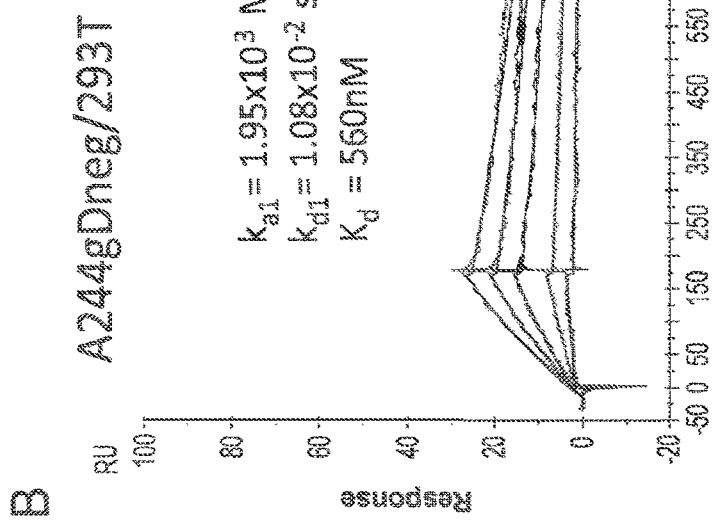
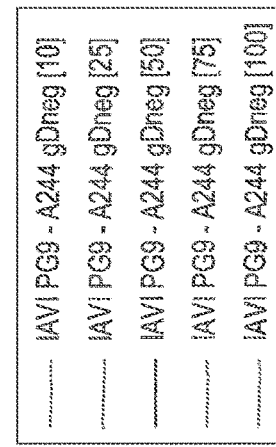
A244A11
$k_a = 1.15 \times 10^4 \, M^{-1}s^{-1}$
$k_d = 1.02 \times 10^{-3} \, s^{-1}$
$K_d = 88.7 nM$
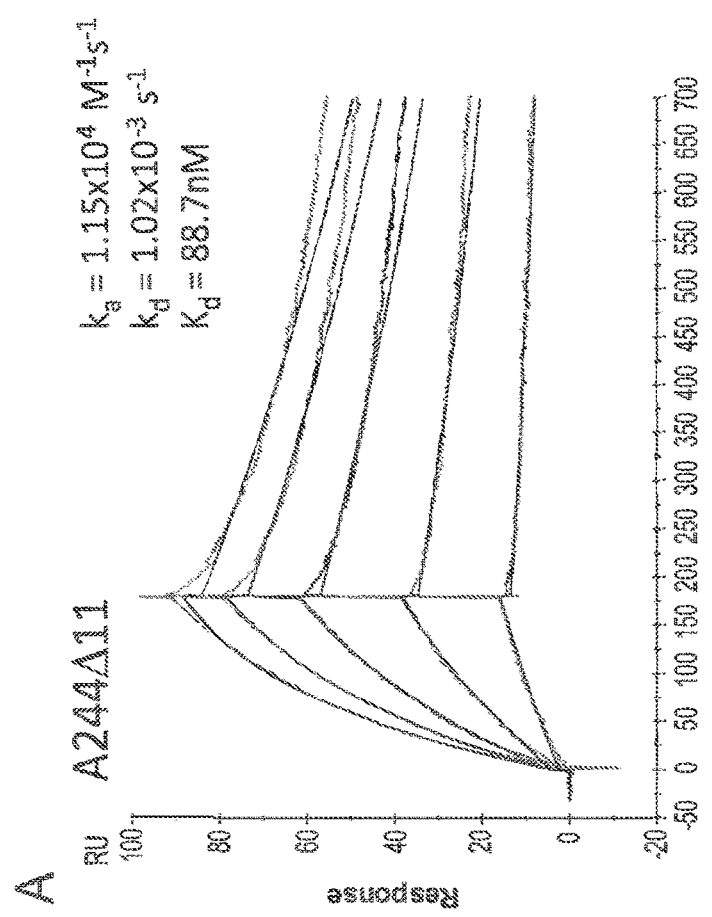
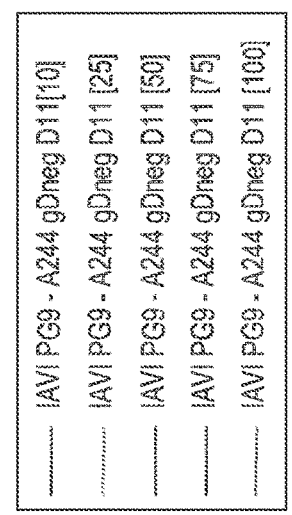
A244gDneg/293T
$k_{a1} = 1.95 \times 10^3 \, M^{-1}s^{-1}$
$k_{d1} = 1.08 \times 10^{-2} \, s^{-1}$
$K_d = 560 nM$

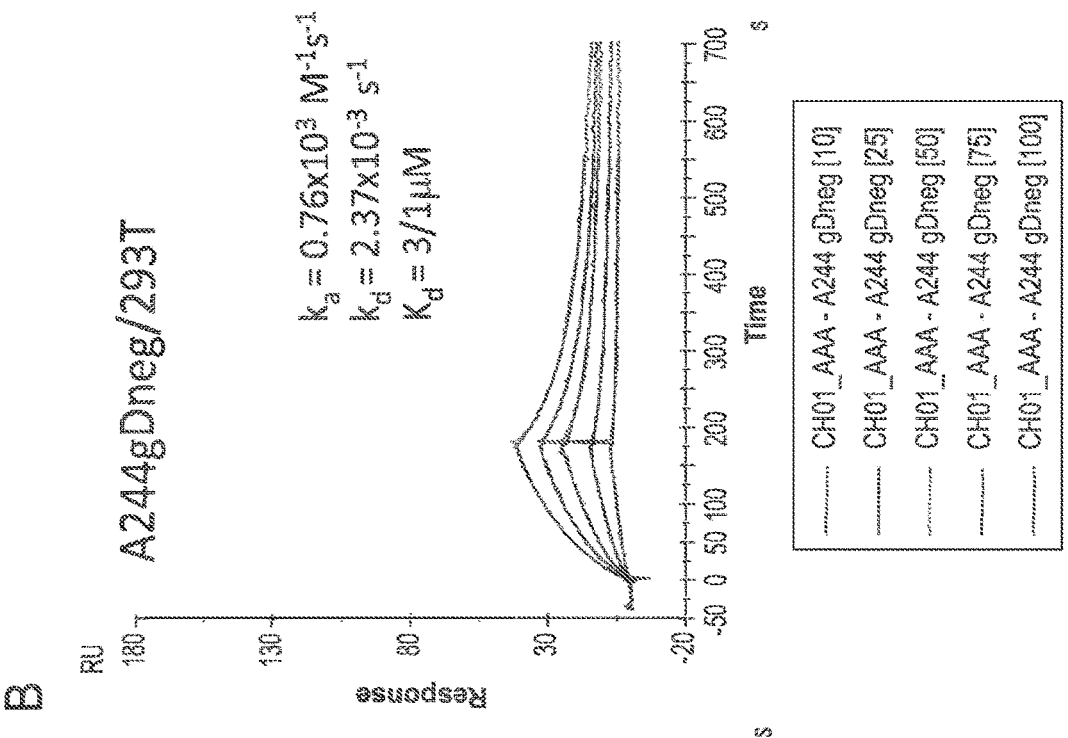
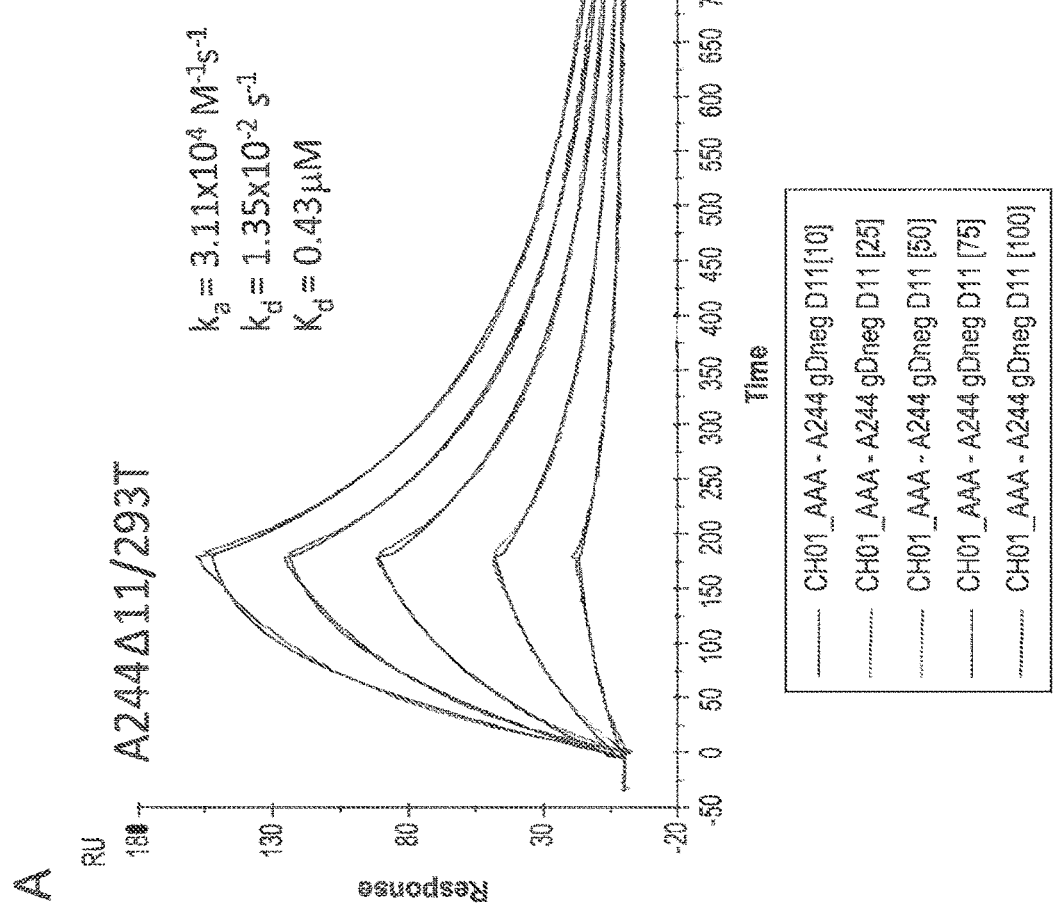
Figures 15A-B

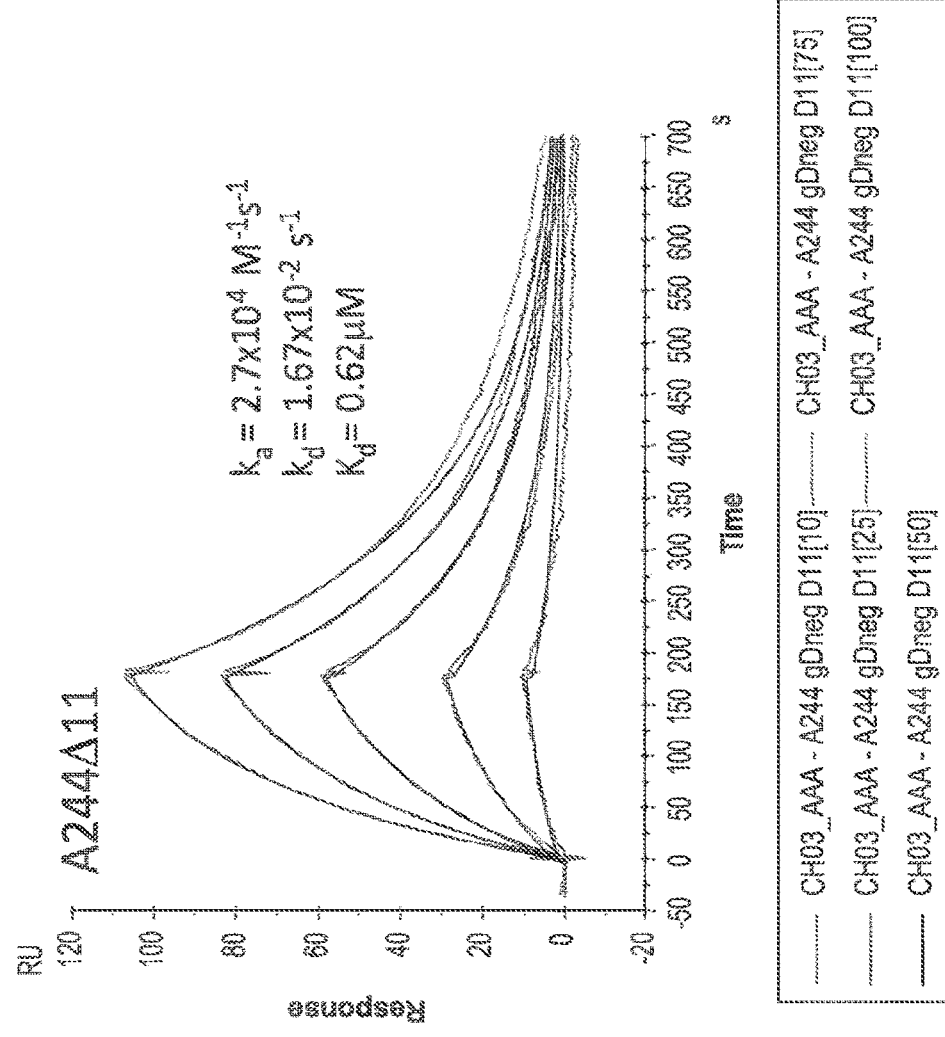

Amino acid and nucleotide sequences the A244 gp120A11 envelope protein.       Figure 19

>A244gp120gDneg-A11
MRVKETQMNWPNLWKWGTLILGLVIICSAVPVWKEADTTLFCASDAKAHETEVHNVWATHACVPTDPNPQEIDLENVTENFN
MWKNNMVEQMQEDVISIWDQSLKPCVKLTPLCVTLHCTNANLTKANLTNVNNRTNVSNIIGNITDEVRNCSFNMTTELRDKK
QKVHALFYKLDIVPIEDNND Amino acid and nucleotide sequences of B63521, B.6240, M.Con-S, C.1086C and C.089C gp120 envelope proteins.

>B.63521_gp120Δ11
MRVKGIRKNYQHLWRWGTMLLGILMICSAVPVWKEATTTLFCASDAKAYDTEVHNVWATHACVPTDPNPQELVLANVTENFN
MWNNTMVEQMHEDIISLWDQSLKPCVKLTPLCVTLNCTDVTNATNINATNINNSSGGVESGEIKNCSFNITTSVRDKVQKEY
ALFYKLDIVPITNESSKYRLISCNTSVLTQACPKVSFEPIPIHYCAPAGFAILKCNNETFNGKGPCINVSTVQCTHGIRPVV
STQLLLNGSLAEKEVIIRSDNFSDNAKNIIVQLKEYVKINCTRPNNNTRKSIHIGPGRAFYATGEIIGNIRQAHCNISRSKW
NDTLKQIAAKLGEQFRNKTIVFNPSSGGDLEIVTHSFNCGGEFFYCNTTKLFNSTWIREGNNGTWNGTIGLNDTAGNDTIIL
PCKIKQIINMWQEVGKAMYAPPIRGQIRCSSNITGLILTRDGGKDDSNGSEILEIFRPGGGDMRDNWRSELYKYKVVRIEPL
GVAPTRARERVVQKEKE

>B.63521_gp120Δ11
aagcttgtcgacaccATGCGCGTGAAGGGCATCCGCAAGAACTACCAGCACCTGTGGCGCTGGGGCACCATGCTGCTGGGCA
TCCTGATGATCTGCTCCGCCGTGCCCGTGTGGAAGGAGGCCACCACCACCCTGTTCTGCGCCTCCGACGCCAAGGCCTACGA
CACCGAGGTGCACAACGTGTGGGCCACCCACGCCTGCGTGCCCACCGACCCCAACCCCCAGGAGCTGGTGCTGGCCAACGTG
ACCGAGAACTTCAACATGTGGAACAACACCATGGTGGAGCAGATGCACGAGGACATCATCTCCCTGTGGGACCAGTCCCTGA
AGCCCTGCGTGAAGCTGACCCCCCTGTGCGTGACCCTGAACTGCACCGACGTGACCAACGCCACCAACATCAACGCCACCAA
CATCAACAACTCCTCCGGCGGCGTGGAGTCCGGCGAGATCAAGAACTGCTCCTTCAACATCACCACCTCCGTGCGCGACAAG
GTGCAGAAGGAGTACGCCCTGTTCTACAAGCTGGACATCGTGCCCATCACCAACGAGTCCTCCAAGTACCGCCTGATCTCCT
GCAACACCTCCGTGCTGACCCAGGCCTGCCCCAAGGTGTCCTTCGAGCCCATCCCCATCCACTACTGCGCCCCCGCCGGCTT
CGCCATCCTGAAGTGCAACAACGAGACCTTCAACGGCAAGGGCCCCTGCATCAACGTGTCCACCGTGCAGTGCACCCACGGC
ATCCGCCCCGTGGTGTCCACCCAGCTGCTGCTGAACGGCTCCCTGGCCGAGAAGGAGGTGATCATCCGCTCCGACAACTTCT
CCGACAACGCCAAGAACATCATCGTGCAGCTGAAGGAGTACGTGAAGATCAACTGCACCCGCCCCAACAACAACACCCGCAA
GTCCATCCACATCGGCCCCGGCCGCGCCTTCTACGCCACCGGCGAGATCATCGGCAACATCCGCCAGGCCCACTGCAACATC
TCCCGCTCCAAGTGGAACGACACCCTGAAGCAGATCGCCGCCAAGCTGGGCGAGCAGTTCCGCAACAAGACCATCGTGTTCA
ACCCCTCCTCCGGCGGCGACCTGGAGATCGTGACCCACTCCTTCAACTGCGGCGGCGAGTTCTTCTACTGCAACACCACCAA
GCTGTTCAACTCCACCTGGATTCGCGAGGGCAACAACGGCACCTGGAACGGCACCATCGGCCTGAACGACACCGCCGGCAAC
GACACCATCATCCTGCCCTGCAAGATCAAGCAGATCATCAACATGTGGCAGGAGGTGGGCAAGGCCATGTACGCCCCCCCCA
TCCGCGGCCAGATCCGCTGCTCCTCCAACATCACCGGCCTGATCCTGACCCGCGACGGCGGCAAGGACGACTCCAACGGCTC
CGAGATCCTGGAGATCTTCCGCCCCGGCGGCGGCGACATGCGCGACAACTGGCGCTCCGAGCTGTACAAGTACAAGGTGGTG
CGCATCGAGCCCCTGGGCGTGGCCCCCACCCGCGCCCGCGAGCGCGTGGTGCAGAAGGAGAAGGAGTAGggatcctctaga_

Figure 20 Cont'd-1

>B.6240_gp120A11
MRVKGIRKNYQHLWRWGIMLLGTLMICSAVPVWKEATTLFCASDAKAYSPEKHNIWATHACVPTDPNPQELVLGNV
TEDFNMWKNNMVEQMHEDIISLWDQSLKPCVKLPLCVTLNCTDLKNSATDTNGISGTNMRTVEQGMETEIKMCSFNITTGI
GNKMQKEYALFYKLDVVPIDSNNNSDNTSYRLISCNTSVTQACPKTSFEPIPIHYCAPAGFAILKCNMKTFSGKGPCKNVS
TVQCTHGIRPVVSTQLLLNGSLAEEEIVIRSENFTNNAKTIIVQLNESVIINCTRPMNNTRKGIHIGLRALYATGDIIGDI
RQAHCNLSSKSWNKTLQQVVRKLREQFGNKTIAFNQSSGGDQEIVKHSFNCGGEFFYCDTTQLFNSTWSSNDTWNSTGVQDN
NITLPCRIKQIINMWQEVGKAMYAPPIQGLISCSSNITGLLLTRDGGTNMTNATEIFRPGGGDMRDNWRSELYKYKVVKIEP
LGTAPTKAKRRVVQREKR

>B.6240_gp120A11□□□□
aagcttgtcgacaccATGCGCGTGAAGGGCATCCGCAAGAACTACCAGCACCTGTGGCGCTGGGGCA
TCATGCTGCTGGGCACCCTGATGATCTGCTCCGCCGTGCCCGTGTGGAAGGAGGCCACCACCCTGTTCTGCGCCTCCGA
CGCCAAGGCCTACTCCCCCGAGAAGCACAACATCTGGGCCACCCACGCCTGCGTGCCCACCGACCCCAACCCCCAGGAGCTG
GTGCTGGGCAACGTGACCGAGGACTTCAACATGTGGAAGAACAACATGGTGGAGCAGATGCACGAGGACATCATCTCCCTGT
GGGACCAGTCCCTGAAGCCCTGCGTGAAGCTGCCCCTGTGCGTGACCCTGAACTGCACCGACCTGAAGAACTCCGCCAC
CGACACCAACGGCATCTCCGGCAACAAGATGCAGAAGGAGTACGCCCTGTTCTACAAGCTGGACGTGGTGCCCATCGACTCCAACA
ACAACTCCGACAACACCTCCTACCGCCTGATCTCCTGCAACACCTCCGTGACCCAGGCCTGCCCCAAGACCTCCTTCGA
GCCCATCCCCATCCACTACTGCGCCCCCGCCGGCTTCGCCATCCTGAAGTGCAACATGAAGACCTTCTCCGGCAAGGGCCCC
TGCAAGAACGTGTCCACCGTGCAGTGCACCCACGGCATCCGCCCCGTGGTGTCCACCCAGCTGCTGCTGAACGGCTCCCTGG
CCGAGGAGGAGATCGTGATCCGCTCCGAGAACTTCACCAACAACGCCAAGACCATCATCGTGCAGCTGAACGAGTCCGTGAT
CAACTGCACCCGCCCCATGAACAACACCCGCAAGGGCATCCACATCGGCCTGCGCGCCCTGTACGCCACCGGCGAC
ATCATCGGCGACATCCGCCAGGCCCACTGCAACCTGTCCTCCAAGTCCTGGAACAAGACCCTGCAGCAGGTGGTGCGCAAGC
TGCGCGAGCAGTTCGGCAACAAGACCATCGCCTTCAACCAGTCCTCCGGCGGCGACCAGGAGATCGTGAAGCACTCCTTCAA
CTGCGGCGGCGAGTTCTTCTACTGCGACACCACCCAGCTGTTCAACTCCACCTGGTCCTCCAACGACACATGGAACTCCACC
GGCGTGCAGGACAACAACATCACCCTGCCCTGCCGCATCAAGCAGATCATCAACATGTGGCAGGAGGTGGGCAAGGCCATGT
ACGCCCCCCCATCCAGGGCCTGATCTCCTGCTCCTCCAACATCACCGGCCTGCTGCTGACCCGCGACGGCGGCACCAACAA
CACCAACGCCACCGAGATCTTCCGCCCCGGCGGCGGCGACATGCGCGACAACTGGCGCTCCGAGCTGTACAAGTACAAGGTG
GTGAAGATCGAGCCCCTGGGCACCGCCCCCACCAAGGCCAAGCGCCGCGTGGTGCAGCGCGAGAAGCGCTAGggatccta
ga >M.CON-S_gp120A11
MRVRGIQRNCQHLWRWGTLILGMLMICSAVPVWKEANTTLFCASDAKAYDTEVHNVWATHACVPTDNPQEIVLENVTENFN

Figure 20 Cont'd-2

MWKNMVEQMHEDIISLWDQSLKPCVKLTPLCVTLNCTNVNVTNTNNTEEKGEIKNCSFNITTEIRDKKQKVYALFYRLDV
VPIDDNNNMSSNYRLINCNTSAITQACPKVSFEPIPIHYCAPAGFAILKCNDKKFNGTGPCKNVSTVQCTHGIKPVVSTQLL
LNGSLAEEEIIIRSENITNNAKTIIVQLNESVEINCTRPNNNTRKSIRIGPGQAFYATGDIIGDIRQAHCNISGTKWNKTLQ
QVAKKLREHFNNKTIIFKPSSGGDLEITTHSFNCRGEFFYCNTSGLFNSTWIGNGTKNNMTNDTITLPCRIKQIINMWQGV
GQAMYAPPIEGKITCKSNITGLLLTRDGGNNNTNETEIFRPGGGDMRDNWRSELYKYKVVKIEPLGVAPTKAKRRVVERERR

>M.CON-S_gp120A11 口口口
aagcttgtcgacaccATGGCCGTGCCGGCCATCCAGGCAGCCAACTGCCAGGGCACCTGTGGGCTGGGCACCCTGATCCTGGGCA
TGCTGATGATCTGCTCCGCCGTGTCCGCCCCGTGTGGGCACCGACCACCCTGTTCTGCGCCCTCCGACGCCAAGGCCTACGA
CACCGAGGTGCACAAGTGTGGGCACCGCCACCCAGCCCCTGCCCACCCGAGATCGTGCTGGAGAACGTG
ACCGAGAACTTCAACATGTGGAAGAACAACATGGTCGAGCAGCAGATGCACGAGGACACATCATCCCTGTGGGACCAGTCCCTGA
AGCCCTGCGTGAAGCTGACCCCCCCTGTGCGTGACCCTGAACTGCACCGAACTGCACCAACACCGA
GGAGAAGGGCGAGATCAAGAACTGCTCCTTCAACATCACCACCGAGATCCGCGACAAGAAGCAGAAGGTGTACGCCCTGTTC
TACCGCCTGGACGTGGTGCCCATCGACGACAACAACAACTCCTCCAACTACCGCCTGATCAACTGCAACACCTCCGCCA
TCACCCAGGCCTGCCCCAAGGTGTCCTTCGAGCCCATCCCCATCCACTACTGCGCACCCGCCGGCTTCGCCATCCTGAAGTG
CAACGACAAGAAGTTCAACGGCACCGGCCCCTGCAAGAACGTGTCCACCGTGCAGTGCACCCACGGCATCAAGCCCGTGGTG
TCCACCCAGCTGCTGCTGAACGGCTCCCTGGCCGAGGAGATCATCATCCGCTCCGAGAACATCATCAACCGCCAAGAACAACGCCAAGA
CCATCATCGTGCAGCTGAACGAGTCCGTGGAGATCAACTGCACCCGCCCCAACAACAACCGCAAGAGTCCATCCGCATCGG
CCCGGGCCAGGCCTTCTACGCCACCGGCGACATCATCGGCGACATCCGCCAGGCCCACTGCAACATCTCCGGCACCAAGTGG
AACAAGACCCTGCAGCAGGTGGCCAAGAAGCTGCGCGAGCACTTCAACAACAAGACCATCATCTTCAAGCCCTCCTCCGGCG
GCGACCTGGAGATCACCACCCACTCCTTCAACTGCCGCGGCGAGTTCTTCTACTGCAACACCAGCGGCCTGTTCAACTCCAC
CTGGATCGGCAACGGCACCAAGAACAACAACAACAACCATGACCAACGACACCATCACCCTGCCCTGCCGCATCAAGCAGATCATCAAC
ATGTGGCAGGGCGTGGGCCAGGCCATGTACGCCCCCCCCATCGAGGGCAAGATCACCTGCAAGTCCAACATCACCGGCCTGC
TGCTGACCCGCGACGGCGGCAACAACAACAACAACGAGACCGAGATCTTCCGCCCCGGCGGCGGCGACATGCGCGACAACTG
GCGCTCCGAGCTGTACAAGTACAAGTGGTGAAGATCGAGCCCCTGGGCGTGGCCCCCACCAAGGCCAAGCGCCGCGTGGTG
GAGCGCGAGAAGCGCTAGggatcctctaga_

>C.1086C_gp120A7
MRVRGIWKNWPQWLIWSIIGFWIGNMEGSVPVWKEAKTTLPCASDAKAYEKEVHNVWATHACVPTDPNPQEMVLANVTENFN
MWKNDMVEQMHEDIISLWDESLKPCVKLTPLCVTLNCTNVKGNESDTSEVRKNCSFKATTELRKDKKHKVHALFYKLDVVPLN
GNSSSSGEYRLINCNTSAITQACPKVSFDPIPLHYCAPAGFAILRCNNKTFMGTGPCRNVSTVQCTHGIKPVVSTQLLLNGS

Figure 20 Cont'd-3

LAEEIIIRSENLTNNAKTIIVHLNESVNIVCTRPNNNTRKSIRIGPGQTFYATGDIIGNIRQAHCNINESKWNNTLQKVGE
ELAKHFPSKTIKFEPSSGGDLEITTHSFNCRGEFFYCNTSDLFNGTYRNGTYNHTGRSSNGTITLQCKIKQIINMWQEVGRA
IYAPPIEGEITCNSNITGLLLLRDGGQSNETNDTETFRPGGGDMRDNWRSELYKYKVVEIKPLGVAPTEAKRRVEREKR

>C.1086C_gp120A7.opt
aagcttgtcgacaccatggcgcgtgcgcccgtgccctccgtgcggggctccacagaactggccccagtggctgatctggtccatcctgggcttctggga
tcggccaacatggagggctccgtgccctgtgggccacgaggaggccaagaggaggccaagaccaccctgttctgcgcctccgacgccaaggcctacga
gaaggagcgcgtgcacaacgtgtgggccacccacgcctgcgtgcccaacctcccccaaagagagatggtgctggccaacgtg
acggagaacttcaacatggagaacgacatggtggagcagacatgccaccaacatcatccctgtgggacgagtcctga
agccctgcgtgaagtgcaccgaccccctgtgcgtgacccagctgaaccgcaacgagctgaaggcaacgagtccgactcctccgaagt
gatgaagaactgctccttcaaggccaactgcctccctccccaggccgagtgaaggacataaccgagtgcaccgagtgcacaagctggac
gtggtgccccctgaacggcaactgcctgaccaccgagtactgcgccgcccgagtgcatcgcacctcgcaatcaccaggcct
gccccaaggtgtccttcgaccccatccccgccggcttcgccatcctgaagccgtgtgtccaccagctg
cttcaaccggcacggccccctgccccgaggagagcatcatcgctcccgagacgcctgaccaacctgaccagcctgccaccatcatcgtgc
ctgctgaacggctcctccctgcgcctctacgcccgaggagacatcgtgcaccctgcaactcctcccaatcaaccccccaagaccccccagccagac
acctgaacgagtccgtaccgcccaccagtgcgacatcatcggcaacatcatccggcaagcactcccaagacatccaggcctccaaccctg
ctctactacggccaccagtgccacaacatcccctacggccccgactctacgcgagagaagtggtggagatcaagaccccccctggaaga
cagaaggtgggcgaggagctcaactgccgcggcccgctcctccaacggcaccatcgagttcttctgcaacaccctgttcaacggcgacaccttcaacg
tcaccacccactccttccaatcgcaggccacccacatgccctgctactactcgccgccatccagggccacggccactaccgcaaccgg
cacctgcagccacccacgccgccatctaccgccccccatcggaggcaccgagggcgacagacgaggcaccacccgaccccggcaccacc
gagtggggggccggcgccagtcaggatccaaggacaccaagaccgagaccccgcccgtgggccgtggccctgggacatccggcgctc
gcgagctgtacaagtacaaggtggtggagatcaagcccccctgggcgcccccaccgaggccaaggcccgccgcggtggtggagcgc
gagaaggcgctaggcgatcctctaga >C.089C_gp120A11
MRVRGMLRNCQQWWIWGILGFWMLMICSVVPVMKEAKTTLFCASDARAYEREVHNVWATHACVPTDPNPQEMVLVNVTENFN
MWKNDMVDQMHEDIISLWDQSLKPCVKLTPLCVILECMNANGTTNNGSVIVNENSTMYGEIQNCSFKVNSEIKGKKQDVYA
LFNSLDIVKLYNNGTSQYRLINCNTSTLTQACPKVSFDPIPIHYCAPAGYAILKCNNKTENGTGPCNNVSTVQCTHGIKPVV
STQLLLNGSLAEGEIIIRSKNLTDNTKTIIVHLNESIKINCIRPNNNTRRSIRIGPGQAFYAANGTVGNIRQAHCNISEGEW
NKTLYRVSRKLAEHFPGKEIKFKPHSGGDLEITTHSFMCRGEFFYCNTSKLFNGTYNGTYMNDTNSTILPCRIKQINMW

Figure 20 Cont'd-4

QEVGQAMYAPPIEGIIACNSTITGLLLTRDGGDKNGSKPEIFRPGGGDMRDNWRSELYKYKVVEIKPLGIAPTKAKRRVVEK
EKTIQKR

>C.089C_gp120A11.000
aagcttgtcgacaccATGGCGCTGTGCCGGGCATGCTGCGGCAGCAGTGGTGGATCTGGGCATCCTGGGCTTCTGGA
TGCTGATGATCTGCTCCGTGGTGCCCGTGTGTGGAAGGAGCCAAGACCACCCTGTTCTGCGCCTCCGACGCCGCTACGA
GCGGGAGGTGCACAACGTGTGGGCCACACCGACCTGCCTGCCGTGCCCAACCCCAGGAGATGGTGCTGGTGAACGTG
ACCGAGAACTTCAACATGTGGAAGAACAACATGGTGGACCAGATGCACGAGGACATCATCTCCCTGTGGGACCAGTCCCTGA
AGCCCTGCGTGAAGCTGACCCCCCTGTGCGTGACCCTGCACTGCACCAACGTGAACAACGGCTCCTGTGAT
CGTGGTGAACGAGAACACTCCACCATCGTACGGCGAGATCCAGAACTGCTCCTTCAAGGTGACTGAACTCCAGACAAG
CAGGACGTGTACGGCCCCTGTTCAACTCCCTGACATCGTGAACATCGTGAAGGTGTCCTTCGACCCCCATCCCCGTGGTATCCCCAGTACTGCGCCCCCGGCTA
GCAACACCTGAACGTGCAACAACAAGACCTTCAACGGCGAACCTCCCTGGCCGAGGGCGAGATCATCATCCGCTTCCACCACCGCCGG
ATCAAGCCCGTGGTGTCCACCCAGCTGCTGCTGAACGGCTCCATCAAGATCAACTGAACTCCATGCCAACAACAACCCCGCCG
CCGACACACCAAGACCATCATCCGGCCGAGTCCGTGCACCTGGCCCTTCTACGCCGTGGGCCAGGCCCTCGTGGCCGAGCATCGTGGGCAACATCGTGGGCAACATC
CTCCATCCCGGCCATCGGCCCCCCTGTCCCCGAACGGCACACTTCCCCCGCCAAGGAGATCAAGTTCA
TCCGAGGGCGAGTGGAACAAGACCTGGAGATCACCACCCACTCCTTCAACTGGAGTTCTTCTACTGCAACACCTCCAA
AGCCGCCATCCGGCGGCGACCTGGAGATCACACCACTACACCAACGACACACCCCCATCGAGGGCCATCAAGCAG
GCTGTTCAACGTGACCCACTCACAACGGCAGCCAGGGCCATGTACGCCCCCATCCCCATCGAGGGCCATCGCAACTCCACCATCA
ATCATCAACACATGTGCAGGAGGTGGGCCGACGGCGGCCGGCGACAAGAACGGCTCCAAGCCCGAGATCTTCCGCCCCGGGGGACATGCG
CCGGCCTGCTGCTGACCCGAGACTCCGAGCTGCTGTACAAGTACAAGGTGGTGGAGATCAAGCCCCCTGGGCATCGCCCCCACCAAGGCCAAGCGC
CGACAACTGGCGCTCCGAGTACCACCCCAGAAGAAGACCATCCAGAAGCGCTAGggatcctctaga Figure 21. Nucleotide and amino acid sequences of B63521, B.6240, M.Con-S, C.1086C and C.089C gp140C envelope proteins.

>B.63521_gp140C
MRVRGIRKNYQHLWRWGTMLLGILMICSAAAQLWVTVYYGVPVWKEATTTLFCASDAKAYDTEVHNVWATHACVPTDPNPQE
LVLANVTENFNMWKNNMTMVEQMHEDIISLWDQSLKPCVKLTPLCVTLNCTDVTNATNINATNINNSSGGVESGEIKNCSFNIT
TSVRDKVQKEYALFYKLDIVPITNESSKYRLISCNTSVLTQACPKVSFEPIPIHYCAPAGFAILKCNNETFNGKGPCINVST
VQCTHGIRPVVSTQLLLNGSLAEKEVIIRSDNFSDNAKNIIVQLKEYVKINCTRPNNMTRKSIHIGPGRAFYATGELIGNIR
QAHCNISRSKWNDTLKQIAAKLGEQFRNKTIVFNPSSGGDLEIVTHSFNCGGEFFYCNTTKLFNSTWIREGNNGTWNGTIGL
NDTAGNDTIILPCKIKQIINMWQEVGKAMYAPPIRGQIRCSSNITGLILITRDGGKDSNGSEILEIFRPGGGDMRDNWRSEL
YKYKVVRIEPLGVAPTRARERVVQKEKEAVGLGAMFLGFLGAAGSTMGAASMTLTVQARQLLSGIVQQNNLLRAIEAQQHM
LQLTVWGIKQLQARVLAVERYLKDQQLLGIWGCSGKLICTTDVPWDTSWSNKTLDDIWGSNMTWMEWEREIDNYTSTIYTLL
EEAQYQQEKNEKELLELDKWASLWNWFDITNWLWYIR

>B.63521_gp140C.opt
ATGCGCGTGAGGGCATCCGCAAGAACTACCAGCACCTGTGGCGCTGGGGCACCATGCTGCTGGGCATCCTGATGATCTGCT
CCGCCGCCCAGCTGTGGGTGACCGTGTACTACGGCGTGCCCGTGTGGAAGGAGGCCACCACCCTGTTCTGCGCCTC
CGACGCCAAGGCCTACGACACCGAGGTGCACAACGTGTGGGCCACCCACGCCTGCGTGCCCACCGACCCCAACCCCCAGGAG
CTGGTGCTGGCCAACGTGACCGAGAACTTCAACATGTGGAAGAACAACATGACCATGGTGGAGCAGATGCACGAGGACATCATCTCC
CTGTGGGACCAGTCCCTGAAGCCCTGCGTGAAGCTGACCCCCCTGTGCGTGACCCTGAACTGCACCGACGTGACCAACGCCAC
CAACATCAACGCCACCAACATCAACAACTCCTCCGGCGTGGAGTCCGGCGAGATCAAGAACTGCTCCTTCAACATCACC
ACCTCCGTGCGCGACAAGGTGCAGAAGGAGTACGCCCTGTTCTACAAGCTGGACATCGTGCCCATCACCAACGAGTCCTCCA
AGTACCGCCTGATCTCCTGCAACACCTCCGTGCTGACCCAGGCTGCCTGCCCCAAGGTGTCCTTCGAGCCCATCCCCATCCACTA
CTGCGCCCCCGCCGGCTTCGCCATCCTGAAGTGCAACAACGAGACCTTCAACGGCAAGGGCCCCTGCATCAACGTGTCCAC
GTGCAGTGCACCCACGGCATCCGCCCCGTGGTGTCCACCCAGCTGCTGCTGAACGGCTCCCTGGCCGAGAAGGAGGTGATCA
TCCGCTCCGACAACTTCTCCGACAACGCCAAGAACATCATCGTGCAGCTGAAGGAGTACGTGAAGATCAACTGCACCCGCCC
CAACAACATGACCCGCAAGTCCATCCACATCGGCCCCGGCCGGGCCTTCTACGCCACCGGCGAGCTGATCGGCAACATCCGC
CAGGCCCACTGCAACATCTCCCGCTCCAAGTGGAACGACACCCTGAAGCAGATCGCCGCCAAGCTGGGCGAGCAGTTCCGCA
ACAAGACCATCGTGTTCAACCCCTCCTCCGGCGGCGACCTGGAGATCGTGACCCACTCCTTCAACTGCGGCGGCGAGTTCTT
CTACTGCAACACCACCAAGCTGTTCAACTCCACCTGGATCCGCGAGGGCAACAACGGCACCTGGAACGGCACCATCGGCCTG
AACGACACCGCCGGCAACGACACCATCATCCTGCCCTGCAAGATCAAGCAGATCATCAACATGTGGCAGGAGGTGGGCAAGG
CCATGTACGCCCCCCCCATCCGCGGCCAGATCCGCTGCTCCTCCAACATCACCGGCCTGATCCTGACCCGCGACGGCGGCAA

Figure 21 Cont'd-1

```
GGACGACTCCAACGGCCTCCGAGATCTTCCGCCCCGGCGGGCGGACATGCCGACAACTGGCGGCTCCGAGCTG
TACAAGTACAAGGTGTGCGGCGCCAGTGTGCGGCCCCCTGGCGTGCTGGGGCGTGGTGCAGAAGGAGAAGG
AGGCCGTGGGCCTGGCCGCCAGTGGCCATGTTCTGCGGCTTCCTGGGCATCGTGTGCAGCAGCAGAACCTGTGCCCGTGCTGCCCAGGCCGGCGCCATCGAGGCCCAGCCATG
CGTGCAGGCCGCCGCCAGCTGCTCTGTCCGGCATCGAGCAGCAGCAGCCCGCCACCGAGCGGCCGTGCTGGGACACCTGAGGACCAGCAGCTGC
CTGCAGCTGACCGGTGTGGGCGTGCTCCGGCAAGCTGATCTGATCGATGGAGTGGAGTGGAGAAGAACTGGAGATCGGCGAGAACGGCGAGATCGACACCTCCAACAAGACCCTGA
CGACATCTGGGGGCTCCAACATGACCTGGATGGAGTGGGAGGCGGAGATCGGCGAGATCGGCGGCGACAACTACACCTCCAACATCTACACCCTGCTG
GAGGAGCCCAGTACCAGCAGGAGAAGAACGAAGGAGCTGCTGGACAAGTGGGCCTCCCTGTGGAACTGGTTCG
ACATCACCAACTGGCTGTGGTACATCCGCTAGGGATCC
```

>B.6240_180C
MRVKGIRKNYQHLWRWGIMRWGIMLLGTMLMICSATEKLWVTVYYGVPVWKEATTTLFCASDAKAYSPEKHNIWATHACVPTD
PNPQELVLGNVTEDFNMWKNNMVEQMHEDIISLWDQSLKPCVKLTPLCVTLNCTDLKNSATDTNGTSGTNNRTVEQGMETEI
KNCSFNITTGIGNKMQKEYALFYKLDVPIDSNNNSDNTSYRLISCNTSVVTQACPKTSFEPIPIHYCAPAGFAILKCNNKT
FSGKGPCKNVSTVQCTHGIRPVVSTQLLLNGSLAEEEIVIRSENFTNNAKTIIVQLNESVIINCTRPNNNTRKGIHIGLGRA
LYATGDIIGDIRQAHCNLSSKSWNKTLQQVVRKLREQFGNKTIAFNQSSGGDETVKHSFNCGGEFFYCDTTQLFNSTWSSN
DTWNSTGVQDNNITLPCRIKQIINMWQEVGKAMYAPPIQGLISCSSNITGLLITRDGGTNNTNATEIFRPGGGDMRDNWRSE
LYKYKVVKIEPLGIAPTKAKERVVQREKEAVGLGAVFIGFLGAAGSTMGAASVTLTVQARQLLSGIVQQQNNLLRAIEAQQH
MLQLTVWGIKQLQARILAVERYLKDQQLLGINGCSGKLICPTAVPWNASWSNKSLTAIWNNMTWMEWEREIDNYTGLIYSLI
EESQIQQEQNEKELLELDKWASLWNWFDITKWLWYIK

>B.6240_140C.opt
ATGCGCGTGAAGGGCATCCGCAAGAACTACCAGCAGAACTGCTGCGCTGGCGCCATCCTGGGCTGCTGCTGGGCA
CCCTGATGATCTGCTCCGCCACCGAGAAGCTGTGGGTGACCGTGTACTACGGCGTGCCCGTGTGGAAGGAGGCCACCAC
CCTGTTCTGCGCCTCCGACGCCAAGGCCTACTCCCCCGAGAAGCACAACATCTGGGCCACCCACGCCTGCGTGCCCACCGAC
CCCAACCCCAGCAGGAGCTGGTGCTGGCAACGTGACCGAGGACTTCAACATGTGGAAGAACAACATGGTGGAGCAGATGCACG
AGGACATCATCTCCCTGTGGGACCAGTCCCTGAAGCCCTGCGTGAAGCTGACCCCCTGTGTGACCCTGAACTGCACCGA
CCTGAAGAACTCCGCCACCGACACCAACGGCACCAGCGGCACCAACAACCGCACCGTGGAGCAGGGCATGGAGACCGAGATC
AAGAACTGCTCCTTCAACATCACCACCGGCATCGGCAACAAGATGCAGAAGGAGTACGCCCTGTTCTACAAGCTGGACGTGG
TGCCCATCGACTCCAACAACAACTCCGACAACACCTCCTACTGCGCCCCCCCGGCTTCGCCATCCTGAAGTGCAACAACAAGACC
CCCAAGAGACCTCCTTCGAGACCGTGCAGTGCACCCACGGCATCCGCCCTGACTACTCCCCCATCCCCATCCACTACTGCGCCCCCGGCTTCGCCATCCTGAAGTGCAACAACAAGACC
```

Figure 21 Cont'd-2

```
TTCTCCGGCAAGGCCCCTCTGCCAAGAACGTGTCCACCGTGCAGTGCACCCACGCCCGTGTGTCCACCAGTGC
TGCTGAACGGCTCCCTGGCCGAGGAGGAGATCAACTGCACCCGCCCGAGAACTTCACCAACAAGCCAAGACCATCGTGCA
GCTGAACGGCAGTCCGTGATCATCAACTGCACCCGCCCCAACAACAACACCCGCCCGCAACCTGCTGGGCCGCCC
CTGTACGGCCACCCGGGCGCCGATCATCGGCGACAGCTCCGGCAACAAGAGACCATCCGGCAACTCCTGCAAGTCCTCCAACTGCCTTCAACCAGTCCTCGGGCGGGCGACCAGGAGAT
AGCAGGTGGTGCGCAAGCTGCGCGAGCAGTTCGGCGAGCAGTTCTTCTACTGCAACAACAGTCCCACCTGGTCCTCCAAC
CGTGAAGCCACTCCTTCAACTGCCGCTGCAGTTCTTCTACTGCAACAACAGTCGCCATCAAGCAGATCATCAAGCATGGCAGG
GACACCTGGAACTGGAACTCCACGGCGTGCAGGACAACAACATCACCTGCCGATCTCGCATCAAGCAGATCATCAAGCATGTGGCAGG
AGTGGGCAAGGCCATGTACGCCCCCCCATCGAGGGCAAGATCACCTGCAAGTCCAACATCACCGGCCTGCTGCTGACCCG
CGACGGCGGCGGCATGCGCGACAACTGGCGCAGCGAGCTGTACAAGTACAAGGTCGTGGTGAAGATCGAGCCCCTGGGCGTCGCCGAG
CTGTACAAGTACAAGGTCGTGAAGATCGAGCCCTGGGCGTGCAGATCAAGCAGCTGCAGACCGTGTGGGGCATCAAGCAGCTGCAGACCGTGTGGGGCATC
AAGCAGCTGCAGACCGTGTGGGGCATCAAGCAGCTGCAGACCGTGTGGGGCCTCCCGGCGCCGCCCGTGACCCT
GACCGTGCAGGCCCGACCGTGTCCGGCATCAAGCTGCTGCTGCTGGCTGCTGCTGCTGCGAGCCCATCGAGCCCCAGCAC
ATGCTGCAGCTGACCGTGTGGGGCATCAAGCAGCTGCAAGCCTGATGGGGCATCAAGCTGCTGAAGGACCAGCAGA
TCCTGGGCATCTGGGGCTGCTCCGGCAAGCTGATCTGCACCACCGCCGTGCCCGTGAACGCTACTCCCTGATC
GACGCCATCTGGAACAACATGACCTGGATGGAGTGGGAGCGCGAGATCGACAACTACACCGGCCTGATCTACTCCCTGATC
GAGGAGTCCCAGATCCAGAATCCAGAAGCAGCTGCAGCGTGTTCGCTGGAGAGTGGACAAGGCTGGACCTGGAACTGGTTCG
ACATCACCAAGTGGCTGTGTGGTACATCAAGTAG
```

```
>M.CON-S_140C
MRVRGIQRNCQHLWRWGTLILGMLMICSAAENLWVTVYYGVPVWKEANTTLFCASDAKAYDTEVHNVWATHACVPTDPNPQE
IVLENVTENFNMWKNNMVEQMHEDIISLWDQSLKPCVILNCTNVNVTNTTNNTEEKGEIKNCSFNITTEIRDKKQ
KVYALFYRLDVVPIDDNNNSSNYRLINCNTSAITQACPKVSFEPIPIHYCAPAGFAILKCMDKKFNGTGPCKNVSTVQCTH
GIKPVVSTQLLLNGSLAEEEITIRSENITNNAKTIIVQLNESVEINCTRPNNNTRKSIRIGPGQAFYATGDIIGDIRQAHCN
ISGTKWNKTLQQVAKKLREHFNNKTIIFKPSSGGDLEITTHSFNCRGEFFYCNTSGLFNSTWIGNGTKNNNNTMDTITLPCR
IKQIINMWQGVGQAMYAPPIEGKITCKSNITGLLLTRDGGNNNTNETEIFRPGGGDMRDNWRSELYKYKVVKIEPLGVAPTK
AKERVVEREKEAVGIGAVFLGFLGAAGSTMGAASITLTVQARQLLSGIVQQQSNLLRAIEAQHLLQLTVWGIKQLQARVLA
VERYLKDQQLLGIWGCSGKLICTTTVPWNSSWSNKSQDEIWDNMTWMEWEREINNYTDIIYSLIEESQNQQEKNEQELLALD
KWASLWNWFDITNWLWYIK
```

Figure 21 Cont'd-3

>M.CON-S_140C.opt
ATGAGGGTCCGGGGAATCCAGGCGCAACTGCCAGTGGGCACGCTGATCCTGGGGATGATGCTGATCTGCA
GCGCGGGCTGAGAACCTGTGGTGACAGTGTACTACGGCGTGCCCTGTGTGTGGAAGGAGGCCAAGACCACCCTGTTCTGCGCCTC
GGACGCGGAAGGCCTACGACGAGGTCCACAACGTGTGGGCTACCCACGCCTGCGTGCCCGTGCCCGTGCCCAATCCTCAGGAG
ATGGTCCTGGAGAACGTGACCGAGAACTTCAACATGTGGAAGAACAACATGGTGGAGCAGATGCACGAGGACATCATCAGCC
TGTGGGACCAGAGCCTGAAGCCCTGCGTGAAGCTGACCCCCTGCGTGACCCTGACCTGCACCAACGTGACCAAGAACATCAGCAA
CACCACGAACACACGGAGGAGAAGGGGGAGATCAAGAACTGCAGCTTCAACGACGTCGTGCCGATCCAGATCAACACCAGGCTGATCA
AAGGTGTACGCCCTGTTCTACCGGCTGGACGTCGTGCCCGATCAAGAACAACATGCCCATCACTCCAGCAACTACAGGCTGATCA
ACTGCAACACCAGCGCGATCACCCAGGCGCCTGCCCTAAGGTGTCGTTCGAGCCCATCCCCATCAAGAGCGTCCGCGCCTGCCCGG
CTTCGCCATCCTGAAGTGCAACGACAAGAAGTTCAAGCGCAACGGCCCCTGGCCGAGGAGGAACTGCAGCGTGCACCAC
GGCATCAAGCCTGTGGTGTCCACCCAGCTGCTGCTGAACGGCAGCCTCGGTGGAGATCAACTGCACCCGCCAACAACAACACGCG
TCACCAACAACGCCAAGACGATCATCCGGACCAGGCGTTCTACCAGGAGCCCTGGAGATCATGGGCGACATCATGGGACATCATGAGC
GAAGAGCATCCGGATCGGACCAAGTGGAACAAGACCCTGAACAACGGCAAGACTGAGCGAGCACTTCAACAAGACCATCATCT
ATCTCGGGGACGAAGTGGAACAAGACCCTGAACAACGGCAAGACTGAGCGAGCACTTCAACAAGACCATCATCT
TCAAGCCCTGTTCAACGGCGGCACCATCGCCCGGGCTGAGACCTTCAACTGCCGCGGGCGCGAGTTCTTCTACTGTAACACGTC
GGGCCCTGTTCAACAGCACCACCCGAGATCTGGCCAGGGCGTGGCCCACCAAACAACCTAAGACCTAGCAACATCACCCTGCCCTGCCGG
ATCAAGCAGATCATCAACATGTGGCAGGGCGTGGGCCGGGCCATGTACGCCCCCCATCGAGGGCAAGATCACGTGCAAGA
GCAACATCACGGGGCCCTGCCTCGACACGAGAGCAATCATCAGGAGCCAGGCGAGTGGGCCATCAGCATCCAGGGCAAAGATCAGCGAGCC
AGACATGAGAGAGGCGAGCGCGAACAGAAGCTGTACAAGGGCTGTACAAGGTCGTGAAGATCGAGGCCCCTGGGCGTGGCACCCAAG
GCCAAGGAGAGGGTCGTGGAGCGGGAGAAGGAGGCCGGCGTGGAAGGTCCCGATCGGCAGGCCAGCACAACCGACGCCAGCCGGCA
GCCACCATGGGGCCGCTCGATCACCCTCGATCGAGCCAGCAGCGCCTGCCATGCCAGCACTGCGCCCACGCCAGCGGCACCAACCT
GCTGAGGCGCATCGAGGGCTGAGGTCATCACCCAGCTGCCTCCGGCATCGTGGGCATCAAGCAGCCAGGCCAGGTGTGCC
GTCGAGCGGCTACCTGAAGGACAACATCAGCAACCGGGAACAGCAGCTGCCATCTGGGCCGGCAGCTGATCTGCACCACCGTGCCCT
GGAACAGCAGCAGCAGAACAAGACCAGGACAACAAGGAGAAGCAGGAGAACCAGCAGGAGGAGAAGAACGAGCAGGAGAGAGATCAACAA
CTACACCGACATCATCTACAGCCTGATCGAGGAAGAACGAGGTGTACATCAAGGTCCTGCCTGTGGCAGGAGAGTGCTGCCGGTGGAC
AAGTGGGCGTCGCGTGAACTGGTTCGACATCACCAACTGGCTGTGGTACATCAAGGTGAGGATCCTCTAGA >C.1086C_140C
MRVRGIWKNWPQWLIWSILGFWIGNMEGSWVTVYYGVPVWKEAKTTLFCASDAKAYEKEVHNVWATHACVPTDPNPQEMVLA
NVTENFNMWKNDMVEQMHEDIISLWDESLKPCVKLTPLCVTLNCTNVKGNESDTSEVMKNCSFKATTELKDKKHKVHALFYK
LDVPLNGNSSSGEYRLINCNTSAITQACPKVSF

Figure 21 Cont'd-4

QLLNGSLAEEEIIRSENLTNNAKTIIVHLNESVNIVCTRPNNNTRKSIRIGPGQTFYATGDIIGNIRQAHCNINESKWNN
TLQKVGEELAKHFPSKTIKFEPSSGGDLEITTHSFNCRGEFFYCNTSDLFNGTYKNGTYNHTGRSSNGTITLQCKIRQIINM
WQEVGRAIYAPPIEGEITCNSNITGLLLRDGGQSNETNDTETFRPGGGDMRDNWRSELYKYKVVEIKPLGVAPTEAKERVV
EREKEAVGIGAVFLGFLGAAGSTMGAASMTLTVQARQLLSGIVQQQSNLLRAIEAQQHMLQLTVWGIKQLQARVLAIERYLK
DQQLLGMWGCSGKLICTTAVPWNSSWSNKSQNEIWGNMTWMQWDREINNYTNTIYRLLEDSQNQQEKNEKDLLALDSWKNLW
NWFDISKWLWYIK
>C.1086C_140C.opt
ATGGCGCGTGCGGCCATCTGGAAGAACTGGCCCAGTGGCTCTGATCTGGTCCATCCTGGGCTTCTGATCGGCAACATGGAGG
GCTCCCGGGTGACCGTGTACTACGGCGTGTGCGCCAAGAGCACGCCAAGAGCCAAGAGCCAAGAGCCAAGGCCTGTTCTGCGACGCCAAGGC
CTACGACGAAGGAGGTGCACAACGTGTGGGCCCTGCGTGCCCACCACGGACACACCCCCAACCCCCAGGAGATGGTGCTGGCC
AACGTGACCGAGAACTTCAACATGTGGAAGAACCACATGGTGGAGCAGATGCACGAGGACATCATCTCCCTGTGGGACGAGT
CCCTGAAGCCCTGCGTGAAGCTGACCCCTGTGCGACCACCTGCAAGGCCACCACCGAGCCTGAACCTGAAGGCAACGAGTCCGACACCTC
CGAGGTGATGAAGAACTGCTCCTTCAACGGCACCACCGAGCTGAAGGACAAGAAGCACAAGGTGCACGCCCTGTTCTACAAG
CTGGACGTGGTGCCCCTGAACGGCAACTCCCTCCTCCCGGCGAGTACTGCGCCGCCCTGATCAACTGCAACACCTCCGCCATCACCC
AGGCCTGCCCCAAGGTGTCCTTTCGACCCCCTGCGACTACTGCGCCGCCCTGGCTTCGCCATCCTGAAGTGCAACAA
CAAGACCTTCAACGGCACGGCTCCCGGCCGAGGAGTCTGTGCCAAGCTGTCCACCGTGCAGTGCACCCACGGCATCAAGCCCGTGGTCTCCACC
CAGCTGCTGCTGAACGGAGTCCGTGAACATCGTGTGCACCAGGAGATCATCATCCGCGGCCCCCAACAACAACACCCGCAAGTCCATCCGGATCGGCCCCGG
CCAGACCTTCTACGCCATCGGCGACATCATCGGCAACATCCGCCAGGCCCACTGCAACATCAACGAGTCCAAGTGGAACAAC
ACCCTGCAGAAGGTGGGCGAGGAGCTGGCCAAGCACTTCCCCTCCAAGACCATCAAGTTCGAGCCCTCCTCCGGCGGCGACC
TGGAGATCACCACCCACTCCTTCAACTGCCGCGGCGAGTTCTTCTACTGCAACACCTCCGACCTGTTCAACGGCACCTACCG
CAACGGCACCTACAACCACACCGGCCGCTCCAGCAACGGCACCATCACCCTGCAGTGCAAGATCCGCCAGATCATCAACATG
TGGCAGGAGGTGGGCCGCGCCATCTACGCCCCCCCCCATCGAGGGCGAGATCACCTGCAACTCCAACATCACCGGCCTGCTGC
TGCGCGACGGCGGCCAGTCCAACGAGACCAACGACACCGAGACCTTCCGCCCCGGCGGCGGCGACATGCGCGACAACTG
GCGCTCCGAGCTGTACAAGTACAAGGTGGTGGAGATCAAGCCCCTGGGCGTGGCCCCCACCGAGGCCAAGGAGCGCGTGGTG
GAGCGCGAGAAGGAGGCCGTGGGCATCGGCGCCGTGTTCCTGGGCTTCCTGGGCGCCGCCGGCTCCACCATGGGCGCCGCCT
CCATGACCCTGACCGTGCAGGCCCGGCAGCTGCTGTCCGGCATCGTGCAGCAGCAGAGCAACCTGCTGCGCGCCATCGAGGC
CCAGCAGCACATGCTGCAGCTGACCGTGTGGGGCATCAAGCAGCTGCAGGCCCGCGTGCTGGCCATCGAGCGCTACCTGAAG
GACCAGCAGCTGCTGGGCATGTGGGCCTGCTCCGGCAAGCTGATCTGCACCACCGCCGTGCCCTGGAACTCCTCCTGGTCCA

Figure 21 Cont'd-5

ACAAGTCCCAGAACGAGATCTGGGCAACATGACCTGGATGCAGTGGGACCGGCGAGATCAACAACTACACCACCATCTA
CCGCCCTGCTGGAGGACTCCCAGAACCAGCAGTGTACATCAAGTAGGGATCCTCTAGA
CGGCCCTGCTGGAGGACTCCCAGAACCAGCAGTGTACATCAAGTAGGGATCCTCTAGA
AACTGGTTCGACATCTCCAAGTGGCTGTGGTACATCAAGTAGGGATCCTCTAGA

>c.089c_140C

MRVRGMLRNCQQWMINGILGFWMLMICSVVGNLWVTVYYGVPVWKEAKTTLFCASDARAYEREVHNVWATHACVPTDPNPQE
MVLVNVTENFNMWKNDMVDQMHEDIISLWDQSLKPCVKLTPLCVILECNNANGTTNNGSVIVNENSTMYGEIQNCSFKVNS
EIKGKKQDVYALFNSLDIVKLYNGTSQYRLINCNTSTLTQACPKVSEDIPIHYCAPAGYAILKCNNKTFNGTGPCNNVST
VQCTHGIKPVVSTQILLNGSLARGEIIIRSKNLIDNTKTIIVHLNESIKNICIRPNNNTRRSTRIGPGQAFYAANGIVGNIR
QAHCNISEGEWNKTLYRVSRKLAEHFPGKEIKFKPHSGGDLEITTHSFNCRGEFFYCNTSKLFNGTYNGTYTMDTNSTIIL
PCRIKQIINMWQEVGQAMYAPPIEGIIACNSTTTGLLLTRDGGDKMGSKPEIFRPGGGDMRDNWRSELYKYKVVEIKPLGIA
PTKAKERVVEKEKTIQKEAVGIGAVFLGFLGAAGSTMGAASITLTVQARQLLSGIVQQQSNLLRAIEAQQHMLQLTVWGIKQ
LQARVLAMERYLQDQQLLGIWGCSGKLICTTAVPWNSSWSNKTLEYIWGNMTWMQNDREIDNYTGIIYDLLEDSQIQQEKNE
KDLLALDSWKNLWSWFSITNWLMYIK

>c.089c_140C.opt

ATGCGCGTGCGCGGCATGCTGCGCAACTGCCAGCAGTGGATCAACGGCATCCTGGGCTTCTGGATGCTGATGATCTGCT
CCGTGGTGGGCAACCTGTGGGTGACCGTGTACTACGGCGTGCCCGTGTGGAAGGAGGCCAAGACCACCCTGTTCTGCGCCTC
CGACGCCCGCGCCTACGAGCGCGAGGTGCACAACGTGTGGGCCACCCACGCCTGCGTGCCCACCGACCCCAACCCCCAGGAG
ATGGTGCTGGTGAACGTGACCGAGAACTTCAACATGTGGAAGAACGACATGGTGGACCAGATGCACGAGGACATCATCTCCC
TGTGGGACCAGTCCCTGAAGCCCTGCGTGAAGCTGACCCCCCTGTGCGTGATCCTGGAGTGCAACAACGCCAACGGCACCAC
CAACAACGGCTCCGTGATCGTGAACGAGAACAGCACCATGTACGGCGAGATCCAGAACTGCTCCTTCAAGGTGAACTCC
GAGATCAAGGGCAAGAAGCAGGACGTGTACGCCCTGTTCAACTCCCTGGACATCGTGAAGCTGTACAACGGCACCTCCC
AGTACCGCCTGATCAACTGCAACACCTCCACCCTGACCCAGGCCTGCCCCAAGGTGTCCTTCGACCCCATCCCCCACTA
CTGCGCCCCCGCCGGCTACGCCATCCTGAAGTGCAACAACAAGACCTTCAACGGCACCGGCCCCTGCAACAACGTGTCCACC
GTGCAGTGCACCCACGGCATCAAGCCCGTGGTGTCCACCCAGATCCTGCTGAACGGCTCCCTGGCCAGGGGCGAGATCATCA
TCCGCTCCAAGAACCTGATCGACAACACCAAGACCATCATCGTGCACCTGAACGAGTCCATCAAGAACATCTGCATCCGCC
CAACAACAACACCCGCCGCTCCATCCGCCCAGGGCGAGTGGAACAAGACCCTGTACCGCGTGTCCCGCAAGCTGGCCGAGCACTTCCCCG
CAGGCAAGGAGATCAAGTTCAAGCCCCACTCCGGCGGCGACCTGGAGATCACCACCCACTCCTTCAACTGCCGCGGCGAGTTCTT

Figure 21 Cont'd-6

CTACTGCAACACCTCCAAGCTGTTCAACGGCACCTACAACGGCACCTACAACAAGGACACCAACTCCACCATCATCCTG
CCCTGCCGGCATCAAGCCAGATCATCAACATGTGGCAGGAGGTGGCCAGGCCCATGTACGCCCCCCCATCGAGGGCATCATCG
CCTGCAACTCCACCATCACCGGCCTGCTGCTGACCCGGCGGGCGACGGGCGACAAGAACGGCTCCAAGCCCGAGATCTTCCGCCC
CGGCGGGCGGACATGCGCCGACAACTGGCCGCTCCGAGCTGTACAAGTACAAGGTGGTGGAGATCAAGCCCCTGGGCATCGCC
CCCACCAAGGCCAAGGAGCGCGTGGTGAGAAGGAGAAGACCATCCAGAAGGAGGCCGTGGGCATCGGCGCCGTGTTCCTGG
GCTTCCTGGGCGCGCGGCTCCAACCTGCCGCCTCCACCATGGGCGCCCTCCATCACCCTGACCCTGCAGGCCCGCCAGTCGTCGTCCGGCAT
CGTGCAGCAGCCCAACCTGCTGGCCATGGAGCCGCTACCTGCAGGACCCAGCACATGCTGCTGGGCATCTGGGCTGCTCCGGCAAGCTGA
CTGCAGGCCCGCCGTGCTGGCCCCTGGGAACTCCCTCCCGGTCCAACAAGACCCTGGAGTACATCTGGGCAACATGACCTGGATGCA
TCTGCACCACCGGCCGTGCCCCTGCCGGCCATCATCTACGACTCATCTGCTGGAGGACTCCCAGATCAGTCCAGCAGGAGAACGAG
GTGGGACCGCGAGATCGACAACTACACCGGGACTCCCTGCTGGAGGACTCCCAGATCAGCAGGAGGAGAACGAG
AAGGACCTGCTGCCCTGGCCCCTGGAAGAACCTGTGGTCCTGGTTCCTCCATCACCAACTGACCTGTGGTACATCAAG

Figure 23

N-terminal sequences of HIV Envs

| | | | | | | | | | | | |
|---|---|---|---|---|---|---|---|---|---|---|---|
| CON-S. Mcon | A | A | E | N | L | W | V | T | V | Y | Y | G |
| A244.AE | A | S | D | N | L | W | V | T | V | Y | Y | G |
| 63521.B | A | A | A | Q | L | W | V | T | V | Y | Y | G |
| 6240.B | A | T | E | K | L | W | V | T | V | Y | Y | G |
| 1086.C | - | - | - | - | - | W | V | T | V | Y | Y | G |
| 089.C | V | V | G | N | L | W | V | T | V | Y | Y | G |

Bold amino acids are hydrophobic. Deletions can be made in any length and in any combination of amino acids to have the effect of the Delta 11 deletion. However, optimal deletions will be of Between 5-11 amino acids. The 1086.C gp120 Env has an N-terminal set of amino acids only 7 aa long and manifests ~ 50% dimer formation when expressed in 293T or CHO cells. Thus it is likely that at least more than 5 aa deletions are needed for prevention of dimer formation. As one instance of the design, 11 residues will be deleted; in another instance, between 2 and 10 residues will be deleted, either in a consecutive strength or selectively; "in yet another instance, a short peptide sequence chosen for stability will be substituted for one or more of the 11 residues.

Figure 25

| Variables/High Risk | Est. HR Quantitative/Categorical/Hazards Quantitative Hazards Categorical | P-value Quantitative/Categorical/Hazards Quantitative Hazards Categorical |
|---|---|---|
| IgA Main Breadth | 1.43/1.51/1.52/1.66 | 0.0275/ns/0.012/ns |
| IgA OOMSA | 1.38/2.63/1.39/2.83 | 0.0315/0.0159/0.0273/0.0102 |
| IgA A1.con.env03 | 3.71/1.57/1.62/4.16 | 0.0019/0.0012/0.0011/0.0007 |
| IgA DRCBL gp140 | 1.34/2.02/1.36/2.07 | 0.0709/0.0499/0.0534/0.0412 |
| IgA C1 CRF1 | 1.69/3.15/1.75/3.26 | 0.0004/0.003/0.0003/0.0022 |
| A32/A244d11 | 1.1/2.33/1.33/2.67 | ns/ns/ns/0.0468 |

| Variables/Lower Risk | Est. HR Quantitative | |
|---|---|---|
| IgG A244gD-293T | 0.71 | 0.0292 |
| IgG A244 K178C | 0.74 | 0.0543 |
| ADCC CM243 AUC | 1.07.96/1.1 | Ns/0.0232/ns |

Figure 26

*Sequences highlighted in red (underlined) above are deleted to make HIV-1 Env gp120_Delta11 mutants, sequences highlighted in blue (double underlined) are C1 region and also deleted.*

HIV-1 Env gp120_Delta11 and deletion of C1 mutants:

>AE.A244_gp120
MRVKETQMNWPNLWKWGTLILGLVIICSASDNLWVTVYYGVPVWKEADTTLFCASDAKAHETEVHNVWATHACVPTDP
NPQEIDLENVTENFNMWKNNMVEQMQEDVISLWDQSLKPCVKLTPPCVTLHCTNANLTKANLTNVNNRTNVSNIIGNI
TDEVRNCSFNMTTELRDKKQKVHALFYKLDIVPIEDNNDSSEYRLINCNTSVIKQPCPKISFDPIPIHYCTPAGYAIL
KCNDKNFNGTGPCKNVSSVQCTHGIKPVVSTQLLLNGSLAEEEIIIRSENLTNNAKTIIVHLNKSVVINCTRPSNNTR
TSITIGPGQVFYRTGDIIGDIRKAYCEINGTEWNKALKQVTEKLKEHFNNKPIIFQPPSGGDLEITMHHFNCRGEFFY
CNTTRLFNNTCIANGTIEGCNGNITLPCKIKQIINMWQGAGQAMYAPPISGTINCVSNITGILLTRDGGATNNTNNET
FRPGGGNIKDNWRNELYKYKVVQIEPLGVAPTRAKRRVVEREKR
>B.63521_gp120
MRVKGIRKNYQHLWRWGTMLLGILMICSAAAQLWVTVYYGVPVWKEATTTLFCASDAKAYDTEVHNVWATHACVPTDP
NPQELVLANVTENFNMWNNTMVEQMHEDIISLWDQSLKPCVKLTPLCVTLNCTDVTNATNINATNINNSSGGVESGEI
KNCSFNITTSVRDKVQKEYALFYKLDIVPITNESSKYRLISCNTSVLTQACPKVSFEPIPIHYCAPAGFAILKCNNET
FNGKGPCINVSTVQCTHGIRPVVSTQLLLNGSLAEKEVIIRSDNFSDNAKNIIVQLKEYVKINCTRPNNNTRKSIHIG
PGRAFYATGEIIGNIRQAHCNISRSKWNDTLKQIAAKLGEQFRNKTIVFNPSSGGDLEIVTHSFNCGGEFFYCNTTKL
FNSTWIREGNNGTWNGTIGLNDTAGNDTIILPCKIKQIINMWQEVGKAMYAPPIRGQIRCSSNITGLILTRDGGKDDS
NGSEILEIFRPGGGDMRDNWRSELYKYKVVRIEPLGVAPTRARERVVQKEKE
>B.62400_gp120
MRVKGIRKNYQHLWRWGIWRWGIMLLGTLMICSATEKLWVTVYYGVPVWKEATTTLFCASDAKAYSPEKHNIWATHAC
VPTDPNPQELVLGNVTEDFNMWKNNMVEQMHEDIISLWDQSLKPCVKLTPLCVTLNCTDLKNSATDTNGTSGTNNRTV
EQGMETEIKNCSFNITTGIGNKMQKEYALFYKLDVVPIDSNNNSDNTSYRLISCNTSVVTQACPKTSFEPIPIHYCAP
AGFAILKCNNKTFSGKGPCKNVSTVQCTHGIRPVVSTQLLLNGSLAEEEIVIRSENFTNNAKTIIVQLNESVIINCTR
PNNNTRKGIHIGLGRALYATGDIIGDIRQAHCNLSSKSWNKTLQQVVRKLREQFGNKTIAFNQSSGGDQEIVKHSFNC
GGEFFYCDTTQLFNSTWSSNDTWNSTGVQDNNITLPCRIKQIINMWQEVGKAMYAPPIQGLISCSSNITGLLLTRDGG
TNNTNATEIFRPGGGDMRDNWRSELYKYKVVKIEPLGIAPTKAKRRVVQREKR

Figure 26 Cont'd-1

>M.CON-S_gp120
MRVRGIQRNCQHLWRWGTLILGMLMICSAAENLWVTVYYGVPVWKEANTTLFCASDAKAYDTEVHNVWATHACVPTDP
NPQEIVLENVTENFNMWKNNMVEQMHEDIISLWDQSLKPCVKLTPLCVTLNCTNVNVTNTTMNTEEKGEIKNCSFNIT
TEIRDKKQKVYALFYRLDVVPIDDNNNSSNYRLINCNTSAITQACPKVSFEPIPIHYCAPAGFAILKCNDKKFNGTG
PCKNVSTVQCTHGIKPVVSTQLLLNGSLAEEEIIRSENITNNAKTIVQLNESVEINCTRPNNMTRKSIRIGPGQAF
YATGDIIGDIRQAHCNISGTKWNKTLQQVAKKLREHFNNKTIIEKPSSGGDLEITTHSFNCRGEFFYCNTSGLFNSTW
IGNGTKWNNNTNDTITLPCRIKQIINMWQGVGQAMYAPPIEGKITCKSNITGLLLTRDGGNMNTNETETFRPGGGDMR
DNWRSELYKYKVKIEPLGVAPTKAKRRVVEREKR

>C.1086C_gp120
MRVRGIMKNWPQNLIWSTLGFWIGNMEGSWVTVYYGVPVWKEAKTTLFCASDAKAYEKEVHNVWATHACVPTDPNPQE
MVLANVTENFNMWKNDMVEQMHEDIISLWDESLKPCVKLTPLCVTLNCTNVKGNESDTSEVMKNCSFKATTELRDKKH
KVHALFYKLDVVPLNGNSSSSGEYRLINCNTSAITQACPKVSFDPIPLHYCAPAGFAILKCNMKTFWGTGPCRNVSTV
QCTHGIKPVVSTQLLLNGSLAEEEIIIRSENLTNNAKTIIVHLNESVNIVCTRPNNNTRKSIRIGPGQTFYATGDIIG
NIRQAHCNINESKWNNTLQKVGEELAKHFPGKEIKFKPHSGGDLEITTHSFNCRGEFFYCNTSDLENGTYRNGTYNHT
GRSSNGTITLQCKIKQIINMWQEVGRATYAPPIEGNITCKSNITGLLLLRDGGQSNETNDTETFRPGGGDMRDNWRSE
LYKYKVVEIKPLGVAPTEAKRRVVEREKR

>C.089C_gp120
MRVRGMIRNCQQWWIWGILGFWMLMICSVWGMLWVTVYYGVPVWKEAKTTLFCASDARAYEREVHNVWATHACVPTDP
NPQEMVLVNVTENFNMWKNDMVDQMHEDIISLWDQSLKPCVKLTPLCVILECNNANGTTNNGSVIVVNENSTMYGEIQ
NCSFKVNSEIKGKKQDVYALFNSLDIVKLYNNGTSQYRLINCNTSLTQACPKVSFDPIPIHYCAPAGYAILKCNNKT
FNGTGPCNNVSTVQCTHGIKPVVSTQLLINGSLAEGEIIIRSKMLTDMTKTIIVHLNESIKINCIRPNNNTRRSIRIG
PGQAFYAANGIVGNIRQAHCNISEGEWNKTLYRVSRKLAEHFPGKEIKFKPHSGGDLEITTHSFNCRGEFFYCNTSKL
FNGTYNGTYTNDTNSTIILPCRIKQIINMWQEVGQAMYAPPIEGILACNSTITGLLLJERDGGDKNGSKPEIERPGGG
DMRDNWRSELYKYKVVEIKPLGIAPTKAKRRVVEKEKTIQKR

Sequences with delta11 and C1 deletion:

>AE.A244_gp120delta11_C1
MRVKETQMNWPNLWKWGTLILGLVIICSAVPVWKEADTLFCASDAKAHETEVHMVWATHACVPTDPNPQEIDLENVT
ENFNMWKNNMVEQTLHCTNANLTKANLTNVNNRTNVSNIIGNITDEVRNCSFNMTTELRDKKQKVHALFYKLDIVPIE
DNWDSSEYRLINCNTSVIKQPCPKISFDPIPIHYCTPAGYAILKCNDKNFNGTGPCKNVSSVQCTHGIKPVVSTQLLL
NGSLAEEEIIIRSENLTNNAKTIVHLNKSVVINCTRPSNNTRTSITIGPGQVFYRTGDIIGDIRKAYCEINGTEWNK

Figure 26 Cont'd-2

ALKQVTEKLKEHENNKPIIFQPPSSGDLEITMHHENCRGEFFYCNTTRLFNNTCIANGTIEGCNGNITLPCKIKQIIN
MWQGAGQAMYAPPISGTINCVSNITGLLLTRDGGATNTNNETFRPGGNIKDNWRNELYKYKVVQIEPLGVAPTRAK
REVVEREKR
>B.63521_gp120delta11_C1
MRVKGIRRNYQHLNRWGTMLLGIMLMICSAVPVWKEATTTLFCASDAKAYDTEVHNVWATHACVPTDPNPQELVLANVT
ENFNMWMNTMVEQTLNCTDVTNATNINATNINNSSGGVESGEIKNCSFNITTSVRDKVQKEYALFYKLDIVPITNESS
KYRLISCNTSVLTQACPKVSFEPIPIHYCAPAGFAILKCNNETFNGKGPCINVSTVQCTHGIRPVVSTQLLLNGSLAE
KEVIIRSDMFSDNAKNIIVQLKEYVKINCTRPMNNTRKSIHIGPGRAFYATGEIIGNIRQAHCNISRSKWNDTLKQIA
AKLGEQFRNKTIVFNPSSGGDLEITVHSFNCGGEFFYCNTTKLFNSTWIREGNNGTWNGTIGLNDTAGNDTIILPCKI
KQIINMWQEVGKAMYAPPIRGQIRCSSNITGLLLTRDGGKDDSMGSEILEIFRPGGGDMRDNWRSELYKYKVVRIEPL
GVAPTRARERVVQREKE
>B.6240_gp120delta11_C1
MRVKGIRRNYQHLWRWGIMLRWGIMLLGTLMICSAVPVWKEATTTLFCASDAKAYSPEKHNIWATHACVPTDPNPQELV
LGNVTEDFNMWKNNMVEQTLNCTDLKNSATDTNGTSGTNMRFVEQGMETEIKNCSFNITTGIGNRMQKEYALFYKLDV
VPIDSNMMSDNTSYRLISCNTSVVTQACPKTSFEPIPIHYCAPAGFAILKCNNMKTFSGKGPCKNVSTVQCTHGIRPVV
STQLLLNGSLAEEEIVIRSENFTNNAKTIIVQLNESVIINCTRPNNNTRKGIHIGLGRALYATGDIIGDIRQAHCNLS
SKSWNKTLQQVVRKLREQFGNKTTAFNQSSGGDQEIVKHSFNCGGEFFYCDTTQLFNSTWSSNDTWNSTGVQDMNITL
PCRIKQIINMWQEVGKAMYAPPIQGLISCSSNITGLLLTRDGGTNNTNATEIFRPGGGDMRDNWRSELYKYKVVKIEP
LGIAPTKAKRRVVQREKR >M.CON-s_gp120delta11_C1
MRVRGIQRNCQHLWRWGTLIIGMLMICSAVPVWKEAMTTLFCASDAKAYDTEVHNVWATHACVPTDPNPQEIVLENVT
ENFNMWKNNMVEQTLNCTNVNVTNTNNTEEKGEIKNCSFNITTEIRDKKQKVYALFYRLDVVPIDDNNNNSSNYRLI
NCMTSAITQACPKVSFEPIPIHYCAPAGFAILKCNDKKFNGTGPCKNVSTVQCTHGIKPVVSTQLLLNGSLAEEEIII
RSENITNNAKTIIVQLNESVEINCTRPNNNTRKSIRIGPGQAFYATGDIIGDIRQAHCNISGTKWNKTLQQVAKKLRE
HFNNKTIIFKPSSGGDLEITTHSFNCGGEFFYCNTSGLFNSTWIGNGTKNMNNTNDTITLPCRIKQIINMWQGVGQAM
YAPPIEGKITCKSNITGLLLTRDGGNNNTNETEIERPGGGMRDNWRSELYKYKVVKIEPLGVAPTKAKRRVVEREKR

Figure 26 Cont'd-3

>C.1086C_gp120delta7_C1
MRVRGIWKNWPQWLIWSILGFWIIGNMEGSVPVWKEAKTTLFCASDAKAYEKEVHNVWATHACVPTDPNPQEMVLANVT
ENFNMWKNDMVEQTLNCTNVKGNESDTSEVMKNCSFKATTELKDKKHKVHALFYKLDVVPLNGNSSSSGEYRLINCNT
SAITQACPKVSFDPIPLHYCAPAGFAILKCNNKTENGTGPCRNVSTVQCTHGIKPVVSTQLLLNGSLAEEIIIRSEM
LTNNAKTIIVHLNESVNIVCTRPNNNTRKSIRIGPGQTFYATGDIIGNIRQAHCNINESKWNNTLQKVGEELAKHFPS
KTIKFEPSSGGDLEITTHSFNCRGEFFYCNTSDLFNGTYRNGTYNHTGRSSNGTIILQCKIKQIINMWQEVGRAIYAP
PIEGEITCNSNITGLLLLRDGGQSNETNDTETERPGGGDMRDNWRSELYKYKVVEIKPLGVAPTEAKRRVVEREKR >C.089C_gp120delta11_C1
MRVRGMLRNCQQWWIWGILGFWMLMICSVVPVWKEAKTTLFCASDARAYEREVHNVWATHACVPTDPNPQEMVLVNVT
ENFNMWKNDMVDQTLECNNAMGTTNNGSVIVVNENSTMYGEIQNCSFKVNSEIRGKKQDVYALENSLDIVKLYNNGTS
QYRLINCNTSTLTQACPKVSFDEIPIHYCAPAGYAILKCNNKTENGTGPCNNVSTVQCTHGIKPVVSTQLLLNGSLAE
GEIIIRSKNLTDNTKTTIVHLNESTKINCIRPNNNTRRSIRIGPGQAFYAANGIVGNIRQAHCNISEGEWNKTLYRVS
RKLAEHFPGKEIKFKPHSGGDLEITTHSFNCRGEFFYCNTSKLFNGTYNGTYTNNDTNSTIILPCRIKQIINMWQEVG
QAMYAPPIEGIIACNSTITGLLLTRDGGDKNGSKPEITRPGGGDMRDNWRSELYKYKVVEIKPLGIAPTKAKRRVVEK
EKTIQKR

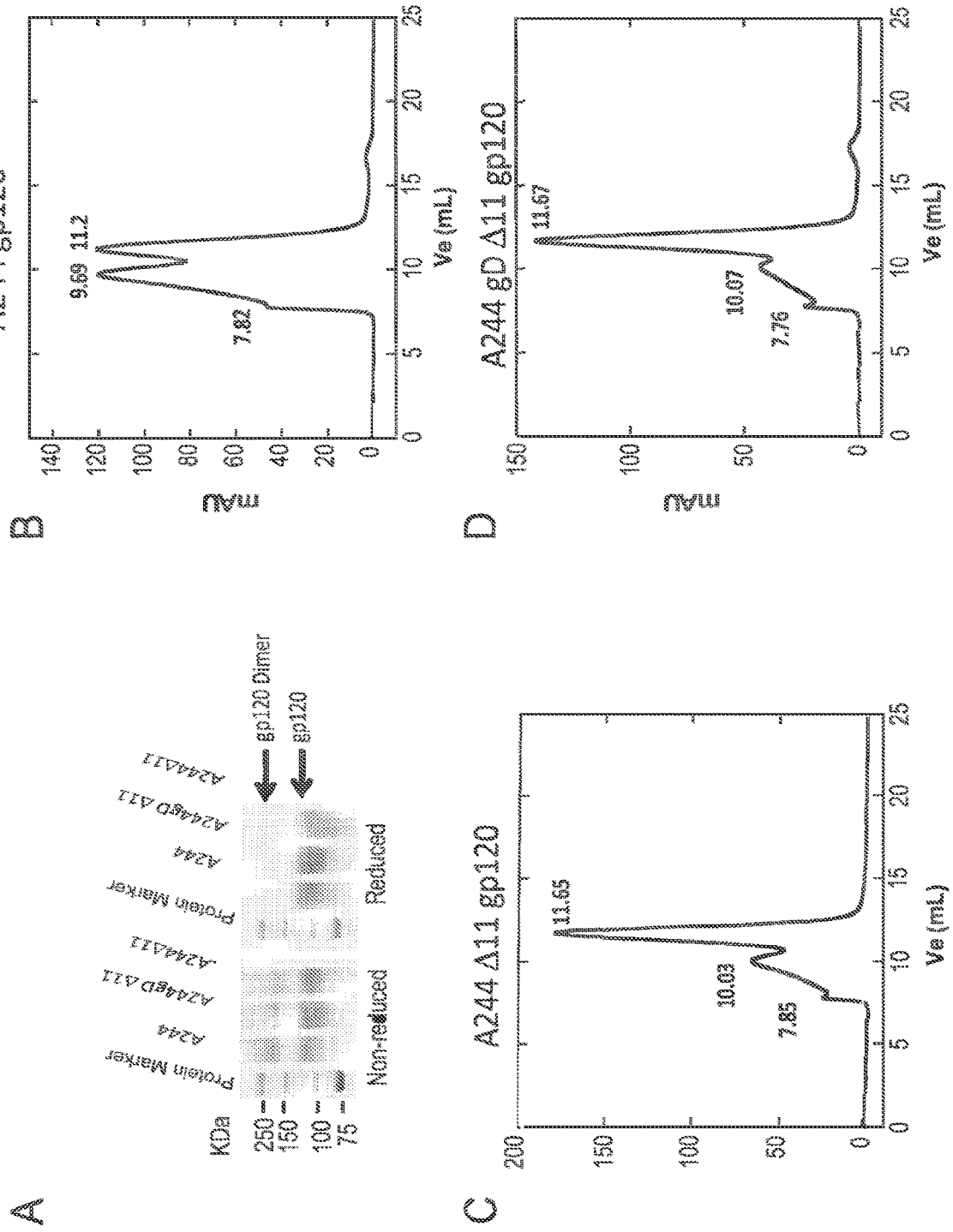
Figures 29A-D

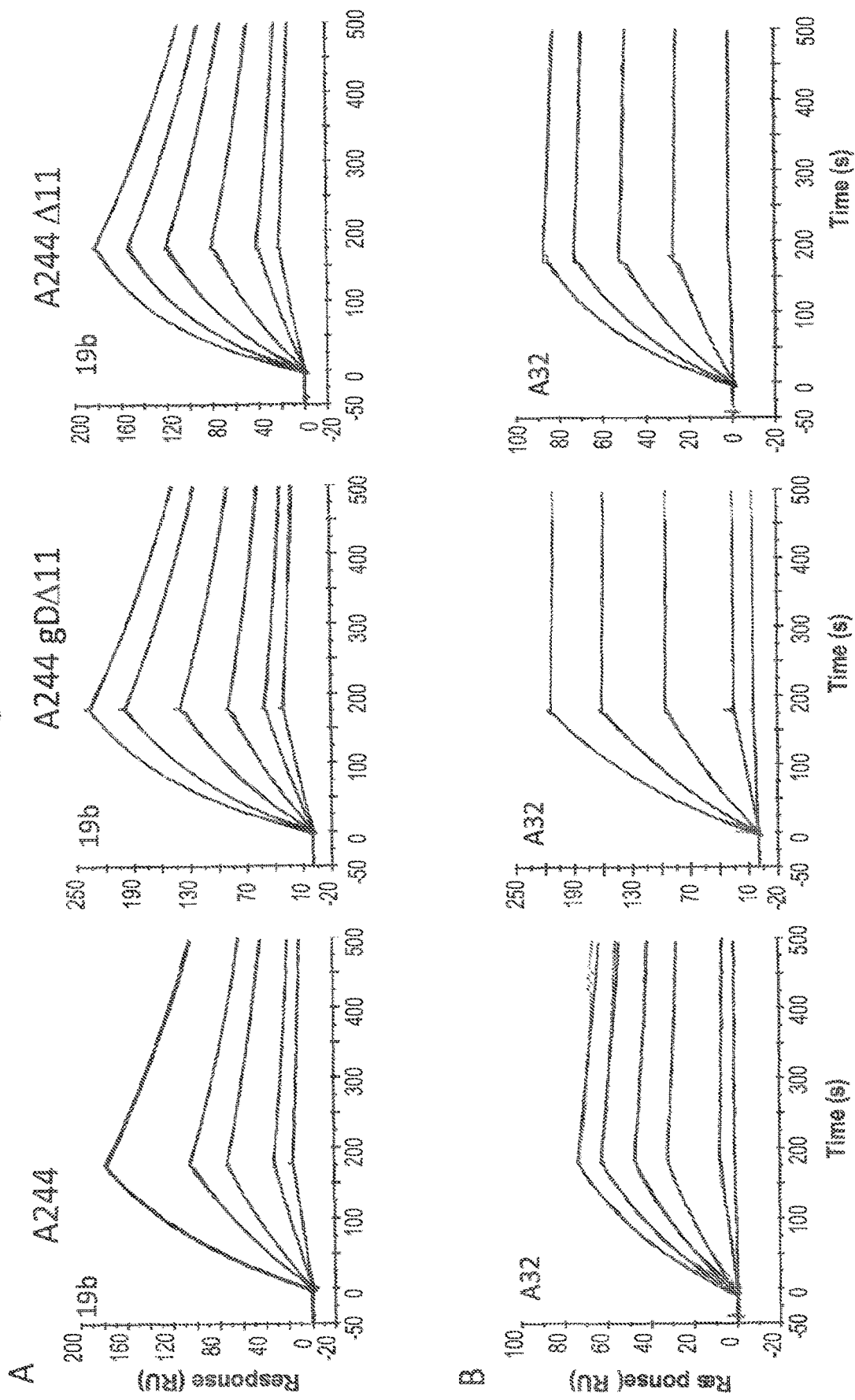
Figures 30A-B

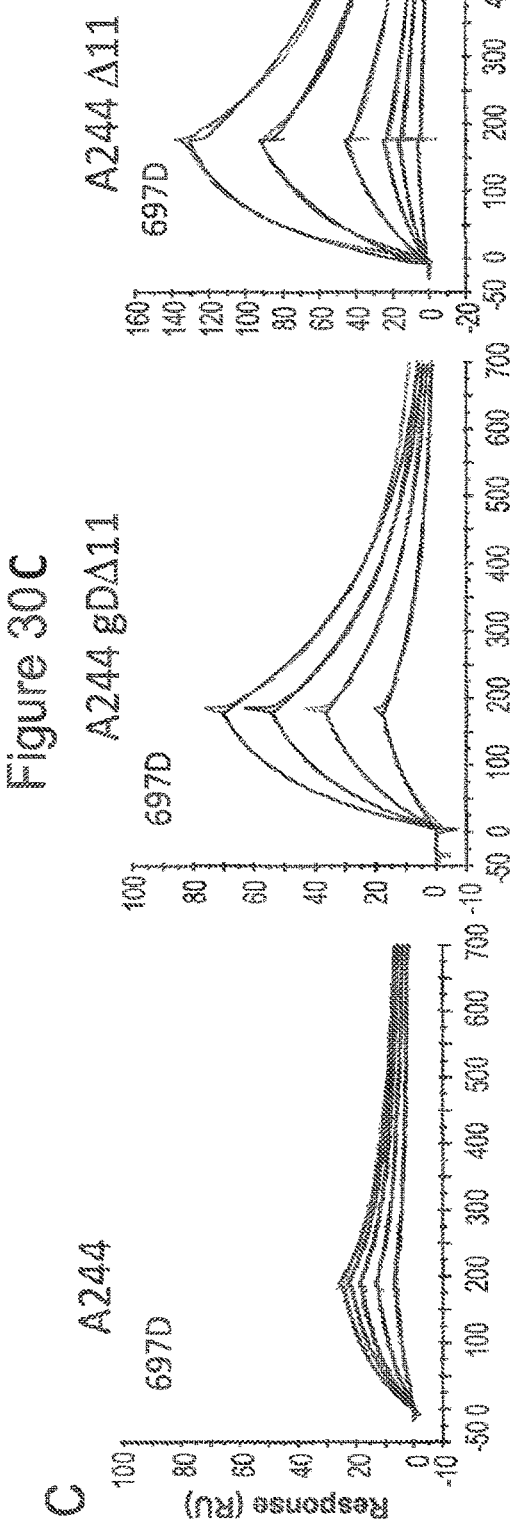
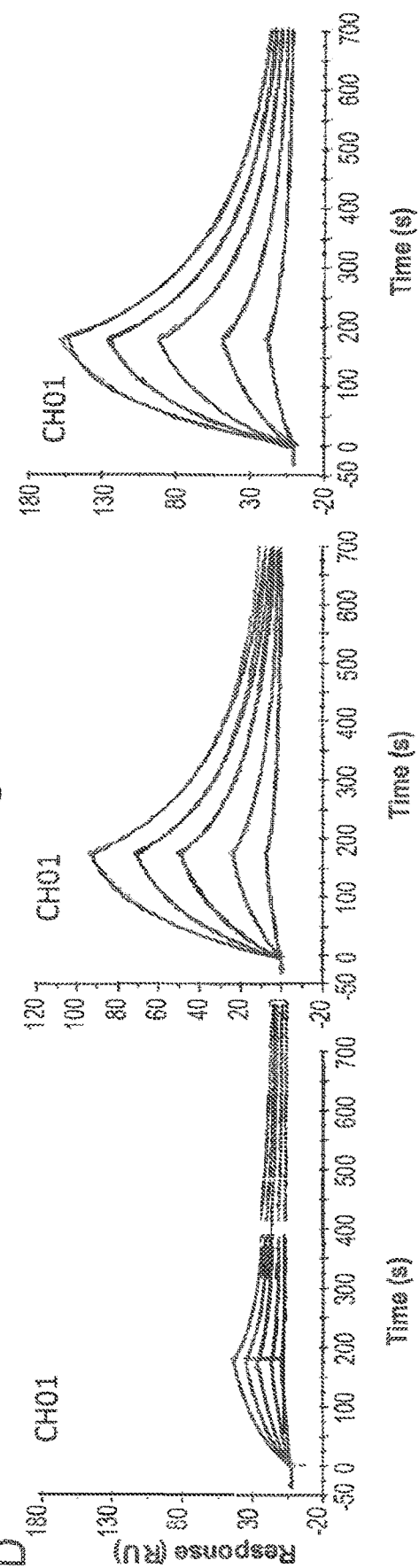
Figure 30C
Figure 30D

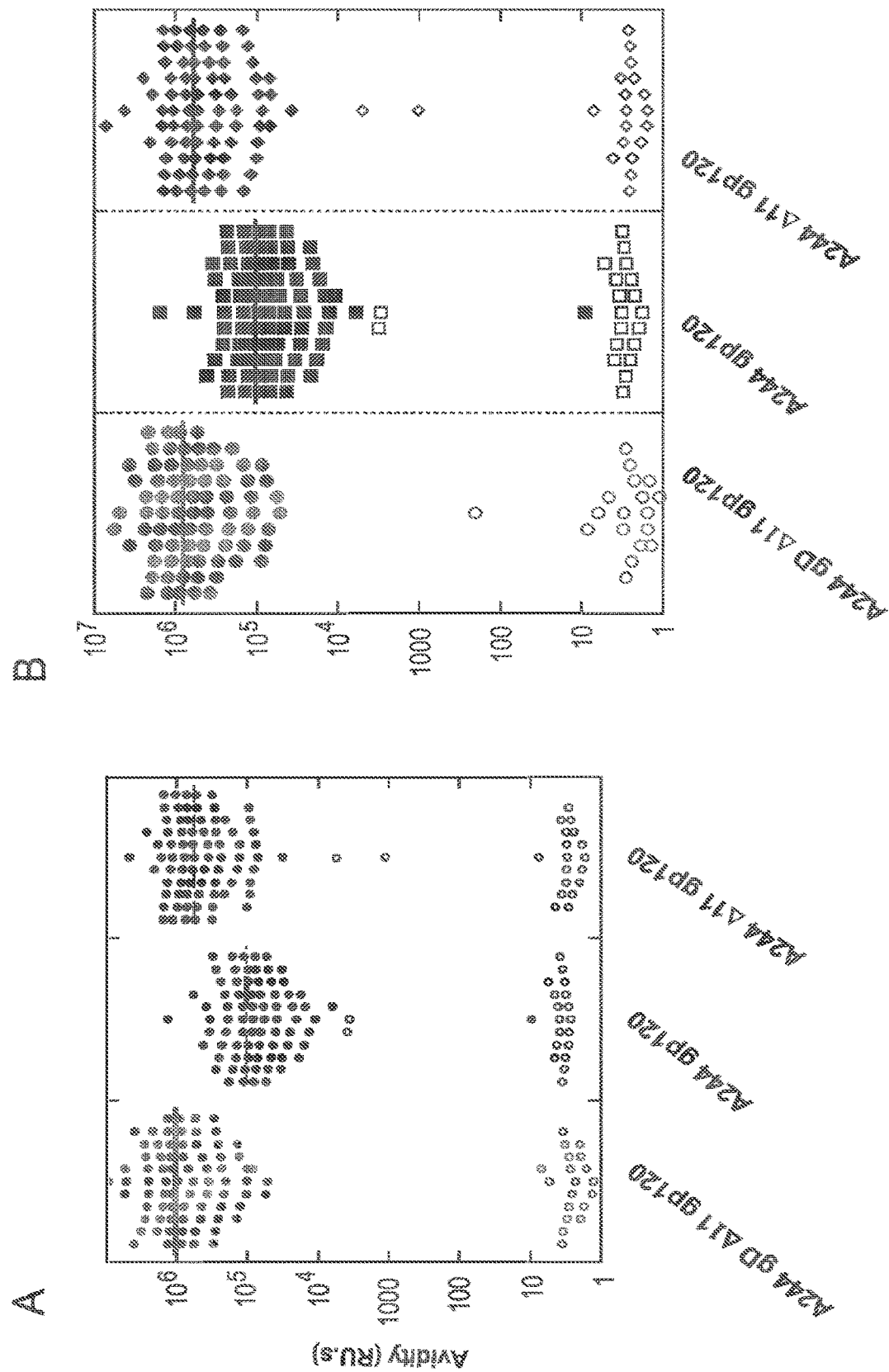
Figures 32A-B

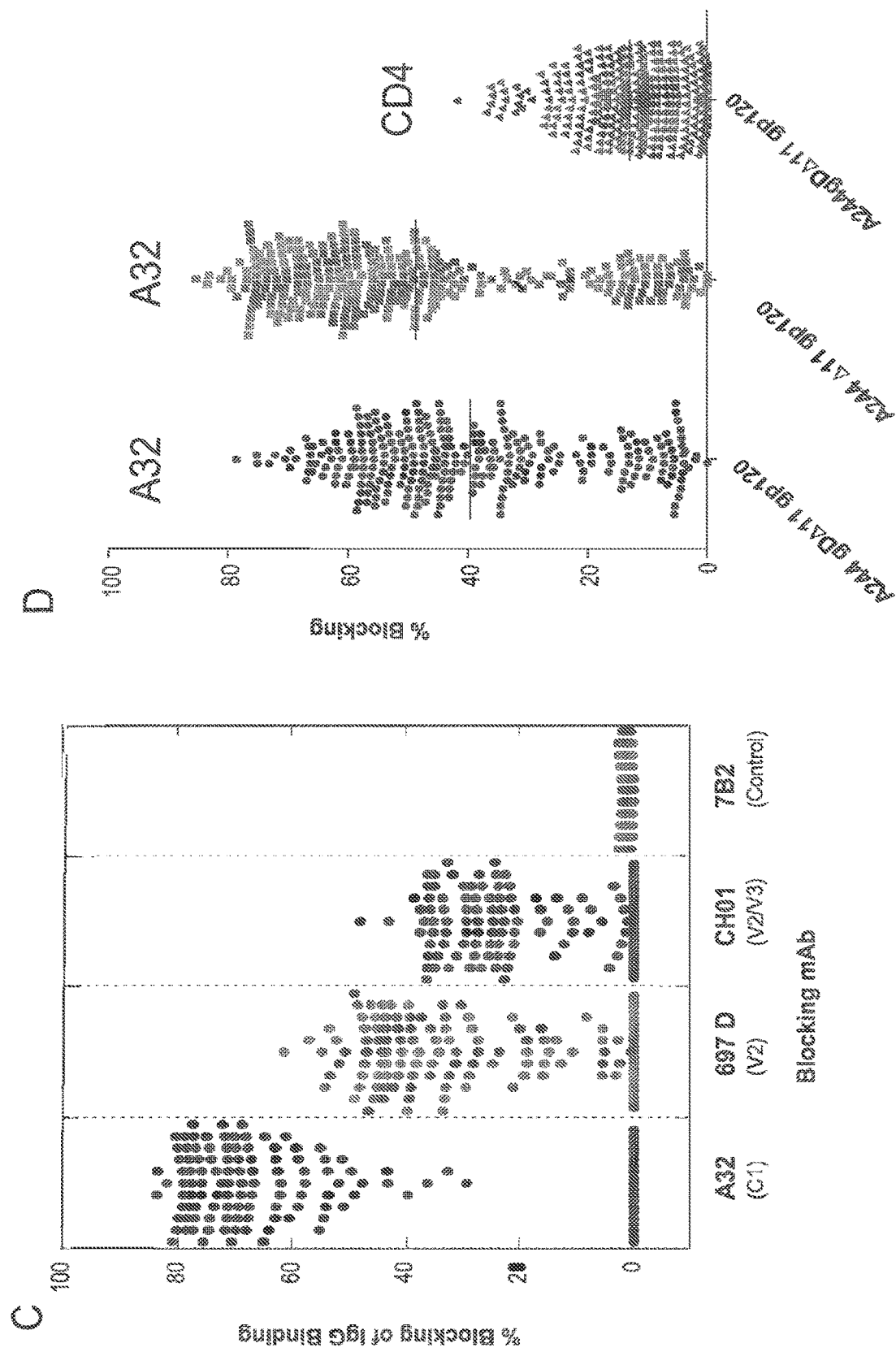
Figures 32C-D

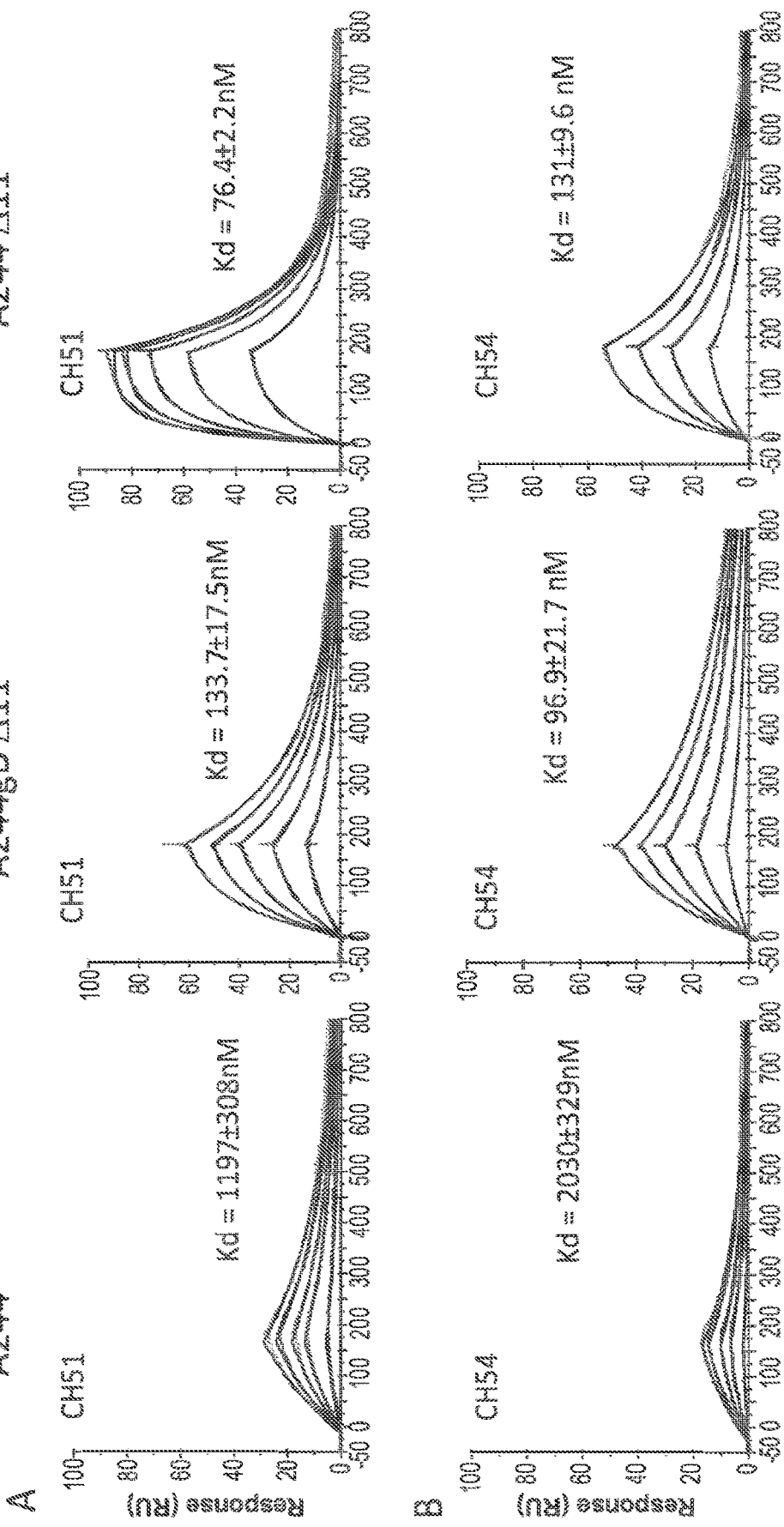
Figures 33A-B

NUCLEIC ACIDS ENCODING HUMAN IMMUNODEFICIENCY VIRUS TYPE 1 (HIV-1) N-TERMINAL DELETED GP120 IMMUNOGENS AND METHODS OF USE

This application is a divisional of U.S. application Ser. No. 14/130,338 filed Apr. 4, 2014, which is the U.S. national phase of International Application No. PCT/US2012/045530 filed 5 Jul. 2012 which designated the U.S. and claims priority from U.S. Provisional Application No. 61/457,906, filed Jul. 5, 2011 and U.S. Provisional Application No. 61/529,137, filed Aug. 30, 2011, the entire contents of each of which are incorporated herein by reference in their entireties.

This invention was made with government support under Grant No. A1067854 awarded by the National Institutes of Health, Bethesda, Md. The government has certain rights in this invention.

SEQUENCE LISTING

The instant application contains a Sequence Listing which has been submitted electronically in ASCII format and is hereby incorporated by reference in its entirety. Said ASCII copy, created on Jun. 27, 2018, is named 1234300_00297US4SL.txt and is 138,923 bytes in size.

TECHNICAL FIELD

The present invention relates, in general, to human immunodeficiency virus (HIV), and, in particular, to a vaccine for HIV-1 and to methods of making and using same.

BACKGROUND

Development of a safe, practical and effective HIV-1 vaccine is one of the highest priorities of the global scientific community (Klausner et al, Science 5628:2036-2039 (2003); Esparza et al, Science Strategic Plan, DOI: 10.1371/journal.pmed.0020025, Policy Forum Vol. 2, February 2005)). While anti-retroviral treatment (ART) has dramatically prolonged the lives of HIV-1 infected patients, anti-retroviral therapy is not yet routinely available in developing countries, and the global rate of spread of HIV-1 continues unabated.

There are multiple components for successful HIV vaccine development. First is the production of HIV envelope constructs that express neutralizing epitopes reflective of the native envelope (Env) to ensure that the regions and epitopes to which it is desired to induce protective antibodies are indeed present on the Env immunogen (i.e., envelope antigenicity). Second, for scalability of Env protein production, it is important to be able to make monomeric Envs that are not disulfide linked. The Sodroski laboratory has previously shown that when gp120 Envs are produced in 293T mammalian cells, there is nearly always a major component of the Env that is disulfide linked (Finzi A, Pacheco B, Zeng, X, Young D K, Kwong, P D, Sodroski, J, J. Virol. Methods 168: 155-161, 2010). This disulfide linked Env has many of the desired epitopes occluded and not available for antibody binding (Finzi A, Pacheco B, Zeng, X, Young D K, Kwong, P D, Sodroski, J, J. Virol. Methods 168: 155-161, 2010). Third, many of the regions of the HIV Env are poorly immunogenic or the responses to these epitopes are down regulated by tolerance mechanisms or represent rare maturation pathways (i.e., are subdominant in nature) (McElrath J, Haynes, B F, Immunity 33:542-54. 2010; Verkoczy L, Kelsoe, G, Moody, M A, Haynes, B F, Current Opinion in Immunology 23:383-390, 2011).

The first and second components described above can be dealt with by immunogen design. The third component is dealt with by taking an optimally antigenic Env and formulating it with appropriate adjuvants to drive an otherwise subdominant antibody response in an immunodominant manner by design of immunogens that can optimally trigger naïve B cell receptors of clonal lineages that can make protective antibodies (Ma, B J, Alam, S M, Go, E P, Lu, X, Desaire, H, Tomaras, G D, Bowman, C, Sutherland, L L, Scearce, R M, Santra, S, Letvin, N L, Kepler, T B, Liao, H X, Haynes, B F, PLoS Pathogens, in press, 2011).

The present invention relates, at least in part, to a gp120 Env design strategy that addresses the first two components of the HIV-1 vaccine problem referenced above: optimal antigenicity and stable gp120 monomer production for scalability of vaccine production.

SUMMARY OF THE INVENTION

The present invention relates generally to HIV. More specifically, the invention relates to a vaccine for HIV-1 and to methods of making and using same.

Objects and advantages of the present invention will be clear from the description that follows.

BRIEF DESCRIPTION OF THE DRAWINGS

FIG. 1. Dissociation constants (Kd) of CH01, PG9, A32 and 697D mAbs binding to RV144 Env.

FIGS. 4A and 4B. Reactivity of the neutralizing V2 mAb 697D (FIG. 4A), and the V2, V3 neutralizing Ab CH03 Fab (FIG. 4B).

FIG. 5. Reactivity of the A32 mAb.

FIG. 12B shows the SPR sensorgrams of CCR5 receptor gp120 binding site mAb 17b binding to either A32 triggered, sCD4 triggered or T8 triggered Env D11 gp120.

FIGS. 13A-13C. Antibody titrations and Kd determinations for mAb 697D (V2 neutralizing); A244$\Delta$11 (FIG. 13A), A244gDneg (FIG. 13B), A244gD/293T (FIG. 13C).

FIGS. 14A-14C. Antibody titrations and Kd determinations for mAb PG9 (V2,V3 conformational); A244Δ11 (FIG. 14A), A244gDneg/293T (FIG. 14B), A244gD/293T (FIG. 14C).

FIGS. 15A-15C. Antibody titrations and Kd determinations for mAb CH01 (V2,V3 conformational); A244Δ11/293T (FIG. 15A), A244gDneg/293T (FIG. 15B), A244gD/293T (FIG. 15C).

FIGS. 16A-16B. Antibody titrations and Kd determinations for mAb CH03 (V2,V3 conformational); A244Δ11 (FIG. 16A), A244gDneg (FIG. 16B).

FIG. 19. Full length nucleotide sequence and amino acid sequence of the Delta 11 gp120 A244 Env protein. Figure discloses SEQ ID NOS 2-3, respectively, in order of appearance.

FIG. 20. Full length nucleotide sequences and amino acid sequences of the Delta11 gp120s of 63521.B, 6240.B, 089.C and the group M consensus Env CON-S gp120, and the Delta7 gp120 of 1086.C. Figure discloses SEQ ID NOS 4-13, respectively, in order of appearance.

FIG. 21. Full nucleotide sequences and amino acid sequences of the full length gp140s of 63521.B, 6240.B, 1086.C, 089.C and the group M consensus Env CON-S gp140. Figure discloses SEQ ID NOS 14-23, respectively, in order of appearance.

FIG. 23. Deleted N-terminal gp120 sequences on Delta 11 Envs. Figure discloses SEQ ID NOS 24-29, respectively, in order of appearance.

FIG. 25. Estimated hazard ratio for cert plasma antibody was measured against A244 gp120, A244gDΔ11 and A244 Δ11 gp120 proteins. The differences in binding responses was significant for A244 gp120 vs A244Δ11 g120 (Student t-test, p<0.001). FIG. 32C) Blocking of RV144 induced IgG binding to A244gDΔ11 gp120 by conformational C1 (A32), V2 (697D, 830A), V3 (19b) and V2/V3 (CH01) antibodies. RV144 IgG samples (n=109) with high and low level (>80 Response Unit measured at 100 ug/mL) of binding to A244D11 gp120 were selected for antibody blocking studies. A control group (n=19) showing no binding to A244 Δ11 gp120 was included to assess non-specific signal in IgG samples. FIG. 32D) ELISA assay showing high level of A32 blocking (mean=39.6%±19.2) by RV144 IgG and low level of CD4 blocking antibodies (mean=13%±8.9). Blocking of IgG from visit 1 were 6.7%±4.2 and 8.9%±7.6 for A32 and CD4 respectively.

FIGS. 33A-33B. RV144 mAbs CH51 and CH54 show higher affinity binding to A244gp120 with Δ11 modification. A244, A244gDΔ11 and A244Δ11 gp120 were each injected at concentrations ranging from 5-25 μg/mL over either CH51 (FIG. 33A) or CH54 (FIG. 33B) captured on anti-Fc immobilized surfaces. Binding of both CH51 and CH54 was an order of magnitude higher for both A244 gp120 with the Δ11 modification than A244 gp120 (left panel) with no modification.

DETAILED DESCRIPTION OF THE INVENTION

Figure 2:
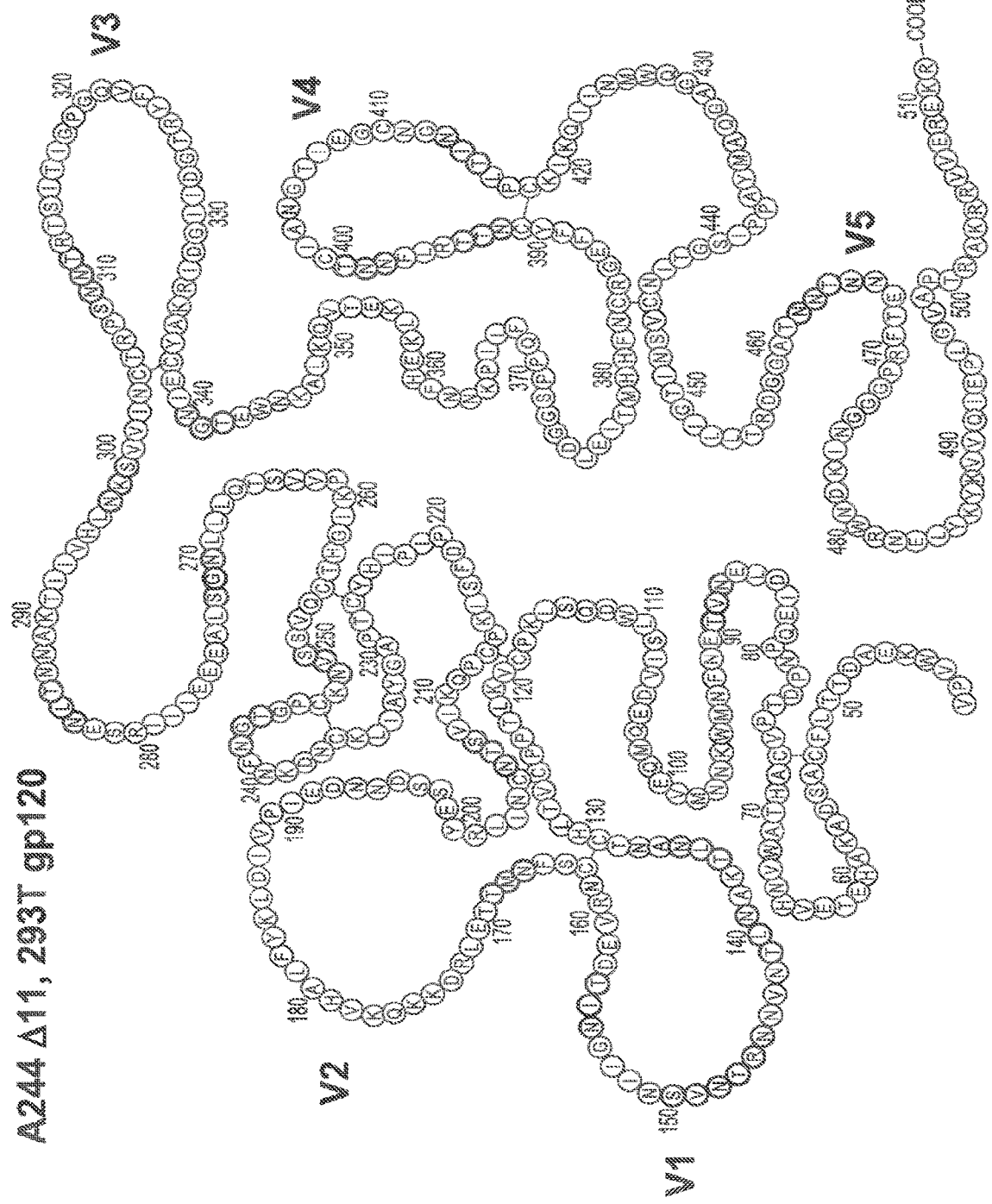
FIG. 2. D11(($\Delta$)11) A244 gp120 design expressed in 293T cells (SEQ ID NO: 1). Green box (more shaded) highlights the effect of gD on Kd of binding to A244 Env.
Figure 3:
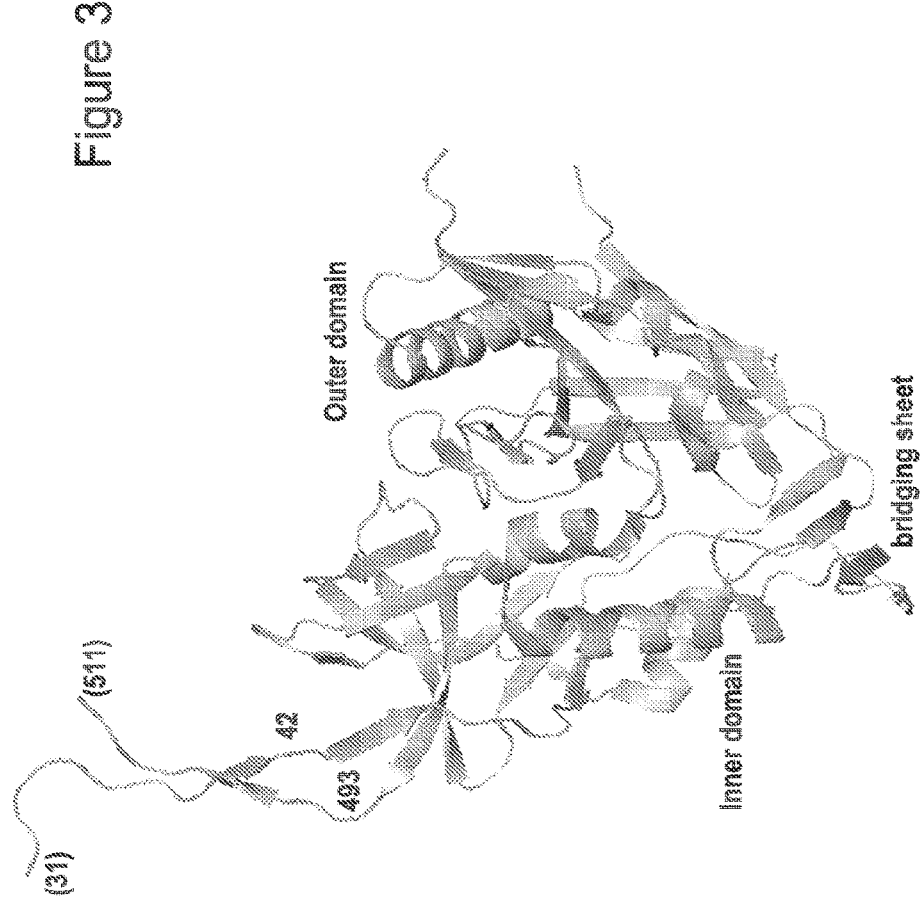
FIG. 3. Black-and-white ribbon diagram of gp120, based on Peter Kwong structure deposited in NCBI database as 3JWD.pdb.
Figure 6:
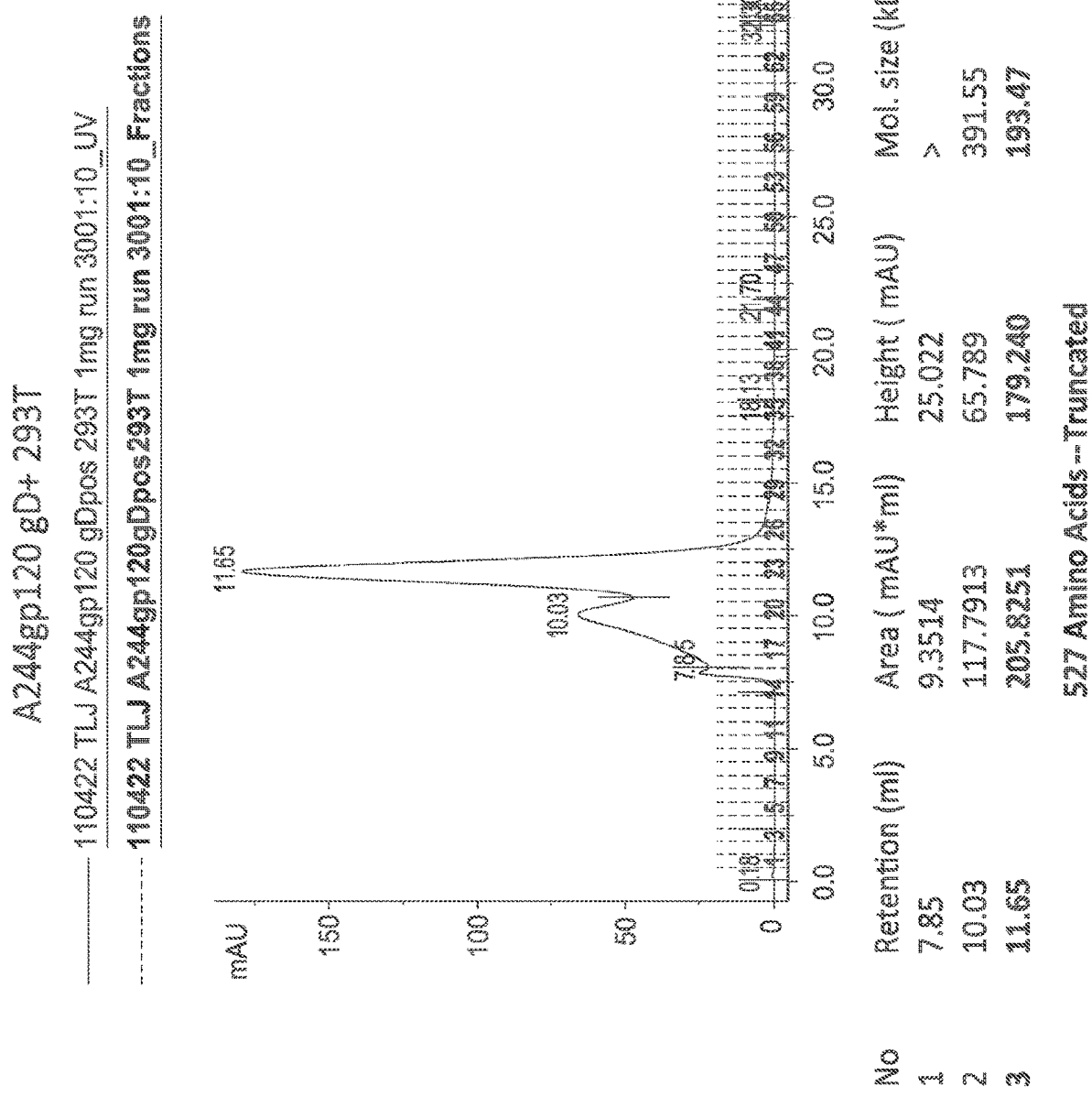
FIG. 6. Fast protein liquid chromatography (FPLC) size exclusion profile of unpurified A244 gp120 gD+ (with 11 amino acid (aa) deletion).
Figure 7:
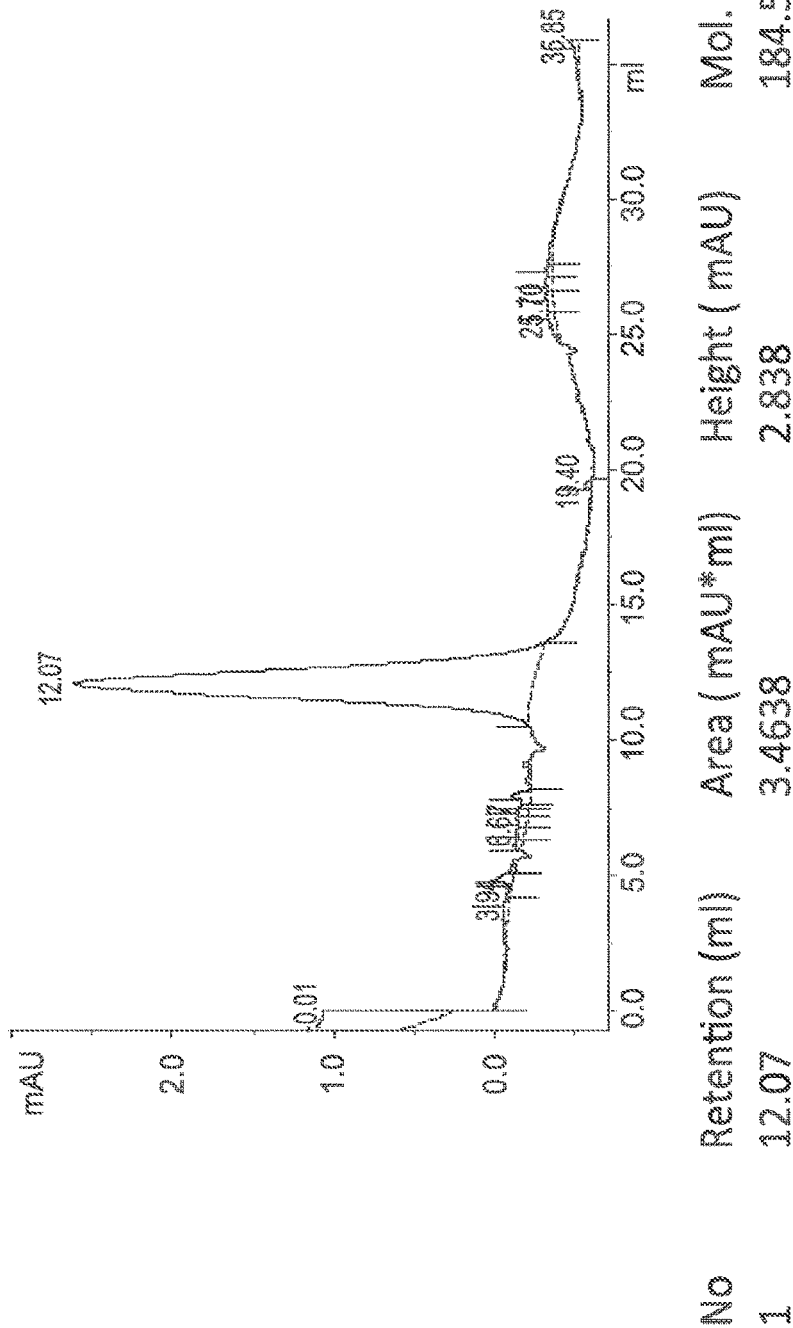
FIG. 7. FPLC size exclusion profile of purified A244 gp120 gD+ (with 11 aa deletion)
Figure 8:
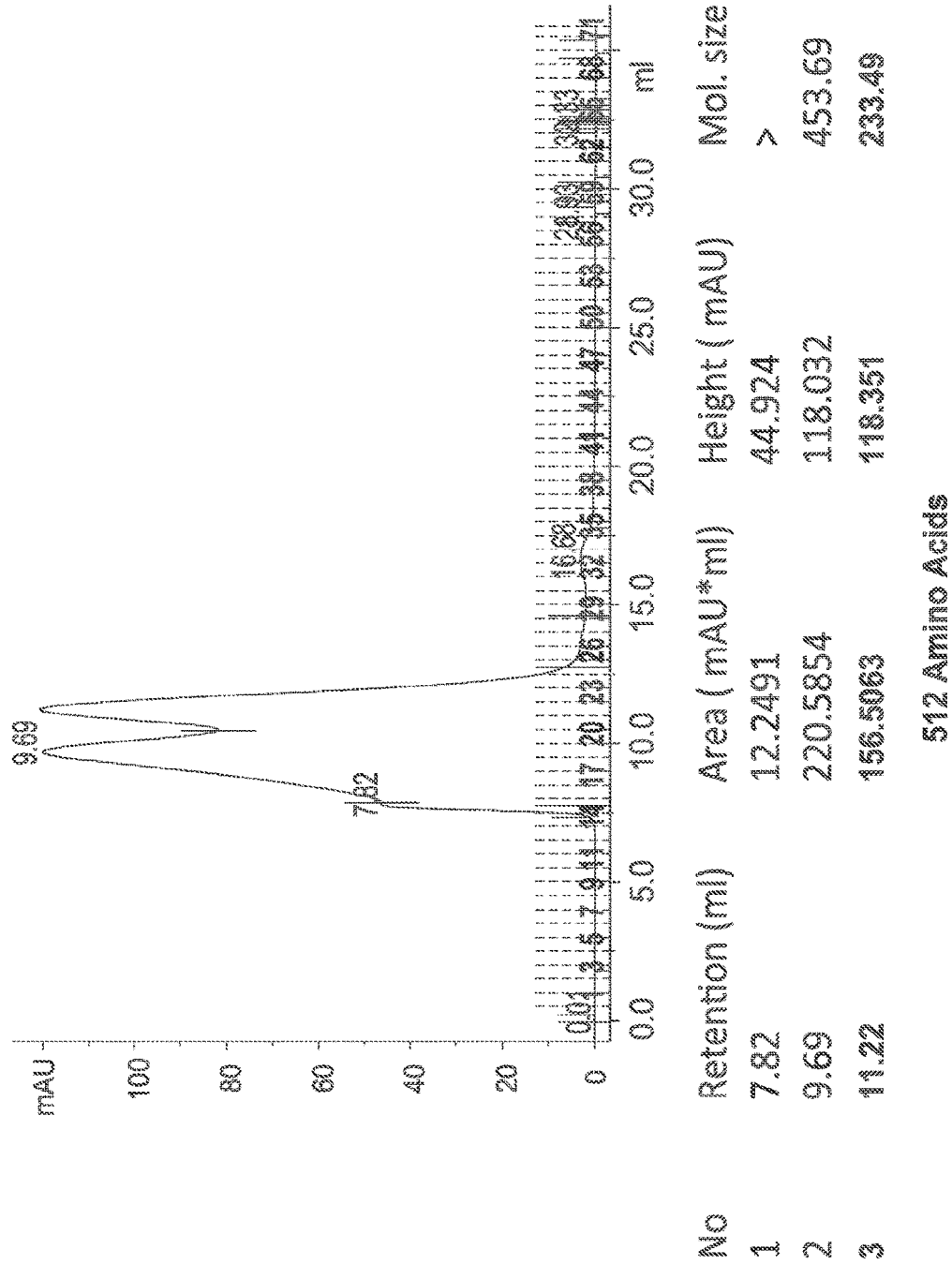
FIG. 8. FPLC size exclusion profile of unpurified A244 gp120 gD negative with the N-terminal 11 aa.
Figure 9:
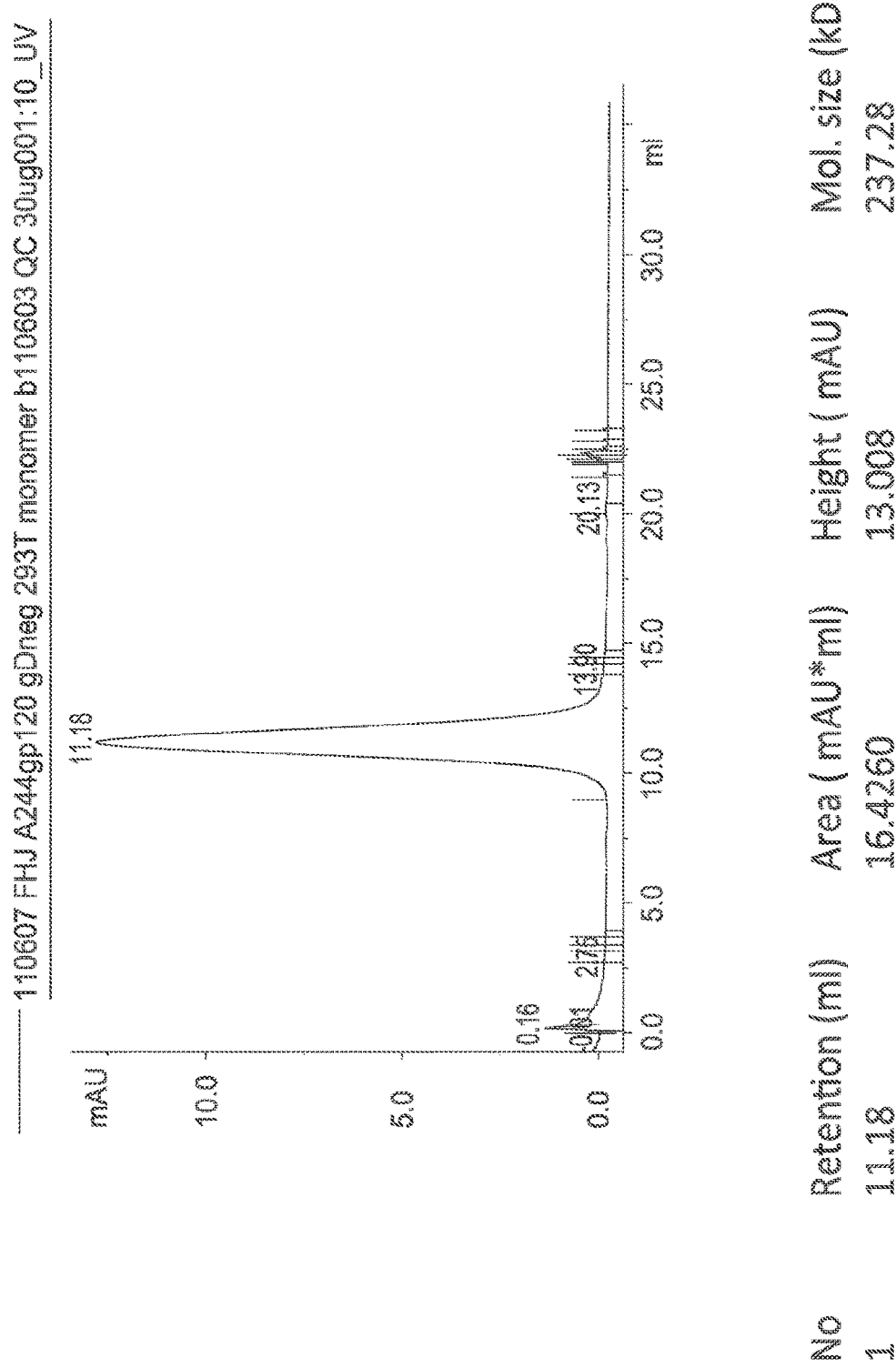
FIG. 9. FPLC size exclusion profile of purified A244 gp120 gD negative with the N-terminal 11 aa.
Figure 10:
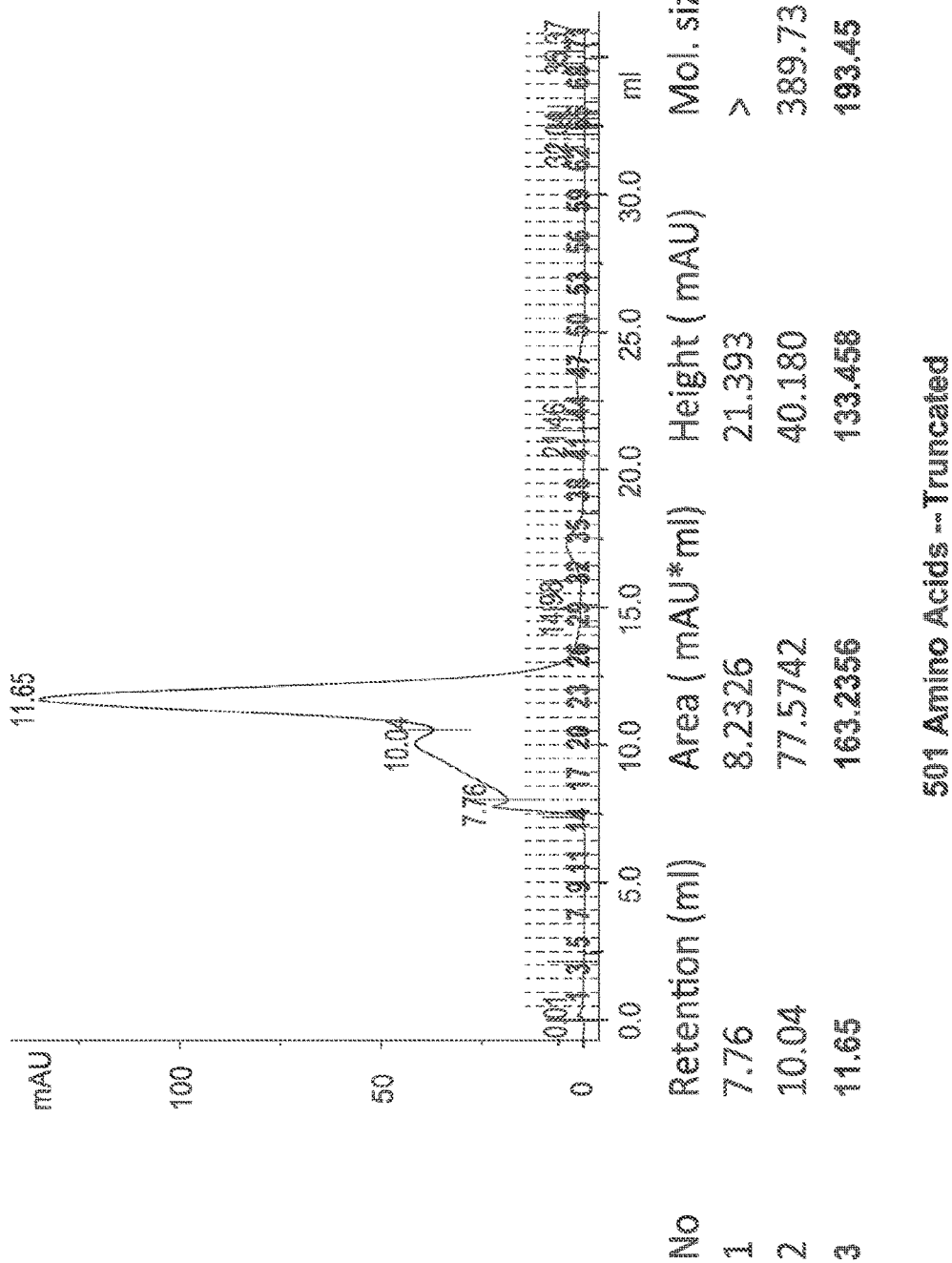
FIG. 10. FPLC size exclusion profile of unpurified gD–A244 gp120 Delta11.
Figure 11:
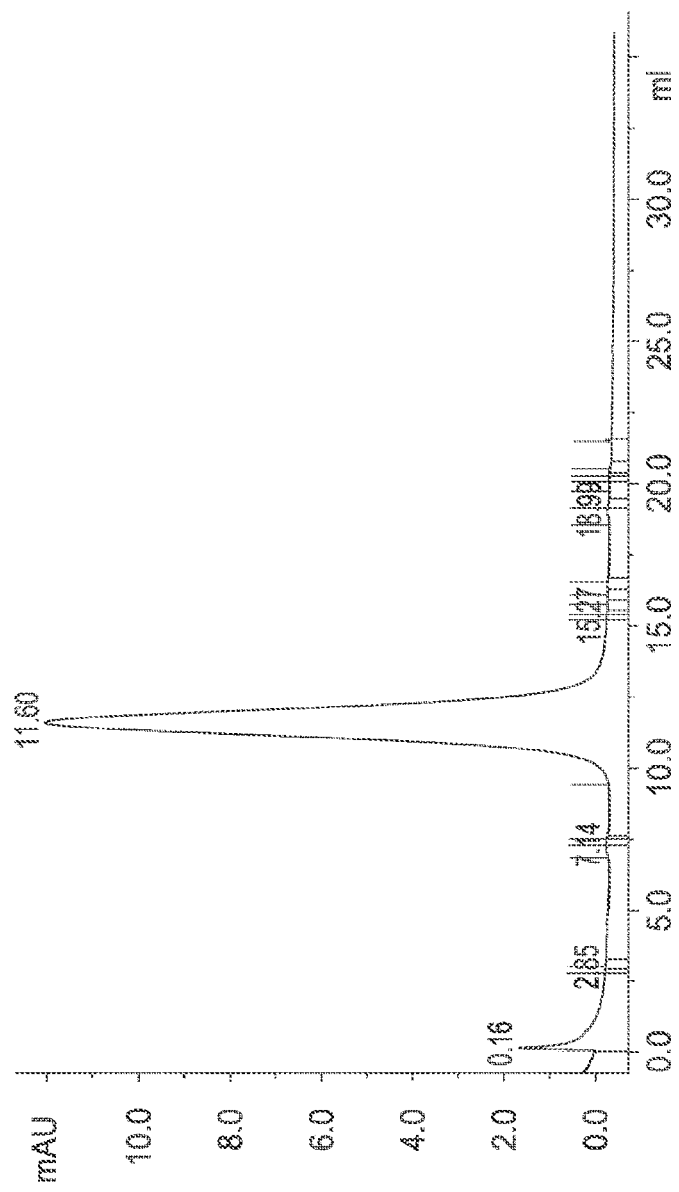
FIG. 11. FPLC size exclusion profile of purified gD–A244 gp120 Delta11.
Figure 12A:
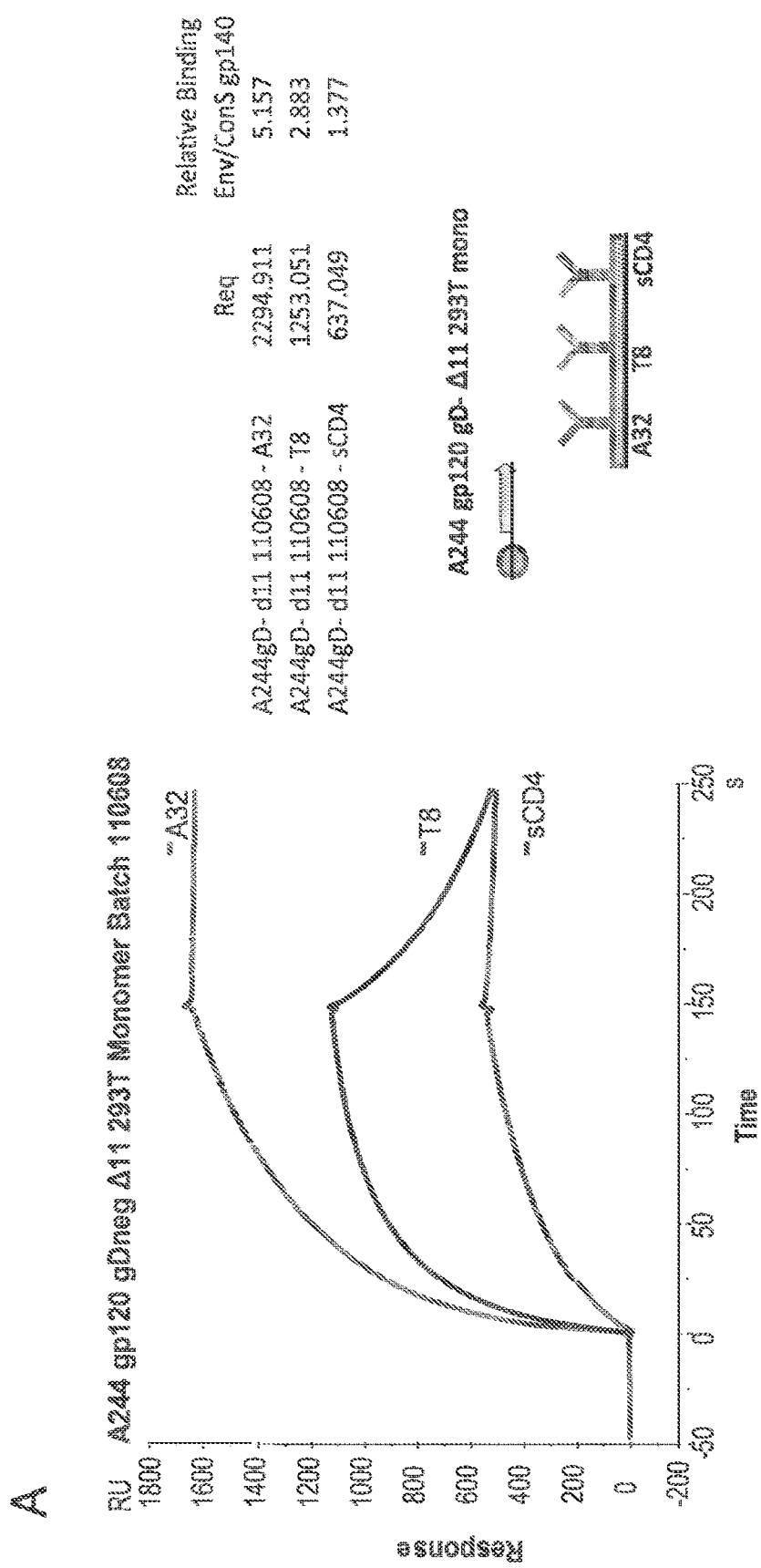
FIGS. 12A and 12B. Surface plasmon resonance (SPR) sensorgrams of the antigenic make-up of the A244 D(delta) negative 11 Env (batch 110608) showing that it binds A32 (C1 conformational), T8 (C1 mAbs and sCD4 recombinant Env) (FIG. 12A).
Figure 12B:
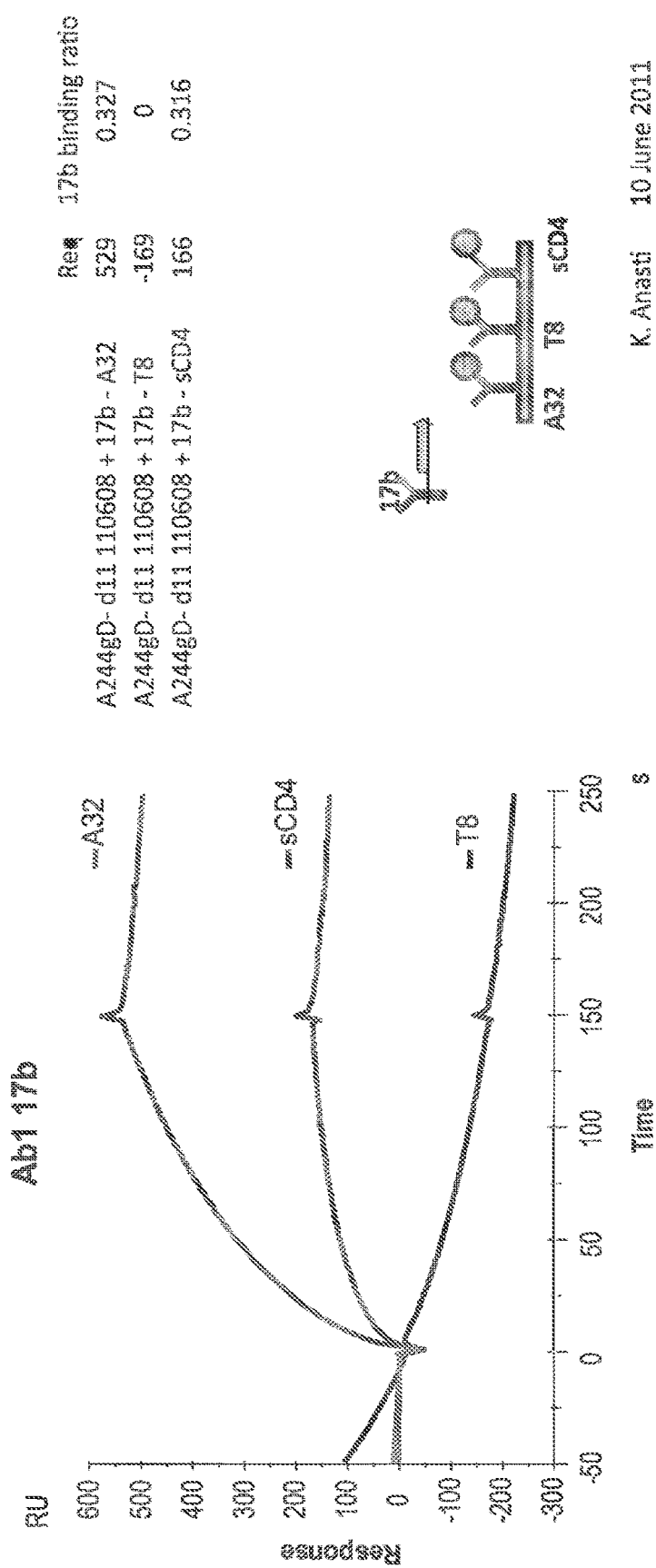
Figure 14C:
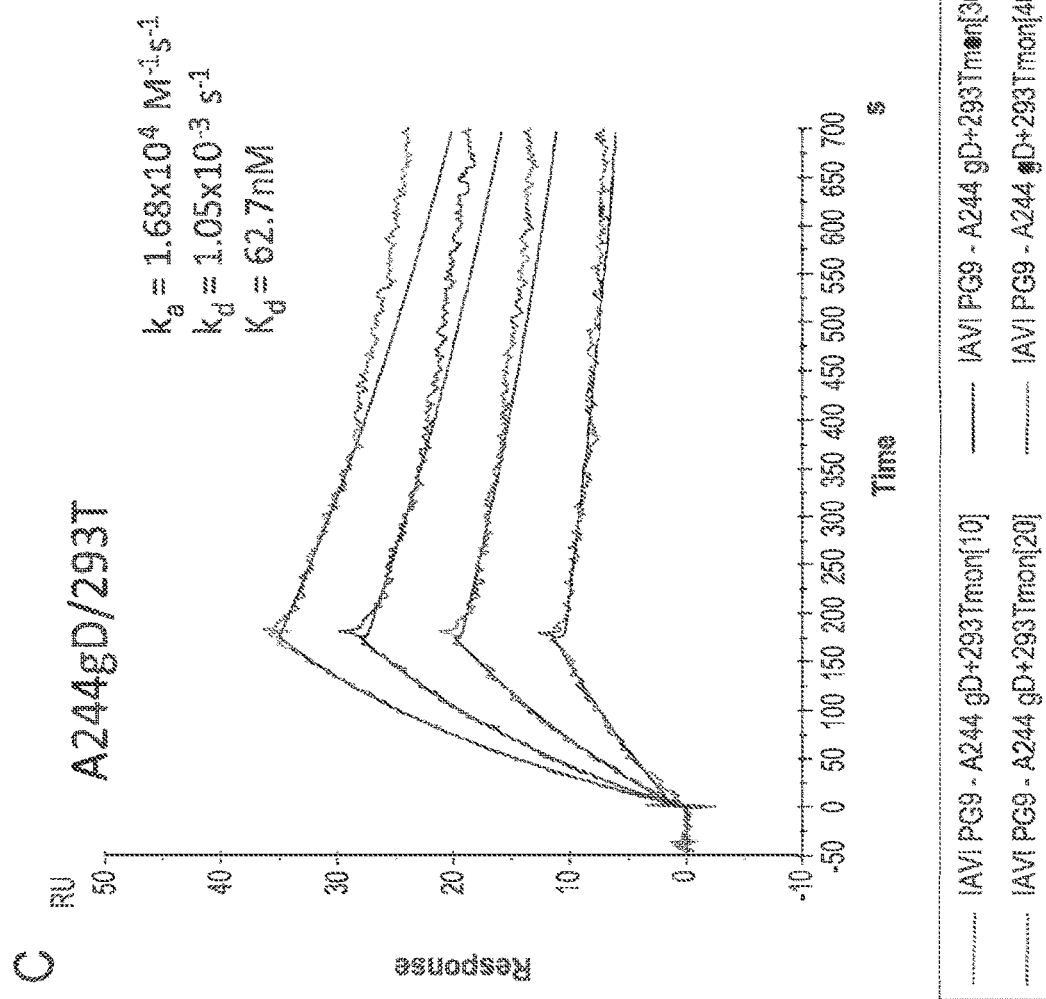
Figure 15C:
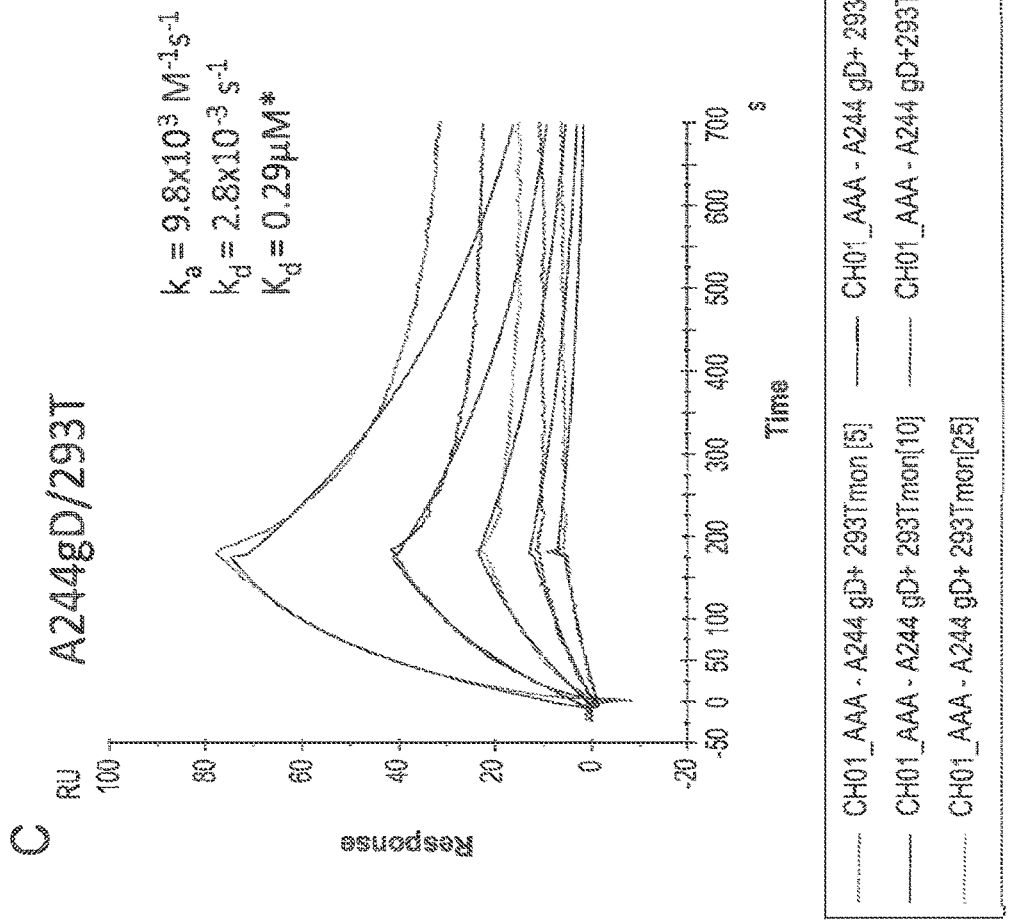
Figure 16B:
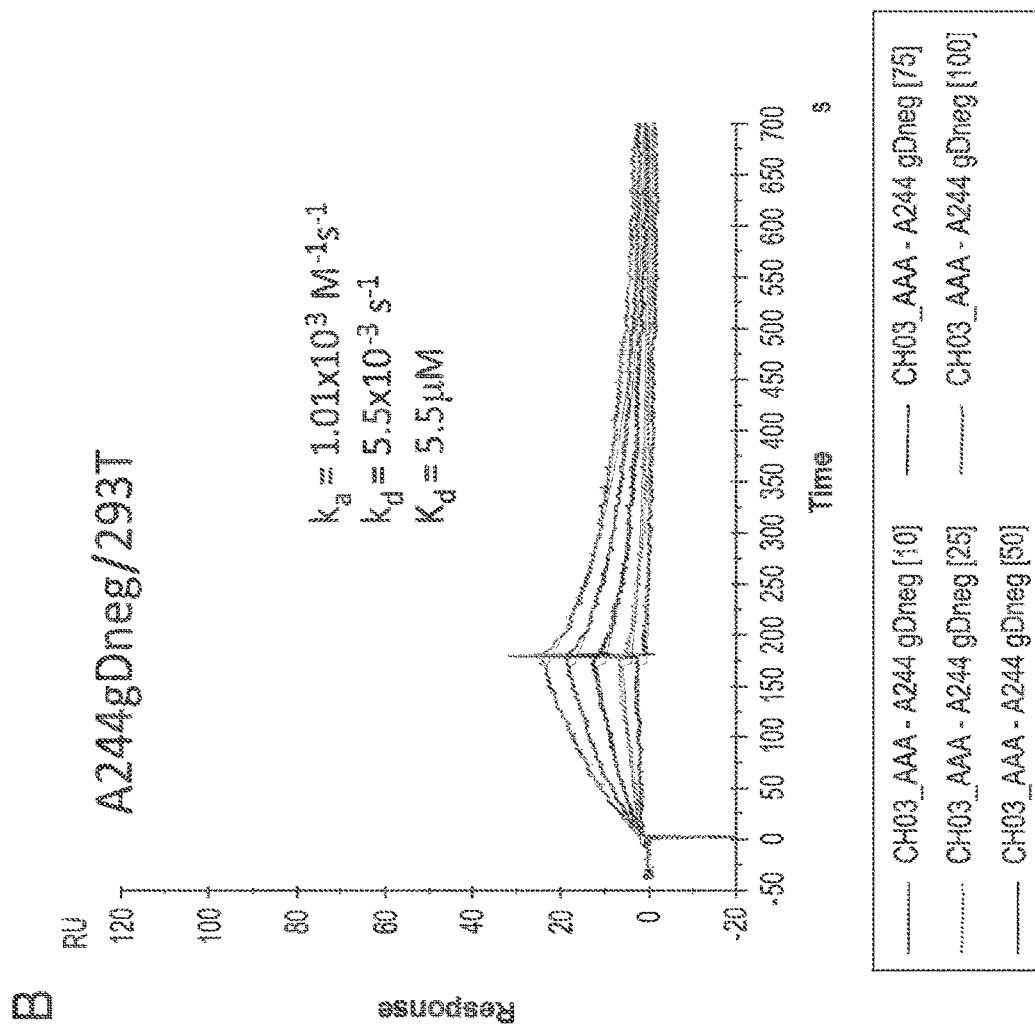
Figure 17A:
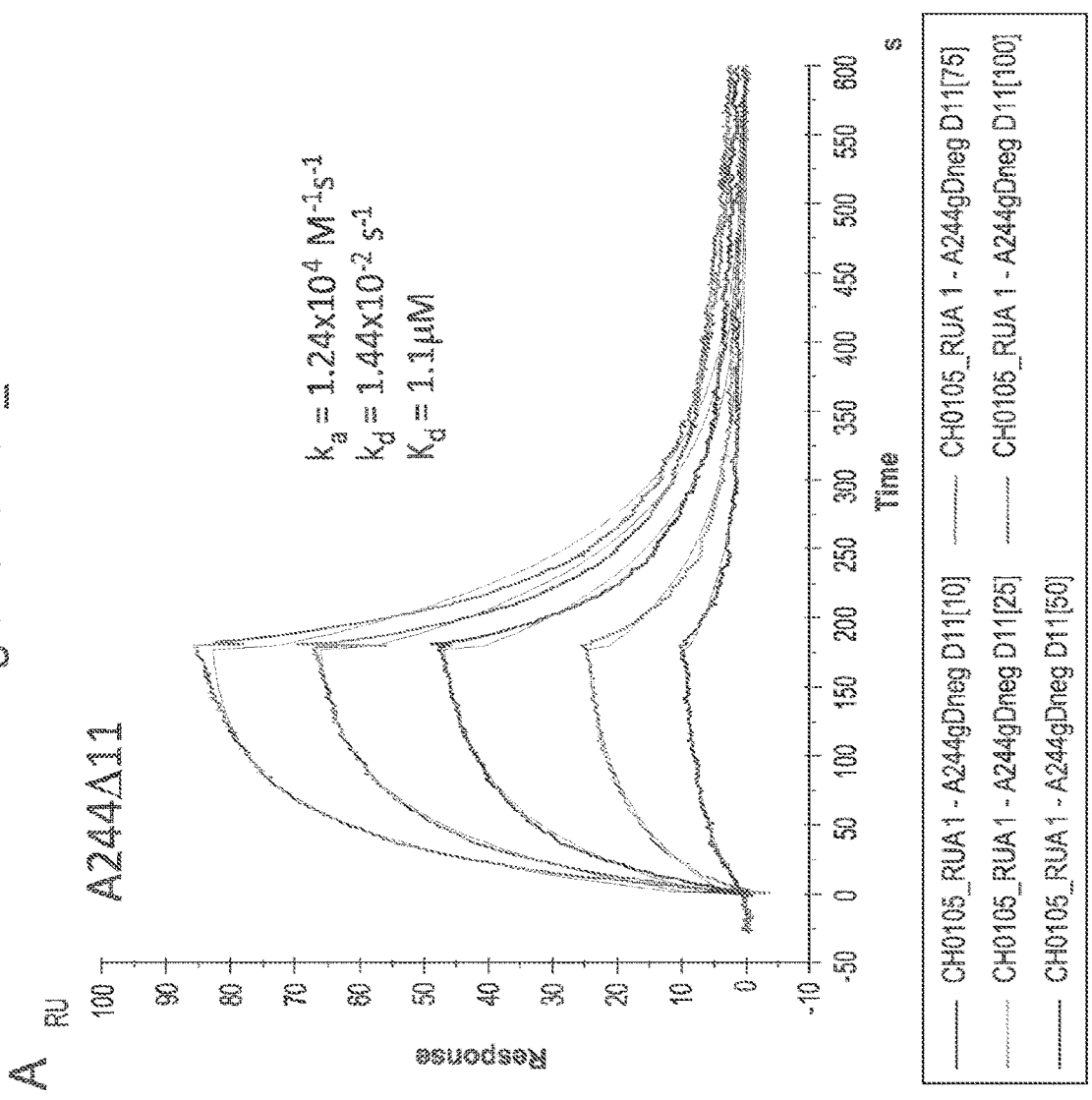
FIGS. 17A and 17B. Binding to CH01-04 RUA1; A244Δ11 (FIG. 17A), A244gDneg (FIG. 17B).
Figure 17B:
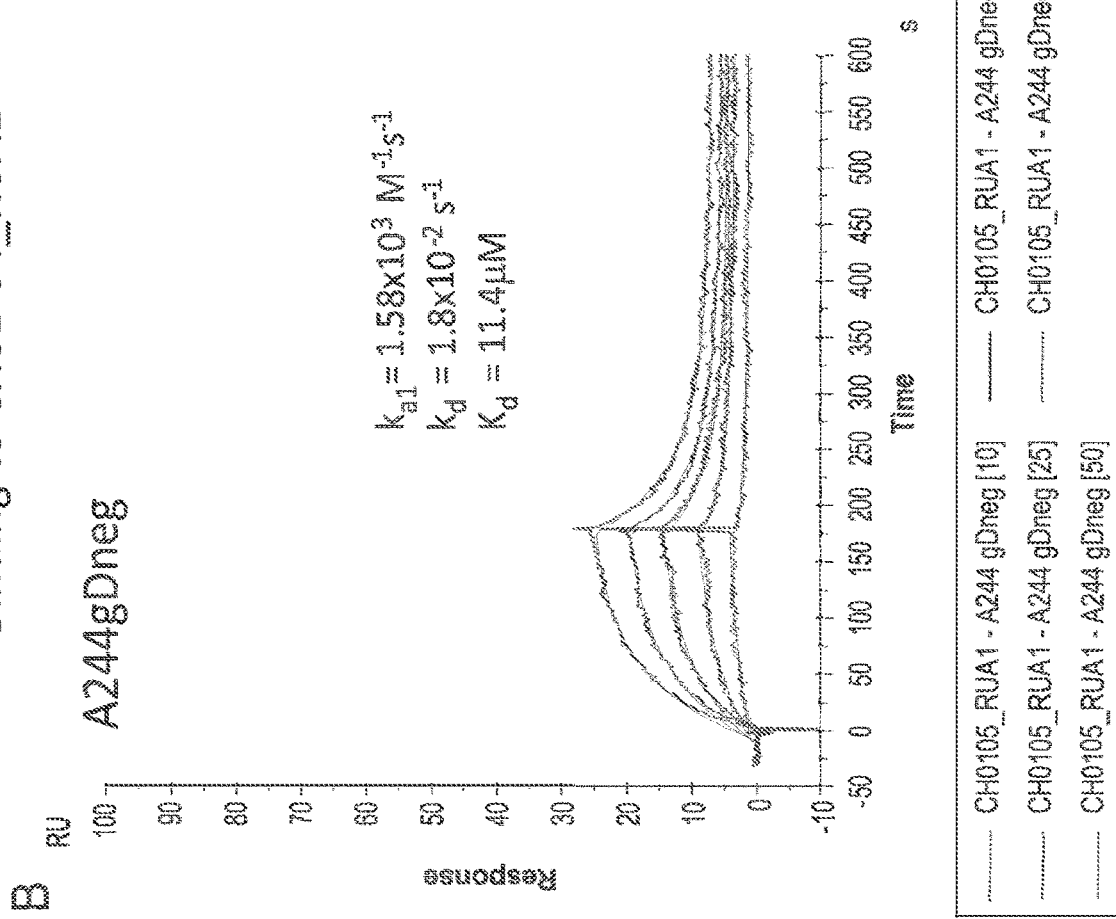
Figure 18A:
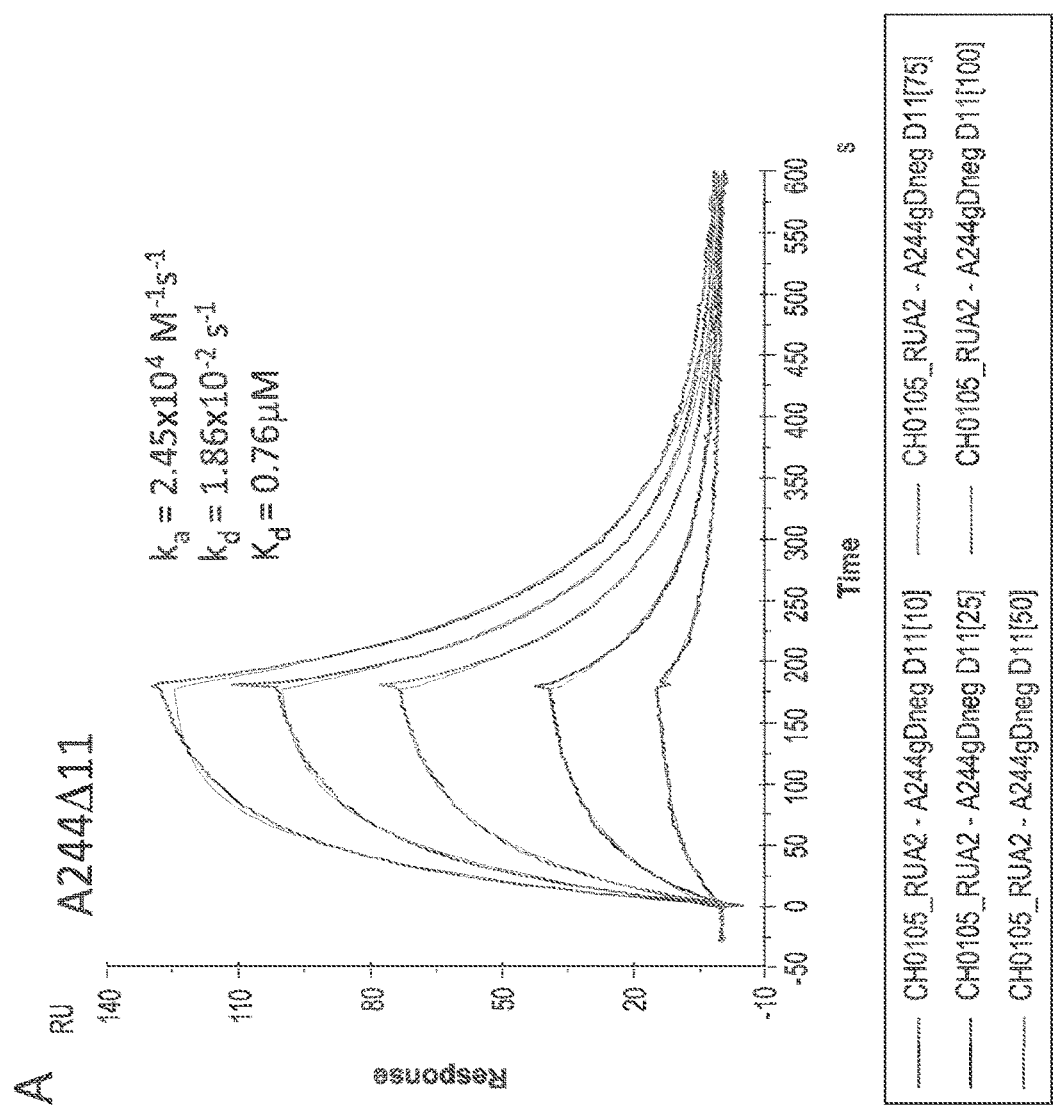
FIGS. 18A and 18B. Binding to CH01-04 RUA2; A244Δ11 (FIG. 18A), A244gDneg/293T (FIG. 18B).
Figure 18B:
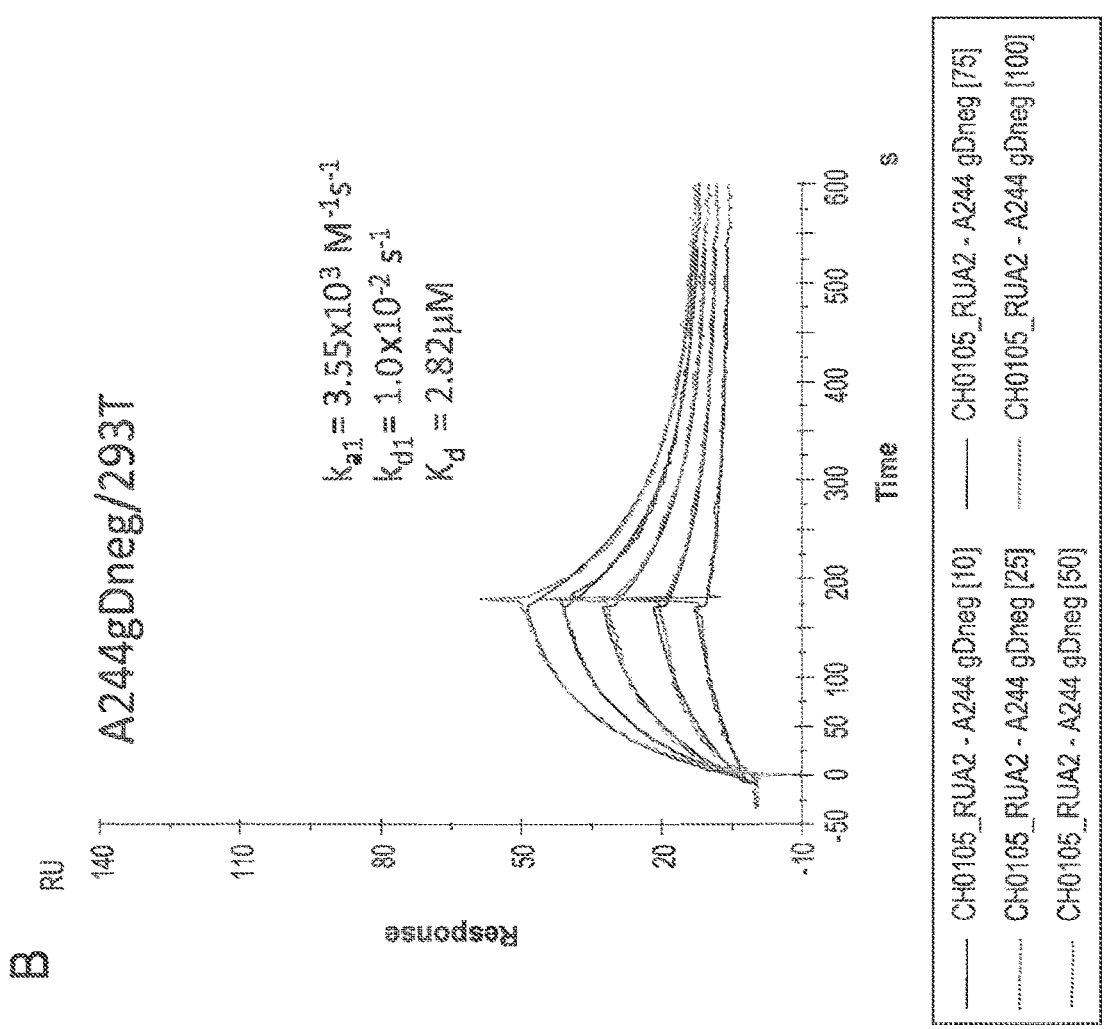
Figure 22:
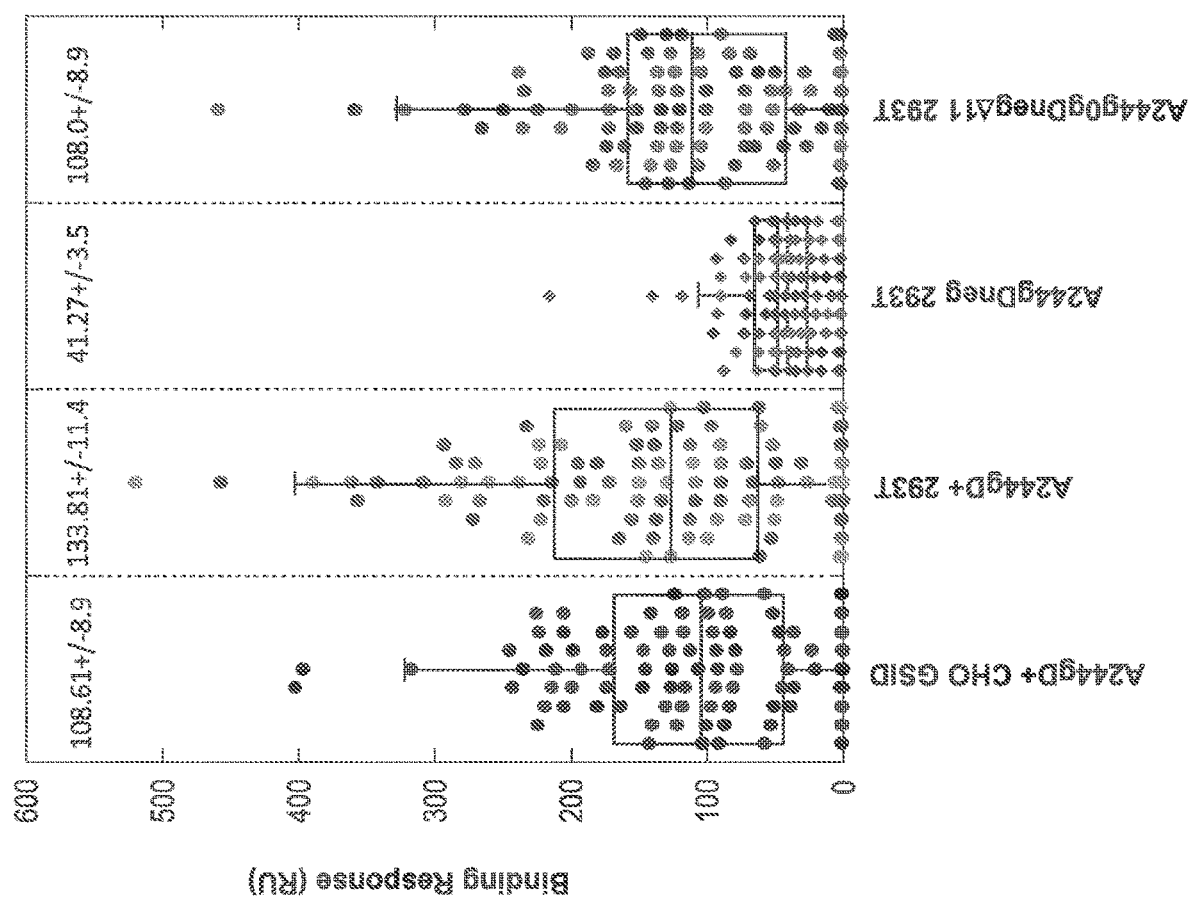
FIG. 22. Binding responses of plasma IgG from RV144 vaccinees in surface plasmon resonance assays. RV144 vaccinees see the same gp120 epitopes on the Delta 11 env as are seen on the gD+A244 Envs, but not on the gD negative A244 Env.
Figure 24:
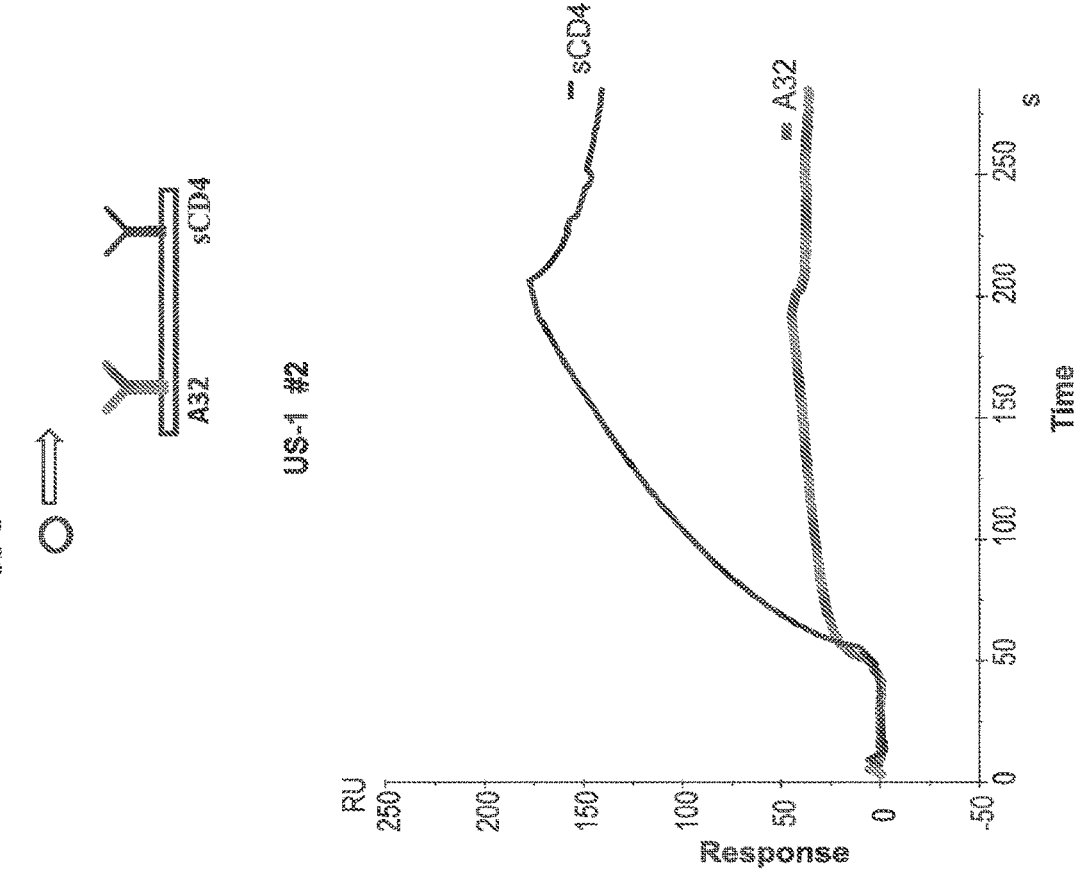
FIG. 24. Differential CD4 and MAb A32 binding to the SIVcpz gp140 Env versus the A244 gp120 Delta 11 Env. Whereas the A244 gp120 binds both sCD4 and the C1 mAb A32 well, the SIVcpz gp140 Env only binds CD4 and not A32. Since the dominant response in the RV144 trial is to C1 region, particularly with regard to the IgA response, and the IgA binding response correlated directly with infection in the RV144 case control immune correlates analysis, then an additional strategy to preventing induction of C1 antibodies is to induce antibodies with an envelope like US1 that doesn't bind A32 but does bind CD4.

The efficacy seen in the RV144 ALVAC prime gp120 B/E boost Thai clinical trial demonstrated that a protective HIV-1 vaccine could be made (Rerks-Ngarm, S et al NEJM 361: 2209-30, 2009). However, the efficacy was modest at 31% and the duration of protection short, demonstrating the need for improvement in level of protection. To improve on the efficacy of RV144 results, it is critical to understand the nature of the immunogens in RV144 and to understand why the trial worked, and to define any immune correlates of protection in the trial.

The gD HSV tag positioned, in the immunogens in RV144, N terminal to the gp120, and in place of the first 11 amino acids of the gp120 expressed coding region, has been implicated as being responsible for effecting the enhanced antigenicity of the A244 gp120 molecule used in the Thai trial. The present invention results, at least in part, from the realization that it was not the 27 amino acid gD tag (Lasky et al, Science 233:209-212 (1986)) that upregulated the gp120 epitopes but, rather, it was the truncation and deletion of the first 11 amino acids of the N-terminus of the gp120 (FIG. 23). Thus, the envelope design in accordance with the present invention involves deletion of residues (e.g., about 11 amino acids) at the N-terminus of the gp120. The result of this deletion on, for example, the A244 gp120 AE envelope is stabilization of the V1V2 conformational neutralizing epitopes, stabilization and enhanced expression of V2,V3 confirmation (so-called quaternary neutralizing epitopes) and enhanced expression of the C1 A32-like ADCC epitope. Moreover, the general strategy of deletion of N-terminal amino acids (e.g., about 11) of gp120 results in gp120s expressed in mammalian cells that are primarily monomeric, as opposed to dimeric, and, therefore, solves the production and scalability problem of commercial gp120 Env vaccine production.

The present invention relates generally to an immunogen, gp120 or gp140, without an N-terminal Herpes Simplex gD tag substituted for amino acids of the N-terminus of gp120, with an HIV leader sequence (or other leader sequence), and without the original about 4 to about 25, preferably about 11, amino acids of the N-terminus of gp120. While the invention includes deletions of various lengths and combinations of amino acids, deletions of between 5-11 amino acids are preferred. The 1086.C gp120 Env has an N-terminal set of amino acids only 7 amino acids long and manifests ~50% dimer formation when expressed in 293T or CHO cells. Thus, it is likely that deletions of greater than 5 amino acids are required for prevention of dimer formation. In one embodiment, 11 residues are deleted; in another embodiment, between 2 and 10 residues are deleted, either consecutive amino acids or selected amino acids; in yet another embodiment, a short peptide sequence chosen for stability is substituted for one or more of the 11 residues.

Advantageously, the Env gp120 or gp140 is a transmitted founder virus Env such as 1086.C, 089.C, 63521.B, 6240.B, 040.B or A1C recombinant transmitted founder Env 707-01-069-2 (see sequences, for example, in U.S. Provisional Application No. 61/344,622 and PCT/US2011/000352). In addition, the 0219.A signature Env of broad Nabs can also be advantageously used, as can transmitted/founder Env sequences derived from a subject with broadly neutralizing antibodies. In addition, N-terminus truncated consensus sequences such as the group M consensus CON-S gp140 or gp120 sequence (Liao et al, Virology 353(2):268 (2006), PCT/US04/30397, U.S. application Ser. Nos. 10/572,638 and 11/896,934) or the gp140 or the gp120 of the mosaic Env sequences (PCT/US2009/004664, U.S. application Ser. Nos. 11/990,222 and 12/192,015) can be used.

The N-terminal gp120 truncation is preferably 11 amino acids in length, however, as noted above, truncations of about 4 to about 25 amino acids can be used. Other combinations of amino acid substitutions can also be used.

The N-terminus truncated gp120 or gp140 envelopes can be formulated as DNAs (Santra S. et al. Nature Med. 16: 324-8, 2010) and as inserts in vectors including rAdenovirus (Barouch D H, et al. Nature Med. 16: 319-23, 2010), recombinant mycobacteria (i.e., BCG or M. smegmatis) (Yu, J S et al. Clinical Vaccine Immunol. 14: 886-093, 2007; ibid 13: 1204-11, 2006), and recombinant vaccinia type of vectors (Santra S. Nature Med. 16: 324-8, 2010). The truncated envelopes can also be administered as a protein boost in combination with a variety of vectored Env primes (i.e., HIV-1 Envs expressed in non-HIV viral or bacterial vectors) (Barefoot B et al. Vaccine 26: 6108-18, 2008), or as protein alone (Liao H C et al Virology 353: 268-82, 2006). The protein can be administered with an adjuvant such as MF59, AS01B, polyI, polyC or alum and administered, for example, subcutaneously or intramuscularly. Alternatively, the protein or vectored Env can be administered mucosally such as via intranasal immunization or by other mucosal route (Torrieri D L et al Mol. Ther. Oct. 19 2010, E put ahead of print).

Immunogens of the invention are suitable for use in generating an immune response in a patient (e.g., a human patient) to HIV-1. The mode of administration of the HIV-1 protein/polypeptide/peptide, or encoding sequence, can vary with the immunogen, the patient and the effect sought, similarly, the dose administered. As noted above, typically, the administration route will be intramuscular or subcutaneous injection (intravenous and intraperitoneal can also be used). Additionally, the formulations can be administered via the intranasal route, or intrarectally or vaginally as a suppository-like vehicle. Optimum dosing regimens can be readily determined by one skilled in the art. The immunogens are preferred for use prophylactically, however, their administration to infected individuals may reduce viral load.

Certain aspects of the invention are described in greater detail in the non-limiting Examples that follow. (U.S. Provisional Application No. 61/457,906 is incorporated herein by reference.)

Example 1

FIG. 1 shows that putting the gD herpes simplex 27 aa tag N-terminal to gp120 AE.92Th023, MN gp120 and A244 gp120 (gp120s used in the Thai HIV vaccine efficacy trial (Lasky et al, Science 233:209-212 (1986); Rerks-Ngarm et al, N. Eng. J. Med. 361:2209-2220 (2009)) and MN and A244 used as gD+, gp120 proteins (Rerks-Ngarm et al, N. Eng. J. Med. 361:2209-2220 (2009)), particularly with A244 gp120, results in upregulation of V2,V3 conformational neutralizing epitopes (CH01, PG9 binding), C1 ADCC A32 mAb binding, and V2 conformational neutralizing Ab binding (mAb 697D). The gD HSV tag is placed N terminal to the gp120 in place of the first 11 amino acids of gp120 expressed coding region. This tag has been implicated as being responsible for effecting the enhanced antigenicity of the A244 gp120 molecule. It has now been shown that the presence of the 27 aa gD tag (Lasky et al, Science 233:209-212 (1986)) has no effect itself on the upregulation of gp120 epitopes. Rather, what is required is truncation of the N-terminus of the gp120 for upregulation of the gp120 epitopes and for production of primarily monomeric gp120 species.

FIG. 2 shows the D11 A244 gp120 design that has been expressed in 293T cells. The N-terminus of the D11 gp120 starts at the VPV . . . aa gp120 sequence.

FIG. 3 shows the black-and-white ribbon diagram of gp120, based on structure from Peter Kwong deposited in the public NCBI database as 3JWD.pdb. The region in this figure that is 31-42 is the region that is deleted in the Delta 11 gp120 Env construct. It includes the full N- and C-terminal segments of gp120 (but not V1-V2 or V3). Residues 31-41 stick out into space, as do residues 494-511. Residues 31-41, are the residues deleted in D11 A244 gp120 which are relatively hydrophobic and which would, in gp160, interact with gp41, likely lead to some misfolding or aggregation of gp120 in the endoplasmic reticulum, so that disulfides form between two gp120s. The C-terminal extension, which would also interact with gp41 (it leads to the cleavage point), is very polar (indeed, charged), so it may help solubilize the expressed protein. The Delta 11 substitution apparently eliminated (or at least partly eliminated) the aggregation aberrant disulfide linkage, and/or misfolding tendency of the whole Env during folding.

FIGS. 4 and 5 show the reactivity of the neutralizing V2 mAb 697D, the V2, V3 neutralizing Ab CH03 Fab (FIG. 4), and the A32 mAb (FIG. 5) binding to A244 gD+gp120, A244 gD negative (with no delta 11 deletion) and A244 gD negative D11 (Delta 11 deletion present with no gD tag present). Data show that each of the three Abs bind better to Delta11 Env gp120 A244 than to Envs with either no gD tag but with the 11 aa N terminus of gp120 (gDneg gp210) or to an Env with the gD tag that has gD substituted for the 11 proximal N-terminal amino acids.

FIGS. 6-11 show the FPLC profiles of unpurified and purified A244 gp120 gD+ (with 11 aa deletion) (FIGS. 6,7), A244 GP120 gD negative with the N-terminal 11 aa (FIGS. 8,9) and gD− A244 gp120 Delta11 (FIGS. 10 and 11). FIGS. 6, 8 and 10 are unpurified post lectin column Envs and FIGS. 7, 9, and 11 are post FPLC purification monomers of each Env. The figures show that after lectin purification columns, the Delta 11 gpD− Env gp120 is the most monomer after lectin column purification and before FPLC and the gD− gp120 without the delta 11 truncation has the most dimers and least monomers of the three Envs. Thus, the Delta11 Env gp120 solves the gp120 production problem by deletion of the 11 N-terminal aa of gp120, thus prohibiting C-C mediated gp120 dimerization.

FIG. 12 shows surface plasmon resonance (SPR) sensorgrams of the antigenic make-up of the A244 D(delta) negative 11 Env (batch 110608) showing that it binds A32 (C1 conformational), T8 (C1 mAbs and sCD4 recombinant Env (FIG. 12A). FIG. 12B shows the SPR sensorgrams of CCR5 receptor gp120 binding site mAb 17b binding to either A32 triggered, sCD4 triggered or T8 triggered env D11 gp120. FIGS. 12A and 12B demonstrate that the Delta 11 Env gp120 expresses the A32 epitope, binds CD4 and as is the case with a functional Env, both A32 and sCD4 upregulate the CCR5 binding site as measured by 17b mAb binding.

FIGS. 13-16 show antibody titrations and Kd determinations for mAbs 697D (V2 neutralizing) (FIG. 13), PG9 (V2,V3 conformational) (FIG. 14), CH01 (V2,V3 conformational) (FIG. 15), CH03 (V2,V3 conformational) (FIG. 16). In all cases the delta (Δ))11 A244 gp120 Env bound the antibodies in question better than did the gD-A244 (with no delta11 deletion) and even bound better than the gD+A244 with both the gD and the delta 11 deletion.

It was of great interest to know how a particular antigen/immunogen binds to the naïve B cell receptor of some of these antibodies. The way this has been accomplished is to revert the mutated CH01-CH04 antibodies back to two candidate reverted unmutated ancestor antibodies (RUAs) that are the putative B cell receptors of naïve B cells (Termed CH01-04 RUA1 and CH01-04 RUA2) and determine the binding of delta11 A244 vs gD− A244 without the delta 11 deletion. It was found that the delta 11 A244 Env bound better to both of the CH01-CH04 clonal lineage RUAs than did the gD− A244 Env without the delta 11 deletion. (See FIGS. 17 and 18.)

FIG. 19 shows the full nucleotide sequence and aa sequence of the Delta (Δ))11 gp120 A244 Envelope protein.

FIG. 20 shows the full nucleotide sequence and aa sequence of the Delta(Δ))11 gp120s of 63521.B, 6240.B, 089.C and the group M consensus Env CON-S gp120, and the Delta (Δ))7 gp120 of 1086.C FIG. 21 shows the full nucleotide sequence and aa sequence of the full gp140s of 63521.B, 6240.B, 1086.C, 089.C and the group M consensus Env CON-S gp140.

FIG. 22 shows the binding responses of plasma IgG from RV144 vaccinees in surface plasmon resonance assays. The median binding response of vaccinee IgG was the same to both the vaccine immunogen gp120 (A244gD CHO GSID) and the delta (Δ)) 11 gp120 (A244gDneg)11 293T) but were 5-fold higher than the Env gp120 without the deletion (A244gDneg 293T). The response to delta (Δ)) 11 gp120 was also similar to the same Env gp120 with the HSV gD peptide tag (A244gD+gp120 293T), both of which have the same Δ11 deletion. These data shows that the RV144 vaccine induced IgGs that bind with higher avidity to delta (Δ)) 11 gp120.

FIG. 23 shows the N-terminal amino acids that are deleted in various Delta 11 gp120 designs. Bold amino acids are hydrophobic. Deletions can be made in any length and in any combination of amino acids to have the effect of the Delta 11 deletion. However, optimal deletions are of between 5-11 amino acids. The 1086.C gp120 Env has an N-terminal set of amino acids only 7 aa long and manifests ~50% dimer formation when expressed in 293T or CHO cells. Thus, it is likely that at least greater than 5 amino acid deletions are needed for prevention of dimer formation.

In one embodiment of the invention, 11 residues are deleted; in another embodiment, between 2 and 10 residues are deleted, either consecutive amino acids or selected amino acids. In yet another embodiment, a short peptide sequence chosen for stability can be substituted for one or more of the 11 residues.

Thus, what these data clearly show is that the delta 11 gp120 Env design is a novel immunogen design that both conveys upon the A244, and likely other Envs, the ability to: 1) be produced as primarily a monomer—thus solving the problem of gp120 Env monomer production for appropriate yield of monomer for scaleup of vaccine protein production, and 2) this delta ($\Delta$))11 mutation has conferred on the remaining gp120 the ability to bind better to C1 and V2 mAbs.

The delta 11 Env design is expected to be applicable to multiple Envs (for examples but not exclusive examples see FIGS. 20 and 21). Moreover, truncations of any length from about 4 aa to about 25 aa are expected to have the same effect. The delta11 gp120s or other truncated versions of gp120 can be administered as proteins, DNAs, and as inserts in a myriad of vectors including rAd5, other rAdenoviruses, recombinant mycobacteria, and a myriad of poxvirus vectors including MVA, NYVAC, and WT vaccinia. In addition attenuated polio virus and the bacterial vector listeria can be used.

The delta 11 and related truncations can as well be made to recombinant gp140 and gp160 constructs that also can be expressed and used in the same manner as Delta 11 gp120s.

Delta 11 Env mutated Env proteins and vectored inserts can thus be used as optimally antigenic Envs for formulation with the most potent adjuvants such as AS01B, MF-59 and polyI, polyC. The plasmids of these Delta 11 Env mutated Env proteins can also be randomly mutated for screens for higher levels of binding to various Env antibody RUAs and intermediate clonal lineage antibodies to improve Env immunogenicity.

Example 2

Epitope specificity in RV144 vaccine recipients were determined using peptide microarray and binding antibody multiplex assays. The vaccine elicited IgG responses were against 4 predominant regions in HIV-1 gp120 Env (C1, V2, V3, and C5). In 20 subjects measured, 100% had IgG responses against the C1 region. Of interest, functional antibody responses (ADCC) were also elicited by RV144 and these responses were epitope mapped to the C1 region (Ferrari, Haynes 2011). RV144 also elicited IgA antibody responses (~60%) and in ~⅓ of these vaccines, the response targets the C1 (CRF1) epitope (as identified by IgG HIV1 Env microarray). The plasma IgA response (Env magnitude and breadth) was a primary variable in the RV144 case control study, along with 5 other primary variables. The anti-Env IgA response showed a statistically significant direct correlation with infection. In further analyses of the secondary variables, the IgA response to several Env (most significantly A1.Congp140) and to the C1 CRF-1 peptide were more strongly correlated with infection. In further analysis of the primary variables, the IgA response was shown to interact (as a variable) with 4 of the other primary variables to directly increase the relative risk of infection. Thus, this work indicates that the anti-IgA Env C1 epitope may either directly contribute to virus replication or may serve to inhibit the protective effects of functional antibody responses (ADCC, neutralization). The C1 epitope chosen for analysis in the case control study was based on the predominance of the IgG response to the C1 region. Therefore, IgA antibodies targeting C1 could directly block functional IgG binding to this region.

A strategy going forward would be to delete the C1 epitope that both IgG and IgA are targeting, while maintaining potentially important epitopes for other functional antibodies (i.e. ADCC directed against V2 targets rather than C1). Another strategy would be to block the C1 region by mutations in the C1 region so that the epitope does not induce antibodies to that region.

Example 3

The RV144 vaccine trial in Thailand demonstrated an estimated vaccine efficacy of 31.2% in preventing HIV-1 acquisition in a heterosexual population (37). A previous trial in high risk intravenous drug users (IVDU) using AIDSVAX B/E® (4, 5, 16, 27) did not show protection (15, 36). The RV144 vaccine is comprised of a canarypox ALVAC prime with the E.92TH023 gp120 membrane anchored insert and AIDSVAX B/E® gp120 boost. This vaccine regimen induced Env antibody responses in 98.6% and CD4 T cell responses in 90.1% of vaccinated subjects (15), and induced Tier 1 virus-, but not Tier 2, neutralizing antibodies (37). The majority (89%) of breakthrough infections in RV144 vaccinees were subtype CRF01_AE (15) suggesting that the immune responses elicited against the clade E gp120 A244 Env protein were involved in lowering infection risk of HIV-1 acquisition.

The target of potentially protective or neutralizing antibodies is the trimeric Env spike, which is sparsely present on HIV-1 virions (30, 47). Neutralizing epitopes presented on gp120 may be masked by glycans, may be exposed only transiently following receptor/co-receptor engagement, or may depend strongly on intact quaternary structures (19, 22, 26). A major hurdle in HIV-1 Env protein vaccine design is the preservation of the structural properties in soluble versions of Env proteins that mimic those on intact viruses (20), particularly when the Env gp120 proteins are expressed as monomers. Furthermore, the gp120 inner domains and the co-receptor binding epitopes can be occluded in dimeric (and probably misfolded) forms of recombinant gp120, which are often produced by mammalian cells together with gp120 monomers (13). Thus, optimal presentation of neutralizing epitopes on gp120 depends critically on its conformational state.

A number of gp120 V2 antibodies have been described that bind well to conformational epitopes on the scaffolded murine leukemia viruses gp70-HIV-1 V1V2 and to other recently described V1V2 scaffold proteins (18, 24, 32, 34, 35). A clonal lineage of V2V3 conformational gp120 broadly neutralizing antibodies (bnAbs) CH01-CH04, that show blocking by the prototype V2V3 conformational gp120 mAb, PG9 and PG16, bind only to a subset of gp120 monomers including clade E A244 gp120 (7). Although previously described as quaternary structure specific mAbs, with preferential binding to membrane anchored trimeric HIV Env (45), PG9 and PG16 bnAbs can bind to both monomeric and trimeric gp140 (9), and as well to monomeric gp120 (7). The PG9 bnAb has been crystallized bound to a V1V2 scaffold protein and shown to bind primarily to the V1V2 C□□ strand and to adjacent glycans (32). Thus the V2V3 conformational bnAbs of which PG9 is a prototype, bind to a conformational peptidoglycan epitope of gp120 V1V2 (32). The RV144 Env, A244-rgp120 (7), a component of AIDSVAX B/E® (4, 27) is among the rare monomeric gp120s to which the CH01-CH04 and PG9 antibodies bind. The unmutated ancestor antibodies of the CH01-CH04 clonal lineage also bind A244 gp120 monomers, with an affinity within the range appropriate for B-cell receptor triggering (7). One unique feature of the RV144 protein gp120 design was that the proteins were constructed with a HSV gD peptide tag and an 11-amino acid (aa) deletion at the gp120 N-terminus (4, 27). Could features of the A244-rgp120 design have contributed to enhanced exposure of V1V2 conformational epitopes on the vaccine proteins? If so, induction of antibodies with specificity for the more prominently exposed epitopes might be observed in RV144 vaccinees. A recently conducted analysis of the RV144 case-control study showed that antibody responses were to the C1, V2, V3 and C5 gp120 regions and that high levels of IgG antibodies to a V1V2 scaffold protein correlated inversely with HIV-1 infection rate in vaccinees (21). Thus, one hypothesis is that addition of the gD tag and/or the Δ11 mutation provided enhanced presentation of certain gp120 epitopes and contributed to the induction of V1V2 antibody responses in RV144 vaccinated subjects.

The studies described below demonstrate that the RV144 gp120 protein immunogen, A244-rgp120, was associated with enhanced antigenicity for C1, V2 and V2V3 conformational epitopes, and that the gp120 N-terminal deletion (Δ11), without the inclusion of HSV gD tag, was sufficient for both the enhanced antigenicity and immunogenicity in humans.

EXPERIMENTAL DETAILS

Proteins and Antibodies

RV144 vaccine immunogen proteins (Table 1 below) A244-rgp120 and MN-rgp120 were produced originally by Genentech, Inc., further developed by VaxGen Inc., and supplied for this study by GSID (Global Solutions for Infectious Diseases, South San Francisco, Calif.). A244 gp120, A244 gDΔ11, A244☐Δ11, A244 gD N160K, MN gDΔ11 and MN gp120 were expressed in 293T cells (Table 1, FIG. 27) and lectin-affinity purified (28) followed by size exclusion chromatography on a Superdex 200 FPLC (GE Healthcare) to homogeneity for monomeric gp120. Expression of additional gp120 proteins with N-terminal deletion included the subtype B (63521 and 6240) and subtype C (C.089C, C.1086) Env proteins described earlier (7, 25, 42). N-terminal deletion for all Env gp120 involved 11 aa, except for C.1086 in which the corresponding shorter N-terminal segment (7aa) of the mature Env protein was deleted. Synagis (MedImmune, Gaithersburg, Md.), anti-RSV mAb, was used as a negative control. The C1 mAb A32 and the V3 mAb 19b were supplied by James Robinson (Tulane University, LA). CH01 mAb as previously described was isolated, and its unmutated ancestor antibodies inferred, from IgG+ memory B cells of a broad neutralizer subject (7). V2 mAb 697D, 830A, 2158, and 697D Fab were provided by S. Zolla-Pazner (New York University, NY) and described previously (17, 18). V2V3 conformational/quaternary mAbs PG9 and PG16 were provided by Dennis Burton (IAVI, and Scripps Research Institute, La Jolla, Calif.) and Peter Kwong (NIH, Bethesda, Calif.).

Surface Plasmon Resonance (SPR) Kinetics and Dissociation Constant ($K_d$) Measurements.

Env gp120 binding $K_d$ and rate constant measurements were carried out on BIAcore 3000 instruments as described earlier (1-3). Anti-human IgG Fc antibody (Sigma Chemicals) was immobilized on a CM5 sensor chip to about 15000 Response Unit (RU), and each antibody was captured to about 50-100 RU on three individual flow cells for replicate analysis, in addition to one flow cell with the control Synagis mAb on the same sensor chip. Non-specific binding of Env gp120 to the control surface and/or blank buffer flow was subtracted for each mAb-gp120 binding interactions. Antibody capture level, which ranged from 50-100 RU, on the sensor surface was optimized for each mAb to minimize rebinding and any associated secondary effects. 697D Fab was directly coupled via amine coupling chemistry to the sensor surfaces, and Env gp120 was flowed and data collected as above. All curve fitting analyses were performed using global fit of multiple titrations to the 1:1 Langmuir model. Mean and standard deviation (s.d.) of rate constants and $K_d$ were calculated from at least three measurements on individual sensor surfaces with equivalent amounts of captured antibody. All data analysis was performed using the BIAevaluation 4.1 analysis software (GE Healthcare).

Isolation and Purification of IgG from Plasma.

Total IgG was isolated from individual RV144 vaccine recipient plasma samples using Protein G resin pre-packed into 96-well depletion plates (GE Healthcare) as previously described (31). Plasma was diluted 2-fold with TBS, pH 7.5, and 200 μl of the diluted sample was added per well. The plates were incubated at room temperature, with shaking, for one hour. The unbound fractions were removed by centrifugation at 700×g for 3 minutes. Wells were then washed 3 times with 2000 of TBS to remove loosely bound material. The IgG bound to the resin was eluted with 2000 of 2.5% glacial acetic acid, pH 2.53, and immediately neutralized with 1200 of 1M Tris-HCL pH 9.0. The eluted IgG fractions were concentrated using Amicon Ultra centrifugal filters (Millipore) with a 30 kDa cut-off. The sample volume was reduced to 500 by centrifugation at 14,000×g in a microcentrifuge pre-cooled to 4° C. A buffer exchange was then performed using 2.5 volumes of PBS, pH 7.5. The concentrated IgG was diluted to the desired volume with PBS and assayed for protein concentration using a NanoDrop 8000 Spectrophotometer (Thermo Fisher Scientific) using the IgG reference setting.

Binding Antibody Multiplex Assays for anti-Env IgG were performed as previously described (41). Briefly, antibody measurements from vaccine plasma (1:200 dilution) were acquired on a Bio-Plex instrument (Bio-Rad) and the readout was expressed as mean fluorescent intensity (MFI) and concentration (m/m1) based on a HIVIG standard curve. Positive and negative controls were included in each assay to ensure specificity and for maintaining consistency and reproducibility between assays. The preset assay criteria for sample reporting were: coefficient of variation (CV) per duplicate values for each sample were A5% and >100 beads counted per sample. To control for Env protein performance, the positive control titer (HIVIG) included on each assay had to be within +/−3 standard deviations of the mean for each antigen (tracked with a Levy-Jennings plot with preset acceptance of titer (calculated with a four-parameter logistic equation, SigmaPlot, Systat Software).

Surface Plasmon Resonance (SPR) Measurements of Plasma IgG Avidity.

RV144 vaccine recipient IgG avidity was measured on a BIAcore 4000 instrument (BIAcore/GE Healthcare) using the multiplex array format (1×16) in which each IgG sample was flowed over duplicate spots of 8 different Env gp120 antigen surfaces. Using a Series S CM5 sensor chip (BIAcore/GE Healthcare) gp120 proteins were amine coupled in duplicate on 16 different spots on four flow channels of the chip. The negative control mAb Synagis was flowed over each surface, and the signal was used to subtract out non-specific interactions with each individual spot. Each of the above listed gp120 Env proteins, including the vaccine immunogens A244-rgp120 and MN-rg120, were immobilized to about 6000-8000 RU using amine coupling chemistry as described earlier (1-3). Antigen surface activity was monitored using the C1 mAb A32 as positive control and an irrelevant anti-RSV (Synagis) mAb as negative control. V1V2 mAb CH01, which is sensitive to N160K substitution, was used as a negative control for antigen spots with A244gD/N160K gp120. An anti-gD Fab was used to monitor binding to the gD peptide tag in Env gp120 with gD and to select IgG samples with low gD reactivity for mAb blocking studies. The IgG samples (n=97) from vaccinee plasma at week 26 (two weeks following final immunization) and week 0 were diluted in PBS to 200 µg/mL and injected over each of the flow cells with replicate spots (2×) at 10 µL/min for an association time of 120 s and a dissociation time of 600s. A random selection of IgG samples collected at visit 0 from 20 vaccinees was also included. Following each binding cycle, surfaces were regenerated with a short injection (20s) of glycine, pH2.5. Each surface activity was monitored by including A32 mAb (20 µg/mL) injection every 20 cycles of IgG samples and surface decay of A32 binding over the entire experimental run was used to normalize binding signal of plasma IgG samples. Non-specific binding of the negative control mAb was subtracted from each IgG sample binding data. Data analyses were performed with BIAevaluation 4000 and BIAevaluation 4.1 software (BIAcore/GE Healthcare) as described earlier for Biacore 3000 (2) and Biacore A100 (38) data analysis respectively. Kinetic binding responses were measured by averaging post-injection response unit (RU) over a 20s window, and dissociation rate constant, $k_d$ (s−1) was measured during the post-injection/buffer wash phase (after the first 20s to allow stabilization of signal) following curve fitting to a Langmuir dissociation equation. The majority of IgG bound with a relatively slow dissociation rate ($<10^{-3}$ s$^{-1}$), and the previously described method for BIAcore A100 ranking of dissociation rates in complex or polyclonal samples as a ratio of response units measured as binding late and stability late (23, 38) was modified to include binding response and dissociation rate constant measurements and as described earlier (14, 21). A relative avidity binding score was calculated for each IgG sample as follows, Avidity score (RU.s)=Binding Response (RU)/$k_d$, s−1, with higher binding responses and slower $k_d$ as an indicator of higher affinity interaction (14).

Antibody Blocking Assay.

Antibody blocking using an ELISA assay was carried out as described earlier (3, 21). 384 well ELISA plates (Costar #3700) were coated with 30 ng/well Env overnight at 4° C. and blocked with assay diluent (PBS containing 4% (w/v) whey protein/15% Normal Goat Serum/0.5% Tween20/0.05% Sodium Azide) for 1 hour at room temperature. All assay steps, were conducted in assay diluent (except substrate step) and incubated for 1 hour at room temperature followed by washing with PBS/0.1% Tween-20. Sera were diluted 1:50 and incubated in quadruplicate wells. For CD4 (binding site) blocking assays, 10 µl of a saturating concentration soluble CD4 (Progenies Pharm Inc.) was added following serum incubation step. 10 µl of biotinylated target mAb was added at the EC50 (determined by a direct binding of biotinylated-mAb to JRFL gp140). Biotin-mAb binding was detected with streptavidin-alkaline phosphatase at 1:1000 (Promega V5591) followed by substrate (CBC buffer+2 mM MgCl$_2$+1 mg/ml p-npp [4-Nitrophenyl phosphate di(2-amino-2-ethyl-1,3-propanediol) salt]), and plates were read at 405 nm at 45 minutes. Quadruplicate wells were background subtracted and averaged. Percent inhibition was calculated as follows: 100−(sera triplicate mean/no inhibition control mean)×100.

SPR antibody blocking using RV144 vaccinee IgG samples was measured on BIAcore 3000 instruments. Env immunogen A244 Δ11 gp120 was immobilized on all flow cells of a CM5 sensor chip to about 5,000-6,000 RU using standard amine coupling chemistry. Blocking antibodies were sequentially injected at predetermined concentration to capture near saturation. A zero baseline was set, and RV144 patient IgGs were injected at 10 µL/min for an association time of 180s and a dissociation time of 600s. Kinetic binding responses were measured 15s after the end of the injection. The IgG samples (n=119) with high and mid-level binding (>80 Response Units) to A244 Δ11 gp120 were selected from a panel of week 26 (two weeks following final immunization) plasma samples that included infected vaccinee (n=41) and uninfected vaccinee (n=205) groups. Randomly selected Visit 0 vaccinee IgG samples (n=19) with no binding to A244Δ11 gp120 were included to assess non-specific interactions. Anti-gp41 mAb 7B2 was used as a negative control blocking antibody. Test antibodies included A32 (C1 region), PG9 and CH01 (V2V3 Conformational/Quaternary), 2158, 697-30D, and 830A (V2), and 19b (V3) mAbs. Following each binding cycle, surfaces were regenerated with a short injection (10-15s) of either Glycine-HCl pH2.0 or 100 mM phosphoric acid. Blocking percentages were calculated from the ratio of binding response after negative control 7B2 mAb block to the binding response after test antibody block [% block=(1−(RU after 7B2 block/RU after test mAb block))*100].

Isolation of Antibodies from RV144 Vaccinee Plasma Memory B Cell.

Monoclonal antibodies CH51 and CH54 were isolated from circulating IgG+ memory B cells obtained from a vaccine recipient (subject 210884) as previously described ((7). Briefly, CD2(neg), CD14(neg), CD16(neg), CD235a (neg), IgD(neg) and IgG(pos) cells were isolated from frozen PBMCs using magnetic activated cell sorting (Miltenyi Biotec, Auburn, Calif.) and resuspended in complete medium containing 2.5 µg/ml oCpG ODN2006 (tlrl-2006, InvivoGen, San Diego, Calif.), 5 µM CHK2 kinase inhibitor (Calbiochem/EMD Chemicals, Gibbstown, N.J.) and EBV (200 µl supernatant of B95-8 cells/$10^4$ memory B cells). After overnight incubation in bulk, cells were distributed into 96-well round-bottom tissue culture plates at a cell density of 8 cells/well in presence of ODN2006, CHK2 kinase inhibitor and irradiated (7500 cGy) CD40 ligand-expressing L cells (5000 cells/well). Cells were re-fed at day 7 and harvested at day 14. Cultures were screened for binding to HIV-1 gp120 envelope glycoproteins contained in the vaccine formulation (Bonsignori et al. manuscript in preparation). Cells from positive cultures were single-cell sorted and PCR was performed as previously described (29, 46). Briefly, reverse transcription (RT) was performed using Superscript III reverse transcriptase (Invitrogen, Carlsbad, Calif.) and human constant region primers for IgG, IgA1, IgA2, IgM, IgD, Igκ, Igλ; separate reactions amplified individual VH, Vκ, and Vλ families from the cDNA template using two rounds of PCR. Products were analyzed with agarose gels (1.2%) and purified with PCR purification kits (QIAGEN, Valencia, Calif.). Products were sequenced in forward and reverse directions using a BigDye® sequencing kit using an ABI 3700 (Applied Biosystems, Foster City, Calif.). Sequence base calling was performed using Phred (10, 11); forward and reverse strands were assembled using an assembly algorithm based on the quality scores at each position (33). The estimated PCR artifact rate was 0.28 or approximately one PCR artifact per five genes amplified. Ig isotype was determined by local alignment with genes of known isotype (40); V, D, and J region genes, CDR3 loop lengths, and mutation rates were identified using SoDA (44) and data were annotated so that matching subject data and sort information was linked to the cDNA sequence and analysis results. Isolated Ig V(D)J gene pairs were assembled by PCR into linear full-length Ig heavy- and light-chain gene expression cassettes (29) and optimized as previously described for binding to the Fcγ-Receptors (39). Human embryonic kidney cell line 293T (ATCC, Manassas, Va.) was grown to near confluence in 6-well tissue culture plates (Becton Dickson, Franklin Lakes, N.J.) and transfected with 2 μg per well of purified PCR-produced IgH and IgL linear Ig gene expression cassettes using Effectene (Qiagen). The supernatants were harvested from the transfected 293T cells after three days of incubation at 37° C. in 5% $CO_2$ and the monoclonal antibodies were purified as previously described (29).

Results

Expression of Gp120 Variants of the RV144 Trial Protein Immunogens

Figure 27:
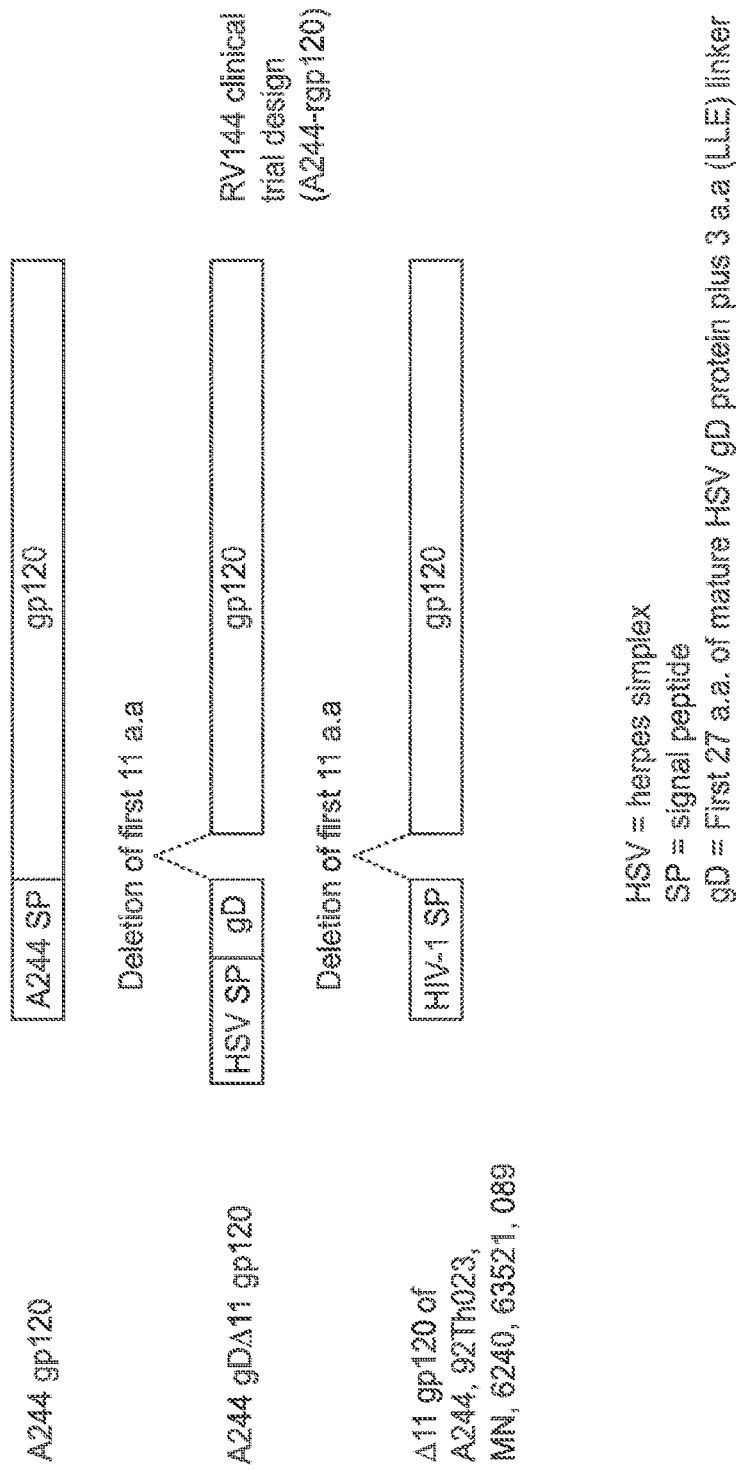

To address the effect of the modifications on the RV144 clinical trial protein Env gp120 antigenicity, the immunogen proteins A244-rgp120 and MN-rgp120 were expressed in 293T cells, with no modifications (A244 gp120 and MN gp120); with only the 11 aa N-terminal deletion (A244Δ11 gp120); or, as in the RV144 Env immunogens, with both the HSV gD peptide tag and the N-terminal deletion (A244 gDΔ11 gp120, MN gDΔ11 gp120) (FIG. 27, Table 1). The E clade 92TH023 gp120 was also expressed either with no modification (92TH023 gp120) or with both Δ11 deletion and gD tag (92TH023 gDΔ11 gp 120, FIG. 27). These Env proteins were compared for gp120 monomer expression and for their binding to mAbs that recognize conformational epitopes on gp120.

Presentation of gp120 Conformational Epitopes on RV144 Vaccine Env gp120 Proteins with the gD Tag and Δ11 Deletion It has been reported previously that one component of the RV144 Env immunogen, A244-rgp120, binds to mAbs with specificity for the gp120 conformational V1V2 epitopes (7, 32). The CH01-CH04 lineage V2V3 bnAbs and PG9 bnAb bound to A244 gp120 with Ds ranging from 100-300 nM (7). Since PG9/PG16 mAbs bind preferentially to native trimers (45) and only to rare gp120 monomers (7), the binding of PG9 and CH01 mAbs suggests that the RV144 Env gp120 might show enhanced expression of conformational epitopes in the V1V2 loops.

Figure 28:
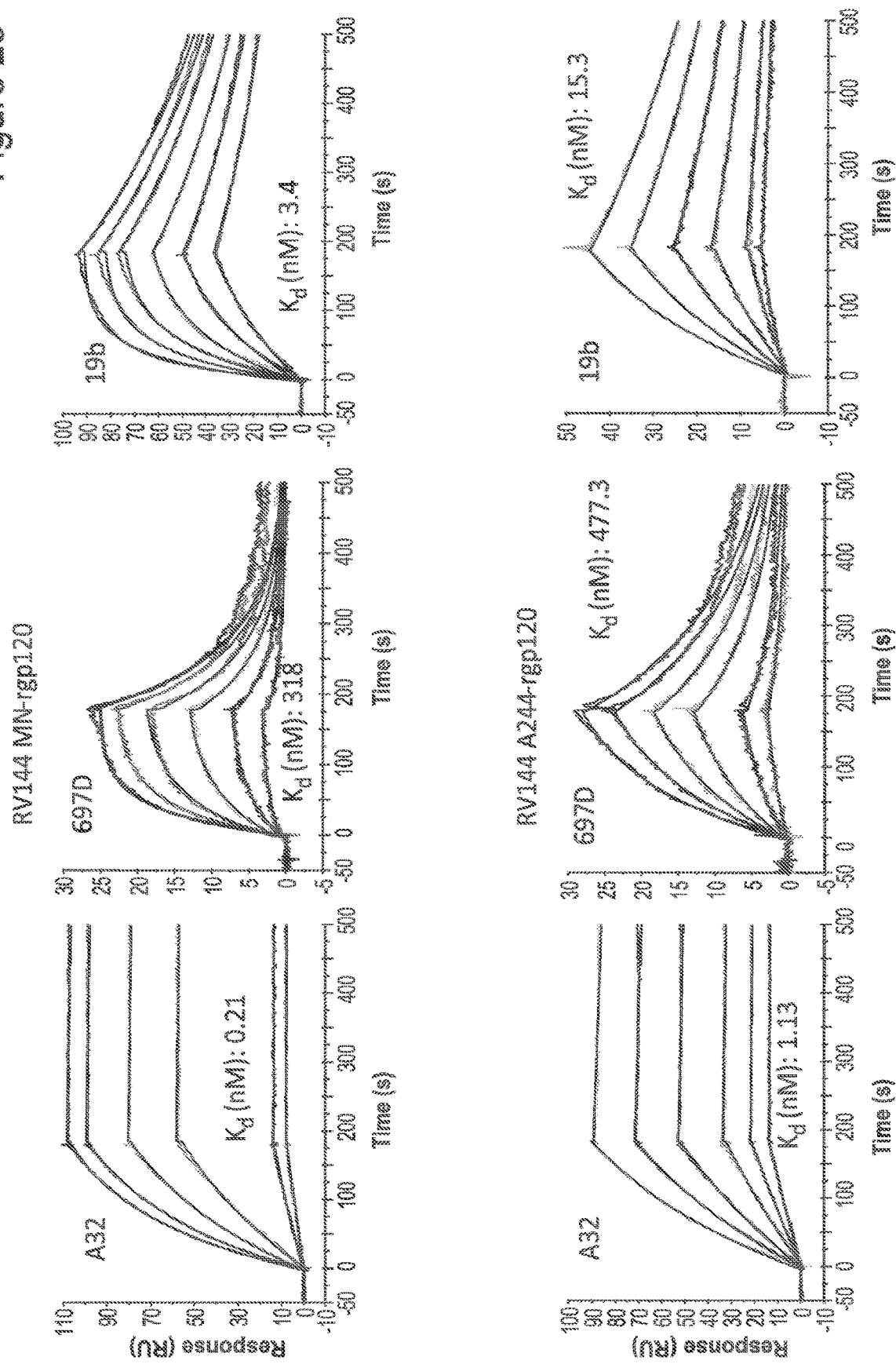

It was found that other conformational epitopes were also presented on both RV144 Env A244-rgp120 and MN-rgp120; the V2 mAb 697-D that does not bind to linear V2 peptides (18) bound to MN- and A244-rgp120 with $K_d$s of 477 nM and 318 nM respectively (FIG. 28) The gp120 C1 mAb A32, which binds to the surface of transmitted/founder infected CD4 T cells and mediates ADCC (12), also bound strongly to the two RV144 Env gp120 proteins, with a relatively higher affinity for MN-rgp120 (FIG. 28). The $K_d$ of the V3 mAb 19b for MN-rgp120 was about 5-fold lower than that of A244-rgp120 but was within the range reported for other V3 mAb binding to Env gp120 proteins (43). Thus, both RV144 vaccine Envelope gp120 immunogens expressed conformational epitopes within the C1, V2 and V2V3 regions of gp120. The presentation of gp120 variable loop conformational epitopes and the recent association of conformational V1V2 antibodies with a lower rate of HIV-1 infection in RV144 (21) raised the question whether the two RV144 vaccine Env modifications—inclusion of the HSV gD peptide tag and/or the N-terminal Δ11 deletion might have led to the enhanced exposure of conformational epitopes within the C1 and V1V2 regions.

The N-Terminal 11 aa Deletion (411) in A244 gp120 Reduces Dimer Formation

Expression of recombinant gp120 produces a substantial amount of disulfide-linked gp120 dimer, in which gp120 inner domain epitopes and the co-receptor binding surface are occluded (13). To determine the effect the two modifications on A244 gp120 might have on protein expression, a comparison was first made of the oligomerization states of the three different A244 gp120 proteins. In reducing SDS-PAGE gel, A244 gp120 proteins migrated as single bands of the expected size; in non-reducing conditions, they gave a mixture of bands that corresponded to monomers and dimers of gp120 (FIG. 29A). Size exclusion chromatography showed that A244 gp120 (FIG. 29B) had more dimer (58±1%) than monomer (38±1%). In contrast, the monomer fraction of Env A244 Δ11 gp120 was enriched by almost two-fold (66±1%) and the dimer fraction was correspondingly reduced (30±1%; monomer to dimer ratio=2.2:1 (Student t test, p<0.001 for monomer fractions in A244 gp120 and A244Δ11 gp120; FIG. 29C). The inclusion of the HSV gD peptide, in addition to the Δ11 modification, in A244 gDΔ11 (FIG. 29D) did not further improve monomer enrichment and gave a similar ratio of monomer to dimer (63±1 and 33±1% respectively) as did A244 Δ11 (Student t test, p=0.11 for monomer fractions in A244gDΔ11 and A244Δ11 gp120). The amount of higher order oligomers or aggregates was the same for all three expressed proteins (about 3-4%) (FIG. 29). A similar profile was observed for the 92TH023 gp120 proteins, with a higher proportion of monomers (~65%) in 92TH023 gp120s with Δ11 and gD tag than without any modifications (~38%). MN gp120 expressed with Δ11 and gD (MN gD gp120) or with no modifications (MN gp120) gave similar proportions of dimers (34% and 31% respectively). Additional gp120 constructs derived from different clades including clade B (625321 and 6240) and clade C (C.089C) were designed to contain their original signal peptide and deletion of the first 11 or 7 (C.1086) amino acid residues, and produced in 293 cells by transient transfection. For each of the above proteins it was found that inclusion of Δ11 alone yielded predominantly monomers, as detected by SDS-PAGE under non-reducing conditions (data not shown) and greater than 90% monomers in gel filtration chromatography analysis. Thus, the N-terminal Δ11 modification alone resulted in markedly lower amounts of gp120 dimer formation when Env proteins were expressed in mammalian cells.

Enhanced Binding of Conformational V2 Antibodies and V2V3 bnAbs to A244 Δ11 gp120 Monomers Monomers of each of the A244 gp120 proteins (A224, A244 Δ11, A244 gDΔ11) were purified to homogeneity following removal of dimeric and aggregate fractions by size exclusion chromatography (SEC). Following SEC fractionation, the monomeric gp120 proteins were stable and did not redistribute into dimer or aggregate fractions. Each of the three purified gp120 monomers bound to CD4 and showed CD4 induced (CD4i) epitope upregulation as assessed by 17b mAb binding (data not shown). A comparison of the binding of the size-fractionated monomeric and dimeric A244 gp120 showed that the binding of the C1 mAb A32 was markedly reduced and the binding of the V2 mAb 697D was near completely lost upon dimer formation. This is consistent with the previously reported results (13) that the V1V2 loop and the N- and C-termini are involved in gp120 dimer formation, and that the epitopes on the Env inner domain are occluded in gp120 dimers.

Figure 30E:
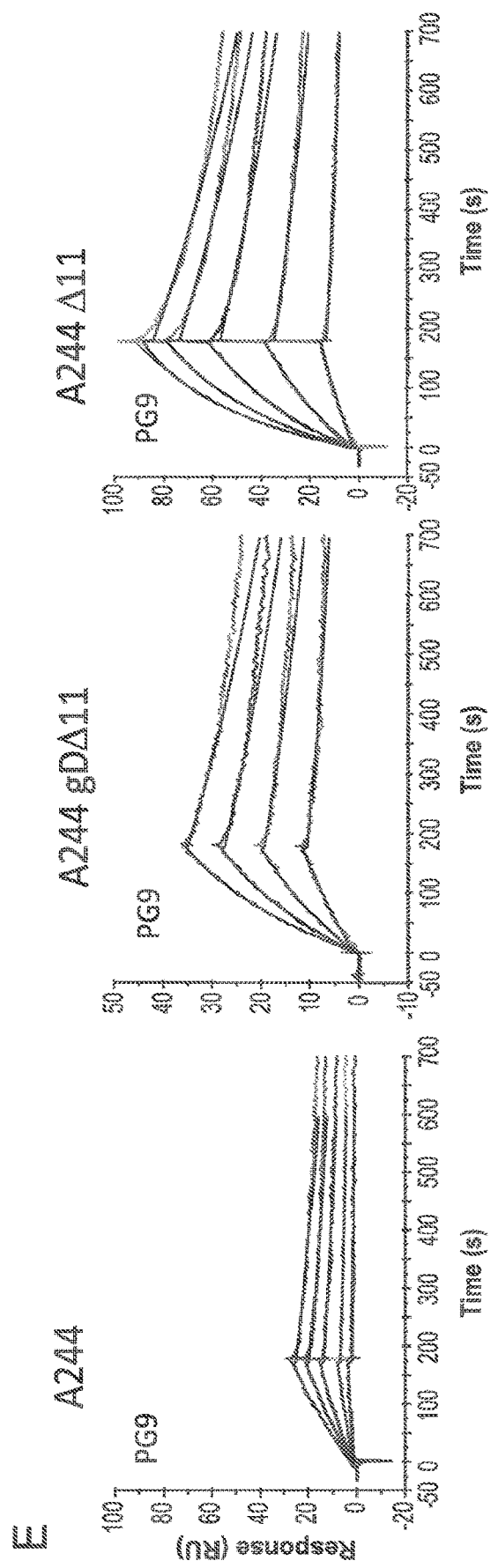

Using a panel of antibodies with specificities that included conformational C1, V2 and V2V3 epitopes, a comparison was made of mAb binding $K_d$ and rate constants for each of the monomeric clade E A244 gp120 proteins, to assess whether the Δ11 and/or gD tag had any effect on Env antigenicity (FIG. 30, Table 2). It was observed that inclusion of Δ11 had no effect on exposure of the V3 loop, since the V3 mAb 19b bound with similar $K_d$ and kinetic rate constants to each of A244 gp120 proteins (Table 2, FIG. 30A). The ADCC mediating C1 mAb A32 (12), however, bound with a 9-fold and 6-fold higher affinity to A244 Δ11 and A244 gDΔ11 respectively than to A244 gp120 (Table 2, FIG. 30B). Similarly, the conformational V2 mAb 697-D (18) bound to A244 gDΔ11 and to A244 Δ11 with nearly an order of magnitude higher affinity (FIG. 30D, Table 2) than to A244 gp120 ($K_d$=218, 157 and 1465 nM, respectively). These differences were also observed using the Fab fragment of the V2 conformational mAb 697-D, which bound to A244 gDΔ11 with 8-fold higher affinity than to unmodified A244 gp120 ($K_d$=690 and 5700 nM respectively). While the dissociation rate constants were similar, the ka (on-rate) was nearly 10-fold higher for binding of 697-D to A244gDΔ11 than to A244 gp120. Two other conformation-dependent V2 mAbs, 2158 and 830A, had higher affinities for A244 gp120 than did 697-D, but both also had higher affinities for A244 with gD and Δ11 modifications (Table 2). In particular, V2 mAb 2158 bound to both A244gDΔ11 and A44Δ11 gp120 with $K_d$~3.7 nM and had approximately 3-fold lower affinity for unmodified A244 gp120 ($K_d$=11.2 nM) (Table 2). Likewise, V2 mAb 830A bound to A244 Δ11gD and to A244Δ11 gp120 about 5-fold more avidly than it did to unmodified A244 gp120 (Table 2). Finally, the affinities of A244Δ11 ($K_d$=278 nM) and A244 gDΔ11 ($K_d$=317 nM) gp120 for V2V3 bNab CH01 were about 5-fold higher than for unmodified A244 gp120 ($K_d$=1638 nM: FIG. 30D, Table 2) and modified Env affinities for PG9, about 3-fold higher ($K_d$=48 nM, 53 nM, and 183 nM for A244Δ11, A244 gDΔ11, and unmodified A244, respectively; FIG. 30E, Table 2).

These results suggest that the conformational V2 and V2V3 epitopes recognized by mAbs 697-D, and CH01 and PG9 are better exposed or conformationally more stable on A244 gp120 proteins with the Δ11 modification and without the inclusion of HSV gD. In most cases, the differences in $K_d$ are due to differences in the association rates, $k_a$, with roughly 10-fold faster rates of both 697D Fab and CH01 mAb for association with gp120 with a Δ11 modification (Table 2). The contribution of ka to the differences in $K_d$ support the notion that exposure of particular conformational epitopes is a critical factor in the enhanced antigenicity.

Figure 31:
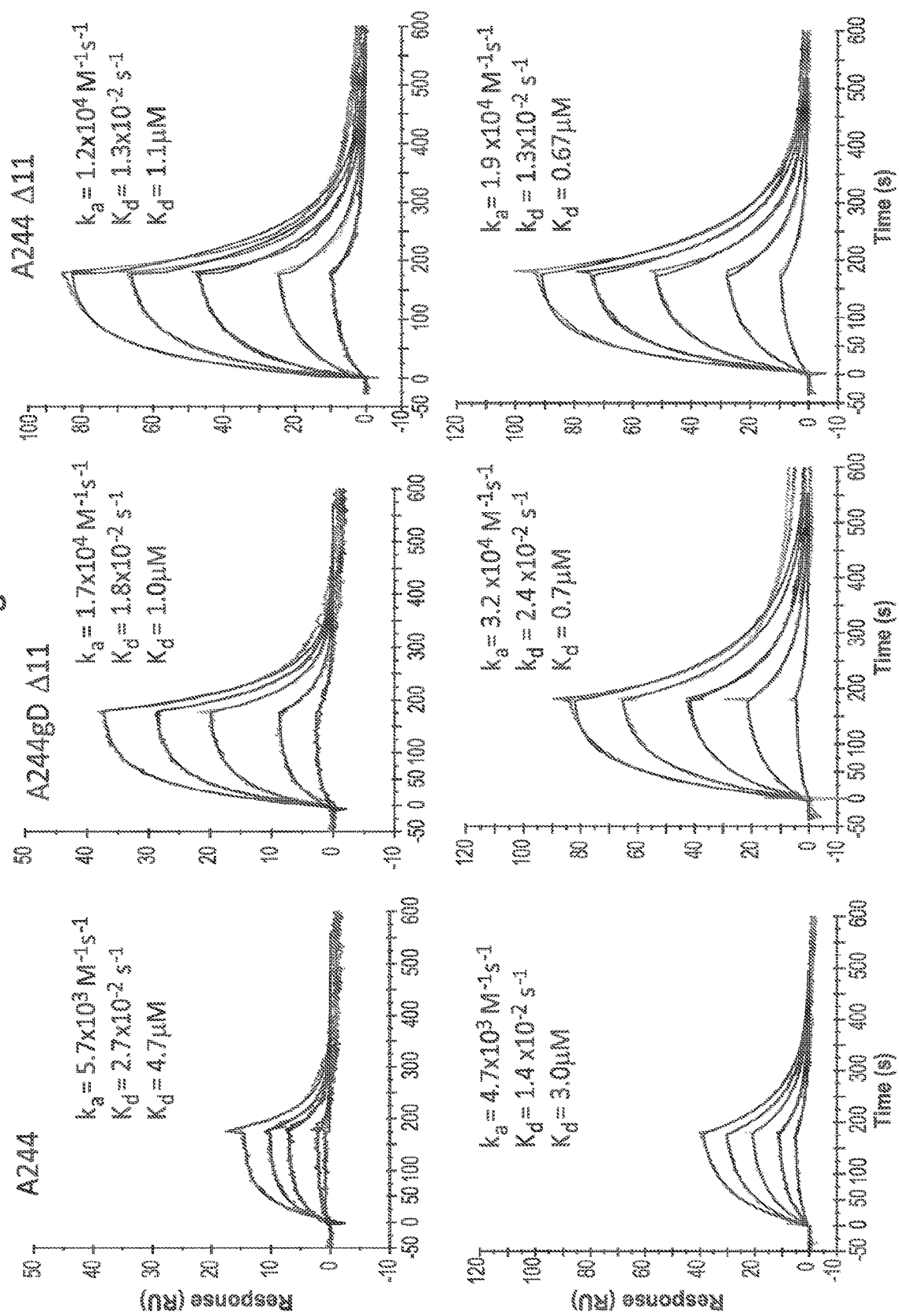

RV144 A244Δ11 Env is Antigenically Reactive with CH01-CH04 Clonal Lineage Unmutated Antibodies Two unmutated ancestor antibodies (UAs) of the mAb CH01-VH04 clonal lineage, CH01_RUA1 and CH01_RUA2, have recently been shown to bind to the RV144 vaccine trial immunogen A244-rgp120 (8). Binding of the CH01-04 UAs to A244Δ11 gp120 was compared with their binding to unmodified A244 gp120. As observed with the mature CH01 mAb, CH01_RUA1 and CH01_RUA2 bound to A244 Δ11 with about 4 to 5-fold higher affinity than to A244 gp120 (FIG. 31); the two CH01 UAs had roughly equivalent $K_d$s for the A244 gp120Δ11 proteins. As observed for the mAbs, the higher affinity of CH01 UAs for A244Δ11 was largely due to relatively faster association rates; the dissociation rates were similar (FIG. 31). This result was interpreted to imply that the Δ11 modification in A244 gp120 results in enhanced exposure of the V2V3 conformational epitopes to the UAs, just as it does for the CH01 lineage mature antibodies.

HSV gD and 411 Modifications have Small Effects on the Antigenicity of MN gp120 and 92TH023 gp120

The results showing the effect of Δ11 modifications on antigenicity of A244 gp120 raises the question whether similar modification of either MN gp120 or the 92TH023 gp120 would influence their antigenicity. The antigenicities of MN and TH023 gp120 Δ11gD were compared with those of the unmodified proteins. The modifications enhanced binding of the C1 mAb A32 and of the V2 mAb 697-D to MN or 92TH023 gp120 by 2-3 fold. PG9 binding to MN and 92TH023 gp120 was unaffected by the presence of gD or Δ11 modification. Thus, in contrast to A244 gp120, the gD and Δ11 modifications had either no effect (conformational V2V3) or a much weaker effect (conformational V2, C1) on the antigenicity of MN or 92TH023 gp120s.

An assessment was made of the effect of an N-terminal Δ11 deletion and gD tag on a clade C Env gp120 (1086). 1086 gp120 monomers with a 7aa deletion of the same region as in A244 gp120 (1086 Δ7 gp120) had the same affinity for A32 (C1), VRC01 (CD4bs) and 19b (V3) mAbs as had the unmodified protein. 1086 gp120 did not bind to PG9 or CH01, as previously reported (7). Binding of the V2 mAbs 697-D and 830A was likewise unaffected by modification. Thus, neither the gD addition nor the N-terminal deletion had any effect on the antigenicity of this clade C gp120 for the antibodies tested. That is, the effects of the Δ11 deletion in the RV144 immunogen apparently depended on the particular gp120 tested.

Plasma IgG from RV144 Vaccinees Bind with Higher Avidity to A244gD Δ11 gp120

The effect of Δ11 modification in enhancing the antigenicity of gp120 conformational epitopes to C1, V2 and V2V3 raises the question, whether antibodies induced by the RV144 immunogen (A244gDΔ11) also bind more avidly to A244 Δ11 than to A244 gp120. IgG was purified from RV144 vaccinee plasma taken two weeks after the final ALVAC/AIDSVAX B/E immunization (week 26) and their relative avidity scores were measured for each of the A244 gp120 proteins in a SPR binding assay. Compared to placebo and pre-vaccination visit 1 IgG samples (no binding), IgG samples from the week-26 vaccinee group bound A244gDΔ11 gp120 with avidity scores that ranged over 2-orders of magnitude (FIG. 32A). The mean avidity scores for both A244 Δ11 and A244 gDΔ11 were, however, significantly higher (p<0.001) than that for A244 gp120 (FIG. 32A). In the HIV-1 binding antibody multiplex assay, a significant difference was found; RV144 plasma IgG showed tighter binding to A244 Δ11 gp120 than did A244 gp120 (p<0.001; FIG. 32B). Thus, the RV144 vaccine gave rise to antibodies with higher magnitude and avidity for A244 gp120 with the Δ11 modification than for unmodified A244 gp120.

Conformational Antibodies to C1, V2 and V2V3 Block RV144 Induced IgG Binding to A244 Δ11 gp120

To assess the specificity of the antibodies induced by RV144 vaccine gp120 immunogens, a measurement was made of the relative level of blocking of vaccinee IgG binding by a panel of mAbs, including those that showed higher affinity for A244 Δ11 gp120. As shown in FIG. 32C, the binding of vaccinee IgG was blocked by each of C1 (A32), V2 (697-D) and the V2V3 (CH01) bnAb, with the strongest blocking observed with A32 (66%). For the V2 epitope, V2 mAbs 2158 and 830A were also used, which show varying levels of overlap with each other; 830A strongly blocks all other V2 mAbs (data not shown). Among these V2 mAbs, blocking of RV144 IgG was strongest with 697-D and 830A, both of which have enhanced binding to A244 with Δ11 modifications (Table 2).

Among the two conformational V2V3 gp120 bnAbs, we found no blocking of RV144 IgG binding by PG9, but detectable blocking (24.6%) by CH01 (FIG. 32C). We also determined blocking of plasma antibodies in ELISA assays for antibodies that inhibit binding of biotinylated mAb A32 and of soluble CD4. In these assays, the mean blocking of A32 and sCD4 binding was 39.6% and 13% respectively (FIG. 32D).

These results suggest that the RV144 vaccine induced a relatively larger proportion of antibodies directed against the conformational C1 (A32) epitope than against epitopes in or around the conformational V2 and V1V2 epitopes recognized by the mAbs 697-D, 830A and the bnAb CH01.

Monoclonal Antibodies from RV144 Vaccinees Recognize Epitopes Enhanced on A244gDΔ11 gp120 Monomers Using previously described methodologies for isolating antibodies from memory B cells (7), two IgG antibodies, CH51 and CH54, were isolated from circulating IgG+ memory B cells of an RV144 vaccine recipient (subject 210884). A32 blocked binding of both CH51 and CH54, suggesting that RV144 derived mAbs bound to epitopes that overlap with the C1 conformational epitope of A32. The overall $K_d$s of CH51 and CH54 mAbs for binding to A244gDΔ11 were higher than that of the C1 mAb A32 (FIG. 33), but both of these RV144 mAbs bound to A244gDΔ11 and A244 Δ11 with an order of magnitude lower $K_d$ than they did to A244 gp120 (FIG. 33A, 33B). Thus, the RV144 vaccinee-derived antibodies (CH51 and CH54) with A32-like specificity showed tighter binding to A244gp120 with the N-terminal deletion and mirrored the overall enhanced avidity detected in RV144 plasma samples with A244gDΔ11.

Summarizing, the RV144 trial showed estimated vaccine efficacy to be 31.2%. Future HIV-1 vaccine efficacy trials will therefore require an improved immunogen design, and analysis of the RV144 immunogens is an important first step. In the work done above, a study has been made of the effects of gp120 design on antigenicity and immunogenicity of the immunogens used in the RV144 HIV-1 vaccine efficacy trial. It has been demonstrated that deletion of the N-terminal amino-acid residues of the A244 gp120 and, to a lesser degree, of the MN gp120, both of which were used as boosts in the trial, enhanced the antigenicity of gp120 conformational epitopes to C1 and V1V2 regions. The enhanced epitopes were immunogenic in the human vaccinees, and they appear to have induced immune responses with higher avidity for these conformational epitopes than for the same epitopes on the unmodified immunogen A244 gp120. It has also been shown that a gD tag, introduced into the AIDSVAX B/E rgp120 as part of early expression and purification strategies (27), does not contribute to the enhancement, as long as the N-terminal deletion is retained. Antigenic enhancement by the N-terminal deletion, Δ11, was more pronounced with A244 (clade E) than with MN (clade B), 92TH023 (clade E), or 1086C (clade C) gp120 proteins, suggesting that these effects may depend strongly on the particular gp120 vaccine immunogen.

The higher proportion of disulfide-linked dimers in the preparations of unmodified A244 rgp120 than in those with a Δ11 deletion (with or without the gD-tag replacement) suggests that the principal effect of removing the N-terminal residues has been to enhance the reliability of folding in the ER. Correctly folded gp120 has no unpaired cysteines, and any inter-chain disulfides must form at the expense of correct intra-chain pairings. That is, at least part of the protein must be misfolded for disulfide-linked dimers to form at all. Even the monomeric protein in any preparation may be conformationally heterogeneous; the proportion of dimer will tend to reflect the degree of misfolding within the monomer population. Because the consequences of the deletion depend on the rest of the gp120 sequence—it had a less marked effect on rgp120 from other isolates—its influence on folding is probably non-specific. The N-terminal 11 residues, which immediately follow the signal-peptide cleavage site in the polypeptide chain, presumably interact with gp41 near the membrane-proximal part of the molecule, and they are unlikely to influence the conformation of most neutralizing epitopes directly, but rather through their effect on the yield of correctly folded protein.

Two observations show that the upregulation of C1, V2, and V1V2 epitopes on A244 gp120 was relevant to the antibody responses induced in the RV144 trial. First, RV144 vaccinee antibodies have been identified that recognize these epitopes in SPR and ELISA blocking assays, and human mAbs have been isolated from RV144 vaccinees that are blocked in their binding to A244 gp120 by the conformational C1 antibody, A32 (6, 21, 48). Moreover, mAb 697-D, which binds to A244 gp120 and the gp70V1V2 Case A2 clade B scaffolded protein, binds to A244 Δ11 gp120 nearly ten-fold more tightly than it does to A244 gp120 with no modifications. Second, the RV144 induced plasma antibody response had a higher avidity for A244 Envs with gD Δ11 or with Δ11 alone than for their unmodified counterparts (FIG. 32). The conformational V2 and V1V2 epitope specificities induced by the vaccine included those that could be blocked by mAbs CH01 and 697D, but not by mAb PG9 (FIG. 32B). Although it has not yet been possible to rescue a V2 mAb against the conformational V2 or V1V2 epitopes selectively recognized by 697-D or CH01, the presence of plasma antibodies with specificities capable of blocking the binding of these mAbs to A244 gp120 has been demonstrated (FIG. 32B). Furthermore, both the A244 gp120 mAbs isolated from RV144 vaccinees (CH51, CH54) bound A244 and MN gp120s, their binding was blocked by A32 and both mediated antibody dependent cellular cytotoxicity (ADCC) to HIV-1 AE_01 infected CD4 T cell targets. Binding of both of these A32-like mAbs (CH51 and CH54) to A244 gp120 was enhanced when the Δ11 deletion was introduced. These data strongly suggest that the observed Δ11-enhanced gp120 antigenicity of RV144 gp120 immunogens played a role in the induction of certain antibody types (C1, V2 and V1V2) in the RV144 vaccinees.

In a RV144 immune correlates analysis, plasma IgA Env antibodies correlated directly with infection rate while V1V2 antibodies correlated inversely with infection rate (21). While ADCC alone did not correlate with infection rate in this analysis, ADCC in the presence of low levels of IgA antibodies did correlate weakly with a lower infection rate, demonstrating an interaction between ADCC-mediating antibodies and high IgA levels for mitigation of any potential protective ADCC response (21). The underlying mechanism of protection in the RV144 trial has yet to be elucidated—the immune correlates study has so far only identified antibody responses that correlate directly (plasma HIV-1 Env IgA) or inversely (plasma Abs binding to gp70-V1V2) with infection risk (21). Subsequent studies are required to determine if either of these antibody types are causal correlates or are surrogate markers of other factors.

Thus, it has been shown that the Δ11 N-terminal deletion on the gp120 Envs used in the AIDSVAX B/E boost of the RV144 HIV-1 vaccine trial enhanced gp120 epitope expression and augmented both antigenicity and immunogenicity for the C1, V2 and V1V2 gp120 regions. The Δ11 deletion (with or without gD) leads to expression of a higher proportion of correctly folded recombinant protein, and the stability and conformational homogeneity of the immunogen is likely to have contributed substantially to its properties. The data suggest that careful attention to Env conformations and antigenicity will be critical when designing immunogens in future trials.

TABLE 1

Env gp120 protein constructs used in the study.

| Env protein | gD peptide | N-terminal deletion |
|---|---|---|
| A244-rgp120* | + | 11 aa |
| MN-rgp120* | + | 11aa |
| A244 gp120 | − | − |
| A244gDΔ11 gp120 | + | 11 aa |
| A244 Δ11 gp120 | + | 11aa |
| MN gp120 | − | − |
| MN gDΔ11 gp120 | + | 11aa |
| 92TH023 gp120 | − | − |
| 92TH023 gDΔ11 gp120 | + | 11aa |
| 63521 Δ11 gp120 | − | 11aa |
| 6240 Δ11 gp120 | − | 11aa |
| O89C Δ11 gp120 | − | 11aa |
| 1086 Δ7 gp120** | − | 7aa |

*RV144 vaccine immunogen proteins A244-rgp120 and MN-rgp120 were produced by Genentech Inc., developed by VaxGen Inc and supplied by GSID.
**1086 Env, in which the corresponding N-terminal segment (7aa) is shorter, was designed with Δ7 deletion.

TABLE 2

Dissociation and kinetic rate constants of antibody binding to E.A244 gp120 proteins.

| Antibody/Protein | Rate Constants/$K_d$ | E.A244 gp120 | E.A244gDΔ11 gp120 | E.A244Δ11 gp120 |
|---|---|---|---|---|
| A32 (C1) | $k_a$ (×10$^3$ M$^{-1}$s$^{-1}$) | 76.8 ± 11.4 | 134 ± 14.0 | 222.6 ± 20.4 |
|  | $k_d$ (×10$^{-3}$ s$^{-1}$) | 0.47 ± 0.05 | 0.133 ± 0.017 | 0.15 ± 0.03 |
|  | $K_d$ (nM) | 6.25 ± 1.4 | 1.0 ± 0.22 | 0.67 ± 0.13 |
| 19b (V3) | $k_a$ (×10$^3$ M$^{-1}$s$^{-1}$) | 130.3 ± 10.5 | 170.3 ± 8.5 | 239.3 ± 19.8 |
|  | $k_d$ (×10$^{-3}$ s$^{-1}$) | 1.54 ± 0.095 | 1.4 ± 0.08 | 1.56 ± 0.08 |
|  | $K_d$ (nM) | 11.8 ± 0.21 | 8.24 ± 0.23 | 6.54 ± 0.38 |
| 697D (V2) | $k_a$ (×10$^3$ M$^{-1}$s$^{-1}$) | 4.9 ± 1.1 | 24.9 ± 5.6 | 26.75 ± 0.71 |
|  | $k_d$ (×10$^{-3}$ s$^{-1}$) | 7.0 ± 1.98 | 5.24 ± 0.54 | 5.18 ± 0.6 |
|  | $K_d$ (nM) | 1465.3 ± 317 | 217.6 ± 45.7 | 156.7 ± 34.0 |
| 830A (V2) | $k_a$ (×10$^3$ M$^{-1}$s$^{-1}$) | 21.8 ± 3.1 | 41.1 ± 1.9 | 59.9 ± 4.6 |
|  | $k_d$ (×10$^{-3}$ s$^{-1}$) | 0.22 ± 0.06 | 0.07 ± 0.003 | 0.088 ± 0.01 |
|  | Kd (nM) | 10.2 ± 3.6 | 1.7 ± 0.16 | 1.56 ± 0.09 |
| 2158 (V2) | $k_a$ (×10$^3$ M$^{-1}$s$^{-1}$) | 16.4 ± 0.98 | 28.7 ± 1.0 | 36.5 ± 1.8 |
|  | $k_d$ (×10$^{-3}$ s$^{-1}$) | 0.19 ± 0.04 | 0.10 ± 0.03 | 0.13 ± 0.04 |
|  | $K_d$ (nM) | 11.2 ± 1.6 | 3.7 ± 0.9 | 3.68 ± 1.1 |
| CH01 (V2V3) | $k_a$ (×10$^3$ M$^{-1}$s$^{-1}$) | 3.73 ± 1.6 | 37.2 ± 15.1 | 49.0 ± 5.4 |
|  | $k_d$ (×10$^{-3}$ s$^{-1}$) | 4.38 ± 0.52 | 9.9 ± 2.8 | 15.6 ± 1.5 |
|  | $K_d$ (nM) | 1639 ± 601 | 277.8 ± 42 | 317 ± 31.9 |
| PG9 (V2V3) | $k_a$ (×10$^3$ M$^{-1}$s$^{-1}$) | 5.0 ± 3.5 | 11.5 ± 0.6 | 10.9 ± 0.9 |
|  | $k_d$ (×10$^{-3}$ s$^{-1}$) | 1.1 ± 0.4 | 0.55 ± 0.03 | 0.57 ± 0.06 |
|  | $K_d$ (nM) | 183 ± 44.0 | 48.1 ± 0.15 | 52.6 ± 2.9 |
| VRC01 (CD4 bs) | $k_a$ (×10$^3$ M$^{-1}$s$^{-1}$) | 17.6 ± 0.52 | 13.3 ± 0.57 | 9.7 ± 0.43 |
|  | $k_d$ (×10$^{-3}$ s$^{-1}$) | 0.28 ± 0.02 | 0.21 ± 0.06 | 0.39 ± 0.03 |
|  | $K_d$ (nM) | 15.7 ± 1.7 | 15.8 ± 3.9 | 36.7 ± 1.4 |

Each of the rate constants and $K_d$ values were derived from at least three measurements on individual flow cells of the same sensor chip or from binding data collected on a different sensor chips. The mean and s.d. of rate constants ($k_a$, $k_d$) and $K_d$ values are reported for each antibody binding to the three different forms of monomeric E.A244 gp120 proteins.

REFERENCES CITED IN EXAMPLE 3

1. Alam, S. M., M. McAdams, D. Boren, M. Rak, R. M. Scearce, F. Gao, Z. T. Camacho, D. Gewirth, G. Kelsoe, P. Chen, and B. F. Haynes. 2007. The role of antibody polyspecificity and lipid reactivity in binding of broadly neutralizing anti-HIV-1 envelope human monoclonal antibodies 2F5 and 4E10 to glycoprotein 41 membrane proximal envelope epitopes. Journal of Immunology 178: 4424-35.
2. Alam, S. M., M. Morelli, S. M. Dennison, H. X. Liao, R. Zhang, S. M. Xia, S. Rits-Volloch, L. Sun, S. C. Harrison, B. F. Haynes, and B. Chen. 2009. Role of HIV membrane in neutralization by two broadly neutralizing antibodies. Proceedings of the National Academy of Sciences of the United States of America 106:20234-9.
3. Alam, S. M., R. M. Scearce, R. J. Parks, K. Plonk, S. G. Plonk, L. L. Sutherland, M. K. Gorny, S. Zolla-Pazner, S. Vanleeuwen, M. A. Moody, S. M. Xia, D. C. Montefiori, G. D. Tomaras, K. J. Weinhold, S. A. Karim, C. B. Hicks, H. X. Liao, J. Robinson, G. M. Shaw, and B. F. Haynes. 2008. Human immunodeficiency virus type 1 gp41 antibodies that mask membrane proximal region epitopes: antibody binding kinetics, induction, and potential for regulation in acute infection. J Virol 82:115-25.
4. Berman, P. W. 1998. Development of bivalent rgp120 vaccines to prevent HIV Type 1 infection. AIDS Res Hum Retroviruses 14:S277-S289.
5. Berman, P. W., Huang, W., Riddle, L. et al. 1999. Development of bivalent (B/E) vaccines able to neutralize CCR5-dependent viruses from the United States and Thailand. Virology 265:1-9.
6. Billings, E. A., KArasavvas, N., de Souza, M. S., Currier, J., Pitisuttithum, P. et al. 2011. Surface Plasmon Resonance Analysis of anti-gp120 V2-specific IgG antibodies generated in the RV144 Thai Trial. AIDS Res Hum Retroviruses 27:21.
7. Bonsignori, M., Hwang, K. K., Chen, X., Tsao, C. Y., Morris, L., Gray, E. et al. 2011. Analysis of a clonal lineage of HIV-1 Envelope V2/V3 conformational epitope-specific broadly neutralizing antibodies and their inferred unmutated common ancestors. J. Virol. 85:9998-10009.
8. Bonsignori, M., X. Wu, M. A. Moody, H. Liao, K. Hwang, J. A. Crump, S. H. Capiga, N. E. Sam, G. D. Tomaras, X. Chen, C. Tsao, S. M. Alam, G. J. Nabel, P. D. Kwong, L. Morris, D. Montefiori, J. R. Mascola, and B. F. Haynes. 2011. Isolation of CD4-Binding Site and V2/V3 Conformational (Quaternary) Broadly Neutralizing Antibodies from the Same HIV-1 Infected African Subject. AIDS Research and Human Retroviruses 27:A120-A120.
9. Davenport, T., Friend D, Ellingson K, Xu H, Caldwell Z, Sellhorn G, Kraft Z, Strong R K, Stamatatos L. 2011. Binding interactions between soluble HIV envelope glycoproteins and quaternary-structure-specific monoclonal antibodies PG9 and PG16. J. Virol. 85:7095-7107.
10. Ewing, B., and P. Green. 1998. Base-calling of automated sequencer traces using phred. II. Error probabilities. Genome Res 8:186-94.
11. Ewing, B., L. Hillier, M. C. Wendl, and P. Green. 1998. Base-calling of automated sequencer traces using phred. I. Accuracy assessment. Genome Res 8:175-85.
12. Ferrari, G., Pollara J, Kozink D, Harms T, Drinker M, Freel S, Moody M A, Alam S M, Tomaras G D, Ochsenbauer C, Kappes J C, Shaw G M, Hoxie J A, Robinson J E, Haynes B F. 2011. An HIV-1 gp120 envelope human monoclonal antibody that recognizes a C1 conformational epitope mediates potent antibody-dependent cellular cytotoxicity (ADCC) activity and defines a common ADCC epitope in human HIV-1 serum. J. Virol. 85:7029-7036.
13. Finzi, A., Pacheco, B., Zeng, X., Do Kwon, Y., Kwong, P. D., Sodroski, J. 2010. Conformatinal characterization of aberrant disulfide-linked HIV-1 gp120 dimers secreted from overexpressing cells. J. Virol. Methods 168:155-161.
14. Flynn, B. J., Kastenmuller, K., Willie-Reece, U., Tomaras, G. D., Alam, S. M., Lindsay, R. W. et al. 2011. Immunization with HIV Gag targeted to dendritic cells followed by recombinant New York Vaccinia virus induces ribust T-cell immunity in nonhuman primates. Proc Natl Acad Sci USA 108:7131-7136.
15. Flynn, N. M., Fortahl, D. N., Harro, C. D., Judson, F. N., Mayer, K. H., Para, M. F., rgp120 HIV Vaccine Study Group. 2005. Placebo-controlled phase 3 trial of a recombinant glycoprotein 120 vaccine to prevent HIV-1 infection. J. Infect. Dis. 191:654-665.
16. Francis, D. P., Gregory, T., McElarath, M. J. et al. 1998. Advancing AIDSVAX to phase 3: safety, immunogenicity, and plans for phase 3. AIDS Res Hum Retroviruses 14:325-331.
17. Gorny, M. K., C. Williams, X. Wang, B. Volsky, T. O'Neal, L. Li, M. S. Seaman, and S. Zolla-Pazner. 2011. Functional and immunochemical cross-reactivity of V2-specific monoclonal antibodies from human immunodeficiency virus type 1-infected individuals. Virology in press.
18. Gorny, M. K., J. P. Moore, A. J. Conley, S. Karwowska, J. Sodroski, C. Williams, S. Burda, L. J. Boots, and S. Zolla-Pazner. 1994. Human anti-V2 monoclonal antibody that neutralizes primary but not laboratory isolates of human immunodeficiency virus type 1. J Virol 68:8312-20.
19. Gorny, M. K., L. Stamatatos, B. Volsky, K. Revesz, C. Williams, X. H. Wang, S. Cohen, R. Staudinger, and S. Zolla-Pazner. 2005. Identification of a new quaternary neutralizing epitope on human immunodeficiency virus type 1 virus particles. J Virol 79:5232-7.
20. Harris, A., Borgnia, M. J., Shi, D., et al. 2011. Trimeric HIV-1 glycoprotein gp140 immunogens and native HIV-1 envelope glysoproteins display the same and open quaternary molecular architectures. Proc Natl Acad Sci USA 108:11440-11445.
21. Haynes, B. F. 2011. Case control study of the RV144 trial for immune correlates: the analysis and way forward AIDS Vaccine Conference 2011, Bangkok, Thailand.
22. Honnen, W. J., C. Krachmarov, S. C. Kayman, M. K. Gorny, S. Zolla-Pazner, and A. Pinter. 2007. Type-specific epitopes targeted by monoclonal antibodies with exceptionally potent neutralizing activities for selected strains of human immunodeficiency virus type 1 map to a common region of the V2 domain of gp120 and differ only at single positions from the clade B consensus sequence. J Virol 81:1424-32.
23. Kasturi, S. P., Skountozi, I., Albrecht, R. A., Koutsonanos, D. et al. 2011. Programming the magnitude and persistence of antibody responses with innate immunity. Nature 470 543-547.
24. Kayman, S. C., Wu, Z., Revesz, K., Chen, H., Kopelman, R., Pinter, A. 1994. Presentation of native epitopes in the V1V2 and V3 regions of human immunodeficiency virus type I gp120 by fusion glycoprotsins containing isolated gp120 domains. J. Virol. 68:400-410.
25. Keele, B. F., E. E. Giorgi, J. F. Salazar-Gonzalez, J. M. Decker, K. T. Pham, M. G. Salazar, C. Sun, T. Grayson, 25. S. Wang, H. Li, X. Wei, C. Jiang, J. L. Kirchherr, F. Gao, J. A. Anderson, L. H. Ping, R. Swanstrom, G. D. Tomaras, W. A. Blattner, et al. 2008. Identification and characterization of transmitted and early founder virus envelopes in primary HIV-1 infection. Proc. Natl. Acad. Sci 105.

26. Kwong, P. D., ML Doyle, DJ Casper, C. Cicala, S. A. Leavitt S. Majeed, T. D. Steenbeke, M. Venturi, I. Chaiken, M. Fung, H. Katinge, P. W. Parren, J. Robinson, D. Van Ryk, L. Wang, D. R. Burton, E. Freire, R. Wyatt, J. Sodroski W. A. Hendrickson, J. Arthos. 2002. HIV-1 evades antibody-mediated neutralization through conformational masking of receptor-binding sites. Nature 420: 678-682.

27. Lasky, L. A., Groopman, J. E., Fennie, C. W. et al. 1986. Neutralization of the AIDS retrovirus by antibodies to a recombinant envelope glycoprotein. Science 233:209-212.

28. Liao, H.-X., L. L. Sutherland, S-M Xia, M. E. Brock, R. M. Scearce, S. Vanleeuwen, M-S. Alam, M. McAdams, E.A. Weaver, Z. T. Camacho, B-J. Ma, Y. Li, J. M. Decker, G. J. Nabel, D. C. Montefiori, B. H. Hahn, B. T. Korber, F. Gao, B. F. Haynes. 2006. A group M consensus envelope glycoprotein induces antibodies that neutralize subsets of subtype B and C HIV-1 primary viruses. Virology 353:268-282.

29. Liao, H. X., M. C. Levesque, A. Nagel, A. Dixon, R. Zhang, E. Walter, R. Parks, J. Whitesides, D. J. Marshall, K. K. Hwang, Y. Yang, X. Chen, F. Gao, S. Munshaw, T. B. Kepler, T. Denny, M. A. Moody, and B. F. Haynes. 2009. High-throughput isolation of immunoglobulin genes from single human B cells and expression as monoclonal antibodies. J Virol Methods 158:171-9.

30. Liu, J., Bartesaghi, A., Borgnia, M. J., Sapiro, G., Subramniam, S. 2008. Molecular architecture of native HIV-1 gp120 trimers. Nature 455:109-113.

31. Liu, P., Overman, R. G., Yates, N. L., Alam, S. M., Vandergrift, N., Chen, Y., Graw, F., Freel, S. A., Kappes, J. C., Ochsenbauer, C., Montefiori, D. C., Gao, F., Perelson, A. S., Cohen, M. S., Haynes, B. F., Tomaras, G. D. 2011. Dynamic antibody specificities and virion concentrations in circulating immune complexes in acute to chronic HIV-1 infection. J. Virol. 85:11196-11207.

32. McLellan, J., Pancera M, Carrico C, Gorman J, Julien J P, Khayat R, Louder R, Pejchal R, Sastry M, Dai K, O'Dell S, Patel N, Shahzad-ul-Hussan S, Yang Y, Zhang B, Zhou T, Zhu J, Boyington J C, Chuang G Y, Diwanji D, Georgiev I, Kwon Y D, Lee D, Louder M K, Moquin S, Schmidt S D, Yang Z Y, Bonsignori M, Crump J A, Kapiga S H, Sam N E, Haynes B F, Burton D R, Koff W C, Walker L M, Phogat S, Wyatt R, Orwenyo J, Wang L X, Arthos J, Bewley C A, Mascola J R, Nabel G J, Schief W R, Ward A B, Wilson I A, Kwong P D. 2011. Structure of HIV-1 gp120 V1/V2 domain with broadly neutralizing antibody PG9. Nature 480:336-343.

33. Munshaw, S., and T. B. Kepler. 2010. SoDA2: a Hidden Markov Model approach for identification of immunoglobulin rearrangements. Bioinformatics 26:867-72.

34. Pinter, A., W. J. Honnen, Y. He, M. K. Gorny, S. Zolla-Pazner, and S. C. Kayman. 2004. The V1/V2 domain of gp120 is a global regulator of the sensitivity of primary human immunodeficiency virus type 1 isolates to neutralization by antibodies commonly induced upon infection. J Virol 78:5205-15.

35. Pinter, A., Honnen, W. J., Kayman, S. C., Trochev, O. Wu, Z. 1998. Potent neutralization of primary HIV-1 isolates by antibodies directed against epitopes present in the V1/V2 domain of HIV-1 gp120. Vaccine 16:1803-1811.

36. Pitisuttithum, P. 2008. HIV vaccine research in Thailand: lessons learned. Expert Rev. Vaccines 7:311-317.

37. Rerks-Ngam, S., Pitisuttithum, P., Nitayaphan, S. et al. 2009. Vaccination with ALVAC and AIDSVAX to prevent HIV-1 infection in Thailand. N. Eng. J. Med. 361:2209-2220.

38. Safsten, P., Klakamp, S. L., Drake, A. W., Karlsson, R., Myszka, D. G. 2006. Screening antibody-antigen interactions in parallel using BIAcore A100. Anal. Biochem. 353:181-190.

39. Shields, R. L., A. K. Namenuk, K. Hong, Y. G. Meng, J. Rae, J. Briggs, D. Xie, J. Lai, A. Stadlen, B. Li, J. A. Fox, and L. G. Presta. 2001. High resolution mapping of the binding site on human IgG1 for Fc gamma RI, Fc gamma MI, Fc gamma MII, and FcRn and design of IgG1 variants with improved binding to the Fc gamma R. J Biol Chem 276:6591-604.

40. Smith, T. F., and M. S. Waterman. 1981. Identification of common molecular subsequences. J Mol Biol 147:195-7.

41. Tomaras, G. D., N. L. Yates, P. Liu, L. Qin, G. G. Fouda, L. L. Chavez, A. C. Decamp, R. J. Parks, V. C. Ashley, J. T. Lucas, M. Cohen, J. Eron, C. B. Hicks, H. X. Liao, S. G. Self, G. Landucci, D. N. Forthal, K. J. Weinhold, B. F. Keele, B. H. Hahn, M. L. Greenberg, L. Morris, S. S. Karim, W. A. Blattner, D. C. Montefiori, G. M. Shaw, A. S. Perelson, and B. F. Haynes. 2008. Initial B-cell responses to transmitted human immunodeficiency virus type 1: virion-binding immunoglobulin M (IgM) and IgG antibodies followed by plasma anti-gp41 antibodies with ineffective control of initial viremia. J Virol 82:12449-63.

42. Tsao, C., et al. 2010. Antigenicity and immuogenicity of transmitted/founder HIV envelope oligomers compared to chronic HIV envelopes. AIDS Res. Hum. Retroviruses 10.01:A27.

43. VanCott, T. C., Bethke, F. R., Polonis, V. R., Gorny, M. K., Zolla-Pazner, S., Redfield R. R., Birx, D. L. 1994. Dissociation rate of antibody-gp120 binding interactions is predictive of V3-mediated neutralization of HIV-1. J. Immunol. 153:449.

44. Volpe, J. M., L. G. Cowell, and T. B. Kepler. 2006. SoDA: implementation of a 3D alignment algorithm for inference of antigen receptor recombinations. Bioinformatics 22:438-44.

45. Walker, L. M., S. K. Phogat, P. Y. Chan-Hui, D. Wagner, P. Phung, J. L. Goss, T. Wrin, M. D. Simek, S. Fling, J. L. Mitcham, J. K. Lehrman, F. H. Priddy, 0. A. Olsen, S. M. Frey, P. W. Hammond, S. Kaminsky, T. Zamb, M. Moyle, W. C. Koff, P. Poignard, and D. R. Burton. 2009. Broad and potent neutralizing antibodies from an African donor reveal a new HIV-1 vaccine target. Science 326:285-9.

46. Wrammert, J., K. Smith, J. Miller, W. A. Langley, K. Kokko, C. Larsen, N. Y. Zheng, I. Mays, L. Garman, C. Helms, J. James, G. M. Air, J. D. Capra, R. Ahmed, and P. C. Wilson. 2008. Rapid cloning of high-affinity human monoclonal antibodies against influenza virus. Nature 453:667-71.

47. Zhu, P., J. Liu, J. Bess, E. Chertova, J. D. Lifson, H. Grise, G. A. Ofek, K. A. Taylor, and K. H. Roux. 2006. Distribution and three-dimensional structure of AIDS virus envelope spikes. Nature 441:847-852.

48. Zolla-Pazner, S., Cardozo, T., Decamp, A., Haynes, B., Kim, J., Kong, X., Michael, N., Rerks-Ngam, S., Williams, C. 2011. V2-reactive Antibodies in RV144 Vaccinees' Plasma. AIDS Res Hum Retroviruses (Abstracts from AIDS Vaccine 2011) 27:A21.

All documents and other information sources cited above are hereby incorporated in their entirety by reference.

SEQUENCE LISTING

<160> NUMBER OF SEQ ID NOS: 41

<210> SEQ ID NO 1
<211> LENGTH: 472
<212> TYPE: PRT
<213> ORGANISM: Human immunodeficiency virus 1

<400> SEQUENCE: 1

```
Val Pro Val Trp Lys Glu Ala Asp Thr Thr Leu Phe Cys Ala Ser Asp
1               5                  10                  15

Ala Lys Ala His Glu Thr Glu Val His Asn Val Trp Ala Thr His Ala
            20                  25                  30

Cys Val Pro Thr Asp Pro Asn Pro Gln Glu Ile Asp Leu Glu Asn Val
        35                  40                  45

Thr Glu Asn Phe Asn Met Trp Lys Asn Asn Met Val Glu Gln Met Gln
    50                  55                  60

Glu Asp Val Ile Ser Leu Trp Asp Gln Ser Leu Lys Pro Cys Val Lys
65                  70                  75                  80

Leu Thr Pro Pro Cys Val Thr Leu His Cys Thr Asn Ala Asn Leu Thr
                85                  90                  95

Lys Ala Asn Leu Thr Asn Val Asn Asn Arg Thr Asn Val Ser Asn Ile
            100                 105                 110

Ile Gly Asn Ile Thr Asp Glu Val Arg Asn Cys Ser Phe Asn Met Thr
        115                 120                 125

Thr Glu Leu Arg Asp Lys Lys Gln Lys Val His Ala Leu Phe Tyr Lys
    130                 135                 140

Leu Asp Ile Val Pro Ile Glu Asp Asn Asn Asp Ser Ser Glu Tyr Arg
145                 150                 155                 160

Leu Ile Asn Cys Asn Thr Ser Val Ile Lys Gln Pro Cys Pro Lys Ile
                165                 170                 175

Ser Phe Asp Pro Ile Pro Ile His Tyr Cys Thr Pro Ala Gly Tyr Ala
            180                 185                 190

Ile Leu Lys Cys Asn Asp Lys Asn Phe Asn Gly Thr Gly Pro Cys Lys
        195                 200                 205

Asn Val Ser Ser Val Gln Cys Thr His Gly Ile Lys Pro Val Val Ser
    210                 215                 220

Thr Gln Leu Leu Leu Asn Gly Ser Leu Ala Glu Glu Ile Ile Ile
225                 230                 235                 240

Arg Ser Glu Asn Leu Thr Asn Asn Ala Lys Thr Ile Ile Val His Leu
                245                 250                 255

Asn Lys Ser Val Val Ile Asn Cys Thr Arg Pro Ser Asn Asn Thr Arg
            260                 265                 270

Thr Ser Ile Thr Ile Gly Pro Gly Gln Val Phe Tyr Arg Thr Gly Asp
        275                 280                 285

Ile Ile Gly Asp Ile Arg Lys Ala Tyr Cys Glu Ile Asn Gly Thr Glu
    290                 295                 300

Trp Asn Lys Ala Leu Lys Gln Val Thr Glu Lys Leu Lys Glu His Phe
305                 310                 315                 320

Asn Asn Lys Pro Ile Ile Phe Gln Pro Pro Ser Gly Gly Asp Leu Glu
                325                 330                 335

Ile Thr Met His His Phe Asn Cys Arg Gly Glu Phe Phe Tyr Cys Asn
            340                 345                 350

Thr Thr Arg Leu Phe Asn Asn Thr Cys Ile Ala Asn Gly Thr Ile Glu
        355                 360                 365
```

```
Gly Cys Asn Gly Asn Ile Thr Leu Pro Cys Lys Ile Lys Gln Ile Ile
    370                 375                 380
Asn Met Trp Gln Gly Ala Gly Gln Ala Met Tyr Ala Pro Pro Ile Ser
385                 390                 395                 400
Gly Thr Ile Asn Cys Val Ser Asn Ile Thr Gly Ile Leu Leu Thr Arg
                405                 410                 415
Asp Gly Gly Ala Thr Asn Asn Thr Asn Asn Glu Thr Phe Arg Pro Gly
                420                 425                 430
Gly Gly Asn Ile Lys Asp Asn Trp Arg Asn Glu Leu Tyr Lys Tyr Lys
                435                 440                 445
Val Val Gln Ile Glu Pro Leu Gly Val Ala Pro Thr Arg Ala Lys Arg
    450                 455                 460
Arg Val Val Glu Arg Glu Lys Arg
465                 470

<210> SEQ ID NO 2
<211> LENGTH: 501
<212> TYPE: PRT
<213> ORGANISM: Human immunodeficiency virus 1

<400> SEQUENCE: 2

Met Arg Val Lys Glu Thr Gln Met Asn Trp Pro Asn Leu Trp Lys Trp
1               5                   10                  15
Gly Thr Leu Ile Leu Gly Leu Val Ile Ile Cys Ser Ala Val Pro Val
                20                  25                  30
Trp Lys Glu Ala Asp Thr Thr Leu Phe Cys Ala Ser Asp Ala Lys Ala
            35                  40                  45
His Glu Thr Glu Val His Asn Val Trp Ala Thr His Ala Cys Val Pro
    50                  55                  60
Thr Asp Pro Asn Pro Gln Glu Ile Asp Leu Glu Asn Val Thr Glu Asn
65                  70                  75                  80
Phe Asn Met Trp Lys Asn Asn Met Val Glu Gln Met Gln Glu Asp Val
                85                  90                  95
Ile Ser Leu Trp Asp Gln Ser Leu Lys Pro Cys Val Lys Leu Thr Pro
            100                 105                 110
Pro Cys Val Thr Leu His Cys Thr Asn Ala Asn Leu Thr Lys Ala Asn
            115                 120                 125
Leu Thr Asn Val Asn Asn Arg Thr Asn Val Ser Asn Ile Ile Gly Asn
    130                 135                 140
Ile Thr Asp Glu Val Arg Asn Cys Ser Phe Asn Met Thr Thr Glu Leu
145                 150                 155                 160
Arg Asp Lys Lys Gln Lys Val His Ala Leu Phe Tyr Lys Leu Asp Ile
                165                 170                 175
Val Pro Ile Glu Asp Asn Asn Asp Ser Ser Glu Tyr Arg Leu Ile Asn
            180                 185                 190
Cys Asn Thr Ser Val Ile Lys Gln Pro Cys Pro Lys Ile Ser Phe Asp
            195                 200                 205
Pro Ile Pro Ile His Tyr Cys Thr Pro Ala Gly Tyr Ala Ile Leu Lys
    210                 215                 220
Cys Asn Asp Lys Asn Phe Asn Gly Thr Gly Pro Cys Lys Asn Val Ser
225                 230                 235                 240
Ser Val Gln Cys Thr His Gly Ile Lys Pro Val Val Ser Thr Gln Leu
                245                 250                 255
Leu Leu Asn Gly Ser Leu Ala Glu Glu Glu Ile Ile Ile Arg Ser Glu
            260                 265                 270
```

Asn Leu Thr Asn Asn Ala Lys Thr Ile Ile Val His Leu Asn Lys Ser
    275                 280                 285

Val Val Ile Asn Cys Thr Arg Pro Ser Asn Asn Thr Arg Thr Ser Ile
    290                 295                 300

Thr Ile Gly Pro Gly Gln Val Phe Tyr Arg Thr Gly Asp Ile Ile Gly
305                 310                 315                 320

Asp Ile Arg Lys Ala Tyr Cys Glu Ile Asn Gly Thr Glu Trp Asn Lys
                325                 330                 335

Ala Leu Lys Gln Val Thr Glu Lys Leu Lys Glu His Phe Asn Asn Lys
                340                 345                 350

Pro Ile Ile Phe Gln Pro Pro Ser Gly Gly Asp Leu Glu Ile Thr Met
            355                 360                 365

His His Phe Asn Cys Arg Gly Glu Phe Phe Tyr Cys Asn Thr Thr Arg
    370                 375                 380

Leu Phe Asn Asn Thr Cys Ile Ala Asn Gly Thr Ile Glu Gly Cys Asn
385                 390                 395                 400

Gly Asn Ile Thr Leu Pro Cys Lys Ile Lys Gln Ile Ile Asn Met Trp
                405                 410                 415

Gln Gly Ala Gly Gln Ala Met Tyr Ala Pro Pro Ile Ser Gly Thr Ile
                420                 425                 430

Asn Cys Val Ser Asn Ile Thr Gly Ile Leu Leu Thr Arg Asp Gly Gly
            435                 440                 445

Ala Thr Asn Asn Thr Asn Asn Glu Thr Phe Arg Pro Gly Gly Gly Asn
    450                 455                 460

Ile Lys Asp Asn Trp Arg Asn Glu Leu Tyr Lys Tyr Lys Val Val Gln
465                 470                 475                 480

Ile Glu Pro Leu Gly Val Ala Pro Thr Arg Ala Lys Arg Arg Val Val
                485                 490                 495

Glu Arg Glu Lys Arg
            500

<210> SEQ ID NO 3
<211> LENGTH: 1533
<212> TYPE: DNA
<213> ORGANISM: Human immunodeficiency virus 1

<400> SEQUENCE: 3
aagcttgtcg acaccatgcg cgtgaaggag acccagatga actggcccaa cctgtggaag    60
tggggcaccc tgatcctggg cctggtgatc atctgctccg ccgtgccgt gtggaaggag    120 gccgacacca ccctgttctg cgcctccgac gccaaggccc acgagaccga ggtgcacaac    180
gtgtgggcca cccacgcctg cgtgcccacc gaccccaacc cccaggagat cgacctggag    240
aacgtgaccg agaacttcaa catgtggaag aacaacatgg tggagcagat gcaggaggac    300
gtgatctccc tgtgggacca gtccctgaag ccctgcgtga agctgacccc ccctgcgtg    360 accctgcact gcaccaacgc caacctgacc aaggccaacc tgaccaacgt gaacaaccgc    420
accaacgtgt ccaacatcat cggcaacatc accgacgagg tgcgcaactg ctccttcaac    480
atgaccaccg agctgcgcga caagaagcag aaggtgcacg ccctgttcta caagctggac    540
atcgtgccca tcgaggacaa caacgactcc tccgagtacc gcctgatcaa ctgcaacacc    600
tccgtgatca gcagccctg ccccaagatc tccttcgacc ccatccccat ccactactgc    660 accccgccg gctacgccat cctgaagtgc aacgacaaga acttcaacgg caccggcccc    720
tgcaagaacg tgtcctccgt gcagtgcacc cacggcatca gcccgtggt gtccacccag    780

```
ctgctgctga acggctccct ggccgaggag gagatcatca tccgctccga gaacctgacc    840
aacaacgcca agaccatcat cgtgcacctg aacaagtccg tggtgatcaa ctgcacccgc    900
ccctccaaca cacccgcac ctccatcacc atcggccccg ccaggtgtt ctaccgcacc      960 ggcgacatca tcggcgacat ccgcaaggcc tactgcgaga tcaacggcac cgagtggaac   1020
aaggccctga agcaggtgac cgagaagctg aaggagcact tcaacaacaa gcccatcatc   1080
ttccagcccc cctccggcgg cgacctggag atcaccatgc accacttcaa ctgccgcggc   1140
gagttcttct actgcaacac cacccgcctg ttcaacaaca cctgcatcgc caacggcacc   1200
atcgagggct gcaacggcaa catcaccctg ccctgcaaga tcaagcagat catcaacatg   1260
tggcagggcg ccggccaggc catgtacgcc ccccccatct ccggcaccat caactgcgtg   1320
tccaacatca ccggcatcct gctgacccgc gacggcggcg ccaccaacaa caccaacaac   1380
gagaccttcc gccccggcgg cggcaacatc aaggacaact ggcgcaacga gctgtacaag   1440
tacaaggtgg tgcagatcga gcccctgggc gtggccccca cccgcgccaa cgccgcgtg    1500 gtggagcgcg agaagcgcta gggatcctct aga                                1533
```

<210> SEQ ID NO 4
<211> LENGTH: 509
<212> TYPE: PRT
<213> ORGANISM: Human immunodeficiency virus 1

<400> SEQUENCE: 4

```
Met Arg Val Lys Gly Ile Arg Lys Asn Tyr Gln His Leu Trp Arg Trp
1               5                   10                  15

Gly Thr Met Leu Leu Gly Ile Leu Met Ile Cys Ser Ala Val Pro Val
            20                  25                  30

Trp Lys Glu Ala Thr Thr Thr Leu Phe Cys Ala Ser Asp Ala Lys Ala
        35                  40                  45

Tyr Asp Thr Glu Val His Asn Val Trp Ala Thr His Ala Cys Val Pro
    50                  55                  60

Thr Asp Pro Asn Pro Gln Glu Leu Val Leu Ala Asn Val Thr Glu Asn
65                  70                  75                  80

Phe Asn Met Trp Asn Asn Thr Met Val Glu Gln Met His Glu Asp Ile
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asp Val Thr Asn Ala Thr Asn Ile
        115                 120                 125

Asn Ala Thr Asn Ile Asn Asn Ser Ser Gly Gly Val Glu Ser Gly Glu
    130                 135                 140

Ile Lys Asn Cys Ser Phe Asn Ile Thr Thr Ser Val Arg Asp Lys Val
145                 150                 155                 160

Gln Lys Glu Tyr Ala Leu Phe Tyr Lys Leu Asp Ile Val Pro Ile Thr
                165                 170                 175

Asn Glu Ser Ser Lys Tyr Arg Leu Ile Ser Cys Asn Thr Ser Val Leu
            180                 185                 190

Thr Gln Ala Cys Pro Lys Val Ser Phe Glu Pro Ile Pro Ile His Tyr
        195                 200                 205

Cys Ala Pro Ala Gly Phe Ala Ile Leu Lys Cys Asn Asn Glu Thr Phe
    210                 215                 220

Asn Gly Lys Gly Pro Cys Ile Asn Val Ser Thr Val Gln Cys Thr His
225                 230                 235                 240
```

```
Gly Ile Arg Pro Val Val Ser Thr Gln Leu Leu Asn Gly Ser Leu
                245                 250                 255

Ala Glu Lys Glu Val Ile Ile Arg Ser Asp Asn Phe Ser Asp Asn Ala
            260                 265                 270

Lys Asn Ile Ile Val Gln Leu Lys Glu Tyr Val Lys Ile Asn Cys Thr
        275                 280                 285

Arg Pro Asn Asn Asn Thr Arg Lys Ser Ile His Ile Gly Pro Gly Arg
    290                 295                 300

Ala Phe Tyr Ala Thr Gly Glu Ile Ile Gly Asn Ile Arg Gln Ala His
305                 310                 315                 320

Cys Asn Ile Ser Arg Ser Lys Trp Asn Asp Thr Leu Lys Gln Ile Ala
                325                 330                 335

Ala Lys Leu Gly Glu Gln Phe Arg Asn Lys Thr Ile Val Phe Asn Pro
            340                 345                 350

Ser Ser Gly Gly Asp Leu Glu Ile Val Thr His Ser Phe Asn Cys Gly
        355                 360                 365

Gly Glu Phe Phe Tyr Cys Asn Thr Thr Lys Leu Phe Asn Ser Thr Trp
    370                 375                 380

Ile Arg Glu Gly Asn Asn Gly Thr Trp Asn Gly Thr Ile Gly Leu Asn
385                 390                 395                 400

Asp Thr Ala Gly Asn Asp Thr Ile Ile Leu Pro Cys Lys Ile Lys Gln
                405                 410                 415

Ile Ile Asn Met Trp Gln Glu Val Gly Lys Ala Met Tyr Ala Pro Pro
            420                 425                 430

Ile Arg Gly Gln Ile Arg Cys Ser Ser Asn Ile Thr Gly Leu Ile Leu
        435                 440                 445

Thr Arg Asp Gly Gly Lys Asp Asp Ser Asn Gly Ser Glu Ile Leu Glu
    450                 455                 460

Ile Phe Arg Pro Gly Gly Gly Asp Met Arg Asp Asn Trp Arg Ser Glu
465                 470                 475                 480

Leu Tyr Lys Tyr Lys Val Val Arg Ile Glu Pro Leu Gly Val Ala Pro
                485                 490                 495

Thr Arg Ala Arg Glu Arg Val Val Gln Lys Glu Lys Glu
            500                 505

<210> SEQ ID NO 5
<211> LENGTH: 1557
<212> TYPE: DNA
<213> ORGANISM: Human immunodeficiency virus 1

<400> SEQUENCE: 5
aagcttgtcg acaccatgcg cgtgaagggc atccgcaaga actaccagca cctgtggcgc      60
tggggcacca tgctgctggg catcctgatg atctgctccg ccgtgcccgt gtggaaggag     120
gccaccacca ccctgttctg cgcctccgac gccaaggcct acgacaccga ggtgcacaac     180
gtgtgggcca cccacgcctg cgtgcccacc gaccccaacc cccaggagct ggtgctggcc     240
aacgtgaccg agaacttcaa catgtggaac aacaccatgg tggagcagat gcacgaggac     300
atcatctccc tgtgggacca gtccctgaag ccctgcgtga agctgacccc cctgtgcgtg     360
accctgaact gcaccgacgt gaccaacgcc accaacatca cgccaccaa catcaacaac     420 tcctccggcg cgtggagtc cggcgagatc aagaactgct ccttcaacat caccacctcc     480
gtgcgcgaca aggtgcagaa ggagtacgcc ctgttctaca gctgcacat cgtgcccatc     540 accaacgagt cctccaagta ccgcctgatc tcctgcaaca cctccgtgct gacccaggcc     600
```

```
tgccccaagg tgtccttcga gcccatcccc atccactact gcgccccgc cggcttcgcc      660 atcctgaagt gcaacaacga gaccttcaac ggcaagggcc cctgcatcaa cgtgtccacc      720
gtgcagtgca cccacggcat ccgccccgtg gtgtccaccc agctgctgct gaacggctcc      780
ctggccgaga aggaggtgat catccgctcc gacaacttct ccgacaacgc caagaacatc      840
atcgtgcagc tgaaggagta cgtgaagatc aactgcaccc gccccaacaa caacacccgc      900
aagtccatcc acatcggccc cggccgcgcc ttctacgcca ccggcgagat catcggcaac      960
atccgccagg cccactgcaa catctcccgc tccaagtgga cgacaccct gaagcagatc     1020 gccgccaagc tgggcgagca gttccgcaac aagaccatcg tgttcaaccc ctcctccggc     1080
ggcgacctgg agatcgtgac ccactccttc aactgcggcg cgagttctt ctactgcaac     1140 accaccaagc tgttcaactc cacctggatt cgcgagggca caacggcac ctggaacggc     1200 accatcggcc tgaacgacac cgccggcaac gacaccatca tcctgccctg caagatcaag     1260
cagatcatca acatgtggca ggaggtgggc aaggccatgt acgccccccc catccgcggc     1320
cagatccgct gctcctccaa catcaccggc ctgatcctga cccgcgacgg cggcaaggac     1380
gactccaacg gctccgagat cctggagatc ttccgccccg gcggcggcga catgcgcgac     1440
aactggcgct ccgagctgta caagtacaag gtggtgcgca tcgagcccct gggcgtggcc     1500
ccaccccgcg cccgcgagcg cgtggtgcag aaggagaagg agtagggatc tctaga        1557

<210> SEQ ID NO 6
<211> LENGTH: 510
<212> TYPE: PRT
<213> ORGANISM: Human immunodeficiency virus 1

<400> SEQUENCE: 6

Met Arg Val Lys Gly Ile Arg Lys Asn Tyr Gln His Leu Trp Arg Trp
1               5                   10                  15

Gly Ile Trp Arg Trp Gly Ile Met Leu Leu Gly Thr Leu Met Ile Cys
            20                  25                  30

Ser Ala Val Pro Val Trp Lys Glu Ala Thr Thr Thr Leu Phe Cys Ala
        35                  40                  45

Ser Asp Ala Lys Ala Tyr Ser Pro Glu Lys His Asn Ile Trp Ala Thr
    50                  55                  60

His Ala Cys Val Pro Thr Asp Pro Asn Pro Gln Glu Leu Val Leu Gly
65                  70                  75                  80

Asn Val Thr Glu Asp Phe Asn Met Trp Lys Asn Asn Met Val Glu Gln
                85                  90                  95

Met His Glu Asp Ile Ile Ser Leu Trp Asp Gln Ser Leu Lys Pro Cys
            100                 105                 110

Val Lys Leu Thr Pro Leu Cys Val Thr Leu Asn Cys Thr Asp Leu Lys
        115                 120                 125

Asn Ser Ala Thr Asp Thr Asn Gly Thr Ser Gly Thr Asn Asn Arg Thr
    130                 135                 140

Val Glu Gln Gly Met Glu Thr Glu Ile Lys Asn Cys Ser Phe Asn Ile
145                 150                 155                 160

Thr Thr Gly Ile Gly Asn Lys Met Gln Lys Glu Tyr Ala Leu Phe Tyr
                165                 170                 175

Lys Leu Asp Val Val Pro Ile Asp Ser Asn Asn Asn Ser Asp Asn Thr
            180                 185                 190

Ser Tyr Arg Leu Ile Ser Cys Asn Thr Ser Val Val Thr Gln Ala Cys
        195                 200                 205
```

Pro Lys Thr Ser Phe Glu Pro Ile Pro Ile His Tyr Cys Ala Pro Ala
    210                 215                 220

Gly Phe Ala Ile Leu Lys Cys Asn Asn Lys Thr Phe Ser Gly Lys Gly
225                 230                 235                 240

Pro Cys Lys Asn Val Ser Thr Val Gln Cys Thr His Gly Ile Arg Pro
                245                 250                 255

Val Val Ser Thr Gln Leu Leu Leu Asn Gly Ser Leu Ala Glu Glu Glu
            260                 265                 270

Ile Val Ile Arg Ser Glu Asn Phe Thr Asn Asn Ala Lys Thr Ile Ile
        275                 280                 285

Val Gln Leu Asn Glu Ser Val Ile Ile Asn Cys Thr Arg Pro Asn Asn
    290                 295                 300

Asn Thr Arg Lys Gly Ile His Ile Gly Leu Gly Arg Ala Leu Tyr Ala
305                 310                 315                 320

Thr Gly Asp Ile Ile Gly Asp Ile Arg Gln Ala His Cys Asn Leu Ser
                325                 330                 335

Ser Lys Ser Trp Asn Lys Thr Leu Gln Gln Val Val Arg Lys Leu Arg
            340                 345                 350

Glu Gln Phe Gly Asn Lys Thr Ile Ala Phe Asn Gln Ser Ser Gly Gly
        355                 360                 365

Asp Gln Glu Ile Val Lys His Ser Phe Asn Cys Gly Gly Glu Phe Phe
    370                 375                 380

Tyr Cys Asp Thr Thr Gln Leu Phe Asn Ser Thr Trp Ser Ser Asn Asp
385                 390                 395                 400

Thr Trp Asn Ser Thr Gly Val Gln Asp Asn Asn Ile Thr Leu Pro Cys
                405                 410                 415

Arg Ile Lys Gln Ile Ile Asn Met Trp Gln Glu Val Gly Lys Ala Met
            420                 425                 430

Tyr Ala Pro Pro Ile Gln Gly Leu Ile Ser Cys Ser Ser Asn Ile Thr
        435                 440                 445

Gly Leu Leu Leu Thr Arg Asp Gly Gly Thr Asn Asn Thr Asn Ala Thr
    450                 455                 460

Glu Ile Phe Arg Pro Gly Gly Gly Asp Met Arg Asp Asn Trp Arg Ser
465                 470                 475                 480

Glu Leu Tyr Lys Tyr Lys Val Val Lys Ile Glu Pro Leu Gly Ile Ala
                485                 490                 495

Pro Thr Lys Ala Lys Arg Arg Val Val Gln Arg Glu Lys Arg
            500                 505                 510

<210> SEQ ID NO 7
<211> LENGTH: 1560
<212> TYPE: DNA
<213> ORGANISM: Human immunodeficiency virus 1

<400> SEQUENCE: 7
aagcttgtcg acaccatgcg cgtgaagggc atccgcaaga actaccagca cctgtggcgc      60
tggggcatct ggcgctgggg catcatgctg ctgggcaccc tgatgatctg ctccgccgtg     120
cccgtgtgga aggaggccac caccaccctg ttctgcgcct ccgacgccaa ggcctactcc     180
cccgagaagc acaacatctg gccacaccac gcctgcgtgc ccaccgaccc caacccccag     240
gagctggtgc tgggcaacgt gaccgaggac ttcaacatgt ggaagaacaa catggtggag     300
cagatgcacg aggacatcat ctccctgtgg gaccagtccc tgaagccctg cgtgaagctg     360
acccccctgt gcgtgaccct gaactgcacc gacctgaaga actccgccac cgacaccaac     420

-continued

```
ggcacctccg gcaccaacaa ccgcaccgtg gagcagggca tggagaccga gatcaagaac    480
tgctccttca acatcaccac cggcatcggc aacaagatgc agaaggagta cgccctgttc    540
tacaagctgg acgtggtgcc catcgactcc aacaacaact ccgacaacac ctcctaccgc    600
ctgatctcct gcaacacctc cgtggtgacc caggcctgcc ccaagacctc cttcgagccc    660
atccccatcc actactgcgc ccccgccggc ttcgccatcc tgaagtgcaa caacaagacc    720
ttctccggca agggcccctg caagaacgtg tccaccgtgc agtgcaccca cggcatccgc    780
cccgtggtgt ccacccagct gctgctgaac ggctccctgg ccgaggagga gatcgtgatc    840
cgctccgaga acttcaccaa caacgccaag accatcatcg tgcagctgaa cgagtccgtg    900
atcatcaact gcacccgccc caacaacaac acccgcaagg gcatccacat cggcctgggc    960
cgcgccctgt acgccaccgg cgacatcatc ggcgacatcc gccaggccca ctgcaacctg   1020
tcctccaagt cctggaacaa gaccctgcag caggtggtgc gcaagctgcg cgagcagttc   1080
ggcaacaaga ccatcgcctt caaccagtcc tccggcggcg accaggagat cgtgaagcac   1140
tccttcaact gcggcggcga gttcttctac tgcgacacca cccagctgtt caactccacc   1200
tggtcctcca cgacacctg gaactccacc ggcgtgcagg acaacaacat caccctgccc   1260
tgccgcatca agcagatcat caacatgtgg caggaggtgg gcaaggccat gtacgccccc   1320
cccatccagg gcctgatctc ctgctcctcc aacatcaccg gctgctgct gacccgcgac   1380 ggcggcacca acaacaccaa cgccaccgag atcttccgcc ccggcggcgg cgacatgcgc   1440
gacaactggc gctccgagct gtacaagtac aaggtggtga agatcgagcc cctgggcatc   1500
gcccccacca aggccaagcg ccgcgtggtg cagcgcgaga gcgctaggg atcctctaga   1560
```

<210> SEQ ID NO 8
<211> LENGTH: 492
<212> TYPE: PRT
<213> ORGANISM: Human immunodeficiency virus 1

<400> SEQUENCE: 8

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Val Pro Val
            20                  25                  30

Trp Lys Glu Ala Asn Thr Thr Leu Phe Cys Ala Ser Asp Ala Lys Ala
        35                  40                  45

Tyr Asp Thr Glu Val His Asn Val Trp Ala Thr His Ala Cys Val Pro
    50                  55                  60

Thr Asp Pro Asn Pro Gln Glu Ile Val Leu Glu Asn Val Thr Glu Asn
65                  70                  75                  80

Phe Asn Met Trp Lys Asn Asn Met Val Glu Gln Met His Glu Asp Ile
                85                  90                  95

Ile Ser Leu Trp Asp Gln Ser Leu Lys Pro Cys Val Lys Leu Thr Pro
            100                 105                 110

Leu Cys Val Thr Leu Asn Cys Thr Asn Val Asn Val Thr Asn Thr Thr
        115                 120                 125

Asn Asn Thr Glu Glu Lys Gly Glu Ile Lys Asn Cys Ser Phe Asn Ile
    130                 135                 140

Thr Thr Glu Ile Arg Asp Lys Lys Gln Lys Val Tyr Ala Leu Phe Tyr
145                 150                 155                 160

Arg Leu Asp Val Val Pro Ile Asp Asp Asn Asn Asn Ser Ser Asn
                165                 170                 175
```

```
Tyr Arg Leu Ile Asn Cys Asn Thr Ser Ala Ile Thr Gln Ala Cys Pro
                180                 185                 190
Lys Val Ser Phe Glu Pro Ile Pro Ile His Tyr Cys Ala Pro Ala Gly
            195                 200                 205
Phe Ala Ile Leu Lys Cys Asn Asp Lys Lys Phe Asn Gly Thr Gly Pro
210                 215                 220
Cys Lys Asn Val Ser Thr Val Gln Cys Thr His Gly Ile Lys Pro Val
225                 230                 235                 240
Val Ser Thr Gln Leu Leu Leu Asn Gly Ser Leu Ala Glu Glu Glu Ile
                245                 250                 255
Ile Ile Arg Ser Glu Asn Ile Thr Asn Asn Ala Lys Thr Ile Ile Val
                260                 265                 270
Gln Leu Asn Glu Ser Val Glu Ile Asn Cys Thr Arg Pro Asn Asn Asn
            275                 280                 285
Thr Arg Lys Ser Ile Arg Ile Gly Pro Gly Gln Ala Phe Tyr Ala Thr
        290                 295                 300
Gly Asp Ile Ile Gly Asp Ile Arg Gln Ala His Cys Asn Ile Ser Gly
305                 310                 315                 320
Thr Lys Trp Asn Lys Thr Leu Gln Gln Val Ala Lys Lys Leu Arg Glu
                325                 330                 335
His Phe Asn Asn Lys Thr Ile Ile Phe Lys Pro Ser Ser Gly Gly Asp
                340                 345                 350
Leu Glu Ile Thr Thr His Ser Phe Asn Cys Arg Gly Glu Phe Phe Tyr
            355                 360                 365
Cys Asn Thr Ser Gly Leu Phe Asn Ser Thr Trp Ile Gly Asn Gly Thr
        370                 375                 380
Lys Asn Asn Asn Asn Thr Asn Asp Thr Ile Thr Leu Pro Cys Arg Ile
385                 390                 395                 400
Lys Gln Ile Ile Asn Met Trp Gln Gly Val Gly Gln Ala Met Tyr Ala
                405                 410                 415
Pro Pro Ile Glu Gly Lys Ile Thr Cys Lys Ser Asn Ile Thr Gly Leu
                420                 425                 430
Leu Leu Thr Arg Asp Gly Gly Asn Asn Asn Thr Asn Glu Thr Glu Ile
            435                 440                 445
Phe Arg Pro Gly Gly Gly Asp Met Arg Asp Asn Trp Arg Ser Glu Leu
        450                 455                 460
Tyr Lys Tyr Lys Val Val Lys Ile Glu Pro Leu Gly Val Ala Pro Thr
465                 470                 475                 480
Lys Ala Lys Arg Arg Val Val Glu Arg Glu Lys Arg
                485                 490
```

<210> SEQ ID NO 9
<211> LENGTH: 1506
<212> TYPE: DNA
<213> ORGANISM: Human immunodeficiency virus 1

<400> SEQUENCE: 9

```
aagcttgtcg acaccatgcg cgtgcgcggc atccagcgca actgccagca cctgtggcgc      60
tggggcaccc tgatcctggg catgctgatg atctgctccg ccgtgcccgt gtggaaggag     120
gccaacacca ccctgttctg cgcctccgac gccaaggcct acgacaccga ggtgcacaac     180
gtgtgggcca cccacgcctg cgtgcccacc gaccccaacc cccaggagat cgtgctggag     240
aacgtgaccg agaacttcaa catgtggaag aacaacatgg tggagcagat gcacgaggac     300
```

```
atcatctccc tgtgggacca gtccctgaag ccctgcgtga agctgacccc cctgtgcgtg    360
accctgaact gcaccaacgt gaacgtgacc aacaccacca caacaccgag gagaagggc    420 gagatcaaga actgctcctt caacatcacc accgagatcc gcgacaagaa gcagaaggtg    480
tacgccctgt tctaccgcct ggacgtggtg cccatcgacg acaacaacaa caactcctcc    540
aactaccgcc tgatcaactg caacacctcc gccatcaccc aggcctgccc caaggtgtcc    600
ttcgagccca tccccatcca ctactgcgcc ccgccggct tcgccatcct gaagtgcaac    660
gacaagaagt tcaacggcac cggcccctgc aagaacgtgt ccaccgtgca gtgcacccac    720
ggcatcaagc ccgtggtgtc cacccagctg ctgctgaacg gctccctggc cgaggaggag    780
atcatcatcc gctccgagaa catcaccaac aacgccaaga ccatcatcgt gcagctgaac    840
gagtccgtgg agatcaactg cacccgcccc aacaacaaca cccgcaagtc catccgcatc    900
ggccccggcc aggccttcta cgccaccggc gacatcatcg gcgacatccg ccaggcccac    960
tgcaacatct ccggcaccaa gtggaacaag accctgcagc aggtggccaa gaagctgcgc    1020
gagcacttca acaacaagac catcatcttc aagccctcct ccggcggcga cctggagatc    1080
accacccact ccttcaactg ccgcggcgag ttcttctact gcaacacctc cggcctgttc    1140
aactccacct ggatcggcaa cggcaccaag aacaacaaca caccaacga caccatcacc    1200 ctgcccctgcc gcatcaagca gatcatcaac atgtggcagg gcgtgggcca ggccatgtac    1260
gcccccccca tcgagggcaa gatcacctgc aagtccaaca tcaccggcct gctgctgacc    1320
cgcgacggcg gcaacaacaa caccaacgag accgagatct ccgccccgg cggcggcgac    1380 atgcgcgaca ctggcgctc cgagctgtac aagtacaagg tggtgaagat cgagcccctg    1440
ggcgtggccc ccaccaaggc caagcgccgc gtggtggagc gcgagaagcg ctagggatcc    1500
tctaga                                                                1506
```

<210> SEQ ID NO 10
<211> LENGTH: 490
<212> TYPE: PRT
<213> ORGANISM: Human immunodeficiency virus 1

<400> SEQUENCE: 10

```
Met Arg Val Arg Gly Ile Trp Lys Asn Trp Pro Gln Trp Leu Ile Trp
1               5                   10                  15

Ser Ile Leu Gly Phe Trp Ile Gly Asn Met Glu Gly Ser Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Ala Asn Val Thr Glu Asn
65                  70                  75                  80

Phe Asn Met Trp Lys Asn Asp Met Val Glu Gln Met His Glu Asp Ile
                85                  90                  95

Ile Ser Leu Trp Asp Glu Ser Leu Lys Pro Cys Val Lys Leu Thr Pro
            100                 105                 110

Leu Cys Val Thr Leu Asn Cys Thr Asn Val Lys Gly Asn Glu Ser Asp
        115                 120                 125

Thr Ser Glu Val Met Lys Asn Cys Ser Phe Lys Ala Thr Thr Glu Leu
    130                 135                 140

Lys Asp Lys Lys His Lys Val His Ala Leu Phe Tyr Lys Leu Asp Val
145                 150                 155                 160
```

Val Pro Leu Asn Gly Asn Ser Ser Ser Gly Glu Tyr Arg Leu Ile
            165                 170                 175

Asn Cys Asn Thr Ser Ala Ile Thr Gln Ala Cys Pro Lys Val Ser Phe
        180                 185                 190

Asp Pro Ile Pro Leu His Tyr Cys Ala Pro Ala Gly Phe Ala Ile Leu
    195                 200                 205

Lys Cys Asn Asn Lys Thr Phe Asn Gly Thr Gly Pro Cys Arg Asn Val
210                 215                 220

Ser Thr Val Gln Cys Thr His Gly Ile Lys Pro Val Val Ser Thr Gln
225                 230                 235                 240

Leu Leu Leu Asn Gly Ser Leu Ala Glu Glu Ile Ile Ile Arg Ser
                245                 250                 255

Glu Asn Leu Thr Asn Asn Ala Lys Thr Ile Ile Val His Leu Asn Glu
            260                 265                 270

Ser Val Asn Ile Val Cys Thr Arg Pro Asn Asn Asn Thr Arg Lys Ser
        275                 280                 285

Ile Arg Ile Gly Pro Gly Gln Thr Phe Tyr Ala Thr Gly Asp Ile Ile
    290                 295                 300

Gly Asn Ile Arg Gln Ala His Cys Asn Ile Asn Glu Ser Lys Trp Asn
305                 310                 315                 320

Asn Thr Leu Gln Lys Val Gly Glu Glu Leu Ala Lys His Phe Pro Ser
                325                 330                 335

Lys Thr Ile Lys Phe Glu Pro Ser Ser Gly Gly Asp Leu Glu Ile Thr
            340                 345                 350

Thr His Ser Phe Asn Cys Arg Gly Glu Phe Phe Tyr Cys Asn Thr Ser
        355                 360                 365

Asp Leu Phe Asn Gly Thr Tyr Arg Asn Gly Thr Tyr Asn His Thr Gly
    370                 375                 380

Arg Ser Ser Asn Gly Thr Ile Thr Leu Gln Cys Lys Ile Lys Gln Ile
385                 390                 395                 400

Ile Asn Met Trp Gln Glu Val Gly Arg Ala Ile Tyr Ala Pro Pro Ile
                405                 410                 415

Glu Gly Glu Ile Thr Cys Asn Ser Asn Ile Thr Gly Leu Leu Leu Leu
            420                 425                 430

Arg Asp Gly Gly Gln Ser Asn Glu Thr Asn Asp Thr Glu Thr Phe Arg
        435                 440                 445

Pro Gly Gly Gly Asp Met Arg Asp Asn Trp Arg Ser Glu Leu Tyr Lys
    450                 455                 460

Tyr Lys Val Val Glu Ile Lys Pro Leu Gly Val Ala Pro Thr Glu Ala
465                 470                 475                 480

Lys Arg Arg Val Val Glu Arg Glu Lys Arg
                485                 490

<210> SEQ ID NO 11
<211> LENGTH: 1500
<212> TYPE: DNA
<213> ORGANISM: Human immunodeficiency virus 1

<400> SEQUENCE: 11
aagcttgtcg acaccatgcg cgtgcgcggc atctggaaga actggcccca gtggctgatc       60
tggtccatcc tgggcttctg gatcggcaac atggagggct ccgtgcccgt gtggaaggag      120
gccaagacca ccctgttctg cgcctccgac gccaaggcct acgagaagga ggtgcacaac      180
gtgtgggcca cccacgcctg cgtgcccacc gaccccaacc cccaggagat ggtgctggcc      240

```
aacgtgaccg agaacttcaa catgtggaag aacgacatgg tggagcagat gcacgaggac    300
atcatctccc tgtgggacga gtccctgaag ccctgcgtga agctgacccc cctgtgcgtg    360
accctgaact gcaccaacgt gaagggcaac gagtccgaca cctccgaggt gatgaagaac    420
tgctccttca aggccaccac cgagctgaag acaagaagc acaaggtgca cgccctgttc    480
tacaagctgg acgtggtgcc cctgaacggc aactcctcct cctccggcga gtaccgcctg    540
atcaactgca acacctccgc catcacccag gcctgcccca aggtgtcctt cgaccccatc    600
cccctgcact actgcgcccc cgccggcttc gccatcctga agtgcaacaa caagaccttc    660
aacggcaccg cccctgccg caacgtgtcc accgtgcagt gcacccacgg catcaagccc    720
gtggtgtcca cccagctgct gctgaacggc tccctggccg aggaggagat catcatccgc    780
tccgagaacc tgaccaacaa cgccaagacc atcatcgtgc acctgaacga gtccgtgaac    840
atcgtgtgca cccgccccaa caacaacacc cgcaagtcca tccgcatcgg ccccggccag    900
accttctacg ccaccggcga catcatcggc aacatccgcc aggccactg caacatcaac    960
gagtccaagt ggaacaacac cctgcagaag gtgggcgagg agctggccaa gcacttcccc   1020
tccaagacca tcaagttcga gccctcctcc ggcggcgacc tggagatcac cacccactcc   1080
ttcaactgcc gcggcgagtt cttctactgc aacacctccg acctgttcaa cggcacctac   1140
cgcaacggca cctacaacca caccggccgc tcctccaacg caccatcac cctgcagtgc   1200
aagatcaagc agatcatcaa catgtggcag gaggtgggcc gcgccatcta cgccccccc    1260
atcgagggcg agatcacctg caactccaac atcaccggcc tgctgctgct gcgcgacggc   1320
ggccagtcca acgagaccaa cgacaccgag accttccgcc ccggcggcgg cgacatgcgc   1380
gacaactggc gctccgagct gtacaagtac aaggtggtgg agatcaagcc cctgggcgtg   1440
gcccccaccg aggccaagcg ccgcgtggtg gagcgcgaga gcgctaggg atcctctaga   1500
```

<210> SEQ ID NO 12
<211> LENGTH: 499
<212> TYPE: PRT
<213> ORGANISM: Human immunodeficiency virus 1

<400> SEQUENCE: 12

Met Arg Val Arg Gly Met Leu Arg Asn Cys Gln Gln Trp Trp Ile Trp
1               5                   10                  15

Gly Ile Leu Gly Phe Trp Met Leu Met Ile Cys Ser Val Val Pro Val
            20                  25                  30

Trp Lys Glu Ala Lys Thr Thr Leu Phe Cys Ala Ser Asp Ala Arg Ala
        35                  40                  45

Tyr Glu Arg Glu Val His Asn Val Trp Ala Thr His Ala Cys Val Pro
    50                  55                  60

Thr Asp Pro Asn Pro Gln Glu Met Val Leu Val Asn Val Thr Glu Asn
65                  70                  75                  80

Phe Asn Met Trp Lys Asn Asp Met Val Asp Gln Met His Glu Asp Ile
                85                  90                  95

Ile Ser Leu Trp Asp Gln Ser Leu Lys Pro Cys Val Lys Leu Thr Pro
            100                 105                 110

Leu Cys Val Ile Leu Glu Cys Asn Asn Ala Asn Gly Thr Thr Asn Asn
        115                 120                 125

Gly Ser Val Ile Val Val Asn Glu Asn Ser Thr Met Tyr Gly Glu Ile
    130                 135                 140

Gln Asn Cys Ser Phe Lys Val Asn Ser Glu Ile Lys Gly Lys Lys Gln

```
            145                 150                 155                 160
Asp Val Tyr Ala Leu Phe Asn Ser Leu Asp Ile Val Lys Leu Tyr Asn
                165                 170                 175

Asn Gly Thr Ser Gln Tyr Arg Leu Ile Asn Cys Asn Thr Ser Thr Leu
            180                 185                 190

Thr Gln Ala Cys Pro Lys Val Ser Phe Asp Pro Ile Pro Ile His Tyr
        195                 200                 205

Cys Ala Pro Ala Gly Tyr Ala Ile Leu Lys Cys Asn Asn Lys Thr Phe
210                 215                 220

Asn Gly Thr Gly Pro Cys Asn Asn Val Ser Thr Val Gln Cys Thr His
225                 230                 235                 240

Gly Ile Lys Pro Val Val Ser Thr Gln Leu Leu Leu Asn Gly Ser Leu
                245                 250                 255

Ala Glu Gly Glu Ile Ile Ile Arg Ser Lys Asn Leu Thr Asp Asn Thr
            260                 265                 270

Lys Thr Ile Ile Val His Leu Asn Glu Ser Ile Lys Ile Asn Cys Ile
        275                 280                 285

Arg Pro Asn Asn Asn Thr Arg Arg Ser Ile Arg Ile Gly Pro Gly Gln
290                 295                 300

Ala Phe Tyr Ala Ala Asn Gly Ile Val Gly Asn Ile Arg Gln Ala His
305                 310                 315                 320

Cys Asn Ile Ser Glu Gly Glu Trp Asn Lys Thr Leu Tyr Arg Val Ser
                325                 330                 335

Arg Lys Leu Ala Glu His Phe Pro Gly Lys Glu Ile Lys Phe Lys Pro
            340                 345                 350

His Ser Gly Gly Asp Leu Glu Ile Thr Thr His Ser Phe Asn Cys Arg
        355                 360                 365

Gly Glu Phe Phe Tyr Cys Asn Thr Ser Lys Leu Phe Asn Gly Thr Tyr
    370                 375                 380

Asn Gly Thr Tyr Thr Asn Asn Asp Thr Asn Ser Thr Ile Ile Leu Pro
385                 390                 395                 400

Cys Arg Ile Lys Gln Ile Ile Asn Met Trp Gln Glu Val Gly Gln Ala
                405                 410                 415

Met Tyr Ala Pro Pro Ile Glu Gly Ile Ile Ala Cys Asn Ser Thr Ile
            420                 425                 430

Thr Gly Leu Leu Leu Thr Arg Asp Gly Gly Asp Lys Asn Gly Ser Lys
        435                 440                 445

Pro Glu Ile Phe Arg Pro Gly Gly Gly Asp Met Arg Asp Asn Trp Arg
    450                 455                 460

Ser Glu Leu Tyr Lys Tyr Lys Val Val Glu Ile Lys Pro Leu Gly Ile
465                 470                 475                 480

Ala Pro Thr Lys Ala Lys Arg Arg Val Val Glu Lys Glu Lys Thr Ile
                485                 490                 495

Gln Lys Arg

<210> SEQ ID NO 13
<211> LENGTH: 1527
<212> TYPE: DNA
<213> ORGANISM: Human immunodeficiency virus 1

<400> SEQUENCE: 13
aagcttgtcg acaccatgcg cgtgcgcggc atgctgcgca actgccagca gtggtggatc    60
tggggcatcc tgggcttctg gatgctgatg atctgctccg tggtgcccgt gtggaaggag   120
```

```
gccaagacca ccctgttctg cgcctccgac gcccgcgcct acgagcgcga ggtgcacaac    180
gtgtgggcca cccacgcctg cgtgcccacc gaccccaacc cccaggagat ggtgctggtg    240
aacgtgaccg agaacttcaa catgtggaag aacgacatgg tggaccagat gcacgaggac    300
atcatctccc tgtgggacca gtccctgaag ccctgcgtga agctgacccc cctgtgcgtg    360
atcctggagt gcaacaacgc caacggcacc accaacaacg gctccgtgat cgtggtgaac    420
gagaactcca ccatgtacgg cgagatccag aactgctcct tcaaggtgaa ctccgagatc    480
aagggcaaga agcaggacgt gtacgccctg ttcaactccc tggacatcgt gaagctgtac    540
aacaacggca cctcccagta ccgcctgatc aactgcaaca cctccaccct gacccaggcc    600
tgccccaagg tgtccttcga ccccatcccc atccactact gcgcccccgc cggctacgcc    660
atcctgaagt gcaacaacaa gaccttcaac ggcaccggcc cctgcaacaa cgtgtccacc    720
gtgcagtgca cccacggcat caagcccgtg gtgtccaccc agctgctgct gaacggctcc    780
ctggccgagg gcgagatcat catccgctcc aagaacctga ccgacaacac caagaccatc    840
atcgtgcacc tgaacgagtc catcaagatc aactgcatcc gccccaacaa caacacccgc    900
cgctccatcc gcatcggccc cggccaggcc ttctacgccg ccaacggcat cgtgggcaac    960
atcgccaggc ccactgcaa catctccgag ggcgagtgga caagaccct gtaccgcgtg    1020
tcccgcaagc tggccgagca cttccccggc aaggagatca gttcaagccc cactccggc    1080
ggcgacctgg agatcaccac ccactccttc aactgccgcg cgagttctt ctactgcaac    1140
acctccaagc tgttcaacgg cacctacaac ggcacctaca ccaacaacga caccaactcc    1200
accatcatcc tgccctgccg catcaagcag atcatcaaca tgtggcagga ggtgggccag    1260
gccatgtacg ccccccccat cgagggcatc atcgcctgca actccaccat caccggcctg    1320
ctgctgaccc gcgacggcgg cgacaagaac ggctccaagc ccgagatctt ccgcccggc    1380
ggcggcgaca tgcgcgacaa ctggcgctcc gagctgtaca agtacaaggt ggtggagatc    1440
aagcccctgg gcatcgcccc caccaaggcc aagcgccgcg tggtggagaa ggagaagacc    1500
atccagaagc gctagggatc ctctaga                                      1527
```

<210> SEQ ID NO 14
<211> LENGTH: 693
<212> TYPE: PRT
<213> ORGANISM: Human immunodeficiency virus 1

<400> SEQUENCE: 14

Met Arg Val Lys Gly Ile Arg Lys Asn Tyr Gln His Leu Trp Arg Trp
1               5                   10                  15

Gly Thr Met Leu Leu Gly Ile Leu Met Ile Cys Ser Ala Ala Ala Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Leu Val Leu Ala Asn Val Thr Glu Asn Phe Asn Met Trp Asn
                85                  90                  95

Asn Thr Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

```
Asn Cys Thr Asp Val Thr Asn Ala Thr Asn Ile Asn Ala Thr Asn Ile
    130                 135                 140

Asn Asn Ser Ser Gly Gly Val Glu Ser Gly Glu Ile Lys Asn Cys Ser
145                 150                 155                 160

Phe Asn Ile Thr Thr Ser Val Arg Asp Lys Val Gln Lys Glu Tyr Ala
                165                 170                 175

Leu Phe Tyr Lys Leu Asp Ile Val Pro Ile Thr Asn Glu Ser Ser Lys
                180                 185                 190

Tyr Arg Leu Ile Ser Cys Asn Thr Ser Val Leu Thr Gln Ala Cys Pro
            195                 200                 205

Lys Val Ser Phe Glu Pro Ile Pro Ile His Tyr Cys Ala Pro Ala Gly
        210                 215                 220

Phe Ala Ile Leu Lys Cys Asn Asn Glu Thr Phe Asn Gly Lys Gly Pro
225                 230                 235                 240

Cys Ile Asn Val Ser Thr Val Gln Cys Thr His Gly Ile Arg Pro Val
                245                 250                 255

Val Ser Thr Gln Leu Leu Leu Asn Gly Ser Leu Ala Glu Lys Glu Val
                260                 265                 270

Ile Ile Arg Ser Asp Asn Phe Ser Asp Asn Ala Lys Asn Ile Ile Val
            275                 280                 285

Gln Leu Lys Glu Tyr Val Lys Ile Asn Cys Thr Arg Pro Asn Asn Asn
        290                 295                 300

Thr Arg Lys Ser Ile His Ile Gly Pro Gly Arg Ala Phe Tyr Ala Thr
305                 310                 315                 320

Gly Glu Ile Ile Gly Asn Ile Arg Gln Ala His Cys Asn Ile Ser Arg
                325                 330                 335

Ser Lys Trp Asn Asp Thr Leu Lys Gln Ile Ala Ala Lys Leu Gly Glu
                340                 345                 350

Gln Phe Arg Asn Lys Thr Ile Val Phe Asn Pro Ser Ser Gly Gly Asp
            355                 360                 365

Leu Glu Ile Val Thr His Ser Phe Asn Cys Gly Gly Glu Phe Phe Tyr
        370                 375                 380

Cys Asn Thr Thr Lys Leu Phe Asn Ser Thr Trp Ile Arg Glu Gly Asn
385                 390                 395                 400

Asn Gly Thr Trp Asn Gly Thr Ile Gly Leu Asn Asp Thr Ala Gly Asn
                405                 410                 415

Asp Thr Ile Ile Leu Pro Cys Lys Ile Lys Gln Ile Ile Asn Met Trp
                420                 425                 430

Gln Glu Val Gly Lys Ala Met Tyr Ala Pro Pro Ile Arg Gly Gln Ile
        435                 440                 445

Arg Cys Ser Ser Asn Ile Thr Gly Leu Ile Leu Thr Arg Asp Gly Gly
450                 455                 460

Lys Asp Asp Ser Asn Gly Ser Glu Ile Leu Glu Ile Phe Arg Pro Gly
465                 470                 475                 480

Gly Gly Asp Met Arg Asp Asn Trp Arg Ser Glu Leu Tyr Lys Tyr Lys
                485                 490                 495

Val Val Arg Ile Glu Pro Leu Gly Val Ala Pro Thr Arg Ala Arg Glu
            500                 505                 510

Arg Val Val Gln Lys Glu Lys Glu Ala Val Gly Leu Gly Ala Met Phe
        515                 520                 525

Leu Gly Phe Leu Gly Ala Ala Gly Ser Ala Met Gly Ala Ala Ser Met
    530                 535                 540
```

```
Thr Leu Thr Val Gln Ala Arg Gln Leu Leu Ser Gly Ile Val Gln Gln
545                 550                 555                 560
Gln Asn Asn Leu Leu Arg Ala Ile Glu Ala Gln Gln His Met Leu Gln
                565                 570                 575
Leu Thr Val Trp Gly Ile Lys Gln Leu Gln Ala Arg Val Leu Ala Val
            580                 585                 590
Glu Arg Tyr Leu Lys Asp Gln Gln Leu Leu Gly Ile Trp Gly Cys Ser
        595                 600                 605
Gly Lys Leu Ile Cys Thr Thr Asp Val Pro Trp Asp Thr Ser Trp Ser
    610                 615                 620
Asn Lys Thr Leu Asp Asp Ile Trp Gly Ser Asn Met Thr Trp Met Glu
625                 630                 635                 640
Trp Glu Arg Glu Ile Asp Asn Tyr Thr Ser Thr Ile Tyr Thr Leu Leu
                645                 650                 655
Glu Glu Ala Gln Tyr Gln Gln Glu Lys Asn Glu Lys Glu Leu Leu Glu
            660                 665                 670
Leu Asp Lys Trp Ala Ser Leu Trp Asn Trp Phe Asp Ile Thr Asn Trp
        675                 680                 685
Leu Trp Tyr Ile Arg
    690

<210> SEQ ID NO 15
<211> LENGTH: 2088
<212> TYPE: DNA
<213> ORGANISM: Human immunodeficiency virus 1

<400> SEQUENCE: 15
atgcgcgtga agggcatccg caagaactac cagcacctgt ggcgctgggg caccatgctg      60
ctgggcatcc tgatgatctg ctccgccgcc gcccagctgt gggtgaccgt gtactacggc     120
gtgcccgtgt ggaaggaggc caccaccacc ctgttctgcg cctccgacgc caaggcctac     180
gacaccgagg tgcacaacgt gtgggccacc cacgcctgcg tgcccaccga ccccaacccc     240
caggagctgg tgctggccaa cgtgaccgag aacttcaaca tgtggaacaa caccatggtg     300
gagcagatgc acgaggacat catctcccty tgggaccagt ccctgaagcc ctgcgtgaag     360
ctgacccccc tgtgcgtgac cctgaactgc accgacgtga ccaacgccac caacatcaac     420
gccaccaaca tcaacaactc ctccggcggc gtggagtccg cgagatcaa gaactgctcc      480 ttcaacatca ccacctccgt gcgcgacaag gtgcagaagg agtacgccct gttctacaag     540
ctggacatcg tgcccatcac caacgagtcc tccaagtacc gcctgatctc ctgcaacacc     600
tccgtgctga cccaggcctg ccccaaggtg tccttcgagc ccatccccat ccactactgc     660
gcccccgccg gcttcgccat cctgaagtgc aacaacgaga ccttcaacgg caagggcccc     720
tgcatcaacg tgtccaccgt gcagtgcacc cacggcatcc gccccgtggt gtccacccag     780
ctgctgctga cggctccct ggccgagaag gaggtgatca tccgctccga caacttctcc     840
gacaacgcca agaacatcat cgtgcagctg aaggagtacg tgaagatcaa ctgcacccgc     900
cccaacaaca cacccgcaa gtccatccac atcggccccg gcgcgccctt ctacgccacc     960
ggcgagatca tcggcaacat ccgccaggcc cactgcaaca tctcccgctc caagtggaac    1020
gacaccctga gcagatcgc cgccaagctg ggcgagcagt tccgcaacaa gaccatcgtg    1080
ttcaacccct cctccggcgg cgacctggag atcgtgaccc actccttcaa ctgcggcggc    1140
gagttcttct actgcaacac caccaagctg ttcaactcca cctggatccg cgagggcaac    1200
aacggcacct ggaacggcac catcggcctg aacgacaccc ccggcaacga caccatcatc    1260
```

```
ctgccctgca agatcaagca gatcatcaac atgtggcagg aggtgggcaa ggccatgtac      1320
gcccccccca tccgcggcca gatccgctgc tcctccaaca tcaccggcct gatcctgacc      1380
cgcgacggcg gcaaggacga ctccaacggc tccgagatcc tggagatctt ccgccccggc      1440
ggcggcgaca tgcgcgacaa ctggcgctcc gagctgtaca agtacaaggt ggtgcgcatc      1500
gagcccctgg gcgtggcccc cacccgcgcc cgcgagcgcg tggtgcagaa ggagaaggag      1560
gccgtgggcc tggcgccat gttcctgggc ttcctgggcg ccgccggctc cgccatgggc       1620
gccgcctcca tgaccctgac cgtgcaggcc cgccagctgc tgtccggcat cgtgcagcag      1680
cagaacaacc tgctgcgcgc catcgaggcc cagcagcaca tgctgcagct gaccgtgtgg      1740
ggcatcaagc agctgcaggc cgcgtgctg ccgtggagc gctacctgaa ggaccagcag        1800
ctgctgggca tctggggctg ctccggcaag ctgatctgca ccaccgacgt gccctgggac      1860
acctcctggt ccaacaagac cctggacgac atctggggct ccaacatgac ctggatggag      1920
tgggagcgcg agatcgacaa ctacacctcc accatctaca ccctgctgga ggaggcccag      1980
taccagcagg agaagaacga gaaggagctg ctggagctgg acaagtgggc ctccctgtgg      2040
aactggttcg acatcaccaa ctggctgtgg tacatccgct agggatcc                   2088
```

<210> SEQ ID NO 16
<211> LENGTH: 693
<212> TYPE: PRT
<213> ORGANISM: Human immunodeficiency virus 1

<400> SEQUENCE: 16

```
Met Arg Val Lys Gly Ile Arg Lys Asn Tyr Gln His Leu Trp Arg Trp
1               5                   10                  15

Gly Ile Trp Arg Trp Gly Ile Met Leu Leu Gly Thr Leu Met Ile Cys
            20                  25                  30

Ser Ala Thr Glu Lys Leu Trp Val Thr Val Tyr Tyr Gly Val Pro Val
        35                  40                  45

Trp Lys Glu Ala Thr Thr Thr Leu Phe Cys Ala Ser Asp Ala Lys Ala
    50                  55                  60

Tyr Ser Pro Glu Lys His Asn Ile Trp Ala Thr His Ala Cys Val Pro
65                  70                  75                  80

Thr Asp Pro Asn Pro Gln Glu Leu Val Leu Gly Asn Val Thr Glu Asp
                85                  90                  95

Phe Asn Met Trp Lys Asn Asn Met Val Glu Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu Asn Cys Thr Asp Leu Lys Asn Ser Ala Thr Asp
    130                 135                 140

Thr Asn Gly Thr Ser Gly Thr Asn Arg Thr Val Glu Gln Gly Met
145                 150                 155                 160

Glu Thr Glu Ile Lys Asn Cys Ser Phe Asn Ile Thr Thr Gly Ile Gly
                165                 170                 175

Asn Lys Met Gln Lys Glu Tyr Ala Leu Phe Tyr Lys Leu Asp Val Val
            180                 185                 190

Pro Ile Asp Ser Asn Asn Asn Ser Asp Asn Thr Ser Tyr Arg Leu Ile
        195                 200                 205

Ser Cys Asn Thr Ser Val Val Thr Gln Ala Cys Pro Lys Thr Ser Phe
    210                 215                 220
```

```
Glu Pro Ile Pro Ile His Tyr Cys Ala Pro Ala Gly Phe Ala Ile Leu
225                 230                 235                 240

Lys Cys Asn Asn Lys Thr Phe Ser Gly Lys Gly Pro Cys Lys Asn Val
            245                 250                 255

Ser Thr Val Gln Cys Thr His Gly Ile Arg Pro Val Val Ser Thr Gln
        260                 265                 270

Leu Leu Leu Asn Gly Ser Leu Ala Glu Glu Ile Val Ile Arg Ser
    275                 280                 285

Glu Asn Phe Thr Asn Asn Ala Lys Thr Ile Ile Val Gln Leu Asn Glu
    290                 295                 300

Ser Val Ile Ile Asn Cys Thr Arg Pro Asn Asn Asn Thr Arg Lys Gly
305                 310                 315                 320

Ile His Ile Gly Leu Gly Arg Ala Leu Tyr Ala Thr Gly Asp Ile Ile
                325                 330                 335

Gly Asp Ile Arg Gln Ala His Cys Asn Leu Ser Ser Lys Ser Trp Asn
                340                 345                 350

Lys Thr Leu Gln Gln Val Val Arg Lys Leu Arg Glu Gln Phe Gly Asn
        355                 360                 365

Lys Thr Ile Ala Phe Asn Gln Ser Ser Gly Gly Asp Gln Glu Ile Val
    370                 375                 380

Lys His Ser Phe Asn Cys Gly Gly Glu Phe Phe Tyr Cys Asp Thr Thr
385                 390                 395                 400

Gln Leu Phe Asn Ser Thr Trp Ser Ser Asn Asp Thr Trp Asn Ser Thr
                405                 410                 415

Gly Val Gln Asp Asn Asn Ile Thr Leu Pro Cys Arg Ile Lys Gln Ile
                420                 425                 430

Ile Asn Met Trp Gln Glu Val Gly Lys Ala Met Tyr Ala Pro Pro Ile
                435                 440                 445

Gln Gly Leu Ile Ser Cys Ser Ser Asn Ile Thr Gly Leu Leu Leu Thr
        450                 455                 460

Arg Asp Gly Gly Thr Asn Asn Thr Asn Ala Thr Glu Ile Phe Arg Pro
465                 470                 475                 480

Gly Gly Gly Asp Met Arg Asp Asn Trp Arg Ser Glu Leu Tyr Lys Tyr
                485                 490                 495

Lys Val Val Lys Ile Glu Pro Leu Gly Ile Ala Pro Thr Lys Ala Lys
                500                 505                 510

Glu Arg Val Val Gln Arg Glu Lys Glu Ala Val Gly Leu Gly Ala Val
        515                 520                 525

Phe Ile Gly Phe Leu Gly Ala Ala Gly Ser Thr Met Gly Ala Ala Ser
530                 535                 540

Val Thr Leu Thr Val Gln Ala Arg Gln Leu Leu Ser Gly Ile Val Gln
545                 550                 555                 560

Gln Gln Asn Asn Leu Leu Arg Ala Ile Glu Ala Gln Gln His Met Leu
                565                 570                 575

Gln Leu Thr Val Trp Gly Ile Lys Gln Leu Gln Ala Arg Ile Leu Ala
            580                 585                 590

Val Glu Arg Tyr Leu Lys Asp Gln Gln Ile Leu Gly Ile Trp Gly Cys
        595                 600                 605

Ser Gly Lys Leu Ile Cys Pro Thr Ala Val Pro Trp Asn Ala Ser Trp
    610                 615                 620

Ser Asn Lys Ser Leu Thr Ala Ile Trp Asn Asn Met Thr Trp Met Glu
625                 630                 635                 640

Trp Glu Arg Glu Ile Asp Asn Tyr Thr Gly Leu Ile Tyr Ser Leu Ile
```

```
                    645                 650                 655
Glu Glu Ser Gln Ile Gln Gln Glu Gln Asn Glu Lys Glu Leu Leu Glu
            660                 665                 670

Leu Asp Lys Trp Ala Ser Leu Trp Asn Trp Phe Asp Ile Thr Lys Trp
        675                 680                 685

Leu Trp Tyr Ile Lys
    690

<210> SEQ ID NO 17
<211> LENGTH: 2082
<212> TYPE: DNA
<213> ORGANISM: Human immunodeficiency virus 1

<400> SEQUENCE: 17
atgcgcgtga agggcatccg caagaactac cagcacctgt ggcgctgggg catctggcgc        60
tggggcatca tgctgctggg caccctgatg atctgctccg ccaccgagaa gctgtgggtg       120
accgtgtact acggcgtgcc cgtgtggaag gaggccacca ccaccctgtt ctgcgcctcc       180
gacgccaagg cctactcccc cgagaagcac aacatctggg ccacccacgc ctgcgtgccc       240
accgacccca cccccagga gctggtgctg gcaacgtga ccgaggactt caacatgtgg        300
aagaacaaca tggtggagca gatgcacgag gacatcatct ccctgtggga ccagtccctg       360
aagccctgcg tgaagctgac ccccctgtgc gtgaccctga actgcaccga cctgaagaac       420
tccgccaccg acaccaacgg cacctccggc accaacaacc gcaccgtgga gcagggcatg       480
gagaccgaga tcaagaactg ctccttcaac atcaccaccg catcggcaa caagatgcag       540 aaggagtacg ccctgttcta caagctggac gtggtgccca tcgactccaa caacaactcc       600
gacaacacct cctaccgcct gatctcctgc aacacctccg tggtgaccca ggcctgcccc       660
aagacctcct tcgagcccat ccccatccac tactgcgccc ccgccggctt cgccatcctg       720
aagtgcaaca acaagacctt ctccggcaag ggccccgca gaacgtgtc caccgtgcag       780 tgcacccacg gcatccgccc cgtggtgtcc acccagctgc tgctgaacgg ctccctggcc       840
gaggaggaga tcgtgatccg ctccgagaac ttcaccaaca cgccaagac catcatcgtg       900 cagctgaacg agtccgtgat catcaactgc acccgcccca caacaacac ccgcaagggc       960 atccacatcg gcctgggccg cgccctgtac gccaccggcg acatcatcgg cgacatccgc      1020
caggcccact gcaacctgtc ctccaagtcc tggaacaaga ccctgcagca ggtggtgcgc      1080
aagctgcgcg agcagttcgg caacaagacc atcgccttca ccagtcctc cggcggcgac      1140 caggagatct gaagcactc cttcaactgc ggcggcgagt tcttctactg cgacaccacc      1200
cagctgttca actccacctg gtcctccaac gacacctgga actccaccgg cgtgcaggac      1260
aacaacatca ccctgccctg ccgcatcaag cagatcatca acatgtggca ggaggtgggc      1320
aaggccatgt acgccccccc catccagggc ctgatctcct gctcctccaa catcaccggc      1380
ctgctgctga cccgcgacgg cggcaccaac aacaccaacg ccaccgagat cttccgcccc      1440
ggcggcggcg acatgcgcga caactggcgc tccgagctgt acaagtacaa ggtggtgaag      1500
atcgagcccc tgggcatcgc ccccaccaag gccaaggagc gcgtggtgca gcgcgagaag      1560
gaggccgtgg gcctgggcgc cgtgttcatc ggcttcctgg gcgccgccgg ctccaccatg      1620
ggcgccgcct ccgtgaccct gaccgtgcag gccgccagc tgctgtccgg catcgtgcag      1680
cagcagaaca acctgctgcg cgccatcgag gcccagcagc acatgctgca gctgaccgtg      1740
tggggcatca agcagctgca ggcccgcatc ctggccgtga gcgctacct gaaggaccag      1800
```

-continued

```
cagatcctgg gcatctgggg ctgctccggc aagctgatct gccccaccgc cgtgccctgg    1860
aacgcctcct ggtccaacaa gtccctgacc gccatctgga caacatgac ctggatggag     1920 tgggagcgcg agatcgacaa ctacaccggc ctgatctact ccctgatcga ggagtcccag    1980
atccagcagg agcagaacga gaaggagctg ctggagctgg acaagtgggc ctccctgtgg    2040
aactggttcg acatcaccaa gtggctgtgg tacatcaagt ag                       2082
```

<210> SEQ ID NO 18
<211> LENGTH: 675
<212> TYPE: PRT
<213> ORGANISM: Human immunodeficiency virus 1

<400> SEQUENCE: 18

```
Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Thr Val Tyr Tyr Gly Val Pro Val Trp Lys Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Asn Val Thr Asn Thr Thr Asn Asn Thr Glu Glu
    130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
            180                 185                 190

Cys Asn Thr Ser Ala Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
    210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Ile Ile Arg Ser Glu
            260                 265                 270

Asn Ile Thr Asn Asn Ala Lys Thr Ile Ile Val Gln Leu Asn Glu Ser
        275                 280                 285

Val Glu Ile Asn Cys Thr Arg Pro Asn Asn Thr Arg Lys Ser Ile
    290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
```

```
                    325                 330                 335
Thr Leu Gln Gln Val Ala Lys Lys Leu Arg Glu His Phe Asn Asn Lys
                340                 345                 350

Thr Ile Ile Phe Lys Pro Ser Ser Gly Gly Asp Leu Glu Ile Thr Thr
            355                 360                 365

His Ser Phe Asn Cys Arg Gly Glu Phe Phe Tyr Cys Asn Thr Ser Gly
        370                 375                 380

Leu Phe Asn Ser Thr Trp Ile Gly Asn Gly Thr Lys Asn Asn Asn Asn
385                 390                 395                 400

Thr Asn Asp Thr Ile Thr Leu Pro Cys Arg Ile Lys Gln Ile Ile Asn
                405                 410                 415

Met Trp Gln Gly Val Gly Gln Ala Met Tyr Ala Pro Pro Ile Glu Gly
                420                 425                 430

Lys Ile Thr Cys Lys Ser Asn Ile Thr Gly Leu Leu Leu Thr Arg Asp
                435                 440                 445

Gly Gly Asn Asn Asn Thr Asn Glu Thr Glu Ile Phe Arg Pro Gly Gly
            450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Glu Arg
                485                 490                 495

Val Val Glu Arg Glu Lys Glu Ala Val Gly Ile Gly Ala Val Phe Leu
            500                 505                 510

Gly Phe Leu Gly Ala Ala Gly Ser Thr Met Gly Ala Ala Ser Ile Thr
        515                 520                 525

Leu Thr Val Gln Ala Arg Gln Leu Leu Ser Gly Ile Val Gln Gln Gln
    530                 535                 540

Ser Asn Leu Leu Arg Ala Ile Glu Ala Gln Gln His Leu Leu Gln Leu
545                 550                 555                 560

Thr Val Trp Gly Ile Lys Gln Leu Gln Ala Arg Val Leu Ala Val Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Thr Val Pro Trp Asn Ser Ser Trp Ser Asn
        595                 600                 605

Lys Ser Gln Asp Glu Ile Trp Asp Asn Met Thr Trp Met Glu Trp Glu
    610                 615                 620

Arg Glu Ile Asn Asn Tyr Thr Asp Ile Ile Tyr Ser Leu Ile Glu Glu
625                 630                 635                 640

Ser Gln Asn Gln Gln Glu Lys Asn Glu Gln Glu Leu Leu Ala Leu Asp
                645                 650                 655

Lys Trp Ala Ser Leu Trp Asn Trp Phe Asp Ile Thr Asn Trp Leu Trp
            660                 665                 670

Tyr Ile Lys
        675

<210> SEQ ID NO 19
<211> LENGTH: 2040
<212> TYPE: DNA
<213> ORGANISM: Human immunodeficiency virus 1

<400> SEQUENCE: 19
atgagggtcc ggggaatcca gcgcaactgc cagcacctct ggaggtgggg cacgctgatc      60
ctggggatgc tgatgatctg cagcgcggct gagaacctgt gggtgacagt gtactacggc     120
```

-continued

```
gtgcctgtgt ggaaggaggc caacaccacc ctgttctgcg cctcggacgc caaggcctac      180
gacacggagg tccacaacgt gtgggctacc cacgcctgcg tgcccaccga ccccaatcct      240
caggagatcg tcctggagaa cgtgaccgag aacttcaaca tgtggaagaa caacatggtg      300
gagcagatgc acgaggacat catcagcctg tgggaccaga gcctgaagcc ctgcgtgaag      360
ctgacccccc tgtgcgtgac cctgaactgc acgaacgtga acgtgaccaa caccacgaac      420
aacacggagg agaaggggga gatcaagaac tgcagcttca acatcaccac cgagatccgg      480
gacaagaagc agaaggtgta cgccctgttc taccggctgg acgtcgtgcc gatcgacgac      540
aacaacaaca actccagcaa ctacaggctg atcaactgca acaccagcgc gatcacccag      600
gcctgcccta aggtgtcgtt cgagcccatc cccatccact actgcgcgcc tgccggcttc      660
gccatcctga agtgcaacga caagaagttc aacggcaccg cccctgcaa gaacgtcagc      720
accgtccagt gcacccacgg catcaagcct gtggtgtcca cccagctgct cctgaacggc      780
agcctggccg aggaggagat catcatcagg agcgagaaca tcaccaacaa cgccaagacg      840
atcatcgtgc agctgaacga gtcggtggag atcaactgca cccggcccaa caacaacacg      900
cggaagagca tccggatcgg ccctggacag gcgttctacg ccacgggcga catcatcggc      960
gacatcaggc aggcccactg caacatctcg ggacgaagt ggaacaagac cctgcagcag     1020
gtcgcgaaga agctgaggga gcacttcaac aacaagacca tcatcttcaa gccgagcagc     1080
ggcggagacc tggagatcac cacgcactcg ttcaactgcc ggggcgagtt cttctactgt     1140
aacacgtcgg gcctgttcaa cagcacctgg atcggcaacg cacgaagaa caacaacaac     1200
actaacgaca ccatcacccct gccctgccgg atcaagcaga tcatcaacat gtggcagggc     1260
gtgggccagg ctatgtacgc ccctcccatc gagggcaaga tcacgtgcaa gagcaacatc     1320
accggcctgc tgctgaccag ggacggcggg aacaacaaca cgaacgagac cgagatcttc     1380
agacctggcg gcggagacat gagagacaac tggcggagcg agctgtacaa gtacaaggtc     1440
gtgaagatcg agcccctggg cgtcgcaccc accaaggcca aggagagggt ggtggagcgg     1500
gagaaggagg cggtcggcat cggcgccgtg ttcctgggct tcctgggagc agccggcagc     1560
accatgggag ccgcctcgat caccctgacc gtgcaggcga ggcagctgct gtccggcatc     1620
gtgcagcagc agtcgaacct gctgagggcc atcgaggccc agcagcacct gctccagctg     1680
accgtgtggg gcatcaagca gctccaggcc agggtgctgg ccgtcgagcg ctacctgaag     1740
gaccagcagc tgctcggcat ctggggctgc agcggcaagc tgatctgcac caccaccgtg     1800
ccctggaaca gcagctggag caacaagagc caggacgaga tctgggacaa catgacctgg     1860
atggagtggg agcgggagat caacaactac accgacatca tctacagcct gatcgaggag     1920
agccagaacc agcaggagaa gaacgagcag agctgctgg cgctggacaa gtgggcgtcg     1980
ctgtggaact ggttcgacat caccaactgg ctgtggtaca tcaagtgagg atcctctaga     2040
```

<210> SEQ ID NO 20
<211> LENGTH: 669
<212> TYPE: PRT
<213> ORGANISM: Human immunodeficiency virus 1

<400> SEQUENCE: 20

Met Arg Val Arg Gly Ile Trp Lys Asn Trp Pro Gln Trp Leu Ile Trp
1               5                   10                  15

Ser Ile Leu Gly Phe Trp Ile Gly Asn Met Glu Gly Ser Trp Val Thr
            20                  25                  30

-continued

Val Tyr Tyr Gly Val Pro Val Trp Lys Glu Ala Lys Thr Leu Phe
        35                  40                  45

Cys Ala Ser Asp Ala Lys Ala Tyr Glu Lys Glu Val His Asn Val Trp
 50                  55                  60

Ala Thr His Ala Cys Val Pro Thr Asp Pro Asn Pro Gln Glu Met Val
 65                  70                  75                  80

Leu Ala Asn Val Thr Glu Asn Phe Asn Met Trp Lys Asn Asp Met Val
                85                  90                  95

Glu Gln Met His Glu Asp Ile Ile Ser Leu Trp Asp Glu Ser Leu Lys
            100                 105                 110

Pro Cys Val Lys Leu Thr Pro Leu Cys Val Thr Leu Asn Cys Thr Asn
            115                 120                 125

Val Lys Gly Asn Glu Ser Asp Thr Ser Glu Val Met Lys Asn Cys Ser
    130                 135                 140

Phe Lys Ala Thr Thr Glu Leu Lys Asp Lys Lys His Lys Val His Ala
145                 150                 155                 160

Leu Phe Tyr Lys Leu Asp Val Val Pro Leu Asn Gly Asn Ser Ser Ser
                165                 170                 175

Ser Gly Glu Tyr Arg Leu Ile Asn Cys Asn Thr Ser Ala Ile Thr Gln
            180                 185                 190

Ala Cys Pro Lys Val Ser Phe Asp Pro Ile Pro Leu His Tyr Cys Ala
        195                 200                 205

Pro Ala Gly Phe Ala Ile Leu Lys Cys Asn Asn Lys Thr Phe Asn Gly
    210                 215                 220

Thr Gly Pro Cys Arg Asn Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Ile Ile Ile Arg Ser Glu Asn Leu Thr Asn Asn Ala Lys Thr
            260                 265                 270

Ile Ile Val His Leu Asn Glu Ser Val Asn Ile Val Cys Thr Arg Pro
        275                 280                 285

Asn Asn Asn Thr Arg Lys Ser Ile Arg Ile Gly Pro Gly Gln Thr Phe
    290                 295                 300

Tyr Ala Thr Gly Asp Ile Ile Gly Asn Ile Arg Gln Ala His Cys Asn
305                 310                 315                 320

Ile Asn Glu Ser Lys Trp Asn Asn Thr Leu Gln Lys Val Gly Glu Glu
                325                 330                 335

Leu Ala Lys His Phe Pro Ser Lys Thr Ile Lys Phe Glu Pro Ser Ser
            340                 345                 350

Gly Gly Asp Leu Glu Ile Thr Thr His Ser Phe Asn Cys Arg Gly Glu
        355                 360                 365

Phe Phe Tyr Cys Asn Thr Ser Asp Leu Phe Asn Gly Thr Tyr Arg Asn
    370                 375                 380

Gly Thr Tyr Asn His Thr Gly Arg Ser Ser Asn Gly Thr Ile Thr Leu
385                 390                 395                 400

Gln Cys Lys Ile Lys Gln Ile Ile Asn Met Trp Gln Glu Val Gly Arg
                405                 410                 415

Ala Ile Tyr Ala Pro Pro Ile Glu Gly Glu Ile Thr Cys Asn Ser Asn
            420                 425                 430

Ile Thr Gly Leu Leu Leu Leu Arg Asp Gly Gly Gln Ser Asn Glu Thr
        435                 440                 445

Asn Asp Thr Glu Thr Phe Arg Pro Gly Gly Gly Asp Met Arg Asp Asn

```
                450           455           460
Trp Arg Ser Glu Leu Tyr Lys Tyr Lys Val Val Glu Ile Lys Pro Leu
465                 470                 475                 480

Gly Val Ala Pro Thr Glu Ala Lys Glu Arg Val Val Glu Arg Glu Lys
                485                 490                 495

Glu Ala Val Gly Ile Gly Ala Val Phe Leu Gly Phe Leu Gly Ala Ala
                500                 505                 510

Gly Ser Thr Met Gly Ala Ala Ser Met Thr Leu Thr Val Gln Ala Arg
        515                 520                 525

Gln Leu Leu Ser Gly Ile Val Gln Gln Gln Ser Asn Leu Leu Arg Ala
        530                 535                 540

Ile Glu Ala Gln Gln His Met Leu Gln Leu Thr Val Trp Gly Ile Lys
545                 550                 555                 560

Gln Leu Gln Ala Arg Val Leu Ala Ile Glu Arg Tyr Leu Lys Asp Gln
                565                 570                 575

Gln Leu Leu Gly Met Trp Gly Cys Ser Gly Lys Leu Ile Cys Thr Thr
                580                 585                 590

Ala Val Pro Trp Asn Ser Ser Trp Ser Asn Lys Ser Gln Asn Glu Ile
                595                 600                 605

Trp Gly Asn Met Thr Trp Met Gln Trp Asp Arg Glu Ile Asn Asn Tyr
        610                 615                 620

Thr Asn Thr Ile Tyr Arg Leu Leu Glu Asp Ser Gln Asn Gln Gln Glu
625                 630                 635                 640

Lys Asn Glu Lys Asp Leu Leu Ala Leu Asp Ser Trp Lys Asn Leu Trp
                645                 650                 655

Asn Trp Phe Asp Ile Ser Lys Trp Leu Trp Tyr Ile Lys
                660                 665

<210> SEQ ID NO 21
<211> LENGTH: 2022
<212> TYPE: DNA
<213> ORGANISM: Human immunodeficiency virus 1

<400> SEQUENCE: 21
atgcgcgtgc gcggcatctg aagaactgg ccccagtggc tgatctggtc catcctgggc      60
ttctggatcg caacatgga gggctcctgg gtgaccgtgt actacggcgt gcccgtgtgg     120
aaggaggcca agaccaccct gttctgcgcc tccgacgcca aggcctacga gaaggaggtg     180
cacaacgtgt gggccaccca cgcctgcgtg cccaccgacc ccaaccccca ggagatggtg     240
ctggccaacg tgaccgagaa cttcaacatg tggaagaacg acatggtgga gcagatgcac     300
gaggacatca tctccctgtg gacgagtcc ctgaagccct gcgtgaagct gacccccctg     360
tgcgtgaccc tgaactgcac caacgtgaag ggcaacgagt ccgacacctc cgaggtgatg     420
aagaactgct ccttcaaggc caccaccgag ctgaaggaca agaagcacaa ggtgcacgcc     480
ctgttctaca gctggacgt ggtgcccctg aacggcaact cctcctcctc cggcgagtac     540
cgcctgatca actgcaacac ctccgccatc acccaggcct gccccaaggt gtccttcgac     600
cccatccccc tgcactactg cgcccccgcc ggcttcgcca tcctgaagtg caacaacaag     660
accttcaacg gcaccggccc ctgccgcaac gtgtccaccg tgcagtgcac ccacggcatc     720
aagcccgtgg tgtccaccca gctgctgctg aacggctccc tggccgagga ggagatcatc     780
atccgctccg agaacctgac caacaacgcc aagaccatca tcgtgcacct gaacgagtcc     840
gtgaacatcg tgtgcacccg ccccaacaac aacacccgca gtccatccg catcggcccc     900
```

-continued

```
ggccagacct tctacgccac cggcgacatc atcggcaaca tccgccaggc ccactgcaac    960
atcaacgagt ccaagtggaa caacaccctg cagaaggtgg gcgaggagct ggccaagcac   1020
ttcccctcca agaccatcaa gttcgagccc tcctccggcg gcgacctgga gatcaccacc   1080
cactccttca actgccgcgg cgagttcttc tactgcaaca cctccgacct gttcaacggc   1140
acctaccgca acggcaccta caaccacacc ggccgctcct ccaacggcac catcaccctg   1200
cagtgcaaga tcaagcagat catcaacatg tggcaggagg tgggccgcgc catctacgcc   1260
ccccccatcg agggcgagat cacctgcaac tccaacatca ccggcctgct gctgctgcgc   1320
gacggcggcc agtccaacga gaccaacgac accgagacct tccgcccgg cggcggcgac   1380 atgcgcgaca actggcgctc cgagctgtac aagtacaagg tggtggagat caagcccctg   1440
ggcgtggccc ccaccgaggc caaggagcgc gtggtggagc gcgagaagga ggccgtgggc   1500
atcggcgccg tgttcctggg cttcctgggc gccgccggct ccaccatggg cgccgcctcc   1560
atgaccctga ccgtgcaggc ccgccagctg ctgtccggca tcgtgcagca gcagtccaac   1620
ctgctgcgcg ccatcgaggc ccagcagcac atgctgcagc tgaccgtgtg gggcatcaag   1680
cagctgcagg cccgcgtgct ggccatcgag cgctacctga aggaccagca gctgctgggc   1740
atgtggggct gctccggcaa gctgatctgc accaccgccg tgccctggaa ctcctcctgg   1800
tccaacaagt cccagaacga gatctggggc aacatgacct ggatgcagtg ggaccgcgag   1860
atcaacaact acaccaacac catctaccgc ctgctggagg actcccagaa ccagcaggag   1920
aagaacgaga aggacctgct ggccctggac tcctggaaga acctgtggaa ctggttcgac   1980
atctccaagt ggctgtggta catcaagtag ggatcctcta ga                      2022
```

<210> SEQ ID NO 22
<211> LENGTH: 682
<212> TYPE: PRT
<213> ORGANISM: Human immunodeficiency virus 1

<400> SEQUENCE: 22

```
Met Arg Val Arg Gly Met Leu Arg Asn Cys Gln Gln Trp Trp Ile Trp
  1               5                  10                  15

Gly Ile Leu Gly Phe Trp Met Leu Met Ile Cys Ser Val Val Gly Asn
             20                  25                  30

Leu Trp Val Thr Val Tyr Tyr Gly Val Pro Val Trp Lys Glu Ala Lys
         35                  40                  45

Thr Thr Leu Phe Cys Ala Ser Asp Ala Arg Ala Tyr Glu Arg Glu Val
     50                  55                  60

His Asn Val Trp Ala Thr His Ala Cys Val Pro Thr Asp Pro Asn Pro
 65                  70                  75                  80

Gln Glu Met Val Leu Val Asn Val Thr Glu Asn Phe Asn Met Trp Lys
                 85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Ile Leu
        115                 120                 125

Glu Cys Asn Asn Ala Asn Gly Thr Thr Asn Asn Gly Ser Val Ile Val
    130                 135                 140

Val Asn Glu Asn Ser Thr Met Tyr Gly Glu Ile Gln Asn Cys Ser Phe
145                 150                 155                 160

Lys Val Asn Ser Glu Ile Lys Gly Lys Lys Gln Asp Val Tyr Ala Leu
                165                 170                 175
```

```
Phe Asn Ser Leu Asp Ile Val Lys Leu Tyr Asn Asn Gly Thr Ser Gln
                180                 185                 190

Tyr Arg Leu Ile Asn Cys Asn Thr Ser Thr Leu Thr Gln Ala Cys Pro
            195                 200                 205

Lys Val Ser Phe Asp Pro Ile Pro Ile His Tyr Cys Ala Pro Ala Gly
        210                 215                 220

Tyr Ala Ile Leu Lys Cys Asn Asn Lys Thr Phe Asn Gly Thr Gly Pro
225                 230                 235                 240

Cys Asn Asn Val Ser Thr Val Gln Cys Thr His Gly Ile Lys Pro Val
                245                 250                 255

Val Ser Thr Gln Leu Leu Leu Asn Gly Ser Leu Ala Glu Gly Glu Ile
            260                 265                 270

Ile Ile Arg Ser Lys Asn Leu Thr Asp Asn Thr Lys Thr Ile Ile Val
        275                 280                 285

His Leu Asn Glu Ser Ile Lys Ile Asn Cys Ile Arg Pro Asn Asn Asn
290                 295                 300

Thr Arg Arg Ser Ile Arg Ile Gly Pro Gly Gln Ala Phe Tyr Ala Ala
305                 310                 315                 320

Asn Gly Ile Val Gly Asn Ile Arg Gln Ala His Cys Asn Ile Ser Glu
                325                 330                 335

Gly Glu Trp Asn Lys Thr Leu Tyr Arg Val Ser Arg Lys Leu Ala Glu
            340                 345                 350

His Phe Pro Gly Lys Glu Ile Lys Phe Lys Pro His Ser Gly Gly Asp
        355                 360                 365

Leu Glu Ile Thr Thr His Ser Phe Asn Cys Arg Gly Glu Phe Phe Tyr
370                 375                 380

Cys Asn Thr Ser Lys Leu Phe Asn Gly Thr Tyr Asn Gly Thr Tyr Thr
385                 390                 395                 400

Asn Asn Asp Thr Asn Ser Thr Ile Ile Leu Pro Cys Arg Ile Lys Gln
                405                 410                 415

Ile Ile Asn Met Trp Gln Glu Val Gly Gln Ala Met Tyr Ala Pro Pro
            420                 425                 430

Ile Glu Gly Ile Ile Ala Cys Asn Ser Thr Ile Thr Gly Leu Leu Leu
        435                 440                 445

Thr Arg Asp Gly Gly Asp Lys Asn Gly Ser Lys Pro Glu Ile Phe Arg
450                 455                 460

Pro Gly Gly Gly Asp Met Arg Asp Asn Trp Arg Ser Glu Leu Tyr Lys
465                 470                 475                 480

Tyr Lys Val Val Glu Ile Lys Pro Leu Gly Ile Ala Pro Thr Lys Ala
                485                 490                 495

Lys Glu Arg Val Val Glu Lys Glu Lys Thr Ile Gln Lys Glu Ala Val
            500                 505                 510

Gly Ile Gly Ala Val Phe Leu Gly Phe Leu Gly Ala Ala Gly Ser Thr
        515                 520                 525

Met Gly Ala Ala Ser Ile Thr Leu Thr Val Gln Ala Arg Gln Leu Leu
530                 535                 540

Ser Gly Ile Val Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
                565                 570                 575

Ala Arg Val Leu Ala Met Glu Arg Tyr Leu Gln Asp Gln Gln Leu Leu
            580                 585                 590

Gly Ile Trp Gly Cys Ser Gly Lys Leu Ile Cys Thr Thr Ala Val Pro
```

```
                595                 600                 605

Trp Asn Ser Ser Trp Ser Asn Lys Thr Leu Glu Tyr Ile Trp Gly Asn
        610                 615                 620

Met Thr Trp Met Gln Trp Asp Arg Glu Ile Asp Asn Tyr Thr Gly Ile
625                 630                 635                 640

Ile Tyr Asp Leu Leu Glu Asp Ser Gln Ile Gln Gln Glu Lys Asn Glu
                645                 650                 655

Lys Asp Leu Leu Ala Leu Asp Ser Trp Lys Asn Leu Trp Ser Trp Phe
            660                 665                 670

Ser Ile Thr Asn Trp Leu Trp Tyr Ile Lys
            675                 680

<210> SEQ ID NO 23
<211> LENGTH: 2046
<212> TYPE: DNA
<213> ORGANISM: Human immunodeficiency virus 1

<400> SEQUENCE: 23
atgcgcgtgc gcggcatgct gcgcaactgc cagcagtggt ggatctgggg catcctgggc      60
ttctggatgc tgatgatctg ctccgtggtg ggcaacctgt gggtgaccgt gtactacggc     120
gtgcccgtgt ggaaggaggc caagaccacc ctgttctgcg cctccgacgc ccgcgcctac     180
gagcgcgagg tgcacaacgt gtgggccacc cacgcctgcg tgcccaccga ccccaacccc     240
caggagatgg tgctggtgaa cgtgaccgag aacttcaaca tgtggaagaa cgacatggtg     300
gaccagatgc acgaggacat catctccctg tgggaccagt ccctgaagcc ctgcgtgaag     360 ctgaccccc  tgtgcgtgat cctggagtgc aacaacgcca acggcaccac caacaacggc     420
tccgtgatcg tggtgaacga gaactccacc atgtacggcg agatccagaa ctgctccttc     480
aaggtgaact ccgagatcaa gggcaagaag caggacgtgt acgccctgtt caactccctg     540
gacatcgtga gctgtacaa  caacggcacc tcccagtacc gcctgatcaa ctgcaacacc     600
tccaccctga cccaggcctg ccccaaggtg tccttcgacc ccatccccat ccactactgc     660
gccccccgcg gctacgccat cctgaagtgc aacaacaaga ccttcaacgg caccggcccc     720
tgcaacaacg tgtccaccgt gcagtgcacc cacggcatca agcccgtggt gtccacccag     780
ctgctgctga cggctcccct ggccgagggc gagatcatca tccgctccaa gaacctgacc     840
gacaacacca gaccatcat  cgtgcacctg aacgagtcca tcaagatcaa ctgcatccgc     900
cccaacaaca cacccgccg  ctccatccgc atcggccccg gccaggcctt ctacgccgcc     960
aacggcatcg tgggcaacat ccgccaggcc cactgcaaca tctccgaggg cgagtggaac    1020
aagaccctgt accgcgtgtc ccgcaagctg gccgagcact cccccggcaa ggagatcaag    1080
ttcaagcccc actccggcgg cgacctggag atcaccaccc actccttcaa ctgccgcggc    1140
gagttcttct actgcaacac ctccaagctg ttcaacggca cctacaacgg cacctacacc    1200
aacaacgaca ccaactccac catcatcctg ccctgccgca tcaagcagat catcaacatg    1260
tggcaggagg tgggccaggc catgtacgcc ccccccatcg agggcatcat cgcctgcaac    1320
tccaccatca ccggcctgct gctgacccgc gacggcggcg acaagaacgg ctccaagccc    1380
gagatcttcc gccccggcgg cggcgacatg cgcgacaact ggcgctccga gctgtacaag    1440
tacaaggtgg tggagatcaa gcccctgggc atcgcccca  ccaaggccaa ggagcgcgtg    1500
gtggagaagg agaagaccat ccagaaggag gccgtgggca tcggcgccgt gttcctgggc    1560
ttcctgggcg ccgccggctc caccatgggc gccgcctcca tcaccctgac cgtgcaggcc    1620
```

```
cgccagctgc tgtccggcat cgtgcagcag cagtccaacc tgctgcgcgc catcgaggcc    1680
cagcagcaca tgctgcagct gaccgtgtgg ggcatcaagc agctgcaggc ccgcgtgctg    1740
gccatggagc gctacctgca ggaccagcag ctgctgggca tctggggctg ctccggcaag    1800
ctgatctgca ccaccgccgt gccctggaac tcctcctggt ccaacaagac cctggagtac    1860
atctggggca acatgacctg gatgcagtgg gaccgcgaga tcgacaacta caccggcatc    1920
atctacgacc tgctggagga ctcccagatc cagcaggaga gaacgagaa ggacctgctg    1980 gccctggact cctggaagaa cctgtggtcc tggttctcca tcaccaactg gctgtggtac    2040
atcaag                                                               2046
```

<210> SEQ ID NO 24
<211> LENGTH: 12
<212> TYPE: PRT
<213> ORGANISM: Human immunodeficiency virus 1

<400> SEQUENCE: 24

Ala Ala Glu Asn Leu Trp Val Thr Val Tyr Tyr Gly
1               5                   10

<210> SEQ ID NO 25
<211> LENGTH: 12
<212> TYPE: PRT
<213> ORGANISM: Human immunodeficiency virus 1

<400> SEQUENCE: 25

Ala Ser Asp Asn Leu Trp Val Thr Val Tyr Tyr Gly
1               5                   10

<210> SEQ ID NO 26
<211> LENGTH: 12
<212> TYPE: PRT
<213> ORGANISM: Human immunodeficiency virus 1

<400> SEQUENCE: 26

Ala Ala Ala Gln Leu Trp Val Thr Val Tyr Tyr Gly
1               5                   10

<210> SEQ ID NO 27
<211> LENGTH: 12
<212> TYPE: PRT
<213> ORGANISM: Human immunodeficiency virus 1

<400> SEQUENCE: 27

Ala Thr Glu Lys Leu Trp Val Thr Val Tyr Tyr Gly
1               5                   10

<210> SEQ ID NO 28
<211> LENGTH: 7
<212> TYPE: PRT
<213> ORGANISM: Human immunodeficiency virus 1

<400> SEQUENCE: 28

Trp Val Thr Val Tyr Tyr Gly
1               5

<210> SEQ ID NO 29
<211> LENGTH: 12
<212> TYPE: PRT
<213> ORGANISM: Human immunodeficiency virus 1

<400> SEQUENCE: 29

Val Val Gly Asn Leu Trp Val Thr Val Tyr Tyr Gly
1               5                   10

<210> SEQ ID NO 30
<211> LENGTH: 512
<212> TYPE: PRT
<213> ORGANISM: Human immunodeficiency virus 1

<400> SEQUENCE: 30

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
                20                  25                  30

Leu Trp Val Thr Val Tyr Tyr Gly Val Pro Val Trp Lys Glu Ala Asp
            35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile Asp Leu Glu Asn Val Thr Glu Asn Phe Asn Met Trp Lys
                85                  90                  95

Asn Asn Met Val Glu Gln Met Gln Glu Asp Val Ile Ser Leu Trp Asp
                100                 105                 110

Gln Ser Leu Lys Pro Cys Val Lys Leu Thr Pro Pro Cys Val Thr Leu
            115                 120                 125

His Cys Thr Asn Ala Asn Leu Thr Lys Ala Asn Leu Thr Asn Val Asn
    130                 135                 140

Asn Arg Thr Asn Val Ser Asn Ile Ile Gly Asn Ile Thr Asp Glu Val
145                 150                 155                 160

Arg Asn Cys Ser Phe Asn Met Thr Thr Glu Leu Arg Asp Lys Lys Gln
                165                 170                 175

Lys Val His Ala Leu Phe Tyr Lys Leu Asp Ile Val Pro Ile Glu Asp
                180                 185                 190

Asn Asn Asp Ser Ser Glu Tyr Arg Leu Ile Asn Cys Asn Thr Ser Val
            195                 200                 205

Ile Lys Gln Pro Cys Pro Lys Ile Ser Phe Asp Pro Ile Pro Ile His
    210                 215                 220

Tyr Cys Thr Pro Ala Gly Tyr Ala Ile Leu Lys Cys Asn Asp Lys Asn
225                 230                 235                 240

Phe Asn Gly Thr Gly Pro Cys Lys Asn Val Ser Ser Val Gln Cys Thr
                245                 250                 255

His Gly Ile Lys Pro Val Val Ser Thr Gln Leu Leu Leu Asn Gly Ser
                260                 265                 270

Leu Ala Glu Glu Glu Ile Ile Ile Arg Ser Glu Asn Leu Thr Asn Asn
            275                 280                 285

Ala Lys Thr Ile Ile Val His Leu Asn Lys Ser Val Val Ile Asn Cys
    290                 295                 300

Thr Arg Pro Ser Asn Asn Thr Arg Thr Ser Ile Thr Ile Gly Pro Gly
305                 310                 315                 320

Gln Val Phe Tyr Arg Thr Gly Asp Ile Ile Gly Asp Ile Arg Lys Ala
                325                 330                 335

Tyr Cys Glu Ile Asn Gly Thr Glu Trp Asn Lys Ala Leu Lys Gln Val
            340                 345                 350

Thr Glu Lys Leu Lys Glu His Phe Asn Asn Lys Pro Ile Ile Phe Gln
    355                 360                 365

```
Pro Pro Ser Gly Gly Asp Leu Glu Ile Thr Met His His Phe Asn Cys
    370                 375                 380

Arg Gly Glu Phe Phe Tyr Cys Asn Thr Thr Arg Leu Phe Asn Asn Thr
385                 390                 395                 400

Cys Ile Ala Asn Gly Thr Ile Glu Gly Cys Asn Gly Asn Ile Thr Leu
                405                 410                 415

Pro Cys Lys Ile Lys Gln Ile Ile Asn Met Trp Gln Gly Ala Gly Gln
            420                 425                 430

Ala Met Tyr Ala Pro Pro Ile Ser Gly Thr Ile Asn Cys Val Ser Asn
        435                 440                 445

Ile Thr Gly Ile Leu Leu Thr Arg Asp Gly Gly Ala Thr Asn Asn Thr
    450                 455                 460

Asn Asn Glu Thr Phe Arg Pro Gly Gly Gly Asn Ile Lys Asp Asn Trp
465                 470                 475                 480

Arg Asn Glu Leu Tyr Lys Tyr Lys Val Val Gln Ile Glu Pro Leu Gly
                485                 490                 495

Val Ala Pro Thr Arg Ala Lys Arg Arg Val Val Glu Arg Glu Lys Arg
            500                 505                 510
```

<210> SEQ ID NO 31
<211> LENGTH: 520
<212> TYPE: PRT
<213> ORGANISM: Human immunodeficiency virus 1

<400> SEQUENCE: 31

```
Met Arg Val Lys Gly Ile Arg Lys Asn Tyr Gln His Leu Trp Arg Trp
1               5                   10                  15

Gly Thr Met Leu Leu Gly Ile Leu Met Ile Cys Ser Ala Ala Ala Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Leu Val Leu Ala Asn Val Thr Glu Asn Phe Asn Met Trp Asn
                85                  90                  95

Asn Thr Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Thr Asn Ala Thr Asn Ala Thr Asn Ala Asn Ile
    130                 135                 140

Asn Asn Ser Ser Gly Gly Val Glu Ser Gly Glu Ile Lys Asn Cys Ser
145                 150                 155                 160

Phe Asn Ile Thr Thr Ser Val Arg Asp Lys Val Gln Lys Glu Tyr Ala
                165                 170                 175

Leu Phe Tyr Lys Leu Asp Ile Val Pro Ile Thr Asn Glu Ser Ser Lys
            180                 185                 190

Tyr Arg Leu Ile Ser Cys Asn Thr Ser Val Leu Thr Gln Ala Cys Pro
        195                 200                 205

Lys Val Ser Phe Glu Pro Ile Pro Ile His Tyr Cys Ala Pro Ala Gly
    210                 215                 220

Phe Ala Ile Leu Lys Cys Asn Asn Glu Thr Phe Asn Gly Lys Gly Pro
```

-continued

```
                225                 230                 235                 240
Cys Ile Asn Val Ser Thr Val Gln Cys Thr His Gly Ile Arg Pro Val
                245                 250                 255

Val Ser Thr Gln Leu Leu Asn Gly Ser Leu Ala Glu Lys Glu Val
            260                 265                 270

Ile Ile Arg Ser Asp Asn Phe Ser Asp Asn Ala Lys Asn Ile Ile Val
            275                 280                 285

Gln Leu Lys Glu Tyr Val Lys Ile Asn Cys Thr Arg Pro Asn Asn Asn
        290                 295                 300

Thr Arg Lys Ser Ile His Ile Gly Pro Gly Arg Ala Phe Tyr Ala Thr
305                 310                 315                 320

Gly Glu Ile Ile Gly Asn Ile Arg Gln Ala His Cys Asn Ile Ser Arg
                325                 330                 335

Ser Lys Trp Asn Asp Thr Leu Lys Gln Ile Ala Ala Lys Leu Gly Glu
            340                 345                 350

Gln Phe Arg Asn Lys Thr Ile Val Phe Asn Pro Ser Ser Gly Gly Asp
        355                 360                 365

Leu Glu Ile Val Thr His Ser Phe Asn Cys Gly Gly Glu Phe Phe Tyr
    370                 375                 380

Cys Asn Thr Thr Lys Leu Phe Asn Ser Thr Trp Ile Arg Glu Gly Asn
385                 390                 395                 400

Asn Gly Thr Trp Asn Gly Thr Ile Gly Leu Asn Asp Thr Ala Gly Asn
                405                 410                 415

Asp Thr Ile Ile Leu Pro Cys Lys Ile Lys Gln Ile Ile Asn Met Trp
            420                 425                 430

Gln Glu Val Gly Lys Ala Met Tyr Ala Pro Pro Ile Arg Gly Gln Ile
        435                 440                 445

Arg Cys Ser Ser Asn Ile Thr Gly Leu Ile Leu Thr Arg Asp Gly Gly
    450                 455                 460

Lys Asp Asp Ser Asn Gly Ser Glu Ile Leu Glu Ile Phe Arg Pro Gly
465                 470                 475                 480

Gly Gly Asp Met Arg Asp Asn Trp Arg Ser Glu Leu Tyr Lys Tyr Lys
                485                 490                 495

Val Val Arg Ile Glu Pro Leu Gly Val Ala Pro Thr Arg Ala Arg Glu
            500                 505                 510

Arg Val Val Gln Lys Glu Lys Glu
        515                 520

<210> SEQ ID NO 32
<211> LENGTH: 521
<212> TYPE: PRT
<213> ORGANISM: Human immunodeficiency virus 1

<400> SEQUENCE: 32

Met Arg Val Lys Gly Ile Arg Lys Asn Tyr Gln His Leu Trp Arg Trp
1               5                   10                  15

Gly Ile Trp Arg Trp Gly Ile Met Leu Leu Gly Thr Leu Met Ile Cys
            20                  25                  30

Ser Ala Thr Glu Lys Leu Trp Val Thr Val Tyr Tyr Gly Val Pro Val
        35                  40                  45

Trp Lys Glu Ala Thr Thr Thr Leu Phe Cys Ala Ser Asp Ala Lys Ala
    50                  55                  60

Tyr Ser Pro Glu Lys His Asn Ile Trp Ala Thr His Ala Cys Val Pro
65                  70                  75                  80
```

```
Thr Asp Pro Asn Pro Gln Glu Leu Val Leu Gly Asn Val Thr Glu Asp
                85                  90                  95

Phe Asn Met Trp Lys Asn Asn Met Val Glu Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu Asn Cys Thr Asp Leu Lys Asn Ser Ala Thr Asp
    130                 135                 140

Thr Asn Gly Thr Ser Gly Thr Asn Asn Arg Thr Val Glu Gln Gly Met
145                 150                 155                 160

Glu Thr Glu Ile Lys Asn Cys Ser Phe Asn Ile Thr Thr Gly Ile Gly
                165                 170                 175

Asn Lys Met Gln Lys Glu Tyr Ala Leu Phe Tyr Lys Leu Asp Val Val
            180                 185                 190

Pro Ile Asp Ser Asn Asn Asn Ser Asp Asn Thr Ser Tyr Arg Leu Ile
        195                 200                 205

Ser Cys Asn Thr Ser Val Val Thr Gln Ala Cys Pro Lys Thr Ser Phe
    210                 215                 220

Glu Pro Ile Pro Ile His Tyr Cys Ala Pro Ala Gly Phe Ala Ile Leu
225                 230                 235                 240

Lys Cys Asn Asn Lys Thr Phe Ser Gly Lys Gly Pro Cys Lys Asn Val
                245                 250                 255

Ser Thr Val Gln Cys Thr His Gly Ile Arg Pro Val Val Ser Thr Gln
            260                 265                 270

Leu Leu Leu Asn Gly Ser Leu Ala Glu Glu Ile Val Ile Arg Ser
        275                 280                 285

Glu Asn Phe Thr Asn Asn Ala Lys Thr Ile Ile Val Gln Leu Asn Glu
    290                 295                 300

Ser Val Ile Ile Asn Cys Thr Arg Pro Asn Asn Thr Arg Lys Gly
305                 310                 315                 320

Ile His Ile Gly Leu Gly Arg Ala Leu Tyr Ala Thr Gly Asp Ile Ile
                325                 330                 335

Gly Asp Ile Arg Gln Ala His Cys Asn Leu Ser Ser Lys Ser Trp Asn
            340                 345                 350

Lys Thr Leu Gln Gln Val Val Arg Lys Leu Arg Glu Gln Phe Gly Asn
        355                 360                 365

Lys Thr Ile Ala Phe Asn Gln Ser Ser Gly Gly Asp Gln Glu Ile Val
    370                 375                 380

Lys His Ser Phe Asn Cys Gly Gly Glu Phe Phe Tyr Cys Asp Thr Thr
385                 390                 395                 400

Gln Leu Phe Asn Ser Thr Trp Ser Ser Asn Asp Thr Trp Asn Ser Thr
                405                 410                 415

Gly Val Gln Asp Asn Asn Ile Thr Leu Pro Cys Arg Ile Lys Gln Ile
            420                 425                 430

Ile Asn Met Trp Gln Glu Val Gly Lys Ala Met Tyr Ala Pro Pro Ile
        435                 440                 445

Gln Gly Leu Ile Ser Cys Ser Ser Asn Ile Thr Gly Leu Leu Leu Thr
    450                 455                 460

Arg Asp Gly Gly Thr Asn Thr Asn Ala Thr Glu Ile Phe Arg Pro
465                 470                 475                 480

Gly Gly Gly Asp Met Arg Asp Asn Trp Arg Ser Glu Leu Tyr Lys Tyr
                485                 490                 495

Lys Val Val Lys Ile Glu Pro Leu Gly Ile Ala Pro Thr Lys Ala Lys
```

```
                500              505              510
Arg Arg Val Val Gln Arg Glu Lys Arg
        515              520

<210> SEQ ID NO 33
<211> LENGTH: 503
<212> TYPE: PRT
<213> ORGANISM: Human immunodeficiency virus 1

<400> SEQUENCE: 33

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
                20                  25                  30

Leu Trp Val Thr Val Tyr Tyr Gly Val Pro Val Trp Lys Glu Ala Asn
            35                  40                  45

Thr Thr Leu Phe Cys Ala Ser Asp Ala Lys Ala Tyr Asp Thr Glu Val
        50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Asn Val Thr Asn Thr Thr Asn Asn Thr Glu Glu
130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
            180                 185                 190

Cys Asn Thr Ser Ala Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Glu Ile Ile Ile Arg Ser Glu
            260                 265                 270

Asn Ile Thr Asn Asn Ala Lys Thr Ile Ile Val Gln Leu Asn Glu Ser
        275                 280                 285

Val Glu Ile Asn Cys Thr Arg Pro Asn Asn Asn Thr Arg Lys Ser Ile
290                 295                 300

Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
                325                 330                 335

Thr Leu Gln Gln Val Ala Lys Lys Leu Arg Glu His Phe Asn Asn Lys
            340                 345                 350
```

```
Thr Ile Ile Phe Lys Pro Ser Gly Gly Asp Leu Glu Ile Thr Thr
            355                 360                 365

His Ser Phe Asn Cys Arg Gly Glu Phe Phe Tyr Cys Asn Thr Ser Gly
    370                 375                 380

Leu Phe Asn Ser Thr Trp Ile Gly Asn Gly Thr Lys Asn Asn Asn Asn
385                 390                 395                 400

Thr Asn Asp Thr Ile Thr Leu Pro Cys Arg Ile Lys Gln Ile Ile Asn
                405                 410                 415

Met Trp Gln Gly Val Gly Gln Ala Met Tyr Ala Pro Pro Ile Glu Gly
                420                 425                 430

Lys Ile Thr Cys Lys Ser Asn Ile Thr Gly Leu Leu Leu Thr Arg Asp
                435                 440                 445

Gly Gly Asn Asn Asn Thr Asn Glu Thr Glu Ile Phe Arg Pro Gly Gly
            450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Arg Arg
                485                 490                 495

Val Val Glu Arg Glu Lys Arg
                500
```

<210> SEQ ID NO 34
<211> LENGTH: 497
<212> TYPE: PRT
<213> ORGANISM: Human immunodeficiency virus 1

<400> SEQUENCE: 34

```
Met Arg Val Arg Gly Ile Trp Lys Asn Trp Pro Gln Trp Leu Ile Trp
1               5                   10                  15

Ser Ile Leu Gly Phe Trp Ile Gly Asn Met Glu Gly Ser Trp Val Thr
                20                  25                  30

Val Tyr Tyr Gly Val Pro Val Trp Lys Glu Ala Lys Thr Thr Leu Phe
            35                  40                  45

Cys Ala Ser Asp Ala Lys Ala Tyr Glu Lys Glu Val His Asn Val Trp
    50                  55                  60

Ala Thr His Ala Cys Val Pro Thr Asp Pro Asn Pro Gln Glu Met Val
65                  70                  75                  80

Leu Ala Asn Val Thr Glu Asn Phe Asn Met Trp Lys Asn Asp Met Val
                85                  90                  95

Glu Gln Met His Glu Asp Ile Ile Ser Leu Trp Asp Glu Ser Leu Lys
                100                 105                 110

Pro Cys Val Lys Leu Thr Pro Leu Cys Val Thr Leu Asn Cys Thr Asn
            115                 120                 125

Val Lys Gly Asn Glu Ser Asp Thr Ser Glu Val Met Lys Asn Cys Ser
    130                 135                 140

Phe Lys Ala Thr Thr Glu Leu Lys Asp Lys Lys His Lys Val His Ala
145                 150                 155                 160

Leu Phe Tyr Lys Leu Asp Val Val Pro Leu Asn Gly Asn Ser Ser Ser
                165                 170                 175

Ser Gly Glu Tyr Arg Leu Ile Asn Cys Asn Thr Ser Ala Ile Thr Gln
                180                 185                 190

Ala Cys Pro Lys Val Ser Phe Asp Pro Ile Pro Leu His Tyr Cys Ala
            195                 200                 205

Pro Ala Gly Phe Ala Ile Leu Lys Cys Asn Asn Lys Thr Phe Asn Gly
            210                 215                 220
```

Thr Gly Pro Cys Arg Asn Val Ser Thr Val Gln Cys Thr His Gly Ile
225                 230                 235                 240

Lys Pro Val Val Ser Thr Gln Leu Leu Leu Asn Gly Ser Leu Ala Glu
            245                 250                 255

Glu Glu Ile Ile Ile Arg Ser Glu Asn Leu Thr Asn Asn Ala Lys Thr
        260                 265                 270

Ile Ile Val His Leu Asn Glu Ser Val Asn Ile Val Cys Thr Arg Pro
    275                 280                 285

Asn Asn Asn Thr Arg Lys Ser Ile Arg Ile Gly Pro Gly Gln Thr Phe
290                 295                 300

Tyr Ala Thr Gly Asp Ile Ile Gly Asn Ile Arg Gln Ala His Cys Asn
305                 310                 315                 320

Ile Asn Glu Ser Lys Trp Asn Asn Thr Leu Gln Lys Val Gly Glu Glu
            325                 330                 335

Leu Ala Lys His Phe Pro Ser Lys Thr Ile Lys Phe Glu Pro Ser Ser
        340                 345                 350

Gly Gly Asp Leu Glu Ile Thr Thr His Ser Phe Asn Cys Arg Gly Glu
    355                 360                 365

Phe Phe Tyr Cys Asn Thr Ser Asp Leu Phe Asn Gly Thr Tyr Arg Asn
370                 375                 380

Gly Thr Tyr Asn His Thr Gly Arg Ser Ser Asn Gly Thr Ile Thr Leu
385                 390                 395                 400

Gln Cys Lys Ile Lys Gln Ile Ile Asn Met Trp Gln Glu Val Gly Arg
            405                 410                 415

Ala Ile Tyr Ala Pro Pro Ile Glu Gly Glu Ile Thr Cys Asn Ser Asn
        420                 425                 430

Ile Thr Gly Leu Leu Leu Arg Asp Gly Gly Gln Ser Asn Glu Thr
    435                 440                 445

Asn Asp Thr Glu Thr Phe Arg Pro Gly Gly Gly Asp Met Arg Asp Asn
450                 455                 460

Trp Arg Ser Glu Leu Tyr Lys Tyr Lys Val Val Glu Ile Lys Pro Leu
465                 470                 475                 480

Gly Val Ala Pro Thr Glu Ala Lys Arg Arg Val Val Glu Arg Glu Lys
            485                 490                 495

Arg

<210> SEQ ID NO 35
<211> LENGTH: 510
<212> TYPE: PRT
<213> ORGANISM: Human immunodeficiency virus 1

<400> SEQUENCE: 35

Met Arg Val Arg Gly Met Leu Arg Asn Cys Gln Gln Trp Trp Ile Trp
1               5                   10                  15

Gly Ile Leu Gly Phe Trp Met Leu Met Ile Cys Ser Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Arg Ala Tyr Glu Arg Glu Val
    50                  55                  60

His Asn Val Trp Ala Thr His Ala Cys Val Pro Thr Asp Pro Asn Pro
65                  70                  75                  80

Gln Glu Met Val Leu Val Asn Val Thr Glu Asn Phe Asn Met Trp Lys
            85                  90                  95

```
Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Ile Leu
            115                 120                 125

Glu Cys Asn Asn Ala Asn Gly Thr Thr Asn Asn Gly Ser Val Ile Val
            130                 135                 140

Val Asn Glu Asn Ser Thr Met Tyr Gly Glu Ile Gln Asn Cys Ser Phe
145                 150                 155                 160

Lys Val Asn Ser Glu Ile Lys Gly Lys Lys Gln Asp Val Tyr Ala Leu
                165                 170                 175

Phe Asn Ser Leu Asp Ile Val Lys Leu Tyr Asn Asn Gly Thr Ser Gln
            180                 185                 190

Tyr Arg Leu Ile Asn Cys Asn Thr Ser Thr Leu Thr Gln Ala Cys Pro
            195                 200                 205

Lys Val Ser Phe Asp Pro Ile Pro Ile His Tyr Cys Ala Pro Ala Gly
            210                 215                 220

Tyr Ala Ile Leu Lys Cys Asn Asn Lys Thr Phe Asn Gly Thr Gly Pro
225                 230                 235                 240

Cys Asn Asn Val Ser Thr Val Gln Cys Thr His Gly Ile Lys Pro Val
                245                 250                 255

Val Ser Thr Gln Leu Leu Leu Asn Gly Ser Leu Ala Glu Gly Glu Ile
            260                 265                 270

Ile Ile Arg Ser Lys Asn Leu Thr Asp Asn Thr Lys Thr Ile Ile Val
            275                 280                 285

His Leu Asn Glu Ser Ile Lys Ile Asn Cys Ile Arg Pro Asn Asn Asn
            290                 295                 300

Thr Arg Arg Ser Ile Arg Ile Gly Pro Gly Gln Ala Phe Tyr Ala Ala
305                 310                 315                 320

Asn Gly Ile Val Gly Asn Ile Arg Gln Ala His Cys Asn Ile Ser Glu
                325                 330                 335

Gly Glu Trp Asn Lys Thr Leu Tyr Arg Val Ser Arg Lys Leu Ala Glu
            340                 345                 350

His Phe Pro Gly Lys Glu Ile Lys Phe Lys Pro His Ser Gly Gly Asp
            355                 360                 365

Leu Glu Ile Thr Thr His Ser Phe Asn Cys Arg Gly Glu Phe Phe Tyr
            370                 375                 380

Cys Asn Thr Ser Lys Leu Phe Asn Gly Thr Tyr Asn Gly Thr Tyr Thr
385                 390                 395                 400

Asn Asn Asp Thr Asn Ser Thr Ile Ile Leu Pro Cys Arg Ile Lys Gln
                405                 410                 415

Ile Ile Asn Met Trp Gln Glu Val Gly Gln Ala Met Tyr Ala Pro Pro
            420                 425                 430

Ile Glu Gly Ile Ile Ala Cys Asn Ser Thr Ile Thr Gly Leu Leu Leu
            435                 440                 445

Thr Arg Asp Gly Gly Asp Lys Asn Gly Ser Lys Pro Glu Ile Phe Arg
            450                 455                 460

Pro Gly Gly Gly Asp Met Arg Asp Asn Trp Arg Ser Glu Leu Tyr Lys
465                 470                 475                 480

Tyr Lys Val Val Glu Ile Lys Pro Leu Gly Ile Ala Pro Thr Lys Ala
                485                 490                 495

Lys Arg Arg Val Val Glu Lys Glu Lys Thr Ile Gln Lys Arg
            500                 505                 510
```

<210> SEQ ID NO 36
<211> LENGTH: 477
<212> TYPE: PRT
<213> ORGANISM: Human immunodeficiency virus 1

<400> SEQUENCE: 36

```
Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Val Pro Val
            20                  25                  30

Trp Lys Glu Ala Asp Thr Thr Leu Phe Cys Ala Ser Asp Ala Lys Ala
        35                  40                  45

His Glu Thr Glu Val His Asn Val Trp Ala Thr His Ala Cys Val Pro
    50                  55                  60

Thr Asp Pro Asn Pro Gln Glu Ile Asp Leu Glu Asn Val Thr Glu Asn
65                  70                  75                  80

Phe Asn Met Trp Lys Asn Asn Met Val Glu Gln Thr Leu His Cys Thr
                85                  90                  95

Asn Ala Asn Leu Thr Lys Ala Asn Leu Thr Asn Val Asn Asn Arg Thr
            100                 105                 110

Asn Val Ser Asn Ile Ile Gly Asn Ile Thr Asp Glu Val Arg Asn Cys
        115                 120                 125

Ser Phe Asn Met Thr Thr Glu Leu Arg Asp Lys Lys Gln Lys Val His
    130                 135                 140

Ala Leu Phe Tyr Lys Leu Asp Ile Val Pro Ile Glu Asp Asn Asn Asp
145                 150                 155                 160

Ser Ser Glu Tyr Arg Leu Ile Asn Cys Asn Thr Ser Val Ile Lys Gln
                165                 170                 175

Pro Cys Pro Lys Ile Ser Phe Asp Pro Ile Pro Ile His Tyr Cys Thr
            180                 185                 190

Pro Ala Gly Tyr Ala Ile Leu Lys Cys Asn Asp Lys Asn Phe Asn Gly
        195                 200                 205

Thr Gly Pro Cys Lys Asn Val Ser Ser Val Gln Cys Thr His Gly Ile
    210                 215                 220

Lys Pro Val Val Ser Thr Gln Leu Leu Leu Asn Gly Ser Leu Ala Glu
225                 230                 235                 240

Glu Glu Ile Ile Ile Arg Ser Glu Asn Leu Thr Asn Asn Ala Lys Thr
                245                 250                 255

Ile Ile Val His Leu Asn Lys Ser Val Val Ile Asn Cys Thr Arg Pro
            260                 265                 270

Ser Asn Asn Thr Arg Thr Ser Ile Thr Ile Gly Pro Gly Gln Val Phe
        275                 280                 285

Tyr Arg Thr Gly Asp Ile Ile Gly Asp Ile Arg Lys Ala Tyr Cys Glu
    290                 295                 300

Ile Asn Gly Thr Glu Trp Asn Lys Ala Leu Lys Gln Val Thr Glu Lys
305                 310                 315                 320

Leu Lys Glu His Phe Asn Asn Lys Pro Ile Ile Phe Gln Pro Pro Ser
                325                 330                 335

Gly Gly Asp Leu Glu Ile Thr Met His His Phe Asn Cys Arg Gly Glu
            340                 345                 350

Phe Phe Tyr Cys Asn Thr Thr Arg Leu Phe Asn Thr Cys Ile Ala
        355                 360                 365

Asn Gly Thr Ile Glu Gly Cys Asn Gly Asn Ile Thr Leu Pro Cys Lys
    370                 375                 380
```

```
Ile Lys Gln Ile Ile Asn Met Trp Gln Gly Ala Gly Gln Ala Met Tyr
385                 390                 395                 400

Ala Pro Pro Ile Ser Gly Thr Ile Asn Cys Val Ser Asn Ile Thr Gly
                405                 410                 415

Ile Leu Leu Thr Arg Asp Gly Gly Ala Thr Asn Asn Thr Asn Asn Glu
            420                 425                 430

Thr Phe Arg Pro Gly Gly Gly Asn Ile Lys Asp Asn Trp Arg Asn Glu
        435                 440                 445

Leu Tyr Lys Tyr Lys Val Val Gln Ile Glu Pro Leu Gly Val Ala Pro
    450                 455                 460

Thr Arg Ala Lys Arg Arg Val Val Glu Arg Glu Lys Arg
465                 470                 475

<210> SEQ ID NO 37
<211> LENGTH: 485
<212> TYPE: PRT
<213> ORGANISM: Human immunodeficiency virus 1

<400> SEQUENCE: 37

Met Arg Val Lys Gly Ile Arg Lys Asn Tyr Gln His Leu Trp Arg Trp
1               5                   10                  15

Gly Thr Met Leu Leu Gly Ile Leu Met Ile Cys Ser Ala Val Pro Val
                20                  25                  30

Trp Lys Glu Ala Thr Thr Thr Leu Phe Cys Ala Ser Asp Ala Lys Ala
            35                  40                  45

Tyr Asp Thr Glu Val His Asn Val Trp Ala Thr His Ala Cys Val Pro
        50                  55                  60

Thr Asp Pro Asn Pro Gln Glu Leu Val Leu Ala Asn Val Thr Glu Asn
65                  70                  75                  80

Phe Asn Met Trp Asn Asn Thr Met Val Glu Gln Thr Leu Asn Cys Thr
                85                  90                  95

Asp Val Thr Asn Ala Thr Asn Ile Asn Ala Thr Asn Ile Asn Asn Ser
            100                 105                 110

Ser Gly Gly Val Glu Ser Gly Glu Ile Lys Asn Cys Ser Phe Asn Ile
        115                 120                 125

Thr Thr Ser Val Arg Asp Lys Val Gln Lys Glu Tyr Ala Leu Phe Tyr
    130                 135                 140

Lys Leu Asp Ile Val Pro Ile Thr Asn Glu Ser Ser Lys Tyr Arg Leu
145                 150                 155                 160

Ile Ser Cys Asn Thr Ser Val Leu Thr Gln Ala Cys Pro Lys Val Ser
                165                 170                 175

Phe Glu Pro Ile Pro Ile His Tyr Cys Ala Pro Ala Gly Phe Ala Ile
            180                 185                 190

Leu Lys Cys Asn Asn Glu Thr Phe Asn Gly Lys Gly Pro Cys Ile Asn
        195                 200                 205

Val Ser Thr Val Gln Cys Thr His Gly Ile Arg Pro Val Val Ser Thr
    210                 215                 220

Gln Leu Leu Leu Asn Gly Ser Leu Ala Glu Lys Glu Val Ile Ile Arg
225                 230                 235                 240

Ser Asp Asn Phe Ser Asp Asn Ala Lys Asn Ile Ile Val Gln Leu Lys
                245                 250                 255

Glu Tyr Val Lys Ile Asn Cys Thr Arg Pro Asn Asn Asn Thr Arg Lys
            260                 265                 270

Ser Ile His Ile Gly Pro Gly Arg Ala Phe Tyr Ala Thr Gly Glu Ile
```

```
                275                 280                 285
Ile Gly Asn Ile Arg Gln Ala His Cys Asn Ile Ser Arg Ser Lys Trp
290                 295                 300
Asn Asp Thr Leu Lys Gln Ile Ala Ala Lys Leu Gly Glu Gln Phe Arg
305                 310                 315                 320
Asn Lys Thr Ile Val Phe Asn Pro Ser Ser Gly Gly Asp Leu Glu Ile
                325                 330                 335
Val Thr His Ser Phe Asn Cys Gly Gly Glu Phe Phe Tyr Cys Asn Thr
            340                 345                 350
Thr Lys Leu Phe Asn Ser Thr Trp Ile Arg Glu Gly Asn Asn Gly Thr
        355                 360                 365
Trp Asn Gly Thr Ile Gly Leu Asn Asp Thr Ala Gly Asn Asp Thr Ile
370                 375                 380
Ile Leu Pro Cys Lys Ile Lys Gln Ile Ile Asn Met Trp Gln Glu Val
385                 390                 395                 400
Gly Lys Ala Met Tyr Ala Pro Pro Ile Arg Gly Gln Ile Arg Cys Ser
                405                 410                 415
Ser Asn Ile Thr Gly Leu Ile Leu Thr Arg Asp Gly Gly Lys Asp Asp
            420                 425                 430
Ser Asn Gly Ser Glu Ile Leu Glu Ile Phe Arg Pro Gly Gly Gly Asp
        435                 440                 445
Met Arg Asp Asn Trp Arg Ser Glu Leu Tyr Lys Tyr Lys Val Val Arg
450                 455                 460
Ile Glu Pro Leu Gly Val Ala Pro Thr Arg Ala Arg Glu Arg Val Val
465                 470                 475                 480
Gln Lys Glu Lys Glu
                485

<210> SEQ ID NO 38
<211> LENGTH: 486
<212> TYPE: PRT
<213> ORGANISM: Human immunodeficiency virus 1

<400> SEQUENCE: 38

Met Arg Val Lys Gly Ile Arg Lys Asn Tyr Gln His Leu Trp Arg Trp
1               5                   10                  15
Gly Ile Trp Arg Trp Gly Ile Met Leu Leu Gly Thr Leu Met Ile Cys
            20                  25                  30
Ser Ala Val Pro Val Trp Lys Glu Ala Thr Thr Thr Leu Phe Cys Ala
        35                  40                  45
Ser Asp Ala Lys Ala Tyr Ser Pro Glu Lys His Asn Ile Trp Ala Thr
    50                  55                  60
His Ala Cys Val Pro Thr Asp Pro Asn Pro Gln Glu Leu Val Leu Gly
65                  70                  75                  80
Asn Val Thr Glu Asp Phe Asn Met Trp Lys Asn Asn Met Val Glu Gln
                85                  90                  95
Thr Leu Asn Cys Thr Asp Leu Lys Asn Ser Ala Thr Asp Thr Asn Gly
            100                 105                 110
Thr Ser Gly Thr Asn Asn Arg Thr Val Glu Gln Gly Met Glu Thr Glu
        115                 120                 125
Ile Lys Asn Cys Ser Phe Asn Ile Thr Thr Gly Ile Gly Asn Lys Met
    130                 135                 140
Gln Lys Glu Tyr Ala Leu Phe Tyr Lys Leu Asp Val Val Pro Ile Asp
145                 150                 155                 160
```

```
Ser Asn Asn Asn Ser Asp Asn Thr Ser Tyr Arg Leu Ile Ser Cys Asn
            165                 170                 175

Thr Ser Val Val Thr Gln Ala Cys Pro Lys Thr Ser Phe Glu Pro Ile
        180                 185                 190

Pro Ile His Tyr Cys Ala Pro Ala Gly Phe Ala Ile Leu Lys Cys Asn
        195                 200                 205

Asn Lys Thr Phe Ser Gly Lys Gly Pro Cys Lys Asn Val Ser Thr Val
        210                 215                 220

Gln Cys Thr His Gly Ile Arg Pro Val Val Ser Thr Gln Leu Leu Leu
225                 230                 235                 240

Asn Gly Ser Leu Ala Glu Glu Glu Ile Val Ile Arg Ser Glu Asn Phe
            245                 250                 255

Thr Asn Asn Ala Lys Thr Ile Ile Val Gln Leu Asn Glu Ser Val Ile
        260                 265                 270

Ile Asn Cys Thr Arg Pro Asn Asn Asn Thr Arg Lys Gly Ile His Ile
        275                 280                 285

Gly Leu Gly Arg Ala Leu Tyr Ala Thr Gly Asp Ile Ile Gly Asp Ile
        290                 295                 300

Arg Gln Ala His Cys Asn Leu Ser Ser Lys Ser Trp Asn Lys Thr Leu
305                 310                 315                 320

Gln Gln Val Val Arg Lys Leu Arg Glu Gln Phe Gly Asn Lys Thr Ile
                325                 330                 335

Ala Phe Asn Gln Ser Ser Gly Gly Asp Gln Glu Ile Val Lys His Ser
            340                 345                 350

Phe Asn Cys Gly Gly Glu Phe Phe Tyr Cys Asp Thr Thr Gln Leu Phe
        355                 360                 365

Asn Ser Thr Trp Ser Ser Asn Asp Thr Trp Asn Ser Thr Gly Val Gln
        370                 375                 380

Asp Asn Asn Ile Thr Leu Pro Cys Arg Ile Lys Gln Ile Ile Asn Met
385                 390                 395                 400

Trp Gln Glu Val Gly Lys Ala Met Tyr Ala Pro Pro Ile Gln Gly Leu
                405                 410                 415

Ile Ser Cys Ser Ser Asn Ile Thr Gly Leu Leu Leu Thr Arg Asp Gly
            420                 425                 430

Gly Thr Asn Asn Thr Asn Ala Thr Glu Ile Phe Arg Pro Gly Gly Gly
            435                 440                 445

Asp Met Arg Asp Asn Trp Arg Ser Glu Leu Tyr Lys Tyr Lys Val Val
        450                 455                 460

Lys Ile Glu Pro Leu Gly Ile Ala Pro Thr Lys Ala Lys Arg Arg Val
465                 470                 475                 480

Val Gln Arg Glu Lys Arg
                485

<210> SEQ ID NO 39
<211> LENGTH: 468
<212> TYPE: PRT
<213> ORGANISM: Human immunodeficiency virus 1

<400> SEQUENCE: 39

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Val Pro Val
            20                  25                  30

Trp Lys Glu Ala Asn Thr Thr Leu Phe Cys Ala Ser Asp Ala Lys Ala
        35                  40                  45
```

-continued

```
Tyr Asp Thr Glu Val His Asn Val Trp Ala Thr His Ala Cys Val Pro
 50                  55                  60
Thr Asp Pro Asn Pro Gln Glu Ile Val Leu Glu Asn Val Thr Glu Asn
 65                  70                  75                  80
Phe Asn Met Trp Lys Asn Asn Met Val Glu Gln Thr Leu Asn Cys Thr
                 85                  90                  95
Asn Val Asn Val Thr Asn Thr Thr Asn Asn Thr Glu Glu Lys Gly Glu
                100                 105                 110
Ile Lys Asn Cys Ser Phe Asn Ile Thr Thr Glu Ile Arg Asp Lys Lys
            115                 120                 125
Gln Lys Val Tyr Ala Leu Phe Tyr Arg Leu Asp Val Val Pro Ile Asp
130                 135                 140
Asp Asn Asn Asn Ser Ser Asn Tyr Arg Leu Ile Asn Cys Asn Thr
145                 150                 155                 160
Ser Ala Ile Thr Gln Ala Cys Pro Lys Val Ser Phe Glu Pro Ile Pro
                165                 170                 175
Ile His Tyr Cys Ala Pro Ala Gly Phe Ala Ile Leu Lys Cys Asn Asp
                180                 185                 190
Lys Lys Phe Asn Gly Thr Gly Pro Cys Lys Asn Val Ser Thr Val Gln
            195                 200                 205
Cys Thr His Gly Ile Lys Pro Val Val Ser Thr Gln Leu Leu Leu Asn
210                 215                 220
Gly Ser Leu Ala Glu Glu Glu Ile Ile Ile Arg Ser Glu Asn Ile Thr
225                 230                 235                 240
Asn Asn Ala Lys Thr Ile Ile Val Gln Leu Asn Glu Ser Val Glu Ile
                245                 250                 255
Asn Cys Thr Arg Pro Asn Asn Asn Thr Arg Lys Ser Ile Arg Ile Gly
                260                 265                 270
Pro Gly Gln Ala Phe Tyr Ala Thr Gly Asp Ile Ile Gly Asp Ile Arg
            275                 280                 285
Gln Ala His Cys Asn Ile Ser Gly Thr Lys Trp Asn Lys Thr Leu Gln
290                 295                 300
Gln Val Ala Lys Lys Leu Arg Glu His Phe Asn Asn Lys Thr Ile Ile
305                 310                 315                 320
Phe Lys Pro Ser Ser Gly Gly Asp Leu Glu Ile Thr Thr His Ser Phe
                325                 330                 335
Asn Cys Arg Gly Glu Phe Phe Tyr Cys Asn Thr Ser Gly Leu Phe Asn
                340                 345                 350
Ser Thr Trp Ile Gly Asn Gly Thr Lys Asn Asn Asn Thr Asn Asp
            355                 360                 365
Thr Ile Thr Leu Pro Cys Arg Ile Lys Gln Ile Ile Asn Met Trp Gln
370                 375                 380
Gly Val Gly Gln Ala Met Tyr Ala Pro Pro Ile Glu Gly Lys Ile Thr
385                 390                 395                 400
Cys Lys Ser Asn Ile Thr Gly Leu Leu Leu Thr Arg Asp Gly Gly Asn
                405                 410                 415
Asn Asn Thr Asn Glu Thr Glu Ile Phe Arg Pro Gly Gly Gly Asp Met
                420                 425                 430
Arg Asp Asn Trp Arg Ser Glu Leu Tyr Lys Tyr Lys Val Val Lys Ile
            435                 440                 445
Glu Pro Leu Gly Val Ala Pro Thr Lys Ala Lys Arg Arg Val Val Glu
450                 455                 460
```

```
Arg Glu Lys Arg
465

<210> SEQ ID NO 40
<211> LENGTH: 466
<212> TYPE: PRT
<213> ORGANISM: Human immunodeficiency virus 1

<400> SEQUENCE: 40

Met Arg Val Arg Gly Ile Trp Lys Asn Trp Pro Gln Trp Leu Ile Trp
1               5                   10                  15

Ser Ile Leu Gly Phe Trp Ile Gly Asn Met Glu Gly Ser Val Pro Val
            20                  25                  30

Trp Lys Glu Ala Lys Thr Thr Leu Phe Cys Ala Ser Asp Ala Lys Ala
        35                  40                  45

Tyr Glu Lys Glu Val His Asn Val Trp Ala Thr His Ala Cys Val Pro
    50                  55                  60

Thr Asp Pro Asn Pro Gln Glu Met Val Leu Ala Asn Val Thr Glu Asn
65                  70                  75                  80

Phe Asn Met Trp Lys Asn Asp Met Val Glu Gln Thr Leu Asn Cys Thr
                85                  90                  95

Asn Val Lys Gly Asn Glu Ser Asp Thr Ser Glu Val Met Lys Asn Cys
            100                 105                 110

Ser Phe Lys Ala Thr Thr Glu Leu Lys Asp Lys Lys His Lys Val His
        115                 120                 125

Ala Leu Phe Tyr Lys Leu Asp Val Val Pro Leu Asn Gly Asn Ser Ser
    130                 135                 140

Ser Ser Gly Glu Tyr Arg Leu Ile Asn Cys Asn Thr Ser Ala Ile Thr
145                 150                 155                 160

Gln Ala Cys Pro Lys Val Ser Phe Asp Pro Ile Pro Leu His Tyr Cys
                165                 170                 175

Ala Pro Ala Gly Phe Ala Ile Leu Lys Cys Asn Asn Lys Thr Phe Asn
            180                 185                 190

Gly Thr Gly Pro Cys Arg Asn Val Ser Thr Val Gln Cys Thr His Gly
        195                 200                 205

Ile Lys Pro Val Val Ser Thr Gln Leu Leu Leu Asn Gly Ser Leu Ala
    210                 215                 220

Glu Glu Glu Ile Ile Ile Arg Ser Glu Asn Leu Thr Asn Asn Ala Lys
225                 230                 235                 240

Thr Ile Ile Val His Leu Asn Glu Ser Val Asn Ile Val Cys Thr Arg
                245                 250                 255

Pro Asn Asn Asn Thr Arg Lys Ser Ile Arg Ile Gly Pro Gly Gln Thr
            260                 265                 270

Phe Tyr Ala Thr Gly Asp Ile Ile Gly Asn Ile Arg Gln Ala His Cys
        275                 280                 285

Asn Ile Asn Glu Ser Lys Trp Asn Asn Thr Leu Gln Lys Val Gly Glu
    290                 295                 300

Glu Leu Ala Lys His Phe Pro Ser Lys Thr Ile Lys Phe Glu Pro Ser
305                 310                 315                 320

Ser Gly Gly Asp Leu Glu Ile Thr Thr His Ser Phe Asn Cys Arg Gly
                325                 330                 335

Glu Phe Phe Tyr Cys Asn Thr Ser Asp Leu Phe Asn Gly Thr Tyr Arg
            340                 345                 350

Asn Gly Thr Tyr Asn His Thr Gly Arg Ser Ser Asn Gly Thr Ile Thr
        355                 360                 365
```

```
Leu Gln Cys Lys Ile Lys Gln Ile Ile Asn Met Trp Gln Glu Val Gly
        370                 375                 380

Arg Ala Ile Tyr Ala Pro Pro Ile Glu Gly Glu Ile Thr Cys Asn Ser
385                 390                 395                 400

Asn Ile Thr Gly Leu Leu Leu Arg Asp Gly Gly Gln Ser Asn Glu
            405                 410                 415

Thr Asn Asp Thr Glu Thr Phe Arg Pro Gly Gly Gly Asp Met Arg Asp
                420                 425                 430

Asn Trp Arg Ser Glu Leu Tyr Lys Tyr Lys Val Val Glu Ile Lys Pro
            435                 440                 445

Leu Gly Val Ala Pro Thr Glu Ala Lys Arg Arg Val Val Glu Arg Glu
450                 455                 460

Lys Arg
465

<210> SEQ ID NO 41
<211> LENGTH: 475
<212> TYPE: PRT
<213> ORGANISM: Human immunodeficiency virus 1

<400> SEQUENCE: 41

Met Arg Val Arg Gly Met Leu Arg Asn Cys Gln Gln Trp Trp Ile Trp
1               5                   10                  15

Gly Ile Leu Gly Phe Trp Met Leu Met Ile Cys Ser Val Val Pro Val
            20                  25                  30

Trp Lys Glu Ala Lys Thr Thr Leu Phe Cys Ala Ser Asp Ala Arg Ala
        35                  40                  45

Tyr Glu Arg Glu Val His Asn Val Trp Ala Thr His Ala Cys Val Pro
    50                  55                  60

Thr Asp Pro Asn Pro Gln Glu Met Val Leu Val Asn Val Thr Glu Asn
65                  70                  75                  80

Phe Asn Met Trp Lys Asn Asp Met Val Asp Gln Ile Leu Glu Cys Asn
                85                  90                  95

Asn Ala Asn Gly Thr Thr Asn Asn Gly Ser Val Ile Val Val Asn Glu
            100                 105                 110

Asn Ser Thr Met Tyr Gly Glu Ile Gln Asn Cys Ser Phe Lys Val Asn
        115                 120                 125

Ser Glu Ile Lys Gly Lys Lys Gln Asp Val Tyr Ala Leu Phe Asn Ser
    130                 135                 140

Leu Asp Ile Val Lys Leu Tyr Asn Asn Gly Thr Ser Gln Tyr Arg Leu
145                 150                 155                 160

Ile Asn Cys Asn Thr Ser Thr Leu Thr Gln Ala Cys Pro Lys Val Ser
                165                 170                 175

Phe Asp Pro Ile Pro Ile His Tyr Cys Ala Pro Ala Gly Tyr Ala Ile
            180                 185                 190

Leu Lys Cys Asn Asn Lys Thr Phe Asn Gly Thr Gly Pro Cys Asn Asn
        195                 200                 205

Val Ser Thr Val Gln Cys Thr His Gly Ile Lys Pro Val Val Ser Thr
    210                 215                 220

Gln Leu Leu Leu Asn Gly Ser Leu Ala Glu Gly Glu Ile Ile Ile Arg
225                 230                 235                 240

Ser Lys Asn Leu Thr Asp Asn Thr Lys Thr Ile Ile Val His Leu Asn
                245                 250                 255

Glu Ser Ile Lys Ile Asn Cys Ile Arg Pro Asn Asn Asn Thr Arg Arg
```

```
                    260                 265                 270
Ser Ile Arg Ile Gly Pro Gly Gln Ala Phe Tyr Ala Ala Asn Gly Ile
        275                 280                 285

Val Gly Asn Ile Arg Gln Ala His Cys Asn Ile Ser Glu Gly Glu Trp
        290                 295                 300

Asn Lys Thr Leu Tyr Arg Val Ser Arg Lys Leu Ala Glu His Phe Pro
305                 310                 315                 320

Gly Lys Glu Ile Lys Phe Lys Pro His Ser Gly Gly Asp Leu Glu Ile
                325                 330                 335

Thr Thr His Ser Phe Asn Cys Arg Gly Glu Phe Phe Tyr Cys Asn Thr
                340                 345                 350

Ser Lys Leu Phe Asn Gly Thr Tyr Asn Gly Thr Tyr Thr Asn Asn Asp
        355                 360                 365

Thr Asn Ser Thr Ile Ile Leu Pro Cys Arg Ile Lys Gln Ile Ile Asn
        370                 375                 380

Met Trp Gln Glu Val Gly Gln Ala Met Tyr Ala Pro Pro Ile Glu Gly
385                 390                 395                 400

Ile Ile Ala Cys Asn Ser Thr Ile Thr Gly Leu Leu Leu Thr Arg Asp
                405                 410                 415

Gly Gly Asp Lys Asn Gly Ser Lys Pro Glu Ile Phe Arg Pro Gly Gly
                420                 425                 430

Gly Asp Met Arg Asp Asn Trp Arg Ser Glu Leu Tyr Lys Tyr Lys Val
            435                 440                 445

Val Glu Ile Lys Pro Leu Gly Ile Ala Pro Thr Lys Ala Lys Arg Arg
        450                 455                 460

Val Val Glu Lys Glu Lys Thr Ile Gln Lys Arg
465                 470                 475
```

What is claimed is:

1. A nucleic acid encoding a recombinant protein comprising an HIV-1 envelope (Env) gp120 or gp140, wherein the original 4 to 25 consecutive amino acids of the N-terminus are deleted, wherein the deleted consecutive amino acids are located immediately after the envelope signal peptide and wherein an N-terminal Herpes Simplex gD tag is not substituted for amino acids of the N-terminus.

2. The nucleic acid according to claim 1, wherein 5 to 11 consecutive amino acids of the N-terminus of the recombinant protein are deleted.

3. The nucleic acid according to claim 1, wherein eleven (11) consecutive amino acids of the N-terminus of the recombinant protein are deleted.

4. The nucleic acid according to claim 1, wherein seven (7) consecutive amino acids of the N-terminus of the recombinant protein are deleted.

5. The nucleic acid according to claim 1, wherein said HIV-1 Env is gp120.

6. The nucleic acid according to claim 5, wherein said HIV-1 Env is A244, 1086.C, 089.C, 63521.B, CONS or 6240.B.

7. The nucleic acid according to claim 5, wherein said HIV-1 Env is 040.B or A1C recombinant Env 707-01-069-2.

8. The nucleic acid according to claim 3, wherein the HIV-1 Env is 63521.B delta 11, A244 delta 11, 6240.B delta 11, MCON-S delta 11, or 089.0 delta 11.

9. The nucleic acid according to claim 4, wherein the HIV-1 Env is 1086.0 delta 7.

10. The nucleic acid according to claim 5, wherein said HIV-1 Env comprises the consecutive amino acids immediately after the signal peptide in SEQ ID NO: 2, SEQ ID NO: 4, SEQ ID NO: 6, SEQ ID NO: 8, SEQ ID NO: 10, or SEQ ID NO: 12.

11. A composition comprising said nucleic acid according to claim 1 and a carrier.

12. A composition comprising a nucleic acid encoding a recombinant protein comprising an HIV-1 Env gp120 and an adjuvant, wherein the original 4 to 25 consecutive amino acids of the N-terminus of the HIV-1 Env gp120 are deleted, wherein the deleted consecutive amino acids are located immediately after the envelope signal peptide and wherein an N-terminal Herpes Simplex gD tag is not substituted for amino acids of the N-terminus of gp120.

13. The composition of claim 12, wherein 5 to 11 consecutive amino acids of the N-terminus of the HIV-1 Env gp120 are deleted.

14. The composition of claim 13, wherein seven (7) or eleven (11) consecutive amino acids of the N-terminus of the HIV-1 Env gp120 are deleted.

15. The composition of claim 12, wherein the recombinant HIV-1 protein comprises the consecutive amino acids immediately after the signal peptide in SEQ ID NO: 2, SEQ ID NO: 4, SEQ ID NO: 6, SEQ ID NO: 8, SEQ ID NO: 10, or SEQ ID NO: 12.

16. A method of inducing an immune response in a subject comprising administering to the subject the composition of claim 12 in an amount sufficient to induce the immune response.

17. The method of claim 16, wherein 5 to 11 consecutive amino acids of the N-terminus of the recombinant HIV-1 Env gp120 encoded by the nucleic acid comprised in the composition are deleted.

18. The method of claim 16, wherein seven (7) or eleven (11) consecutive amino acids of the N-terminus of the recombinant HIV-1 Env gp120 encoded by the nucleic acid comprised in the composition are deleted.

19. The method of claim 16, wherein the recombinant HIV-1 Env gp120 encoded by the nucleic acid comprised in the composition protein comprises the consecutive amino acids immediately after the signal peptide in SEQ ID NO: 2, SEQ ID NO: 4, SEQ ID NO: 6, SEQ ID NO: 8, SEQ ID NO: 10, or SEQ ID NO: 12.

20. A method of inducing an immune response in a subject comprising administering to said subject said nucleic acid according to claim 1 in an amount and manner sufficient to induce the immune response.

21. The method of claim 20, wherein 5 to 11 consecutive amino acids of the N-terminus of the recombinant HIV-1 Env encoded by the nucleic acid are deleted.

22. The method of claim 20, wherein seven (7) or eleven (11) consecutive amino acids of the N-terminus of the recombinant HIV-1 Env encoded by the nucleic acid are deleted.

23. The method of claim 20, wherein the recombinant HIV-1 Env comprises the consecutive amino acids immediately after the signal peptide in SEQ ID NO: 2, SEQ ID NO: 4, SEQ ID NO: 6, SEQ ID NO: 8, SEQ ID NO: 10, or SEQ ID NO: 12.

24. A vector comprising the nucleic acid according to claim 1.

25. The vector according to claim 24 wherein said vector is a rAdenovirus, recombinant mycobacteria or recombinant vaccinia type vector.

* * * * *